US007816367B2

(12) United States Patent
Akerman et al.

(10) Patent No.: US 7,816,367 B2
(45) Date of Patent: Oct. 19, 2010

(54) COMPOUNDS, PHARMACEUTICAL COMPOSITIONS AND METHODS FOR USE IN TREATING METABOLIC DISORDERS

(75) Inventors: Michelle Akerman, San Francisco, CA (US); Jonathan Houze, San Mateo, CA (US); Daniel C. H. Lin, Redwood City, CA (US); Jiwen Liu, Foster City, CA (US); Jian Luo, Brisbane, CA (US); Julio C. Medina, San Carlos, CA (US); Wei Qiu, Foster City, CA (US); Jeffrey D. Reagan, Millbrae, CA (US); Rajiv Sharma, Fremont, CA (US); Stephen J. Shuttleworth, Buckinghamshire (GB); Ying Sun, Albany, CA (US); Jian Zhang, Foster City, CA (US); Liusheng Zhu, Burlingame, CA (US); Jinqian Liu, Palo Alto, CA (US); Zhihua Ma, San Mateo, CA (US); Yingcai Wang, Fremont, CA (US); Michael J. Schmitt, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 1087 days.

(21) Appl. No.: 10/591,214

(22) PCT Filed: Feb. 24, 2005

(86) PCT No.: PCT/US2005/005815

§ 371 (c)(1),
(2), (4) Date: Aug. 28, 2006

(87) PCT Pub. No.: WO2005/086661

PCT Pub. Date: Sep. 22, 2005

(65) Prior Publication Data

US 2007/0142384 A1   Jun. 21, 2007

Related U.S. Application Data

(60) Provisional application No. 60/548,741, filed on Feb. 27, 2004, provisional application No. 60/601,579, filed on Aug. 12, 2004.

(51) Int. Cl.
A61K 31/44 (2006.01)
C07D 213/02 (2006.01)
(52) U.S. Cl. ...................... 514/277; 546/341
(58) Field of Classification Search ........................ None
See application file for complete search history.

(56) References Cited

U.S. PATENT DOCUMENTS

| 3,507,881 | A | 4/1970 | Sandberg et al. |
| 4,760,089 | A | 7/1988 | Chambers et al. |
| 6,037,367 | A | 3/2000 | Christensen, IV et al. |
| 6,506,757 | B1 | 1/2003 | Tajima et al. |
| 6,645,939 | B1 | 11/2003 | Durette et al. |
| 6,710,063 | B1 | 3/2004 | Chao et al. |
| 6,723,740 | B2 | 4/2004 | Chao et al. |
| 6,875,780 | B2 | 4/2005 | Auerbach et al. |
| 6,939,875 | B2 | 9/2005 | Auerbach et al. |
| 6,964,983 | B2 | 11/2005 | Auerbach et al. |
| 7,338,960 | B2 | 3/2008 | Bell et al. |
| 7,345,068 | B2 | 3/2008 | Endou et al. |
| 2004/0058965 | A1 | 3/2004 | Momose et al. |
| 2005/0089866 | A1 | 4/2005 | Hinuma et al. |
| 2005/0119256 | A1 | 6/2005 | Endo et al. |
| 2006/0003344 | A1 | 1/2006 | Houseknecht et al. |
| 2006/0004012 | A1 | 1/2006 | Akerman et al. |
| 2006/0270724 | A1 | 11/2006 | Houze et al. |

FOREIGN PATENT DOCUMENTS

| AU | 27141/77 | 1/1979 |
| AU | 52306/93 | 6/1994 |
| CA | 2111035 | 6/1994 |
| DE | 27 33 305 | 7/1977 |
| DE | 42 41 632 A1 | 6/1994 |
| DE | 199 41 567 A1 | 4/2000 |
| EP | 0 250 264 A1 | 12/1987 |
| EP | 0 414 289 B1 | 2/1991 |
| EP | 1 357 115 A1 | 10/2003 |
| EP | 1 380 562 A1 | 1/2004 |
| EP | 1 535 915 A1 | 6/2005 |
| EP | 1 559 422 A1 | 8/2005 |
| EP | 1 630 152 A1 | 3/2006 |
| JP | 10-316641 | 12/1998 |
| JP | 2001 242165 A | 9/2001 |
| JP | 2002 003368 A | 1/2002 |
| WO | WO 93/23040 | 11/1993 |
| WO | WO 93/23041 | 11/1993 |
| WO | WO 95/01326 | 1/1995 |
| WO | WO 95/01348 | 1/1995 |
| WO | WO 96/40097 | 12/1996 |
| WO | WO 97/10819 | 3/1997 |
| WO | WO 97/12853 | 4/1997 |
| WO | WO 97/12867 | 4/1997 |
| WO | WO 99/11255 | 3/1999 |
| WO | WO 99/30709 | 6/1999 |
| WO | WO 99/62871 | 12/1999 |

(Continued)

OTHER PUBLICATIONS

Vincent et al, Analytical Chemistry (1997), 69(21), 4419-4428.*

(Continued)

Primary Examiner—Zinna N Davis
(74) Attorney, Agent, or Firm—Bernard Friedrichsen

(57) ABSTRACT

The present invention provides compounds useful, for example, for modulating insulin levels in a subject and that have the general formula $Q-L^1-P-L^2-M-X-L^3-A$ wherein the definitions of the variables Q, $L^1$, P, $L^2$, M, X, $L^3$ and A are provided herein. The present invention also provides compositions and methods for use of the compounds, for instance, for treatment of type II diabetes.

25 Claims, 1 Drawing Sheet

FOREIGN PATENT DOCUMENTS

Figure 1:
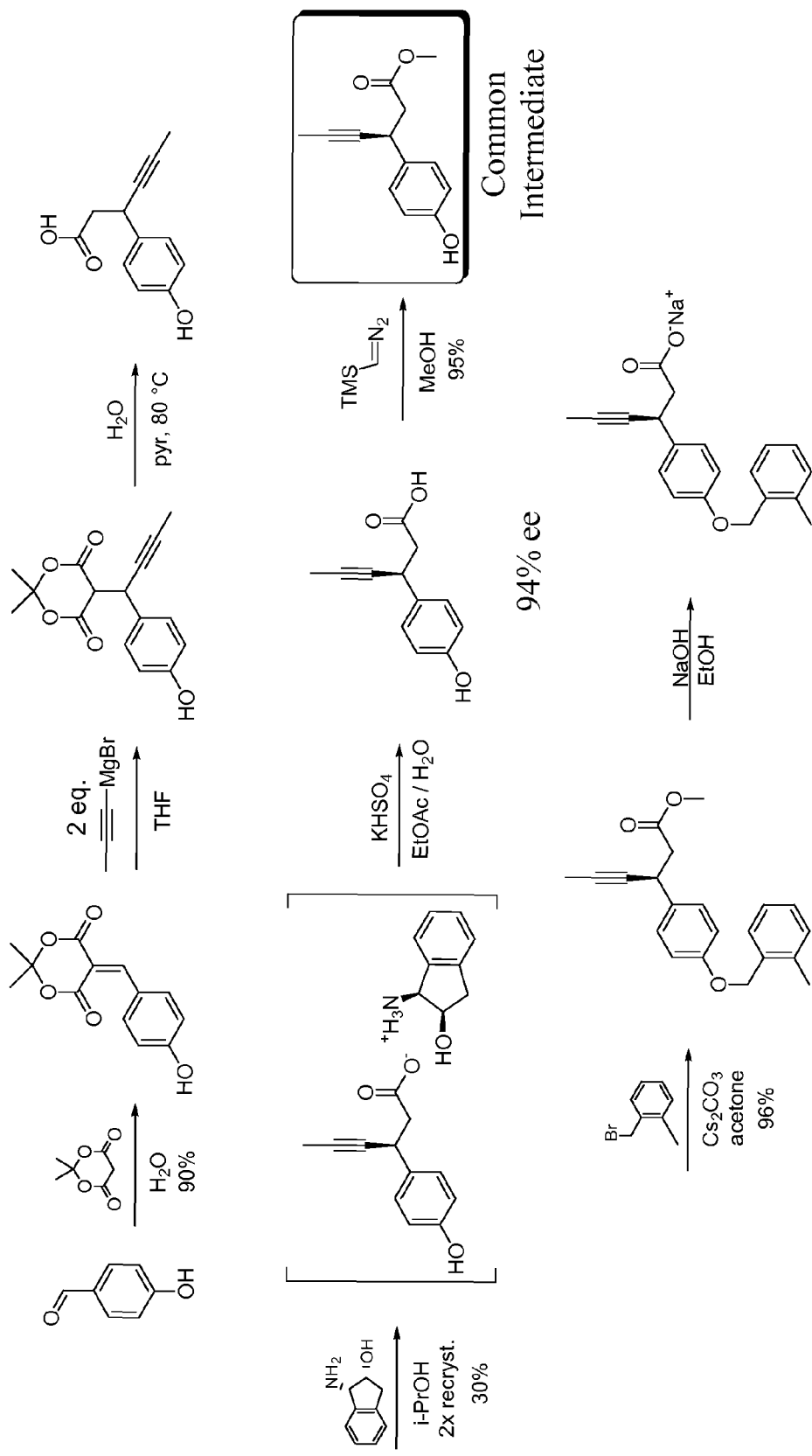

| | | |
|---|---|---|
| WO | WO 00/63196 | 10/2000 |
| WO | WO 00/64876 | 11/2000 |
| WO | WO 00/68223 A1 | 11/2000 |
| WO | WO 00/74666 | 12/2000 |
| WO | WO 01/00603 A1 | 1/2001 |
| WO | WO 01/36351 A2 | 5/2001 |
| WO | WO 01/36365 A2 | 5/2001 |
| WO | WO 02/053547 A1 | 7/2002 |
| WO | WO 02/057783 A2 | 7/2002 |
| WO | WO 02/062774 | 8/2002 |
| WO | WO 02/100403 | 12/2002 |
| WO | WO 02/100812 A1 | 12/2002 |
| WO | WO 03/068959 A1 | 8/2003 |
| WO | WO 03/074050 A1 | 9/2003 |
| WO | WO 03/099793 A1 | 12/2003 |
| WO | WO 2004/000315 A1 | 12/2003 |
| WO | WO 2004/000915 | 12/2003 |
| WO | WO 2004/022551 A1 | 3/2004 |
| WO | WO 2004/041266 A1 | 5/2004 |
| WO | WO 2004/092117 A1 | 10/2004 |
| WO | WO 2004/106276 A1 | 12/2004 |
| WO | WO 2005/051890 A1 | 6/2005 |
| WO | WO 2005/058848 A1 | 6/2005 |
| WO | WO 2005/063725 A1 | 6/2005 |
| WO | WO 2005/063729 A1 | 7/2005 |
| WO | WO 2005/087710 A1 | 9/2005 |
| WO | WO 2006/001092 A1 | 1/2006 |
| WO | WO 2006/011615 A1 | 2/2006 |
| WO | WO 2006/083612 A1 | 8/2006 |
| WO | WO 2006/083781 A1 | 8/2006 |

OTHER PUBLICATIONS

West, Anthony R., Solid State Chemistry and its Applications, Wiley, New York, 1988, pp. 358 & 365.*

Booth, C. J. et al., "The Synthesis and Transition Temperatures of Novel Low Molar Mass Chosesteric materials Derives from (R)-2-(4-Hydroxyphenoxy)propanoic Acid," Mol. Cryst. Liq. Cryst., vol. 210, pp. 31-57 (1992).

Booth, C. J. et al., "The Influence of the Liquid Crystalline Core Geometry on the Mesogenicity of Novel Chiral 2-(4-Substituted-phenoxy)propanonitriles," Liquid Crystals, vol. 16(6), pp. 925-940, (1994).

Bachmann, et al., "The Synthesis of an Analog of the Sex Hormones", Jnl. Amer. Chem. Soc., 64: 94-97 (1942).

Berthelot, et al., "Synthesis and Pharmacological Evaluation of γ-Aminobutyric Acid Analogues. New Ligand for $GABA_B$ Sites", Jnl. Med. Chem., 30: 743-746 (1987).

Boyle, et al., "Applications of the spiroannulation of tetralins with alkynes; towards new anti-estrogenic compounds", Jnl. Chem. Soc., Perkin Trans. Org. and Bioorg. Chem., 18: 2707-2711 (1997).

Briscoe, et al., "The Orphan G Protein-Coupled Receptor GPR40 Is Activated by Medium and Long Chain Fatty Acids", Jnl. of Biol. Chem., 278: 11303-11311 (2003).

Briscoe, et al., "Pharmacological regulation of insulin secretion in MIN6 cells through the fatty acid receptor GPR40: identification of agonist and antagonist small molecules", Brit. Jnl. of Pharm., 148: 619-628 (2006).

Burnop, et al., "Fused Carbon Rings. Part XIX. Experiments on the Synthesis of Tetracyclic Compounds of the Sexual Hormonal Type", Jnl. Chem. Soc., 727-735 (1940).

Chatterjee, et al., "Studies on Nucleophilic Ring Opening of Some Epoxides in Polar Protic Solvents", Tetr., 33: 85-94 (1977).

Collins, et al., "The Structure and Function of Oestrogens. IX. Synthesis of the trans Isomer of 5,5,10b-Trimethy1-4b,5,6,10b,11,12-hexahydrochrysene-2,8-diol", Aust. Jnl. Chem., 41: 735-744 (1988).

Deb, et al., "A Stereocontrolled Synthesis of (1'RS,2'SR)-3-Oxo-3',4'-dihydrospiro[cyclopentane-1,1'(2'H)-naphthalen]-2-ylacetic Acid and its Methoxy Analogues", Jnl. Chem. Res. S., 12: 406 (1985).

DeWolf, et al., "Inactivation of Dopamine β-Hydroxylase by β-Ethynyltyramine: Kinetic Characterization and Covalent Modification of an Active Site Peptide", Biochem., 28: 3833-3842 (1989).

Egan, et al., "Naphthalenes as inhibitors of myeloperoxidase: Direct and indirect mechanisms of inhibition", Agents and Actions, 29¾, 266-276 (1990).

Frey, et al., "Total Synthesis of Pentacyclic Diterpenoid Tropone Hainanolidol," Aust. Jnl. Chem., 53: 819-830 (2000).

Galemmo, et al., "The Development of a Novel Series of (Quinolin-2-ylmethoxy) phenyl-Containing Compounds as High-Affinity Leukotriene Receptor Antagonists. 3. Structural Variation of the Acidic Side Chain To Give Antagonists of Enhanced Potency", Jnl. Med. Chem., 33: 2828-2841 (1990).

Garrido, et al., "Synthesis and activity of small molecule GPR40 agonists," Bioorg. and Med. Chem. Lett., 16: 1840-1845 (2006).

Ghosal, et al., "Stereospecific Synthesis of 9bβ-Carbomethoxy-7-Methoxy-2,3,3aα,4,5,9bβHexahydro-1H-Benz[e]Inden-2-one; An Intermediate Towards Physiologically Active Compounds," Tet. Lett., 17: 1463-1464 (1977).

Guthrie, et al., "Synthesis in the Series of Diterpene Alkaloids VI. A Simple Synthesis of Atisine," Tet. Lett., 38: 4645-4654 1966.

Haigh, et al., "Non-thiazolidinedione Antihyperglycaemic Agents. Part 3: The Effects of Stereochemistry on the Potency of α-Methoxy-β-phenylpropanoic Acids," Bioorg. & Med. Chem., 7: 821-830 (1999).

Hares, et al., "Synthetic Studies of Tricyclospirodienones; Model Chemistry for Novel Mimics of Steroid Substrates", Jnl. Chem. Soc. Perkin Trans. 1: Org. and Bioorg. Chem., 13 1481-1492 (1993).

Iizuka, et al., "β-Substituted Phenethylamines as High Affinity Mechanism-Based Inhibitors of Dopamine β-Hydroxylase", Jnl. Med. Chem., 31: 704-706 (1988).

Ishikawa, et al., "Actions of the novel oral antidiabetic agent HQL-975 in insulin-resistant non-insulin—dependent diabetes mellitus model animals", Diabetes Rsh. and Clin. Pract., 41: 101-111 (1998).

Ishikawa, et al., "Effects of the novel oral antidiabetic agent HQL-975 on Glucose and Lipid Metabolism in Diabetic db/db Mice," Arzneim. Forsch. Drug Rsh., 48 (I),: 245-250 (1998).

Itoh, et al., "Free fatty acids regulate insulin secretion from pancreatic β cells through GPR40," Nature, 422: 173-176 (2003).

Johns, et al., "Total Synthesis of Estrajervatetraene," Jnl. Org. Chem., 44: 958-961 (1979).

Kolasa, et al., "Symmetrical Bis(heteroarylmethoxyphenyl) alkylcarboxylic Acids as Inhibitors of Leukotriene Biosynthesis," Jnl. Med. Chem., 43: 3322-3334 (2000).

Kotarsky, et al., "A human cell surface receptor activated by free fatty acids and thiazolidinedione drugs", Biochem. and Biophys. Rsh. Comm., 301: 406-410 (2003).

Kuchar, et al., "Benzyloxyarylaliphatic Acids: Synthesis and Quantitative Relations Between Structure and Antiinflammatory Activity", Collection Czech. Chem., Commun., 47: 2514-2524 (1982).

Kuchar, et al., "The Effects of Lopophilicity on the Inhibition of Denaturation of Serum Albumin and on the Activation of Fibrinolysis Observed with a Series of Benzyloxyarylaliphatic Acids", Collection Czech. Chem, Commun., 48: 1077-1088 (1983).

Lin, et al., "The Discovery of Acylated β-Amino Acids as Potent and Orally Bioavailable VLA-4 Antagonists," Bioorg. & Med. Chem. Lett., 12: 611-614 (2002).

Liu, et al., "Synthesis and Biological Activity of L-Tyrosine-based PPARγ Agonists with Reduced Molecular Weight", Bioorg. & Med. Chem. Lett., 11: 3111-3113 (2001).

Nilsson, et al., "Identification of a free fatty acid receptor, $FFA_2R$, expressed on leukocytes and activated by short-chain fatty acids, "Biochem. and Biophys. Rsh. Commun., 303 1047-1052 (2003).

Oliver, et al., "A selective peroxisome proliferator-activated receptor δ agonist promotes reverse cholesterol transport", PNAS, 98: 5306-5311 (2001).

Poitout, V., "The ins and outs of fatty acids on the pancreatic β cell", Trends in Endocrin. and Metab., 14: 201-203 (2003).

Ray, et al., "Synthesis of Some Angularly Cyclopentanone Fused Hydrophenanthrene and Hydrofluorene Derivatives by Acid-Catalyzed Intramolecular C-Alkylation of γ, σ-Unsaturated α'-Diazomethyl Ketones", Synth. Commun., 21: 1223-1242 (1991).

Sandberg, et al., "N-Aminoalkylsuccinimides as local anaesthetics", Acta Pharmaceutica Suecica, 17: 169-176 (1980).

Sanyal, et al., "A Novel Synthesis of a Tricyclo $(7.5.0^{1,5}.0^{1,9})$ Tetradecane Ring System Related to Gascardic Acid," *Tet. Lett.*, 25: 2187-2190 (1978).

Sarma, et al., "Synthetic Studies on Terpenoids. Parts XVIII.[1,2] Stereocontrolled Synthesis of (±)-1,2,3,4,4a,9,10,10aα-Octahydro-1α-methylphenanthrene-1β,4aβ-dicarboxylic acid and the 7-Methoxy Analogue: A Potential Intermediate for Diterpenoid Syntheses", *Jnl. Chem. Soc. Perkin Trans. I: Organic and Bioorg. Chem.*, 7: 722-727 (1976).

Sawzdargo, et al., "A Cluster of Four Novel Human G Protein-Coupled Receptor Genes Occurring in Close Proximity to CD22 Gene on Chromosome 19q13.1", *Biochem. and Biophys. Rsh. Commun.*, 239: 543-547 (1997).

Shaw, et al., "Enantioselective Synthesis of (+)-(2S,3S)-3-Ethynyltyrosine", *Tet. Lett.*, 31: 5081-5084 (1990).

Shiotani, et al., "Synthesis of 1,3-Bridged 1,2,3,4,5,6-Hexahydro-2,6-methano-3-benzazocine Derivatives[1]" *Chem. Pharm. Bull.*, 28: 1928-1931 (1980).

Waid, et al., "Constrained Amino Acids. An Approach to the Synthesis of 3-Substituted Prolines," *Tet. Lett.*, 37: 4091-4094 (1996).

Search Report by National Center of the Intellectual Property "Sakpatenti" of Georgia for copending application in Georgia No. AP 2005 009637 completed Apr. 8, 2008, and English translation of the search report document.

STN searches for English language equivalents of Russian documents cited in search report (11 pages).

Russian language document from foreign attorneys showing English language equivalents of Russian patent documents (7 pages).

Supplementary Partial European Search Report for copending EP 05723623 by European Patent Office completed on Sep. 7, 2007.

Austrian Patent Office Search Report for Copending Application in Singapore completed Jan. 2, 2009.

* cited by examiner

COMPOUNDS, PHARMACEUTICAL COMPOSITIONS AND METHODS FOR USE IN TREATING METABOLIC DISORDERS

RELATED APPLICATIONS

This application is a 371 of PCT/US05/05815 filed Feb. 24, 2005 which claims the benefit of U.S. provisional application No. 60/548,741, filed Feb. 27, 2004, and U.S. provisional application No. 60/601,579, filed Aug. 12, 2004, which are incorporated herein by reference in their entireties.

1. FIELD OF THE INVENTION

The present invention relates to compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

2. BACKGROUND OF THE INVENTION

The production of insulin is central to the regulation of carbohydrate and lipid metabolism. Insulin imbalances lead to conditions such as type II diabetes mellitus, a serious metabolic disease that afflicts around 5% of the population in Western Societies and over 150 million people worldwide. Insulin is secreted from pancreatic β cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors ("GPCRs"). GPCRs are membrane proteins characterized as having seven putative transmembrane domains that respond to a variety of molecules by activating intra-cellular signaling pathways critical to a diversity of physiological functions. GPR40 was first identified as an orphan receptor (i.e., a receptor without a known ligand) from a human genomic DNA fragment. Sawzdargo et al. (1997) *Biochem. Biophys. Res. Commun.* 239: 543-547. GPR40 is highly expressed in pancreatic β cells and insulin-secreting cell lines. GPR40 activation is linked to modulation of the $G_q$ family of intra-cellular signaling proteins and concomitant induction of elevated calcium levels. It has been recognized that fatty acids serve as ligands for GPR40, and that fatty acids regulate insulin secretion through GPR40. Itoh et al. (2003) *Nature* 422:173-176; Briscoe et al. (2003) *J. Biol. Chem.* 278: 11303-11311; Kotarsky et al. (2003) *Biochem. Biophys. Res. Commun.* 301: 406-410.

The prevalence of type II diabetes, obesity, hypertension, cardiovascular disease and dyslipidemia underscores the need for new therapies to effectively treat or prevent these conditions.

3. SUMMARY OF THE INVENTION

Provided herein are compounds, pharmaceutical compositions and methods useful for treating or preventing a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema.

In one aspect, the compounds of the invention have the general formula (I):

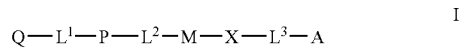

$$Q-L^1-P-L^2-M-X-L^3-A \qquad I$$

wherein Q is hydrogen, aryl, heteroaryl, ($C_1$-$C_6$)alkyl or ($C_2$-$C_6$)heteroalkyl; $L^1$ is a bond, ($C_1$-$C_4$)alkylene, ($C_2$-$C_4$)heteroalkylene, O, S(O)$_m$, N($R^1$), C(O)—($C_5$-$C_7$)heterocycloalkylene, ($C_1$-$C_4$)alkylene-SO$_2$N($R^2$), ($C_1$-$C_4$)alkylene-N($R^2$)SO$_2$ or C(O)N($R^2$); P is an aromatic ring, a heteroaromatic ring, ($C_3$-$C_8$)heterocycloalkylene or ($C_3$-$C_8$)cycloalkylene; $L^2$ is a bond, ($C_1$-$C_6$)alkylene, ($C_2$-$C_6$)heteroalkylene, O, S(O)$_m$, N($R^1$), C(O)N($R^2$), SO$_2$N($R^2$), ($C_1$-$C_4$)alkylene-C(O)N($R^2$), ($C_1$-$C_4$)alkylene-N($R^2$)C(O), ($C_2$-$C_4$)alkenylene-C(O)N($R^2$), ($C_2$-$C_4$)alkenylene-N($R^2$)C(O), ($C_1$-$C_4$)alkylene-SO$_2$N($R^2$), ($C_1$-$C_4$)alkylene-N($R^2$)SO$_2$, ($C_2$-$C_4$)alkenylene-SO$_2$N($R^2$) or ($C_2$-$C_4$)alkenylene-N($R^2$)SO$_2$; M is an aromatic ring, a heteroaromatic ring, ($C_5$-$C_8$)cycloalkylene, aryl($C_1$-$C_4$)alkylene or heteroaryl($C_1$-$C_4$)alkylene; X is $CR^3R^4$, N($R^5$), O or S(O)$_n$; $L^3$ is a bond, ($C_1$-$C_5$)alkylene or ($C_2$-$C_5$)heteroalkylene, provided that $L^3$ is not a bond when $L^2$ is a bond; A is —CO$_2$H, tetrazol-5-yl, —SO$_3$H, —PO$_3$H$_2$, —SO$_2$NH$_2$, —C(O)NHSO$_2$CH$_3$, —CHO, —C(O)$R^6$, —C(O)NHR$^6$, —C(O)NHOR$^7$, thiazolidinedion-yl, hydroxyphenyl or pyridyl; $R^1$ is ($C_1$-$C_6$)alkyl or ($C_2$-$C_6$)heteroalkyl; $R^2$ is hydrogen, ($C_1$-$C_6$)alkyl or ($C_2$-$C_6$)heteroalkyl; $R^3$ is cyano, aryl, heteroaryl, ($C_1$-$C_8$)alkyl, ($C_2$-$C_8$)alkenyl, ($C_2$-$C_8$)alkynyl, —NR$^8$R$^9$, —C(O)NR$^{10}$R$^{11}$, —NR$^{12}$C(O)$R^3$ or —NR$^{12}$S(O)$_p$R$^{13}$; $R^4$ is hydrogen, cyano, aryl, heteroaryl, ($C_1$-$C_8$)alkyl, ($C_2$-$C_8$)alkenyl or ($C_2$-$C_8$)alkynyl, optionally $R^3$ and $R^4$ are combined to form a 3-, 4-, 5-, 6- or 7-membered ring containing from zero to three heteroatoms selected from N, O and S; $R^5$ hydrogen, aryl, heteroaryl, ($C_1$-$C_8$)alkyl, ($C_2$-$C_8$)alkenyl, ($C_2$-$C_8$)alkynyl or ($C_3$-$C_8$)cycloalkyl; $R^6$ is heteroaryl; $R^7$ is hydrogen or ($C_1$-$C_5$)alkyl; $R^8$ and $R^9$ are independently hydrogen, ($C_1$-$C_5$)alkyl, oxy($C_1$-$C_5$)alkyl or carboxy($C_1$-$C_5$)alkyl, optionally, $R^8$ and $R^9$ are combined to form a 4-, 5-, 6- or 7-membered ring containing the nitrogen atom to which they are attached and from 0 to 2 additional heteroatoms selected from N, O and S; $R^{10}$, $R^{11}$ and $R^{12}$ are independently selected from hydrogen, aryl, heteroaryl, ($C_1$-$C_8$)alkyl, ($C_2$-$C_8$)heteroalkyl, ($C_3$-$C_8$)cycloalkyl and ($C_3$-$C_8$)heterocycloalkyl, optionally, $R^{10}$ and $R^{11}$ are combined to form a 4-, 5-, 6- or 7-membered ring containing the nitrogen atom to which they are attached and from 0 to 2 additional heteroatoms selected from N, O and S; $R^{13}$ is aryl, heteroaryl, ($C_1$-$C_8$)alkyl, ($C_2$-$C_8$)heteroalkyl, ($C_3$-$C_8$)cycloalkyl or ($C_3$-$C_8$)heterocycloalkyl; the subscripts m and n are independently 0, 1 or 2; and the subscript p is 1 or 2; and wherein the compound is other than 3-(4-(4-methoxybenzyloxy)phenyl)pent-4-ynoic acid; β-ethenyl-4-phenylmethoxy-benzenepropanoic acid; 4-(2-quinolinylmethoxy)-β-[4-(2-quinolinylmethoxy)phenyl]-benzenepropanoic acid; N-[4-(benzoylamino)phenyl]-N-phenyl-glycine; 3-(4-(isopentyloxy)benzamido)-3-phenylpropanoate; 3-(4-isobutoxybenzamido)-3-phenylpropanoate; (R)-2-((1R,4R)-4-isopropylcyclohexanecarboxamido)-3-phenylpropanoic acid; (R)-3-(4-(benzyloxy)phenyl)-2-(tert-butoxycarbonyl)propanoic acid; 3-(4-chlorophenyl)-3-(furan-2-carboxamido)

propanoic acid; 3-(3,4-dimethoxyphenyl)-3-(furan-2-carboxamido)propanoic acid; 3-(4-chlorobenzamido)-3-(4-(dimethylamino)phenyl)propanoic acid; 3-(2-(2-(3,4-dimethylphenoxy)ethylthio)-1H-benzo[d]imidazol-1-yl)propanoic acid; {2-Bromo-4-[(3,4-dichloro-phenyl)-hydrazonomethyl]-6-ethoxy-phenoxy}-acetic acid; 2-(4-(2-(2-(4-chlorophenyl)furan-5-carboxamido)ethyl)phenoxy)-2-methylpropanoic acid; 5-(3-(3,4-dimethoxyphenyl)-5-(2-fluorophenyl)-4,5-dihydropyrazol-1-yl)-5-oxopentanoic acid; 2-(2-(3-(3,4-dihydro-2H-benzo[b][1,4]dioxepin-7-yl)-2-methyl-4-oxo-4H-chromen-7-yloxy)acetamido)acetic acid; 3-(4'-Bromo-biphenyl-4-yl)-4-phenyl-butyric acid; 3-(4'-Bromo-biphenyl-4-yl)-3-phenylsulfanyl-propionic acid; 3-(5-(2-chloro-6-fluoro-4-(trifluoromethyl)phenoxy)-2,4-dinitrophenyl)propanoic acid; 3-(3-(2-chloro-4-(trifluoromethyl)phenoxy)phenyl)propanoic acid; 3-(4-(4-methoxybenzyloxy)phenyl)pent-4-ynoic acid; 3-(4-(4-methoxybenzyloxy)phenyl)-5-(trimethylsilyl)pent-4-ynoic acid; β,β-dimethyl-4-[[[4 methyl-2-[4-(trifluoromethyl)phenyl]-5-thiazolyl]methyl]thio]-benzenepropanoic acid; β-amino-4-[(4-bromo-2,5-dihydro-2-methyl-5-oxo-1-phenyl-1H-pyrazol-3-yl)methoxy]-3-methoxy-benzenepropanoic acid; or salt thereof.

The compounds of the invention include pharmaceutically acceptable salts, solvates or prodrugs thereof.

In certain embodiments, the present invention provides a compound having the formula (Ia):

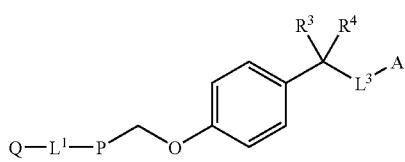

where Q, $L^1$, P, $L^3$, A, $R^3$ and $R^4$ are as defined with regard to formula I above.

In certain embodiments, the present invention provides a compound having the formula (Ib):

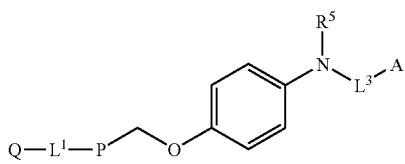

where Q, $L^1$, P, $L^3$, A and $R^5$ are as defined with regard to formula I above.

In another aspect, the compounds of the inventions have the general formula (II):

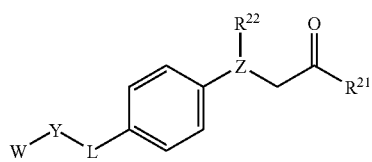

wherein Z is

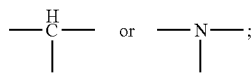

$R^{21}$ is —H, —OH, —NHS($O_2$)$CH_3$, heteroaryl, or —NH—heteroaryl; $R^{22}$ is —($C_2$-$C_8$)alkyl, —($C_3$-$C_8$)alkenyl, —NR$^{23}$R$^{24}$, substituted or unsubstituted aryl, substituted or unsubstituted heteroaryl, —C≡N, or —C≡C—$R^{25}$, or optionally where Z is a nitrogen atom, $R^{22}$ is —H; $R^{23}$ and $R^{24}$ are independently —H, —($C_1$-$C_5$)alkyl, or —($C_1$-$C_5$)oxyalkyl; $R^{25}$ is —H, —($C_1$-$C_5$)alkyl, -hetero($C_1$-$C_5$)alkyl, —($C_1$-$C_5$)oxyalkyl, substituted or unsubstituted aryl, or substituted or unsubstituted heteroaryl; L is —O—, —S—, or —N($R^{26}$)—; $R^{26}$ is —H, —($C_1$-$C_5$)alkyl, substituted or unsubstituted aryl($C_1$-$C_{10}$)alkyl, substituted or unsubstituted aryl, or substituted or unsubstituted heteroaryl; Y is absent or is —$CH_2$—, —$CH_2CH_2$—, —CH=CH—, —C(O)$CH_2$—, —C(O)$CH_2CH_2$—, —C(O)CH=CH—, —S($O_2$)—, —S($O_2$)$CH_2$—, —S($O_2$)$CH_2CH_2$—, —S($O_2$)CH=CH—, or —C(O)—; W is a substituted or unsubstituted aryl or substituted or unsubstituted heteroaryl.

In another aspect, the invention provides pharmaceutical compositions comprising a pharmaceutically acceptable carrier, diluent or excipient and a compound of formula I, Ia, Ib or II.

In another aspect, the invention provides methods for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease atherosclerosis, kidney disease, ketoacidosis, nephropathy, diabetic neuropathy, diabetic retinopathy, sexual dysfunction, thrombotic disorders, dermatopathy, dyspepsia, hypoglycemia, hypertension, cancer and edema comprising administering to a subject in need thereof a therapeutically effective amount of a compound of formula I, Ia, Ib or II.

In another aspect, the invention provides methods for treating or preventing a disease or condition responsive to the modulation of GPR40 comprising administering to a subject in need thereof a therapeutically effective amount of a compound of formula I, Ia, Ib or II.

In another aspect, the invention provides methods for treating or preventing a disease or condition mediated, regulated or influenced by pancreatic P cells comprising administering to a subject in need thereof a therapeutically effective amount of a compound of formula I, Ia, Ib or II.

In another aspect, the invention provides methods for modulating GPR40 function in a cell, comprising contacting a cell with a compound of formula I, Ia, Ib or II.

In another aspect, the invention provides methods for modulating GPR40 function comprising contacting GPR40 with a compound of formula I, Ia, Ib or II.

In another aspect, the invention provides methods for modulating circulating insulin concentration in a subject, comprising administering a compound of formula I, Ia, Ib or II to the subject.

Other objects, features and advantages of the invention will become apparent to those skilled in the art from the following description and claims.

4. BRIEF DESCRIPTION OF THE FIGURES

FIG. 1 provides a scheme for synthesis of exemplary compounds of the invention.

5. DETAILED DESCRIPTION OF THE INVENTION

5.1 Abbreviations and Definitions

The terms "treat", "treating" and "treatment", as used herein, are meant to include alleviating or abrogating a condition or disease and/or its attendant symptoms and alleviating. The terms "prevent", "preventing" and "prevention", as used herein, refer to a method of delaying or precluding the onset of a condition or disease and/or its attendant symptoms, barring a subject from acquiring a condition or disease or reducing a subject's risk of acquiring a condition or disease.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity and the age, weight, etc., of the subject to be treated.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

As used herein, the term "GPR40-mediated condition or disorder" and the like refer to a condition or disorder characterized by inappropriate, for example, less than or greater than normal, GPR40 activity. A GPR40-mediated condition or disorder may be completely or partially mediated by inappropriate GPR40 activity. However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia and edema.

The term "alkyl", by itself or as part of another substituent, means, unless otherwise stated, a straight or branched chain, or cyclic hydrocarbon radical, or combination thereof, which is fully saturated, having the number of carbon atoms designated (e.g., $C_1$-$C_{10}$ means one to ten carbons). Examples of alkyl groups include methyl, ethyl, n-propyl, isopropyl, n-butyl, t-butyl, isobutyl, sec-butyl, cyclohexyl, (cyclohexyl)methyl, cyclopropyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —$CH_2CH_2CH_2CH_2$—. Typically, an alkyl (or alkylene) group will have from 1 to 24 carbon atoms, with those groups having 12 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups that can be the same or different.

The term "heteroalkyl," by itself or in combination with another term, means, unless otherwise stated, a stable straight or branched chain, or cyclic hydrocarbon radical, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S may be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, and —$CH_2$—CH=N—$OCH_3$. Up to two heteroatoms may be consecutive, such as, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group is a oxyalkyl group. For instance, $(C_2-C_5)$oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, and the like.

The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl," by themselves or in combination with other terms, represent, unless otherwise stated, cyclic versions of "alkyl" and "heteroalkyl," respectively. Thus, the terms "cycloalkyl" and "heterocycloalkyl" are meant to be included in the terms "alkyl" and "heteroalkyl," respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "cycloalkylene" and "heterocycloalkylene," by themselves or in combination with other terms, represent, unless otherwise stated, cyclic versions of "alkylene" and "heteroalkylene," respectively. Thus, the terms "cycloalkylene" and "heterocycloalkylene" are meant to be included in the terms "alkylene" and "heteroalkylene," respectively. Additionally, for heterocycloalkylene, one or more heteroatoms can occupy positions at which the heterocycle is attached to the remainder of the molecule. Typically, a cycloalkylene or heterocycloalkylene will have from 3 to 9 atoms forming the ring, more typically, 4 to 7 atoms forming the ring, and even more typically, 5 or 6 atoms will form the cycloalkylene or hetercycloalkylene ring.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo $(C_1-C_4)$alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, alkyl substituted with (2m'+1) halogen atoms, where m' is the total number of carbon atoms in the alkyl group. For example, the term "perhalo$(C_1-C_4)$alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, dibenzofuryl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl or quinolyl group which is unsubstituted or substituted.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical, unless otherwise indicated. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR', halogen, —OC(O)R', —C(O)R', —CO$_2$R', —CONR'R", —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C(NH$_2$)=NR', —SiR'R"R''', —S(O)R', —SO$_2$R', —SO$_2$NR'R", —NR"SO$_2$R, —CN and —NO$_2$, in a number ranging from zero to three, with those groups having zero, one or two substituents being particularly preferred. R', R" and R''' each independently refer to hydrogen, unsubstituted $(C_1-C_8)$alkyl and heteroalkyl, unsubstituted aryl, aryl substituted with one to three halogens, unsubstituted alkyl, alkoxy or thioalkoxy groups, halo$(C_1-C_4)$alkyl, or aryl-$(C_1-C_4)$alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —OC(O)R', —C(O)R', —CO$_2$R', —CONR'R", —OC(O)NR'R", —NR"C(O)R', —NR"CO$_2$R', —NR'—SO$_2$NR"R'", —S(O)R', —SO$_2$R', —SO$_2$NR'R", —NR"SO$_2$R, —CN and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR"CO$_2$R', —NR'—SO$_2$NR"R'", —SO$_2$R', —SO$_2$NR'R", —NR"SO$_2$R, —CN and —NO$_2$.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl. Otherwise, R' is as defined above.

As used herein, the term "heteroatom" is meant to include oxygen (O), nitrogen (N), and sulfur (S).

As used herein, the phrase "bioisostere of —CO$_2$H" is meant that the substituent —CO$_2$H may be optionally replaced with bioisosteric replacements such as:

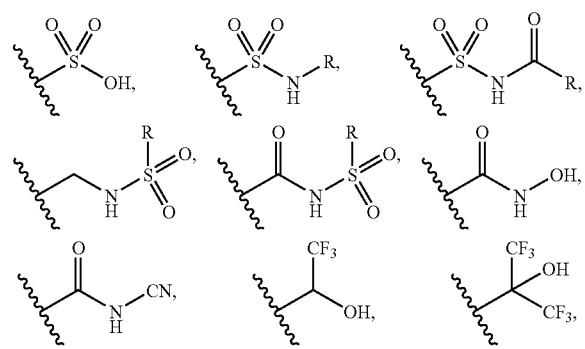

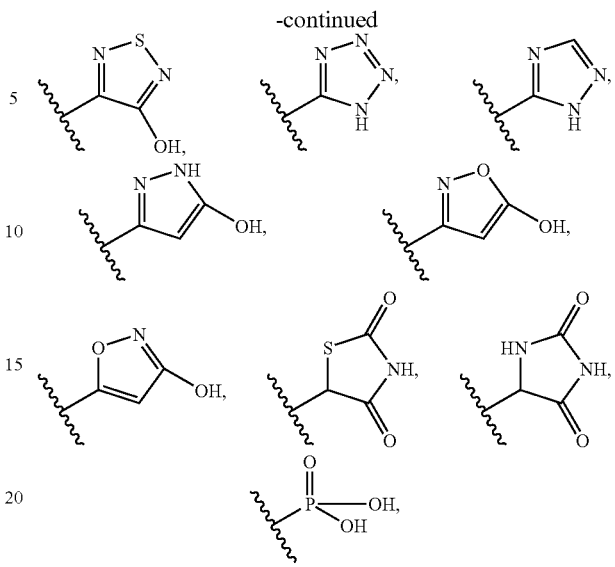

-continued and the like. See, e.g., *The Practice of Medicinal Chemistry*, Wermuth, C. G., Ed., Academic Press: New York, 1996, p. 203.

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al. (1977) *J. Pharm. Sci.* 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate.

Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, enantiomers, diastereomers, geometric isomers and individual isomers are all intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. It should be noted that if the stereochemistry of a structure or a portion of a structure is not indicated with, for example, bold or dashed lines, the structure or portion of the structure is to be interpreted as encompassing all stereoisomers of it.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al. (1997) *Tetrahedron* 33:2725; Eliel, E. L., *Stereochemistry of Carbon Compounds* (McGraw-Hill, NY, 1962), and Wilen, S. H., *Tables of Resolving Agents and Optical Resolutions* p. 268 (E. L. Eliel, Ed., Univ. of Notre Dame Press, Notre Dame, Ind., 1972).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention.

5.2 Embodiments of the Invention

In one aspect, a class of compounds that modulate GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject. The compounds find use as therapeutic agents for modulating diseases and conditions responsive to modulation of GPR40 and/or mediated by GPR40 and/or mediated by pancreatic β cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglylceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema. Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

5.2.1 Compounds

In one aspect, the present invention provides a compound having the formula (I):

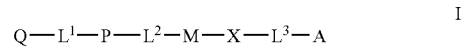

I where Q, $L^1$, P, $L^2$, M, X, $L^3$ and A are defined below.

Q is hydrogen, aryl, heteroaryl, ($C_1$-$C_6$)alkyl or ($C_2$-$C_6$)heteroalkyl.

In preferred embodiments, Q is aryl.

In further preferred embodiments, Q is 4-(trifluoromethyl)phenyl or p-tolyl.

$L^1$ is a bond, $(C_1$-$C_4)$alkylene, $(C_2$-$C_4)$heteroalkylene, O, $S(O)_m$, $N(R^1)$, $C(O)$—$(C_5$-$C_7)$heterocycloalkylene, $(C_1$-$C_4)$alkylene-$SO_2N(R^1)$, $(C_1$-$C_4)$alkylene-$N(R^2)SO_2$ or $C(O)N(R^2)$.

In certain embodiments, $L^1$ is a bond, $(C_1$-$C_4)$alkylene, $(C_2$-$C_4)$heteroalkylene, O, $S(O)_m$, $N(R^1)$ or $C(O)N(R^2)$.

In certain embodiments, $L^1$ is a bond, O or $N(R^1)$.

In preferred embodiments, $L^1$ is a bond.

P is an aromatic ring, a heteroaromatic ring, $(C_3$-$C_8)$heterocycloalkylene or $(C_3$-$C_8)$cycloalkylene. In certain embodiments where P is an aromatic ring, the term aromatic includes aryl. In other embodiments where P is a heteroaromatic ring, the term heteroaromatic includes heteroaryl.

In some embodiments, P is an aromatic ring or a heteroaromatic ring.

In certain embodiments, P is a monocyclic aromatic ring or a monocyclic heteroaromatic ring.

In some embodiments, P is a selected from the group consisting of benzene, naphthalene, pyrrole, pyrazole, imidazole, pyrazine, oxazole, isoxazole, thiazole, furan, thiophene, pyridine, pyrimidine, pyridazine, benzothiazole, purine, benzimidazole, benzoxazole, triazole, oxadiazole, thiadiazole, benzooxadiazole, dibenzofuran, indole, indazole, carbazole, carboline, isoquinoline, quinoxaline and quinoline. For example, P can be benzene, naphthalene, pyrrole, pyrazine, pyridine, pyrimidine, pyridazine, purine, indole, carboline, isoquinoline, quinoxaline or quinoline. In some embodiments, P is a benzene, thiazole, or oxazole ring.

In preferred embodiments, $L^1$ is a bond, O or $N(R^1)$ and P is an aromatic ring or a heteroaromatic ring.

$L^2$ is a bond, $(C_1$-$C_6)$alkylene, $(C_2$-$C_6)$heteroalkylene, oxymethylene, O, $S(O)_m$, $N(R^1)$, $C(O)N(R^2)$, $SO_2N(R^2)$, $(C_1$-$C_4)$alkylene-$C(O)N(R^2)$, $(C_1$-$C_4)$alkylene-$N(R^2)$—$C_4)$alkenylene-$C(O)N(R^2)$, $(C_2$-$C_4)$alkenylene-$N(R^1)C(O)$, $(C_1$-$C_4)$alkylene-$SO_2N(R^2)$, $(C_1$-$C_4)$alkylene-$N(R^2)SO_2$, $(C_2$-$C_4)$alkenylene-$SO_2N(R^2)$ or $(C_2$-$C_4)$alkenylene-$N(R^2)SO_2$.

In certain embodiments, L is a bond, $(C_1$-$C_6)$alkylene, $(C_2$-$C_6)$heteroalkylene, oxymethylene, O, $S(O)_m$, $N(R^1)$, $C(O)N(R^2)$, $SO_2N(R^2)$, $(C_1$-$C_4)$alkylene-$C(O)N(R^2)$, $(C_2$-$C_4)$alkenylene-$C(O)N(R^2)$, $(C_1$-$C_4)$alkylene-$SO_2N(R^2)$ or $(C_2$-$C_4)$alkenylene-$SO_2N(R^2)$.

In certain embodiments, $L^2$ is $(C_2$-$C_6)$heteroalkylene.

In some embodiments, $L^2$ is $(C_2$-$C_4)$heteroalkylene.

In some embodiments, $L^1$ is a bond, O or $N(R^1)$ and $L^2$ is $(C_2$-$C_6)$heteroalkylene.

In certain embodiments, L is oxymethylene or thiomethylene.

In preferred embodiments, $L^1$ is a bond and $L^2$ is oxymethylene or thiomethylene.

M is an aromatic ring, a heteroaromatic ring, $(C_5$-$C_8)$cycloalkylene, aryl$(C_1$-$C_4)$alkylene or heteroaryl$(C_1$-$C_4)$alkylene. In certain embodiments where M is an aromatic ring, the term aromatic includes aryl. In other embodiments where M is a heteroaromatic ring, the term heteroaromatic includes heteroaryl.

In some embodiments, M is an aromatic ring or a heteroaromatic ring.

In some embodiments, M is a $(C_5$-$C_8)$cycloalkylene.

In certain embodiments, M is a monocyclic aromatic, a monocyclic heteroaromatic ring or $(C_5$-$C_8)$cycloalkylene.

In some embodiments, M is an unsubstituted monocyclic aromatic ring or an unsubstituted monocyclic heteroaromatic ring.

In certain embodiments, M is a benzene ring or a heteroaromatic ring.

In preferred embodiments, M is a benzene ring.

In preferred embodiments, P is an aromatic ring or a heteroaromatic ring and M is an aromatic ring, a heteroaromatic ring or $(C_5$-$C_8)$cycloalkylene.

X is $CR^3R^4$, $N(R^5)$, O or $S(O)_n$.

In preferred embodiments, X is $CR^3R^4$ or $N(R^5)$.

In further preferred embodiments, X is $CHR^3$.

In certain embodiments, M is a substituted or unsubstituted benzene ring and X is para to $L^2$.

In certain preferred embodiments, M is an aromatic ring, a heteroaromatic ring or $(C_5$-$C_8)$cycloalkylene and X is $CR^3R^4$ or $N(R^5)$.

In preferred embodiments, P is an aromatic ring or a heteroaromatic ring and X is $CR^3R^4$ or $N(R^5)$.

$L^3$ is a bond, $(C_1$-$C_5)$alkylene or $(C_2$-$C_5)$heteroalkylene, provided that $L^3$ is not a bond when $L^2$ is a bond.

In some embodiments, $L^3$ is $(C_1$-$C_5)$alkylene or $(C_2$-$C_5)$heteroalkylene.

In certain embodiments, $L^3$ is $(C_1$-$C_3)$alkylene.

In some embodiments, $L^3$ is methylene.

In certain embodiments, $L^3$ is a methylene substituted with a monocyclic aryl or monocyclic heteroaryl.

In certain embodiments, X is $CR^3R^4$ or $N(R^5)$, and $L^3$ is substituted or unsubstituted methylene.

In preferred embodiments, $L^2$ is $(C_2$-$C_4)$heteroalkylene and $L^3$ is $(C_1$-$C_3)$alkylene.

In certain preferred embodiments, $L^1$ is a bond, O or $N(R^1)$, $L^2$ is $(C_2$-$C_4)$heteroalkylene and $L^3$ is $(C_1$-$C_3)$alkylene.

A is —$CO_2H$, tetrazol-5-yl, —$SO_3H$, —$PO_3H_2$, —$SO_2NH_2$, —$C(O)NHSO_2CH_3$, —CHO, —$C(O)R^6$, —$C(O)NHR^6$, —$C(O)NHOR^7$, thiazolidinedion-yl, hydroxyphenyl or pyridyl.

In certain embodiments, A is a bioisostere of —$CO_2H$.

In certain embodiments, A is —$CO_2H$ or tetrazol-5-yl, —$C(O)NHSO_2CH_3$ or —$C(O)NHR^6$.

In some embodiments, A is —$CO_2H$ or tetrazol-5-yl.

In preferred embodiments, A is —$CO_2H$ or a salt thereof.

In some embodiments, P is an aromatic ring or a heteroaromatic ring and A is —$CO_2H$.

In certain embodiments, X is $CR^3R^4$ or $N(R^5)$ and A is —$CO_2H$.

In preferred embodiments, M is an aromatic ring, a heteroaromatic ring or $(C_5$-$C_8)$cycloalkylene and A is —$CO_2H$ or tetrazol-5-yl.

In certain preferred embodiments, M is an aromatic ring, a heteroaromatic ring or $(C_5$-$C_8)$cycloalkylene, X is $CR^3R^4$ or $N(R^5)$, $L^3$ is $(C_1$-$C_5)$alkylene or $(C_2$-$C_5)$heteroalkylene and A is —$CO_2H$.

$R^1$ is $(C_1$-$C_6)$alkyl, aryl$(C_1$-$C_3)$ alkyl or $(C_2$-$C_6)$heteroalkyl.

In certain embodiments, $R^1$ is $(C_1$-$C_6)$alkyl or $(C_2$-$C_6)$heteroalkyl.

$R^2$ is hydrogen, $(C_1$-$C_6)$alkyl or $(C_2$-$C_6)$heteroalkyl.

$R^3$ is cyano, aryl, heteroaryl, $(C_1$-$C_8)$alkyl, $(C_2$-$C_8)$alkyl, $(C_2$-$C_8)$alkenyl, $(C_3$-$C_8)$alkenyl, $(C_2$-$C_8)$alkynyl, $(C_3$-$C_8)$alkynyl, —$NR^8R^9$, —$C(O)NR^{10}R^{11}$, —$NR^{12}C(O)R^{13}$ or —$NR^{12}S(O)_pR^{13}$.

In certain embodiments, $R^3$ is cyano, aryl, heteroaryl, $(C_1$-$C_8)$alkyl, $(C_2$-$C_8)$alkenyl, $(C_2$-$C_8)$alkynyl, —$NR^8R^9$, —$C(O)NR^{10}R^{11}$, —$NR^{12}C(O)R^{13}$ or —$NR^{12}S(O)_pR^{13}$.

In some embodiments, $R^3$ is cyano, aryl, heteroaryl, $(C_1$-$C_8)$alkyl, $(C_2$-$C_6)$alkenyl, $(C_2$-$C_6)$alkynyl or —$NR^8R^9$.

In certain embodiments, $R^3$ is cyano, heteroaryl, $(C_2$-$C_6)$alkenyl or $(C_2$-$C_6)$alkynyl.

In certain embodiments, $R^3$ is $(C_2-C_8)$alkyl, $(C_3-C_8)$alkenyl or $(C_3-C_8)$alkynyl.

In some embodiments, $R^3$ is aryl or heteroaryl.

In certain preferred embodiments, $R^3$ is tetrazolyl, thiazolyl, pyrazolyl, isoxazolyl, oxazolyl, pyrrolyl, thienyl or prop-1-ynyl.

In certain embodiments, $R^3$ is tetrazolyl, thiazolyl, or prop-1-ynyl.

$R^4$ is hydrogen, cyano, aryl, heteroaryl, $(C_1-C_8)$alkyl, $(C_2-C_8)$alkenyl or $(C_2-C_8)$alkynyl.

Optionally, $R^3$ and $R^4$ are combined to form a 3-, 4-, 5-, 6- or 7-membered ring containing from zero to three heteroatoms selected from N, O and S. The ring formed by combining $R^3$ and $R^4$ may be a saturated or unsaturated ring.

In some embodiments, $R^4$ is hydrogen or methyl.

In preferred embodiments, $R^4$ is hydrogen.

In further preferred embodiments, $R^3$ is cyano, aryl, heteroaryl, $(C_1-C_8)$alkyl, $(C_2-C_8)$alkyl, $(C_2-C_8)$alkenyl, $(C_3-C_8)$alkenyl, $(C_2-C_8)$alkynyl, $(C_3-C_8)$alkynyl or $-NR^8R^9$ and $R^4$ is hydrogen.

$R^5$ is hydrogen, aryl, $(C_1-C_8)$alkyl, $(C_2-C_8)$alkenyl, $(C_2-C_8)$alkynyl or $(C_3-C_8)$cycloalkyl.

$R^6$ is heteroaryl.

$R^7$ is hydrogen or $(C_1-C_5)$alkyl.

$R^8$ and $R^9$ are independently hydrogen, $(C_1-C_5)$alkyl, oxy$(C_1-C_5)$alkyl or carboxy$(C_1-C_5)$alkyl.

Optionally, $R^8$ and $R^9$ are combined to form a 4-, 5-, 6- or 7-membered ring containing the nitrogen atom to which they are attached and from 0 to 2 additional heteroatoms selected from N, O and S. The ring formed by combining $R^8$ and $R^9$ may be a saturated, unsaturated or aromatic ring.

$R^{10}$, $R^{11}$ and $R^{12}$ are independently selected from hydrogen, aryl, heteroaryl, $(C_1-C_8)$alkyl, $(C_2-C_8)$heteroalkyl, $(C_3-C_8)$cycloalkyl and $(C_3-C_8)$heterocycloalkyl.

Optionally, $R^{10}$ and $R^{11}$ are combined to form a 4-, 5-, 6- or 7-membered ring containing the nitrogen atom to which they are attached and from 0 to 2 additional heteroatoms selected from N, O and S. The ring formed by combining $R^{10}$ and $R^{11}$ may be a saturated, unsaturated or aromatic ring.

$R^{13}$ is aryl, heteroaryl, $(C_1-C_8)$alkyl, $(C_2-C_8)$heteroalkyl, $(C_3-C_8)$cycloalkyl or $(C_3-C_8)$heterocycloalkyl.

The subscripts m and n are independently 0, 1 or 2.

The subscript p is 1 or 2.

In some embodiments, P is an aromatic ring or a heteroaromatic ring, X is $CR^3R^4$ and $R^3$ is cyano, aryl, heteroaryl, $(C_1-C_8)$alkyl, $(C_2-C_8)$alkenyl, $(C_2-C_8)$alkynyl or $-NR^8R^9$.

In some embodiments, A is $-CO_2H$, X is $CR^3R^4$ and $R^3$ is cyano, aryl, heteroaryl, $(C_1-C_8)$alkyl, $(C_2-C_8)$alkenyl, $(C_2-C_8)$alkynyl or $-NR^8R^9$.

In certain embodiments, when P and M are benzene, at least two of $L^2$, X and $L^3$ are other than $CH_2$.

In certain embodiments, the compounds of formula I do not include 3-(4-(4-methoxybenzyloxy)phenyl)pent-4-ynoic acid; β-ethenyl-4-phenylmethoxy-benzenepropanoic acid; 4-(2-quinolinylmethoxy)-β-[4-(2-quinolinylmethoxy)phenyl]-benzenepropanoic acid; N-[4-(benzoylamino)phenyl]-N-phenyl-glycine; 3-(4-(isopentyloxy)benzamido)-3-phenylpropanoate; 3-(4-isobutoxybenzamido)-3-phenylpropanoate; (R)-2-((1R,4R)-4-isopropylcyclohexanecarboxamido)-3-phenylpropanoic acid; (R)-3-(4-(benzyloxy)phenyl)-2-(tert-butoxycarbonyl)propanoic acid; 3-(4-chlorophenyl)-3-(furan-2-carboxamido)propanoic acid; 3-(3,4-dimethoxyphenyl)-3-(furan-2-carboxamido)propanoic acid; 3-(4-chlorobenzamido)-3-(4-(dimethylamino)phenyl)propanoic acid; 3-(2-(2-(3,4-dimethylphenoxy)ethylthio)-1H-benzo[d]imidazol-1-yl)propanoic acid; {2-Bromo-4-[(3,4-dichloro-phenyl)-hydrazonomethyl]-6-ethoxy-phenoxy}-acetic acid; 2-(4-(2-(2-(4-chlorophenyl)furan-5-carboxamido)ethyl)phenoxy)-2-methylpropanoic acid; 5-(3-(3,4-dimethoxyphenyl)-5-(2-fluorophenyl)-4,5-dihydropyrazol-1-yl)-5-oxopentanoic acid; 2-(2-(3-(3,4-dihydro-2H-benzo[b][1,4]dioxepin-7-yl)-2-methyl-4-oxo-4H-chromen-7-yloxy)acetamido)acetic acid; 3-(4'-Bromo-biphenyl-4-yl)-4-phenyl-butyric acid; 3-(4'-Bromo-biphenyl-4-yl)-3-phenylsulfanyl-propionic acid; 3-(5-(2-chloro-6-fluoro-4-(trifluoromethyl)phenoxy)-2,4-dinitrophenyl)propanoic acid; 3-(3-(2-chloro-4-(trifluoromethyl)phenoxy)phenyl)propanoic acid; 3-(4-methoxybenzyloxy)phenyl)pent-4-ynoic acid; or 3-(4-(4-methoxybenzyloxy)phenyl)-5-(trimethylsilyl)pent-4-ynoic acid, salts thereof, or esters thereof.

In certain embodiments, it is to be understood that compounds of formula I do not include compounds wherein P is a 1,2-azole ring when Q is aryl or heteroaryl, $L^1$ is a bond, M is a monocyclic aromatic ring, X is $N(R^5)$, O or $S(O)_n$, and A contains a carbonyl group.

In certain embodiments, it is to be understood that compounds of formula I do not include compounds wherein P is furan or thiophene when Q is aryl, $L^1$ is a bond, M is an aromatic ring, X is $CR^3R^4$, O or $S(O)_n$ and A contains a carbonyl group.

The compounds of the invention include pharmaceutically acceptable salts, solvates or prodrugs thereof.

In certain embodiments, ester prodrugs are preferred.

Those of skill in art will understand that, unless otherwise indicated, divalent groups such as $C(O)N(R^2)$, $SO_2N(R^2)$, $(C_1-C_4)$alkylene-$C(O)N(R^2)$ and the like, both possible orientations of the groups are permitted. For example, in formula I where $L^2$ is $C(O)N(R^2)$, the carbon atom may be attached to P or to M, as shown:

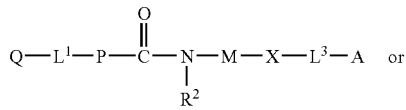

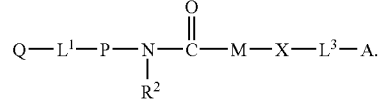

As another example, in formula I where $L^2$ is $(C_1-C_4)$alkylene-$C(O)N(R^2)$ in formula Ia, the alkylene group may be attached to P or to M, as shown:

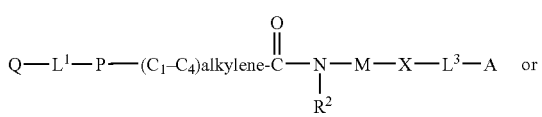

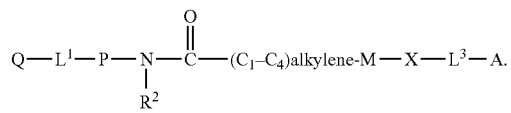

In certain embodiments, the present invention provides a compound having the formula (Ia):

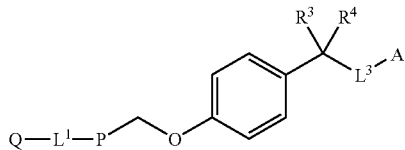

where Q, $L^1$, P, $L^3$, A $R^3$ and $R^4$ are as defined with regard to formula I above.

In some embodiments of formula Ia, Q is substituted or unsubstituted benzene, and $L^1$ is a bond, $(C_1-C_4)$alkylene, O or $S(O)_m$.

In some embodiments, P is selected from the group consisting of benzene, naphthalene, pyrrole, imidazole, pyrazine, oxazole, thiazole, pyridine, pyrimidine, pyridazine, benzothiazole, purine, benzimidazole, indole, indazole, carbazole, carboline, isoquinoline, quinoxaline and quinoline.

In certain embodiments where P is benzene, Q is hydrogen, aryl, heteroaryl or $(C_1-C_6)$alkyl, and $L^1$ is a bond, $(C_1-C_4)$alkylene, O or $S(O)_m$.

In some embodiments, $L^3$ is $(C_1-C_5)$alkylene. In certain embodiments, $L^3$ is methylene.

In certain embodiments, $R^3$ is cyano, aryl, heteroaryl, $(C_2-C_8)$alkyl; $(C_3-C_8)$alkenyl, $(C_3-C_8)$alkynyl, $-NR^8R^9$, $-C(O)NR^{10}R^{11}$, $-NR^{12}C(O)R^{13}$ or $-NR^{12}S(O)_pR^{13}$ and $R^4$ is hydrogen, cyano, aryl, heteroaryl, $(C_1-C_8)$alkyl, $(C_2-C_8)$alkenyl or $(C_2-C_8)$alkynyl.

In certain embodiments, $R^3$ is cyano, an unsubstituted aryl or heteroaryl monocyclic ring, $(C_2-C_8)$alkyl, $(C_3-C_8)$alkenyl, $(C_3-C_8)$alkynyl, or $-C(O)NR^{10}R^{11}$, $R^4$ is hydrogen, and P is selected from the group consisting of benzene, naphthalene, pyrrole, imidazole, pyrazine, oxazole, thiazole, pyridine, pyrimidine, pyridazine, benzothiazole, purine, benzimidazole, indole, indazole, carbazole, carboline, isoquinoline, quinoxaline and quinoline.

In some embodiments, $R^3$ is cyano, an unsubstituted aryl or heteroaryl monocyclic ring, $(C_3-C_8)$alkenyl, $(C_3-C_8)$alkynyl, $-C(O)NR^{10}R^{11}$, $R^4$ is hydrogen, and $L^3$ is methylene.

In certain embodiments, Q is aryl, heteroaryl, $(C_1-C_6)$alkyl or $(C_2-C_6)$heteroalkyl, $L^1$ is a bond, $(C_1-C_4)$alkylene, $(C_2-C_4)$heteroalkylene, $S(O)_m$, $N(R^1)$, $(C_1-C_4)$alkylene-$SO_2N(R^2)$, $(C_1-C_4)$alkylene-$N(R^2)SO_2$ or $C(O)N(R^2)$, P is selected from the group consisting of benzene, naphthalene, pyrrole, imidazole, pyrazine, oxazole, thiazole, pyridine, pyrimidine, pyridazine, benzothiazole, purine, benzimidazole, indole, indazole, carbazole, carboline, isoquinoline, quinoxaline and quinoline, $R^3$ is cyano, an unsubstituted aromatic or heteroaromatic monocyclic ring, $(C_2-C_8)$alkyl, $(C_3-C_8)$alkenyl, $(C_3-C_8)$alkynyl, or $-C(O)NR^{10}R^{11}$, $R^4$ is hydrogen, and $L^3$ is methylene.

In certain embodiments, the present invention provides a compound having the formula (Ib):

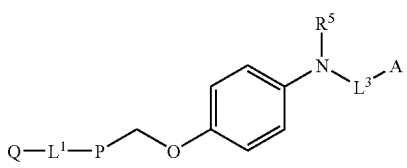

where Q, $L^1$, P, $L^3$, A and $R^5$ are as defined with regard to formula I above.

In some embodiments of formula Ib, P is selected from the group consisting of benzene, naphthalene, pyrrole, imidazole, pyrazine, oxazole, thiazole, furan, thiophene, pyridine, pyrimidine, pyridazine, benzothiazole, purine, benzimidazole, indole, indazole, carbazole, carboline, isoquinoline, quinoxaline and quinoline.

In certain embodiments, $R^5$ is an unsubstituted or substituted benzene.

In another aspect, the present invention provides a compound having the formula (II):

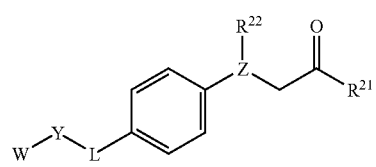

where $R^{21}$, $R^{22}$, Z, L, Y and W are defined below.

$R^{21}$ is $-H$, $-OH$, $-NHS(O_2)CH_3$, heteroaryl, or $-NH$-heteroaryl.

In certain embodiments, $R^{21}$ is $-OH$, $-NHS(O_2)CH_3$, $-NH$-tetrazolyl, or tetrazolyl.

In certain embodiments, $R^{21}$ is tetrazolyl, pyrimidinyl, or pyridinyl.

In preferred embodiments, $R^{21}$ is $-OH$, or a salt thereof.

$R^{22}$ is $-H$, $-(C_2-C_8)$alkyl, $-(C_3-C_8)$alkenyl, $-NR^{23}R^{24}$, substituted or unsubstituted aryl, substituted or unsubstituted heteroaryl, $-C\equiv N$, or $-C\equiv C-R^{25}$.

In some embodiments, $R^{22}$ is $-(C_2-C_8)$alkyl, $-(C_3-C_8)$alkenyl, $-NR^{23}R^{24}$, substituted or unsubstituted aryl, substituted or unsubstituted heteroaryl, $-C\equiv N$, or $-C\equiv C-R^{25}$.

In certain embodiments, $R^{22}$ is $-(C_2-C_3)$alkyl, $-NR^{23}R^{24}$, substituted or unsubstituted phenyl, $-CH=C(CH_3)_2$, $-CH_2CH=CH_2$, or $-C\equiv C-R^{25}$.

In other embodiments, $R^{22}$ is unsubstituted aryl or unsubstituted heteroaryl. In other embodiments, $R^{22}$ is substituted aryl and the substitution onto the aryl is unsubstituted $-(C_1-C_5)$alkyl, $-(C_1-C_5)$oxyalkyl, or -halo$(C_1-C_5)$alkyl.

In certain embodiments, $R^{22}$ is $-C\equiv C-R^{25}$ and $R^{25}$ is $-(C_1-C_5)$alkyl having 0 or 1 heteroatoms.

In preferred embodiments, $R^{22}$ is $-C\equiv CCH_3$.

In some embodiments, $R^{22}$ is $-CH=C(CH_3)_2$, or $-CH_2CH=CH_2$.

$R^{23}$ and $R^{24}$ are independently $-H$, $-(C_1-C_5)$alkyl, or $-(C_1-C_5)$oxyalkyl.

$R^{25}$ is $-H$, $-(C_1-C_5)$alkyl, -hetero$(C_1-C_5)$alkyl, $-(C_1-C_5)$oxyalkyl, substituted or unsubstituted aryl, or substituted or unsubstituted heteroaryl.

In some embodiments, $R^{25}$ is —($C_1$-$C_5$)alkyl, —($C_1$-$C_5$)oxyalkyl, substituted or unsubstituted aryl, or substituted or unsubstituted heteroaryl.

In some embodiments, $R^{25}$ is -hetero($C_1$-$C_5$)alkyl that does not contain Si.

In some embodiments, $R^{25}$ is unsubstituted phenyl.

In other embodiments, $R^{25}$ is a substituted phenyl.

In preferred embodiments, $R^{25}$ is methyl.

Z is

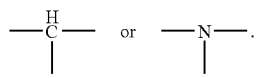

In some embodiments, Z is nitrogen. In other embodiments, Z is carbon.

L is —O—, —S—, or —N($R^{26}$)—. In some embodiments, L is —O—. In other embodiments, L is —S—. In other embodiments, L is —N($R^{26}$)—.

In certain embodiments, Z is nitrogen and L is —N($R^{26}$)—.

$R^{26}$ is —H, —($C_1$-$C_5$)alkyl, substituted or unsubstituted aryl($C_1$-$C_{10}$)alkyl, substituted or unsubstituted aryl, or substituted or unsubstituted heteroaryl.

In certain embodiments, $R^{26}$ is —H, substituted or unsubstituted aryl($C_1$-$C_{10}$)alkyl or substituted or unsubstituted aryl.

In some embodiments, $R^{26}$ is —H.

In other embodiments, $R^{26}$ is substituted or unsubstituted phenyl.

Y is absent or is —$CH_2$—, —$CH_2CH_2$—, —CH=CH—, —C(O)$CH_2$—, —C(O)$CH_2CH_2$—, —C(O)CH=CH—, —S($O_2$)—, —S($O_2$)$CH_2$—, —S($O_2$)$CH_2CH_2$—, —S($O_2$)CH=CH—, or —C(O)—.

In certain embodiments, Y is —$CH_2$—, —$CH_2CH_2$—, —CH=CH—, —C(O)$CH_2$—, —C(O)$CH_2CH_2$—, —C(O)CH=CH—, —S($O_2$)—, —S($O_2$)$CH_2$—, —S($O_2$)$CH_2CH_2$—, —S($O_2$)CH=CH—.

In some embodiments Y is —$CH_2$—.

In some embodiments L is —O— or —S—, and Y is —$CH_2$—, —$CH_2CH_2$—.

W is substituted or unsubstituted aryl or substituted or unsubstituted heteroaryl.

For example and without limitation, W can be a ring such as a benzene, naphthalene, pyrrole, pyrazole, imidazole, pyrazine, oxazole, isoxazole, thiazole, furan, thiophene, pyridine, pyrimidine, pyridazine, benzothiazole, purine, benzimidazole, benzoxazole, triazole, oxadiazole, thiadiazole, benzooxadiazole, dibenzofuran, indole, indazole, carbazole, carboline, isoquinoline, quinoxaline or quinoline, and so forth.

In some embodiments, W is a substituted or unsubstituted monocyclic aryl ring or a substituted or unsubstituted monocyclic heteroaryl ring.

In some embodiments, W is substituted or unsubstituted fused aryl bicyclic ring or substituted or unsubstituted fused heteroaryl bicyclic ring. In certain embodiments, W is an 8- to 11-membered fused aryl bicyclic ring or an 8- to 11-membered fused heteroaryl bicyclic ring.

In other embodiments, W is a substituted or unsubstituted 5- or 6-membered aryl ring or substituted or unsubstituted 5- or 6-membered heteroaryl ring.

In certain embodiments where W is a substituted aryl or heteroaryl ring, the substituting group can be a halogen, substituted or unsubstituted ($C_1$-$C_{10}$)alkyl, substituted or unsubstituted hetero($C_1$-$C_{10}$)alkyl, substituted or unsubstituted halo($C_1$-$C_{10}$)alkyl, substituted or unsubstituted aryl($C_1$-$C_{10}$)alkyl, substituted or unsubstituted aryl, or substituted or unsubstituted heteroaryl.

In some embodiments, W is a 5-membered ring having two or more heteroatoms.

In certain embodiments, W is a 5-membered ring selected from the group consisting of

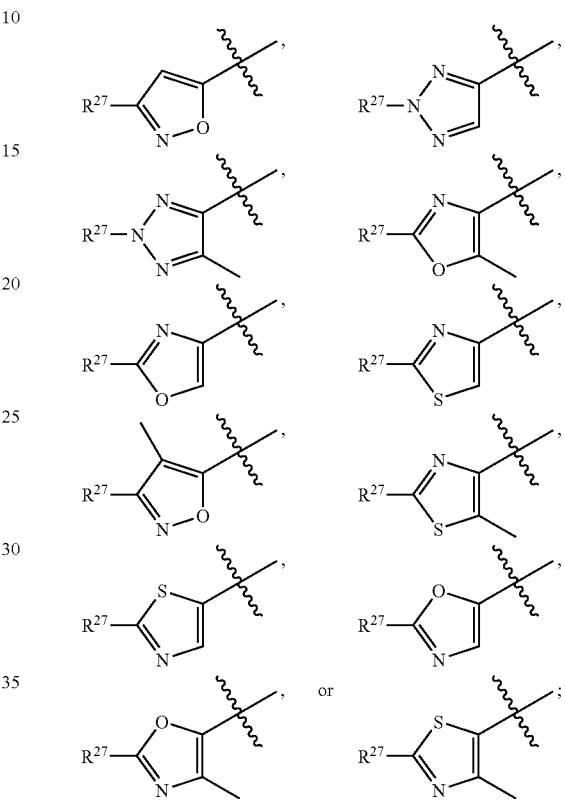

and $R^{27}$ is substituted or unsubstituted ($C_1$-$C_{10}$)alkyl, substituted or unsubstituted hetero($C_1$-$C_{10}$)alkyl, substituted or unsubstituted halo($C_1$-$C_{10}$)alkyl, substituted or unsubstituted aryl($C_1$-$C_{10}$)alkyl, substituted or unsubstituted aryl, or substituted or unsubstituted heteroaryl.

In some embodiments where Z is

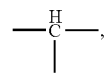

$R^{21}$ is —OH, L is —O—, —S—, or —N($R^{26}$)—, and Y is —$CH_2$—, —$CH_2CH_2$—, —CH=CH—, —C(O)$CH_2$—, —C(O)$CH_2CH_2$—, —C(O)CH=CH—, or —C(O)—, then W is not furan or thiophene.

In certain embodiments, W is a substituted or unsubstituted phenyl.

In some embodiments, Z is carbon and $R^{22}$ is —($C_2$-$C_8$)alkyl, —($C_3$-$C_8$)alkenyl, substituted or unsubstituted aryl, substituted or unsubstituted heteroaryl, or —C≡C—$R^{25}$ In some embodiments where Z is carbon, W is a benzene ring, $R^{22}$ is —C≡C—$R^{25}$, $R^{25}$ is -hetero($C_1$-$C_5$)alkyl, L is —O— or —S—, then any heteroatom in $R^{25}$ is not Si.

In some embodiments, where $R^{21}$ is —OH, L is —O—, Y is —CH$_2$—, and W is para-methoxyphenyl, $R^{22}$ is —C≡C—$R^{25}$, then $R^{25}$ is not —H.

In certain embodiments, where L is —N($R^{26}$)—, Z is nitrogen, $R^{22}$ is a phenyl, $R^{26}$ is hydrogen or a phenyl and W is a phenyl, then Y is not —C(O)—.

It will be apparent that in embodiments of formula II where Z is

and $R^{22}$ is —(C$_2$-C$_8$)alkyl, —(C$_3$-C$_8$)alkenyl, —NR$^{23}$R$^{24}$, substituted or unsubstituted aryl, substituted or unsubstituted heteroaryl, —C≡N, or —C≡C—R$^{25}$, then the carbon at Z is a chiral carbon as shown:

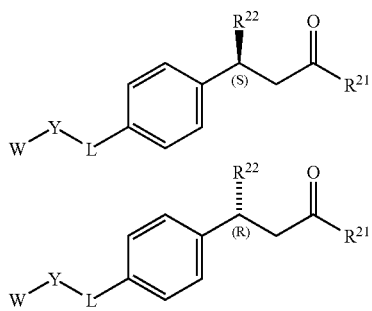

Thus, a compound of the invention can be an S-enantiomer, an R-enantiomer, or a mixture of both an S-enantiomer and an R-enantiomer.

In preferred embodiments, a compound is an S-enantiomer.

In certain embodiments, $R^{21}$ is —OH; L is —O—, or —S—; and Y is —CH$_2$—, or —CH$_2$CH$_2$—.

In some embodiments where Z is nitrogen, then W is not a 1,2-azole ring.

In certain other embodiments, the present invention provides a compound having the formula (III):

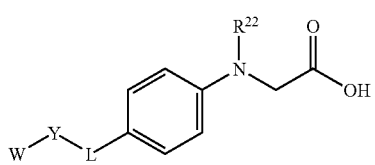

or a pharmaceutically acceptable salt, hydrate or prodrug thereof, where $R^{22}$, L, Y, and W are as defined with regard to formula II above.

In some embodiments, $R^{22}$ is —H, —(C$_2$-C$_3$)alkyl, —NR$^{23}$R$^{24}$, or substituted or unsubstituted phenyl.

In certain embodiments, L is —O—, —S—, or —N(R$^{26}$)—.

In some embodiments, $R^{26}$ is —H, substituted or unsubstituted aryl(C$_1$-C$_{10}$)alkyl or substituted or unsubstituted aryl.

In some embodiments, Y is —CH$_2$—, —CH$_2$CH$_2$—, —CH=CH—, —C(O)CH$_2$—, —C(O)CH$_2$CH$_2$—, —C(O)CH=CH—, —S(O$_2$)CH$_2$—, —S(O$_2$)CH$_2$CH$_2$—, —C(O)—, or —S(O$_2$)CH=CH—.

In some embodiments, W is a substituted or unsubstituted 5- or 6-membered aryl ring or substituted or unsubstituted 5- or 6-membered heteroaryl ring with the proviso if $R^{22}$ is phenyl, L is —O—, —S—, or —N(R$^{26}$)—, and W is a benzene ring then Y may not be —C(O)—.

In some embodiments, L is —N(R$^{26}$)—, and $R^{26}$ is hydrogen.

In certain embodiments, W is not a 1,2-azole ring.

In other embodiments, the compound of formula III is selected from the group consisting of

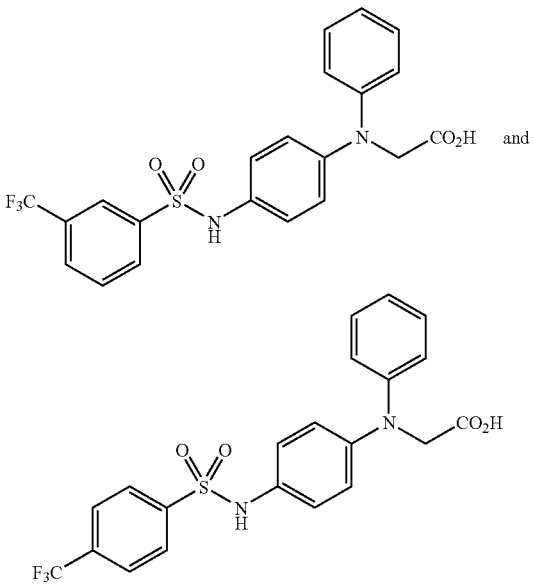

or a salt thereof.

In further embodiments, the present invention provides a compound of formula II or a pharmaceutically acceptable salt, solvate or prodrug thereof, wherein $R^{21}$ is —OH, —NHS(O$_2$)CH$_3$, —NH-tetrazolyl, or tetrazolyl; $R^{22}$ is —(C$_2$-C$_8$)alkyl, —NR$^{23}$R$^{24}$; substituted or unsubstituted phenyl, —CH=C(CH$_3$)$_2$, —CH$_2$CH=CH$_2$, or —C≡C—R$^{25}$; $R^{23}$ and $R^{24}$ are independently —H, —(C$_1$-C$_5$)alkyl, or —(C$_1$-C$_5$)oxyalkyl; $R^{25}$ is —H, —(C$_1$-C$_5$)alkyl, —(C$_1$-C$_5$)oxyalkyl, substituted or unsubstituted aryl, or substituted or unsubstituted heteroaryl; Z is

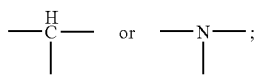

L is —O—, —S—, or —N(R$^{26}$)—; $R^{26}$ is —H, —(C$_1$-C$_5$) alkyl substituted or unsubstituted aryl(C$_1$-C$_{10}$)alkyl, substituted or unsubstituted aryl, or substituted or unsubstituted heteroaryl; Y is —CH$_2$—, —CH$_2$CH$_2$—, —CH=CH—, —C(O)CH$_2$—, —C(O)CH$_2$CH$_2$—, —C(O)CH=CH—, —S(O$_2$)CH$_2$—, —S(O$_2$)CH$_2$CH$_2$—, or —S(O$_2$)CH=CH—; and W is a substituted or unsubstituted 5- or 6-membered aryl ring or substituted or unsubstituted 5- or 6-membered heteroaryl ring.

In certain embodiments, the present invention provides compounds according to formula (IV):

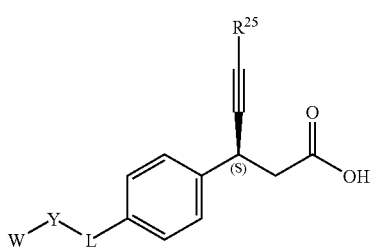

IV or a pharmaceutically acceptable salt, hydrate or prodrug thereof, wherein $R^{25}$, W, Y, and L are defined as in the preceding paragraph.

In some embodiments, $R^{25}$ is methyl.

In some embodiments, L is —O— or —S— and Y is —CH$_2$— or —CH$_2$CH$_2$—.

In some embodiments, W is a 5-membered ring selected from the group consisting of

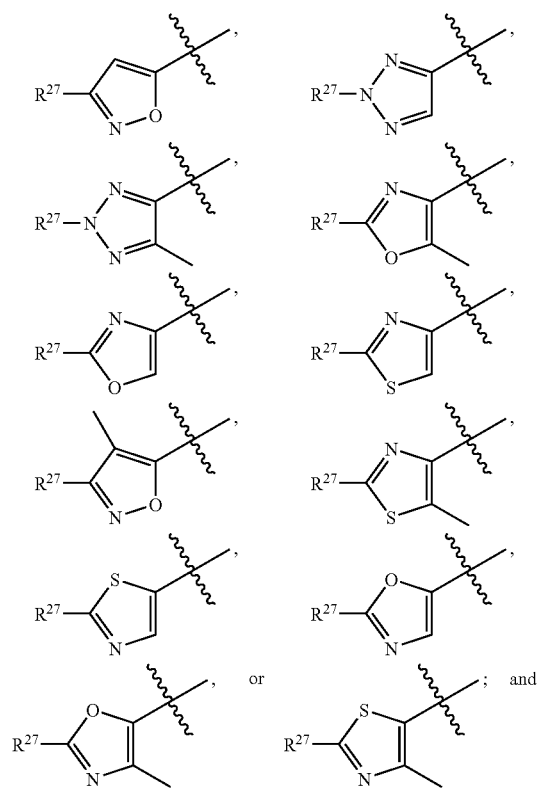

$R^{27}$ is substituted or unsubstituted (C$_1$-C$_{10}$)alkyl, substituted or unsubstituted hetero(C$_1$-C$_{10}$)alkyl, substituted or unsubstituted halo(C$_1$-C$_{10}$)alkyl, substituted or unsubstituted aryl (C$_1$-C$_{10}$)alkyl, substituted or unsubstituted aryl, or substituted or unsubstituted heteroaryl.

In certain embodiments, $R^{27}$ is substituted phenyl.

In other embodiments, $R^{27}$ is unsubstituted phenyl.

In some embodiments, the present invention provides compounds according to formula (V):

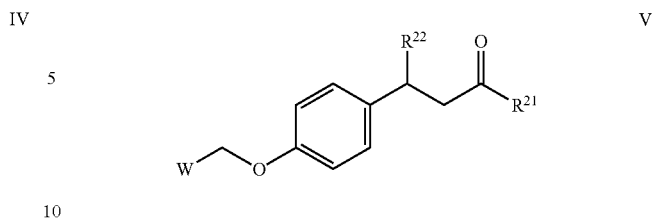

V or a pharmaceutically acceptable salt, hydrate or prodrug thereof, where $R^{21}$, $R^{22}$ and W are defined as in the paragraph preceding that providing the structure of the compounds of formula IV.

In some embodiments, $R^{21}$ is —OH, or a salt thereof.

In some embodiments, W is substituted phenyl.

In certain embodiments, W is substituted with substituted or unsubstituted (C$_1$-C$_{10}$)alkyl, substituted or unsubstituted hetero(C$_1$-C$_{10}$)alkyl, substituted or unsubstituted halo(C$_1$-C$_{10}$)alkyl, substituted or unsubstituted aryl(C$_1$-C$_{10}$)alkyl, substituted or unsubstituted aryl, or substituted or unsubstituted heteroaryl.

In other embodiments, W is a 5-membered ring selected from the group consisting of

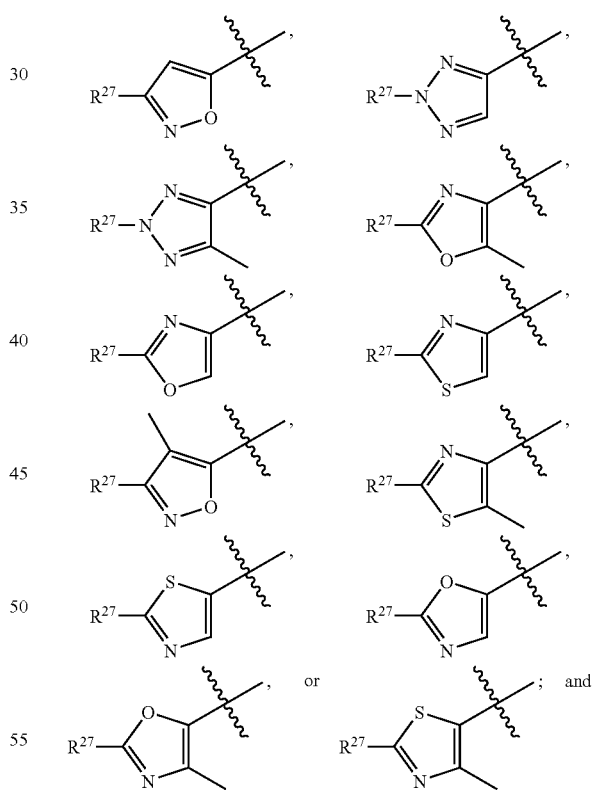

$R^{27}$ is hydrogen, substituted or unsubstituted (C$_1$-C$_{10}$)alkyl, substituted or unsubstituted hetero(C$_1$-C$_{10}$)alkyl, substituted or unsubstituted halo(C$_1$-C$_{10}$)alkyl, substituted or unsubstituted aryl(C$_1$-C$_{10}$)alkyl, substituted or unsubstituted aryl, or substituted or unsubstituted heteroaryl.

In certain embodiments, a compound of formula V is a racemate. In certain embodiments, the compound of formula V comprises a mixture of (S) and (R) enantiomers.

In certain embodiments, the present invention provides compounds having the formula (Va):

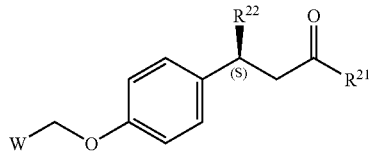

Va where $R^{21}$, $R^{22}$ and W are defined above in formula V.

In other embodiments, the compound has the formula (Vb):

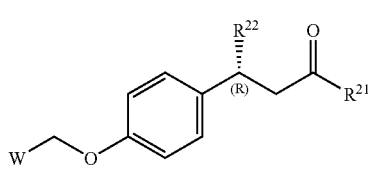

Vb where $R^{21}$, $R^{22}$ and W are defined above in formula V.

In certain embodiments, the present invention provides compounds according to formula (VI):

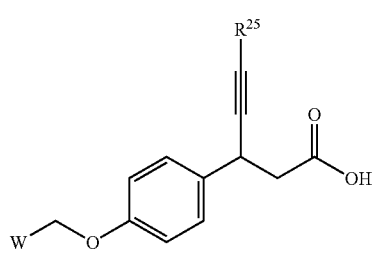

VI or a pharmaceutically acceptable salt, solvate or prodrug thereof, where $R^{25}$ and W are defined in the paragraph preceding that providing the structure of the compounds of formula IV.

In some embodiments, $R^{25}$ is methyl.

In some embodiments, W is a 5-membered ring selected from the group consisting of

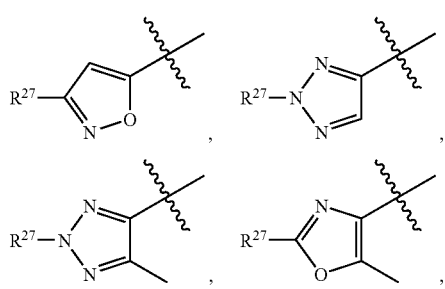

-continued

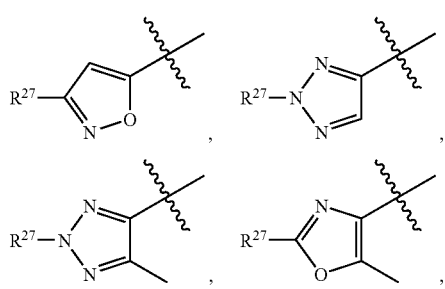

$R^{27}$ is hydrogen, substituted or unsubstituted $(C_1-C_{10})$alkyl, substituted or unsubstituted hetero$(C_1-C_{10})$alkyl, substituted or unsubstituted halo$(C_1-C_{10})$alkyl, substituted or unsubstituted aryl$(C_1-C_{10})$alkyl, substituted or unsubstituted aryl, or substituted or unsubstituted heteroaryl.

In certain embodiments, the compound of formula VI comprises a stereomerically pure S-enantiomer. In other embodiments, the compound of formula VI comprises a stereomerically pure R-enantiomer. In yet other embodiments, the compound of formula VI comprises a mixture of S- and R-enantiomers.

In certain embodiments, the present invention provides compounds according to formula (VII):

VII or a pharmaceutically acceptable salt, hydrate or prodrug thereof, wherein each $R^{28}$ is independently selected from the group consisting of substituted or unsubstituted $(C_1-C_{10})$alkyl, substituted or unsubstituted hetero$(C_1-C_{10})$alkyl, substituted or unsubstituted halo$(C_1-C_{10})$alkyl, substituted or unsubstituted aryl$(C_1-C_{10})$alkyl, substituted or unsubstituted aryl, and substituted or unsubstituted heteroaryl, the subscript q is an integer from 0 to 5, and $R^{25}$ is as defined above in the paragraph preceding that providing the structure of the compounds of formula IV.

In some embodiments, the subscript q is 0, 1, or 2.

In other embodiments, $R^{28}$ is a methoxy, ethoxy, trihalomethyl, methyl, halo, or cyano group and the subscript q is 1 or 2.

In other embodiments, $R^{28}$ is a phenyl, methoxyphenyl, methylphenyl, trihalomethylphenyl, benzyl, phenoxy, ethoxyphenyl, cyanophenyl, halophenyl, halobenzyl, pyridyl, methoxybenzyl, or pyryl group and the subscript q is 1 or 2.

In other embodiments, $R^{25}$ is methyl.

In certain embodiments, the compound of formula VII comprises a stereomerically pure S-enantiomer. In other embodiments, the compound of formula VII comprises a stereomerically pure R-enantiomer. In yet other embodiments, the compound of formula VII comprises a mixture of S- and R-enantiomers.

In other embodiments, the formula is selected from the group consisting of

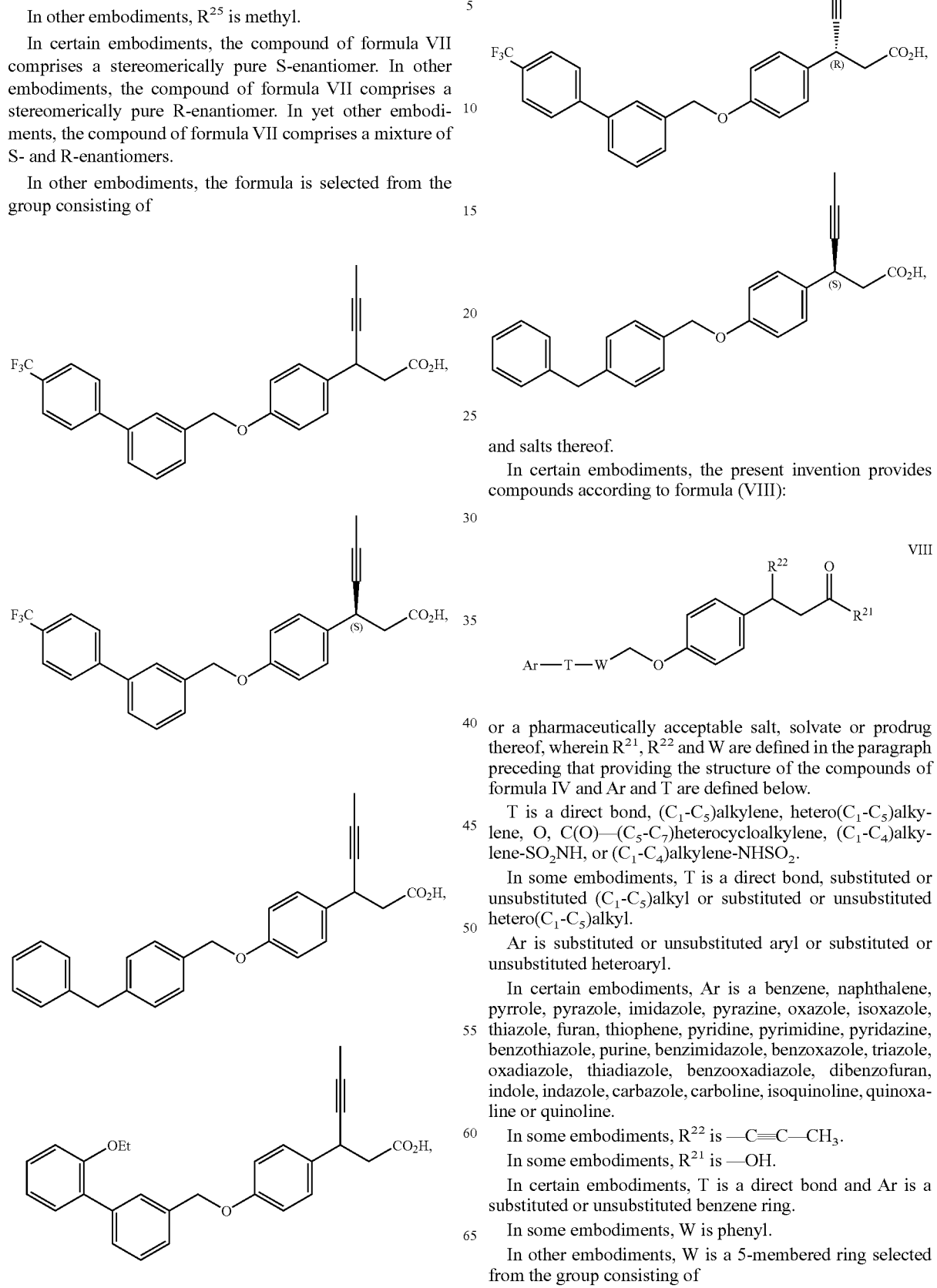

and salts thereof.

In certain embodiments, the present invention provides compounds according to formula (VIII):

or a pharmaceutically acceptable salt, solvate or prodrug thereof, wherein $R^{21}$, $R^{22}$ and W are defined in the paragraph preceding that providing the structure of the compounds of formula IV and Ar and T are defined below.

T is a direct bond, $(C_1-C_5)$alkylene, hetero$(C_1-C_5)$alkylene, O, C(O)—$(C_5-C_7)$heterocycloalkylene, $(C_1-C_4)$alkylene-SO$_2$NH, or $(C_1-C_4)$alkylene-NHSO$_2$.

In some embodiments, T is a direct bond, substituted or unsubstituted $(C_1-C_5)$alkyl or substituted or unsubstituted hetero$(C_1-C_5)$alkyl.

Ar is substituted or unsubstituted aryl or substituted or unsubstituted heteroaryl.

In certain embodiments, Ar is a benzene, naphthalene, pyrrole, pyrazole, imidazole, pyrazine, oxazole, isoxazole, thiazole, furan, thiophene, pyridine, pyrimidine, pyridazine, benzothiazole, purine, benzimidazole, benzoxazole, triazole, oxadiazole, thiadiazole, benzooxadiazole, dibenzofuran, indole, indazole, carbazole, carboline, isoquinoline, quinoxaline or quinoline.

In some embodiments, $R^{22}$ is —C≡C—CH$_3$.

In some embodiments, $R^{21}$ is —OH.

In certain embodiments, T is a direct bond and Ar is a substituted or unsubstituted benzene ring.

In some embodiments, W is phenyl.

In other embodiments, W is a 5-membered ring selected from the group consisting of

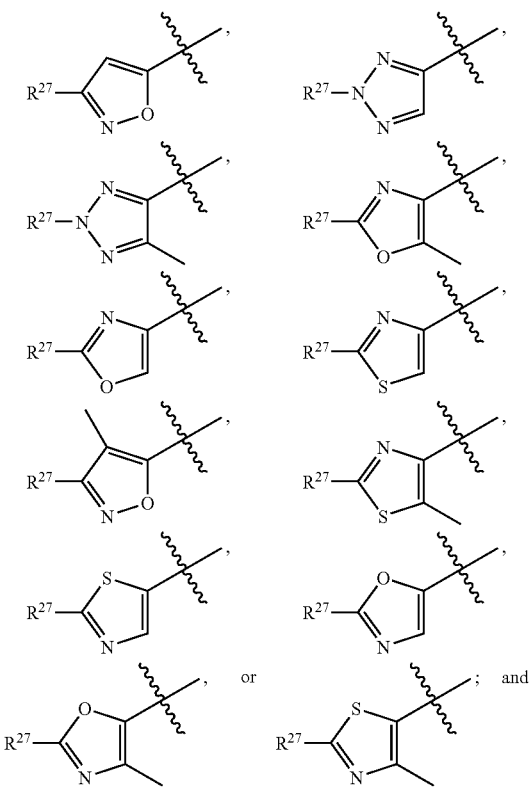

and R²⁷ is Ar-T-.

In certain embodiments, the compound of formula VIII comprises a stereomerically pure S-enantiomer. In other embodiments, the compound of formula VIII comprises a stereomerically pure R-enantiomer. In yet other embodiments, the compound of formula VIII comprises a mixture of S- and R-enantiomers.

In certain embodiments, the compound is selected from the group consisting of:

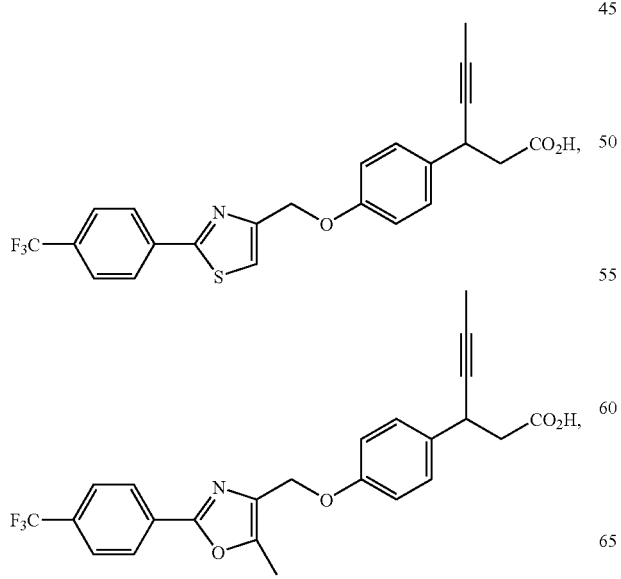

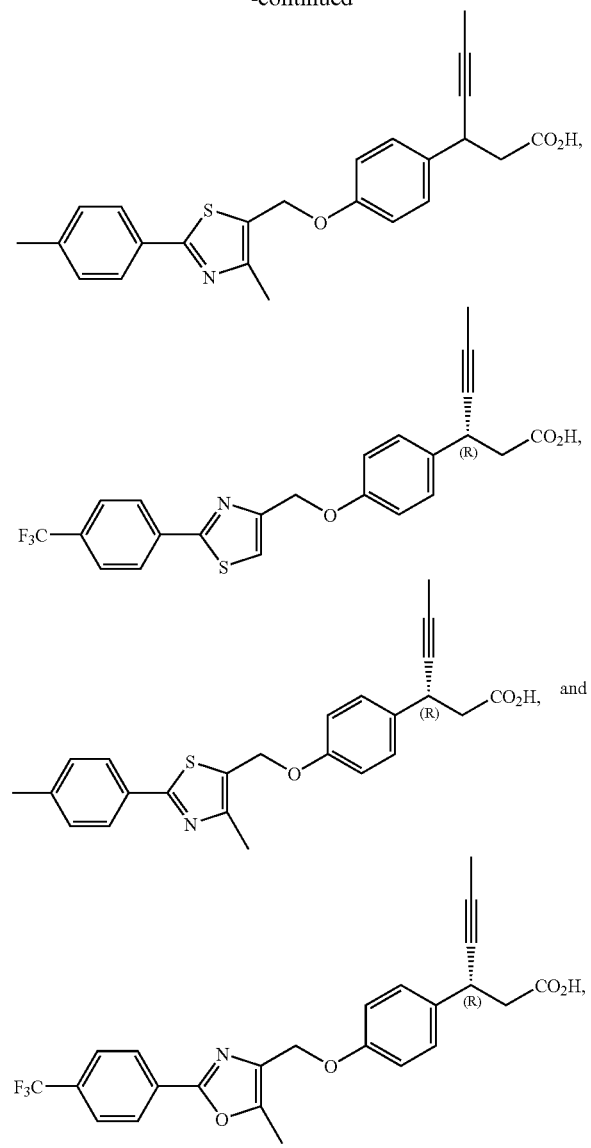

or a salt thereof.

In certain embodiments, the present invention provides compounds according to formula (IX)

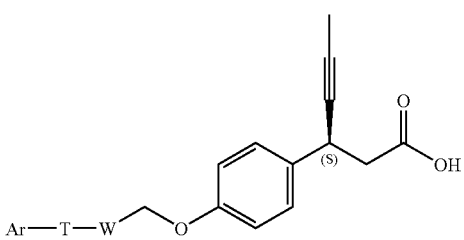

or a pharmaceutically acceptable salt, hydrate or prodrug thereof, wherein W, T and Ar are as defined above in formula VIII.

In some embodiments, the compound has the formula:

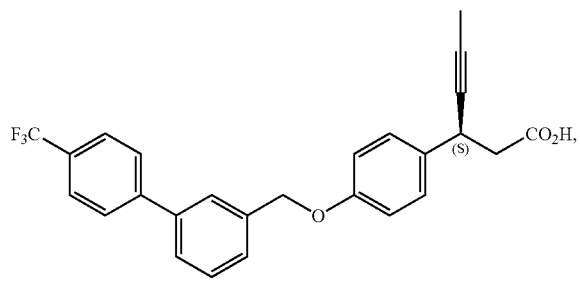

or a salt thereof.

In an embodiment, the compound is selected from the group consisting of:

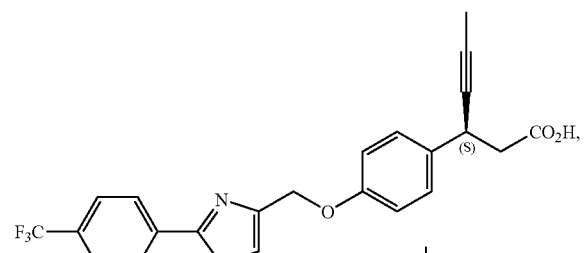

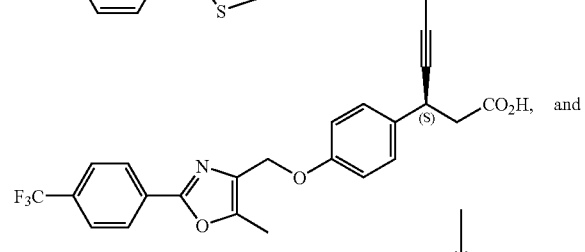

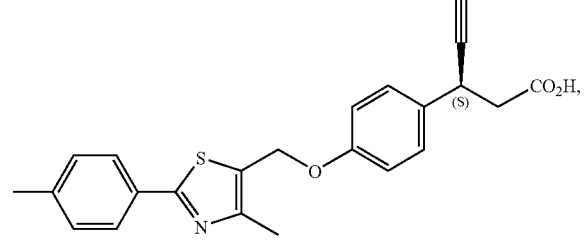

or a salt thereof.

In certain embodiments, the present invention provides compounds, for example, of formula III, IV, VI, VII, or IX, that include a bioisostere of —$CO_2H$ in place of —$CO_2H$. For illustration, compounds that include a bioisostere of —$CO_2H$ in place of the —$CO_2H$ on examplary compound 27.1, described in the examples below, can include the following:

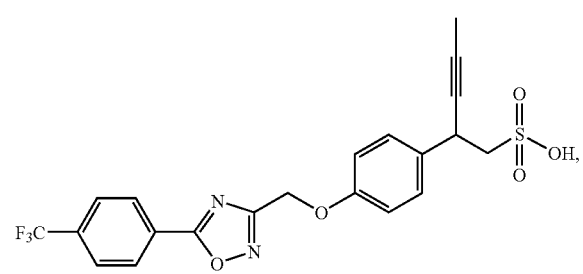

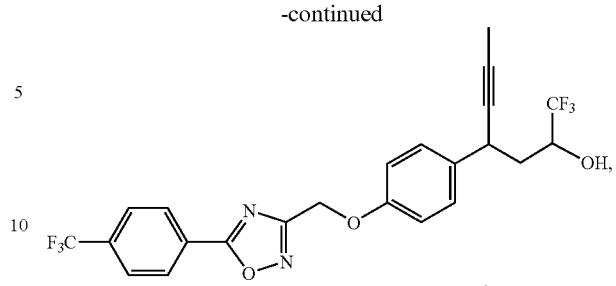

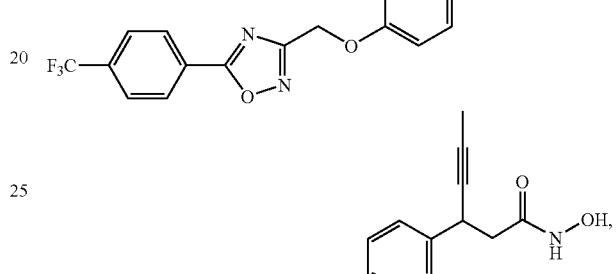

and the like, without limitation, as recognized by those of skill in the art. See, e.g., *The Practice of Medicinal Chemistry*, Wermuth, C. G., Ed., Academic Press: New York, 1996, incorporated herein by reference in its entirety.

In certain embodiments, the invention provides compounds according to the above formulas so long as the compound is not one of the following acids, or salt thereof, including:

3-(4-(4-methoxybenzyloxy)phenyl)pent-4-ynoic acid;
β-ethenyl-4-phenylmethoxy-benzenepropanoic acid;
4-(2-quinolinylmethoxy)-β-[4-(2-quinolinylmethoxy)phenyl]-benzenepropanoic acid;
N-[4-(benzoylamino)phenyl]-N-phenyl-glycine;
3-(4-(isopentyloxy)benzamido)-3-phenylpropanoate;
3-(4-isobutoxybenzamido)-3-phenylpropanoate;
(R)-2-((1R,4R)-4-isopropylcyclohexanecarboxamido)-3-phenylpropanoic acid;
(R)-3-(4-(benzyloxy)phenyl)-2-(tert-butoxycarbonyl)propanoic acid;
3-(4-chlorophenyl)-3-(furan-2-carboxamido)propanoic acid;
3-(3,4-dimethoxyphenyl)-3-(furan-2-carboxamido)propanoic acid;
3-(4-chlorobenzamido)-3-(4-(dimethylamino)phenyl)propanoic acid;
3-(2-(2-(3,4-dimethylphenoxy)ethylthio)-1H-benzo [d]imidazol-1-yl)propanoic acid;
{2-Bromo-4-[(3,4-dichloro-phenyl)-hydrazonomethyl]-6-ethoxy-phenoxy}-acetic acid;
2-(4-(2-(2-(4-chlorophenyl)furan-5-carboxamido)ethyl) phenoxy)-2-methylpropanoic acid;
5-(3-(3,4-dimethoxyphenyl)-5-(2-fluorophenyl)-4,5-dihydropyrazol-1-yl)-5-oxopentanoic acid;

2-(2-(3-(3,4-dihydro-2H-benzo[b][1,4]dioxepin-7-yl)-2-methyl-4-oxo-4H-chromen-7-yloxy)acetamido)acetic acid;

3-(4'-Bromo-biphenyl-4-yl)-4-phenyl-butyric acid;

3-(4'-Bromo-biphenyl-4-yl)-3-phenylsulfanyl-propionic acid;

3-(5-(2-chloro-6-fluoro-4-(trifluoromethyl)phenoxy)-2,4-dinitrophenyl)propanoic acid;

3-(3-(2-chloro-4-(trifluoromethyl)phenoxy)phenyl)propanoic acid;

3-(4-(4-methoxybenzyloxy)phenyl)pent-4-ynoic acid;

3-(4-(4-methoxybenzyloxy)phenyl)-5-(trimethylsilyl)pent-4-ynoic acid;

β,β-dimethyl-4-[[[4-methyl-2-[4-(trifluoromethyl)phenyl]-5-thiazolyl]methyl]thio]-benzenepropanoic acid; or β-amino-4-[(4-bromo-2,5-dihydro-2-methyl-5-oxo-1-phenyl-1H-pyrazol-3-yl)methoxy]-3-methoxy-benzenepropanoic acid.

5.2.2 Preparation of the Compounds

The compounds of the invention can be prepared by a variety of synthetic or semisynthetic techniques. FIG. 1 and the Examples in Section 6 below provide a variety of synthesis routes to the compounds provided herein. Appropriate starting materials can be prepared by techniques known or apparent to those of skill in the art or the starting materials may be commercially available. One of skill in the art will understand that the synthetic routes can be modified to use different starting materials or alternative reagents and that suitable adjustments in conditions (e.g., temperatures, solvents, etc.) can be made to accomplish the desired transformations. Additionally, one of skill in the art will recognize that protecting groups may be necessary for the preparation of certain compounds and will be aware of those conditions compatible with a selected protecting group. Accordingly, the exemplary methods and the examples described herein are illustrative of the present invention and are not to be construed as limiting the scope thereof.

5.2.3 Compositions

In another aspect, the invention provides pharmaceutical compositions suitable for pharmaceutical use comprising one or more compounds of the invention and a pharmaceutically acceptable carrier, excipient or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier or excipient is compatible with the other ingredients of the formulation and not deleterious to the recipient thereof.

In certain embodiments, the present invention provides a pharmaceutical composition comprising a compound of formula II, wherein $R^{22}$ comprises an alkynyl containing Si, and where $R^{21}$, L, Y, and W are as defined above in formula II.

In some embodiments, the Si atom is substituted with up to three alkyl groups.

In some embodiments, $R^{22}$ is —C≡C—Si(CH$_3$)$_3$.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixers. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452 and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

5.2.4 Methods of Use

In another aspect, the invention provides methods of treating or preventing a disease or condition selected from the group consisting of type II diabetes, obesity, hyperglycemia, glucose intolerance, insulin resistance, hyperinsulinenia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema, comprising administering to a subject in need thereof a therapeutically effective amount of a compound or composition of the invention.

In one embodiment, the disease or condition is type II diabetes.

In another aspect, the present invention provides a method for treating a disease or condition responsive to the modulation of GPR40 comprising administering to a subject in need thereof a therapeutically effective amount of a compound or composition of the invention.

In some embodiments, the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, the disease or condition is type II diabetes.

In some embodiments, the disease or condition is obesity.

In some embodiments, the disease or condition is hypertension.

In some embodiments of administering the compounds or compositions or the invention, the compound or composition is administered orally.

In other embodiments, the compound or composition is administered parentally.

In other embodiments, the compound or composition is administered in combination with a second therapeutic agent.

In other embodiments, the second therapeutic agent is an insulin sensitizing agent, such as metformin or a thiazolidinedione, for example.

In another aspect, the invention provides methods of treating or preventing a disease or disorder responsive to modulation of GPR40 comprising administering to a subject having such a disease or disorder, a therapeutically effective amount of one or more of the subject compounds or compositions.

In yet another aspect, the invention provides methods of treating or preventing a GPR40-mediated condition, disease or disorder comprising administering to a subject having such a condition, disease or disorder, a therapeutically effective amount of one or more of the subject compounds or compositions.

In yet another aspect, the invention provides methods of modulating GPR40 comprising contacting a cell with one or more of the subject compounds or compositions.

For example, in some embodiments, a cell that constitutively expresses GPR40 is contacted with one or more of the subject compounds or compositions.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefor, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat); and (c) antidiabetic agents such as insulin and insulin mimetics, sulfonylureas (e.g., glyburide, meglinatide), biguanides, e.g., metformin (Glucophage®), α-glucosidase inhibitors (acarbose), insulin sensitizers, e.g., thiazolidinone compounds, rosiglitazone (Avandia®), troglitazone (Rezulin®), ciglitazone, pioglitazone (Actos®) and englitazone.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject, comprising administering a compound or composition of the invention.

In some embodiments, the insulin concentration is increased.

In other embodiments, the insulin concentration is decreased.

In certain embodiments, a compound, or composition comprising a compound, according to formula II wherein $R^{22}$ comprises an alkylyl containing Si, and where $R^{21}$, L, Y, and W are as defined above in formula II, may be used.

In some embodiments, the Si atom is substituted with up to three alkyl groups.

In some embodiments, $R^{22}$ is —C≡C—Si(CH$_3$)$_3$.

The following examples are offered by way of illustration and are not intended to limit the scope of the invention. Those of skill in the art will readily recognize a variety of noncritical parameters that could be modified to yield essentially similar results.

6. EXAMPLES

6.1 Example 1

This example illustrates the preparation of (3S)-3-(4-Hydroxy-phenyl)-hex-4-ynoic acid methyl ester.

Scheme 1.1

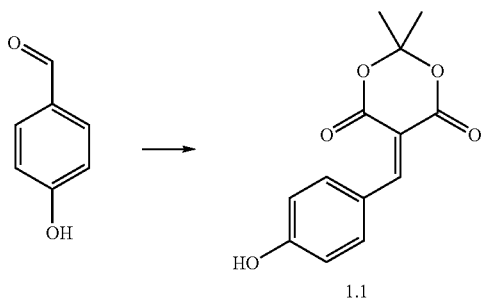

5-(4-Hydroxy-benzylidene)-2,2-dimethyl-[1,3]dioxane-4,6-dione (1.1). Condensation with Meldrum's acid is carried out according to the method of Bigi et. al. (2001) *Tetr. Lett.* 42: 5203-5205. A 2L pear-shaped flask was charged with 4-hydroxybenzaldehyde (50 g, 409 mmol) and water (400 mL). The flask was placed in a water bath at 75° C. and Meldrum's acid (62 g, 430 mmol) was added as a slurry in 400 mL of water. The reaction mixture was agitated for 2 h then cooled in an ice bath for 2 hours. The product was collected by filtration and rinsed with cold water. After drying thoroughly, 95 g (94%) of adduct 1.1 was obtained as a fine yellow powder. $^1$H NMR(500 MHz)(DMSO-$d_6$) δ 9.75 (br s, 1H); 8.27 (s, 1H); 8.24 (d, 2H, J=10 Hz); 6.98 (d, 2H, J=10 Hz); 1.76 (s, 6H). MS ESI (pos.) m/e: 519.0 (2M+Na).

Scheme 1.2

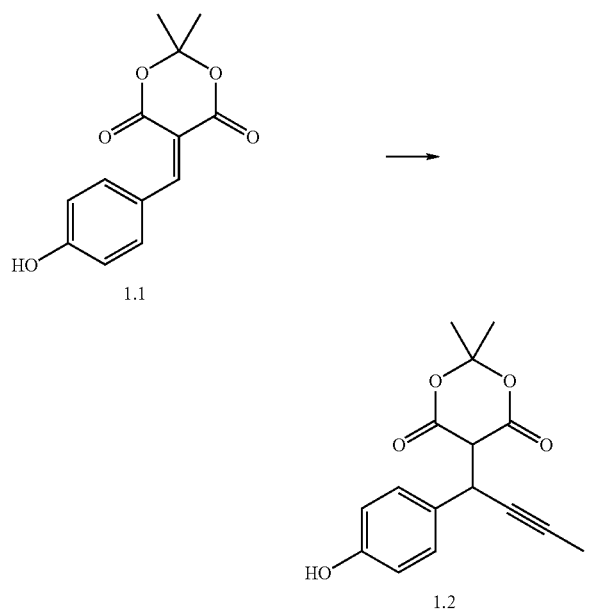

(+/−)-5-[1-(4-Hydroxy-phenyl)-but-2-ynyl]-2,2-dimethyl-[1,3]dioxane-4,6-dione (1.2). An oven-dried 3L 3-neck flask equipped with a mechanical stirrer, nitrogen inlet, nitrogen outlet and placed in a room-temperature water bath. After purging with nitrogen for 20 minutes, a solution of 1-propynylmagnesium bromide in THF (0.5 N, 600 mL) was added by cannula. In a separate oven-dried and nitrogen-flushed 500 mL RB flask, compound 1.1 (35 g, 142 mmol) was dissolved in anhydrous THF (350 mL) with gentle warming. The solution of 1.1 was then added over 15 minutes. Over the course of the addition, the reaction mixture changed to a thick, yellow suspension. After the addition was complete, the reaction mixture was stirred for 15 minutes and then quenched with aqueous NH$_4$Cl (0.6N, 750 mL) and diluted with hexanes (800 mL). The layers were separated and the organic layer discarded. The aqueous layer was acidified to pH ~2 with saturated aqueous KHSO$_4$ and extracted with ethyl acetate (2×400 mL). The combined extracts were washed with saturated brine, dried over MgSO$_4$, filtered, and concentrated to a light yellow solid (37 g, 91%). $^1$H NMR(500 MHz)(acetone-$d_6$) δ 8.26 (s, 1H); 7.39 (d, 2H, J=8.5 Hz); 6.76 (d, 2H, J=8.4 Hz); 4.73 (br s, 1H); 4.46 (d, 1H, J=2.4 Hz); 1.82 (s, 3H); 1.81 (s, 3H); 1.64 (s, 3H). MS ESI (pos.) m/e: 599.0 (2M+Na).

Scheme 1.3

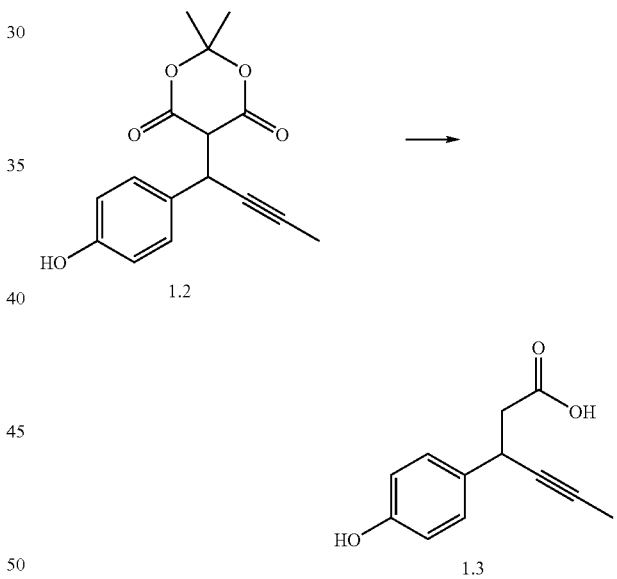

(+/−)-3-(4-Hydroxy-phenyl)-hex-4-ynoic acid (1.3). A 1L RB flask was charged with compound 1.2 (37 g), diethyl ketone (160 mL), and water (80 mL). The suspension was heated to reflux for 48 h. After cooling, the aqueous layer was saturated with NaCl$_{(s)}$ and separated. The organic layer was dried over MgSO$_4$, filtered, and concentrated to a light brown oil which was crystallized from hot ethyl acetate:hexanes (1:2). After collecting and drying, the product was obtained as an off-white powder (20.3 g, 77%). $^1$H NMR(500 MHz) (DMSO-$d_6$) δ 12.2 (s, 1H); 9.27 (s, 1H); 7.12 (d, 2H, J=8.5 Hz); 6.67 (d, 2H, J=8.6 Hz); 3.87 (m, 1H); 2.54 (m, 2H); 1.82 (d, 3H, J=2.4 Hz). MS ESI (pos.) m/e: 205.1 (M+H); 227.1 (M+Na).

Scheme 1.4

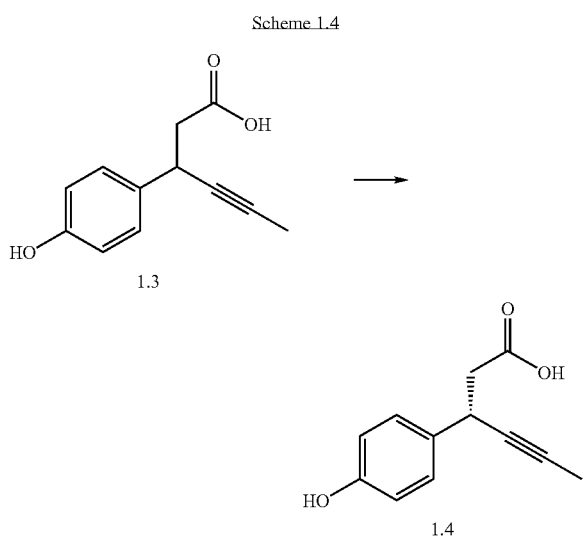

(3S)-3-(4-Hydroxy-phenyl)-hex-4-ynoic acid (1.4). A 5L RB flask was charged with compound 1.3 (66.4 g, 325 mmol) and 2-propanol (1 L) and then heated to 70° C. (1S,2R)-1-amino-2-indanol (46.1 g, 309 mmol) was dissolved in 2-propanol (1 L) with gentle warming. The solution of amine was added to the dissolved carboxylic acid and the resulting solution was allowed to cool to room temperature. After 16 h, the crystals were collected and dried. The salt was re-suspended in 2 L of 2-propanol and dissolved by heating to reflux. After allowing to cool to room temperature, the salt was collected after 16 h. A small sample of the salt was decomposed with aqueous acid and the free carboxylic acid was analyzed by chiral HPLC (Daicel ChiralPAK AD-H column, eluant: 0.1% TFA in 90:10 hexanes:2-propanol) and was found to have 75% ee. The salt was re-suspended in 1.5 L of 2-propanol and dissolved by heating to reflux. After allowing to cool to room temperature, the salt was collected after 16 h. This material was found to have 96% ee by chiral HPLC. This material was suspended in ethyl acetate (300 mL) and water (100 mL). Saturated aqueous KHSO$_4$ (100 mL) was added with vigorous mixing. After two clear layers were obtained, the layers were separated and the aqueous layer extracted with ethyl acetate (100 mL). The combined extracts were washed with saturated brine, dried over MgSO$_4$, filtered, and concentrated to a light yellow oil which crystallized on drying in vacuo. Compound 1.4 was obtained as an off-white solid (23.5 g, 35%).

Scheme 1.5

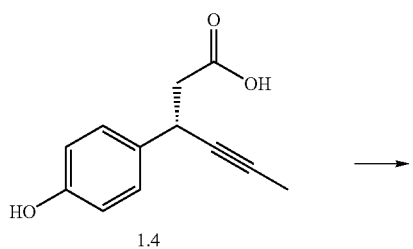

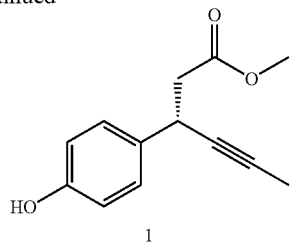

(3S)-3-(4-Hydroxy-phenyl)-hex-4-ynoic acid methyl ester (1). Phenol 1.4 (23.5 g, 115 mmol) was dissolved in acetone (230 mL) and treated with KHCO$_3$ (11.5 g, 115 mmol). After 15 minutes, methyl iodide (5 mL, 80 mmol) was added, and the reaction stirred at 40° C. for 14 h. An additional portion of methyl iodide (3 mL, 48 mmol) was added and heating was continued for 24 h. Potassium salts were removed by filtration and thoroughly rinsed with acetone. The filtrate was concentrated to an oil which was purified by filtration through a 1 cm plug of silica gel. Elution with 2.5% MeOH in dichloromethane followed by concentration provided phenol 1 (21.5 g, 85%) as a light yellow oil. $^1$H NMR(500 MHz) (acetone-d$_6$) δ 8.2 (br s, 1H); 7.20 (d, 2H, J=9.5 Hz); 6.77 (d, 2H, J=9.0 Hz); 3.98 (m, 1H); 3.60 (s, 3H); 2.65 (m, 2H); 1.78 (d, 3H, J=2.5 Hz). MS ESI (pos.) m/e: 219.1 (M+H); 241.1 (M+Na).

6.2 Example 2

This example illustrates the preparation of (3S)-3-[4-(4'-Trifluoromethyl-biphenyl-3-ylmethoxy)-phenyl]-hex-4-ynoic acid sodium salt.

Scheme 2.1

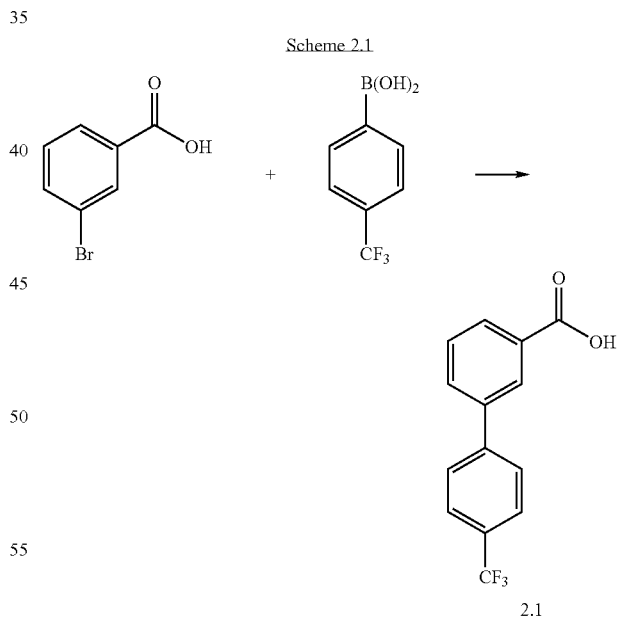

3-(4-Trifluoromethylphenyl)-benzoic acid (2.1). The Suzuki coupling was carried out according to the method of Dyer et al. (2001) *Tetrahedron Letters* 42: 1765-1767. Commercially available 4-(Trifluoromethyl)phenylboronic acid (15 g, 78.7 mmol) and 3-bromobenzoic acid (15.1 g, 75 mmol) were suspended in 2-propanol:water (1:4, 72 mL). 10% Pd/C (1.5 g) was added followed by aqueous Na$_2$CO$_3$ (39 mL, 20% by wt.). The resulting mixture was heated at 70°

C. for 4 hours. The precipitate was filtered and rinsed with 20% aqueous Na₂CO₃ solution. The filtrate was diluted with water and acidified to pH=2. The white solid was filtered and dried in vacuo. The crude material (2.1) (19.69 g) was used in the next step without further purification.

Scheme 2.2

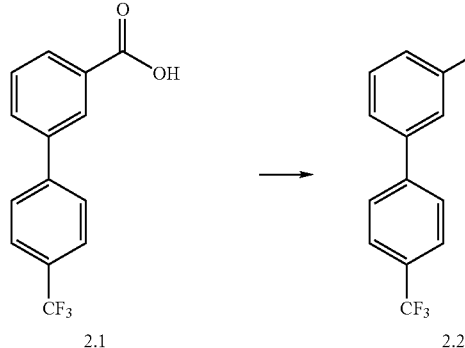

3-(4-Trifluoromethylphenyl)-benzyl alcohol (2.2). The carboxylic acid 2.1 (13.3 g, 50 mmol) in anhydrous THF (100 mL) was added dropwise to LiAlH₄ (2.9 g, 75 mmol) in anhydrous THF (150 mL) at 0° C. over 30 minutes. The resulting mixture was slowly warmed to room temperature and stirred for 4 hours. The reaction was slowly quenched with water (2.9 mL) at 0° C., 15% NaOH aqueous solution (2.9 mL) and another portion of water (8.7 mL). The mixture was dried over Na₂SO₄ and concentrated to give a white solid (11.9 g). The crude product (2.2) was used in the next step without further purification.

Scheme 2.3

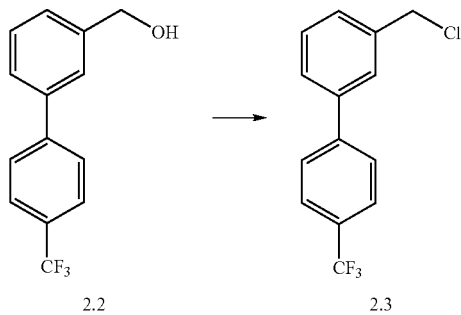

3-(4-Trifluoromethylphenyl)-benzyl chloride (2.3). The alcohol 2.2 (15 g, 59.5 mmol) was dissolved in anhydrous dichloromethane (100 mL). Thionyl chloride (10 mL) was slowly added dropwise to the above solution. The resulting mixture was stirred at room temperature for 24 hours. The organic solvent was removed under vacuo. The residue was then purified by flash chromatography (SiO₂ gel 60, eluted with 20% DCM in hexanes). Fractions containing the desired product 2.3 were combined and concentrated to a white solid (14.0 g). ¹H NMR (400 MHz) (CDCl₃) δ 7.73 (4H, s); 7.65 (1H, s); 7.58 (1H, s); 7.52-7.28 (2H, m); 4.69 (2H, s).

Scheme 2.4

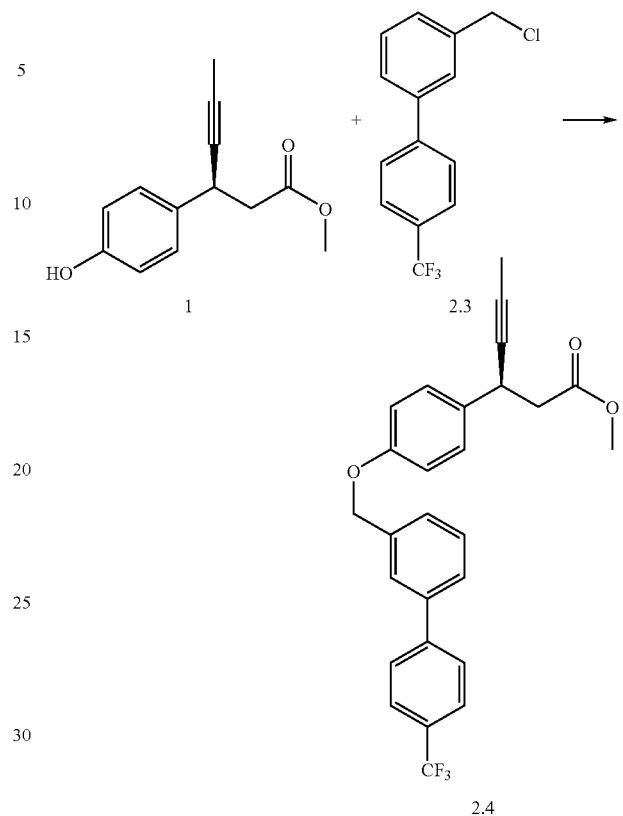

(3S)-3-[4-(4'-Trifluoromethyl-biphenyl-3-ylmethoxy)-phenyl]-hex-4-ynoic acid methyl ester (2.4). Benzyl chloride 2.3 (28.0 g, 103 mmol) and phenol 1 (21.5 g, 98 mmol) were dissolved in acetone (150 mL) and treated with Cs₂CO₃ (39.9 g, 122 mmol). The reaction was stirred at 50° C. for 16 h then filtered and concentrated to an pale yellow oil which was purified by column chromatography (silica gel, 33% to 66% dichloromethane in hexanes). Eluant containing compound 2.4 was concentrated to a colorless oil (40.0 g, 92%).

Scheme 2.4

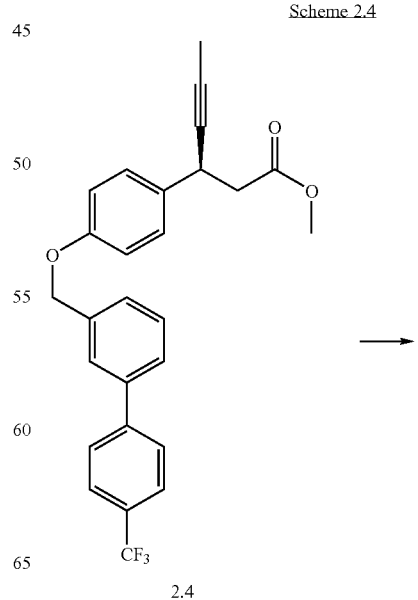

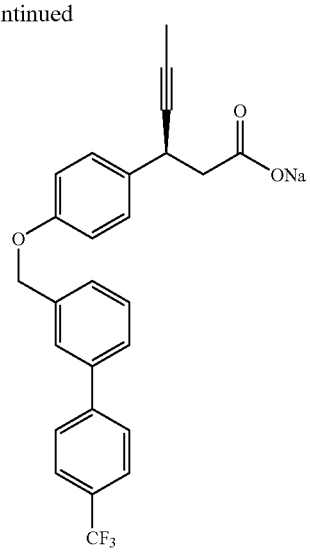

2

(3S)-3-[4-(4'-Trifluoromethyl-biphenyl-3-ylmethoxy)-phenyl]-hex-4-ynoic acid sodium salt (2). Methyl ester 2.4 was dissolved in diethyl ether (50 mL). Sodium trimethylsilanolate (0.78 g, 7 mmol) was added in one portion and the reaction mixture stirred for 48 h. The precipitate was collected by filtration and recrystallized from ethyl acetate:hexanes. After drying in vacuo, the desired sodium salt was obtained as a white powder (1.3 g). $^1$H NMR (500 MHz) (CD$_3$OD) δ 7.82 (d, 2H, J=8.5 Hz); 7.75-7.73 (m, 3H); 7.62 (m, 1H); 7.32 (d, 2H, J=8.5 Hz); 6.94 (d, 2H, J=8.5 Hz); 5.15 (s, 2H); 4.03 (m, 1H); 2.52 (dd, 1H, J=8.2, 14.5 Hz); 2.45 (dd, 1H, J=7.0, 14.0 Hz); 1.79 (d, 3H, J=2.5 Hz).

6.3 Example 3

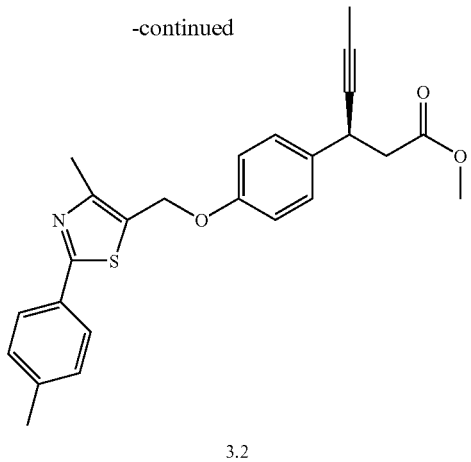

3.2

(3S)-3-[4-(4-Methyl-2-p-tolyl-thiazol-5-ylmethoxy)-phenyl]-hex-4-ynoic acid methyl ester (3.2). Compound 3.1 was prepared according to the method described in Example 2 starting from the commercial available 4-methyl-2-(4-methylphenyl)-1,3-thiazole-5-carboxylic acid. The chloride 3.1 (250 mg, 1.1 mmol) and phenol 1 (230 mg, 1.1 mmol) were dissolved in anhydrous DMF (5 mL). Finely powdered Cs$_2$CO$_3$ (650 mg, 2.2 mmol) was then added and the reaction mixture was stirred at room temperature for 14 h. The reaction was poured into water and extracted with ethyl acetate (15 mL×3). The organic phases were combined, dried over Na$_2$SO$_4$, and concentrated in vacuo to a residue which was used in the next step without further purification.

Scheme 3.1

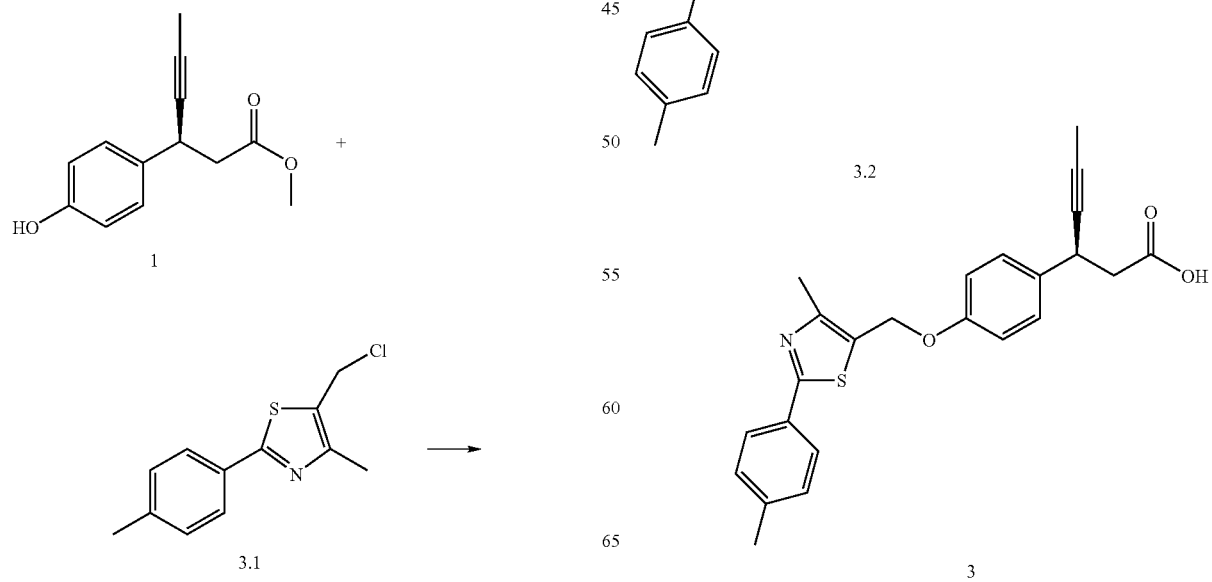

(S)-3-[4-(4-Methyl-2-p-tolyl-thiazol-5-ylmethoxy)-phenyl]-hex-4-ynoic acid (3). Ester 3.2 was dissolved in THF/MeOH/10% NaOH$_{(aq)}$ (1:1:1) solution (15 mL). After stirring at room temperature over 30 minutes, the mixture was acidified with 1N HCl (aq.) until pH=4. The aqueous phase was extracted with ethyl acetate and the combined organic phases were dried over Na$_2$SO$_4$ and concentrated. The crude residue was triturated with 20% ethyl acetate in hexanes (20 mL). The precipitate was filtered and compound 3 was acquired as a pale yellow powder (315 mg, 0.8 mmol). MS ESI m/e: 406 (M−H). $^1$H NMR (500 MHz) (CDCl$_3$) δ 7.86 (2H, d, J=7.5 Hz); 7.36 (2H, d, J=9 Hz); 7.26 (2H, d, J=8 Hz); 6.96 (2H, d, J=8.5 Hz); 5.18 (2H, s); 4.1 (1H, m); 2.77 (2H, m); 2.52 (3H, s); 2.42 (3H, s); 1.86 (3H, s).

6.4 Example 4

This example illustrates the preparation of 3-{4-[2-(2,6-Dichloro-benzyl)-thiazol-4-ylmethoxy]-phenyl}-hex-4-ynoic acid.

centrated in vacuo and the residue dissolved in THF/MeOH/10% NaOH$_{(aq)}$ (1:1:1) solution (6 mL). The resulting mixture was stirred at room temperature for 30 minutes. The mixture was acidified with 1N HCl$_{(aq.)}$ until pH=4. The aqueous phase was extracted with ethyl acetate. The organic phases were combined, dried over Na$_2$SO$_4$, and concentrated in vacuo. The crude residue was triturated with 20% ethyl acetate in hexanes (10 mL). The precipitate was filtered and acid 4 was acquired as a pale yellow powder (55 mg, 0.12 mmol). MS ESI m/e: 460 (M−H). $^1$H NMR (400 MHz) (CDCl$_3$) δ 7.40-7.19 (6H, m); 6.94-6.79 (2H, m); 5.18 (2H, s); 4.73 (2H, s); 4.1-4.06 (1H, m); 2.77 (2H, m); 1.85 (3H, s).

6.5 Example 5

This example illustrates the preparation of 3-[4-(2-Methyl-5-phenyl-furan-3-ylmethoxy)-phenyl]-hex-4-ynoic acid.

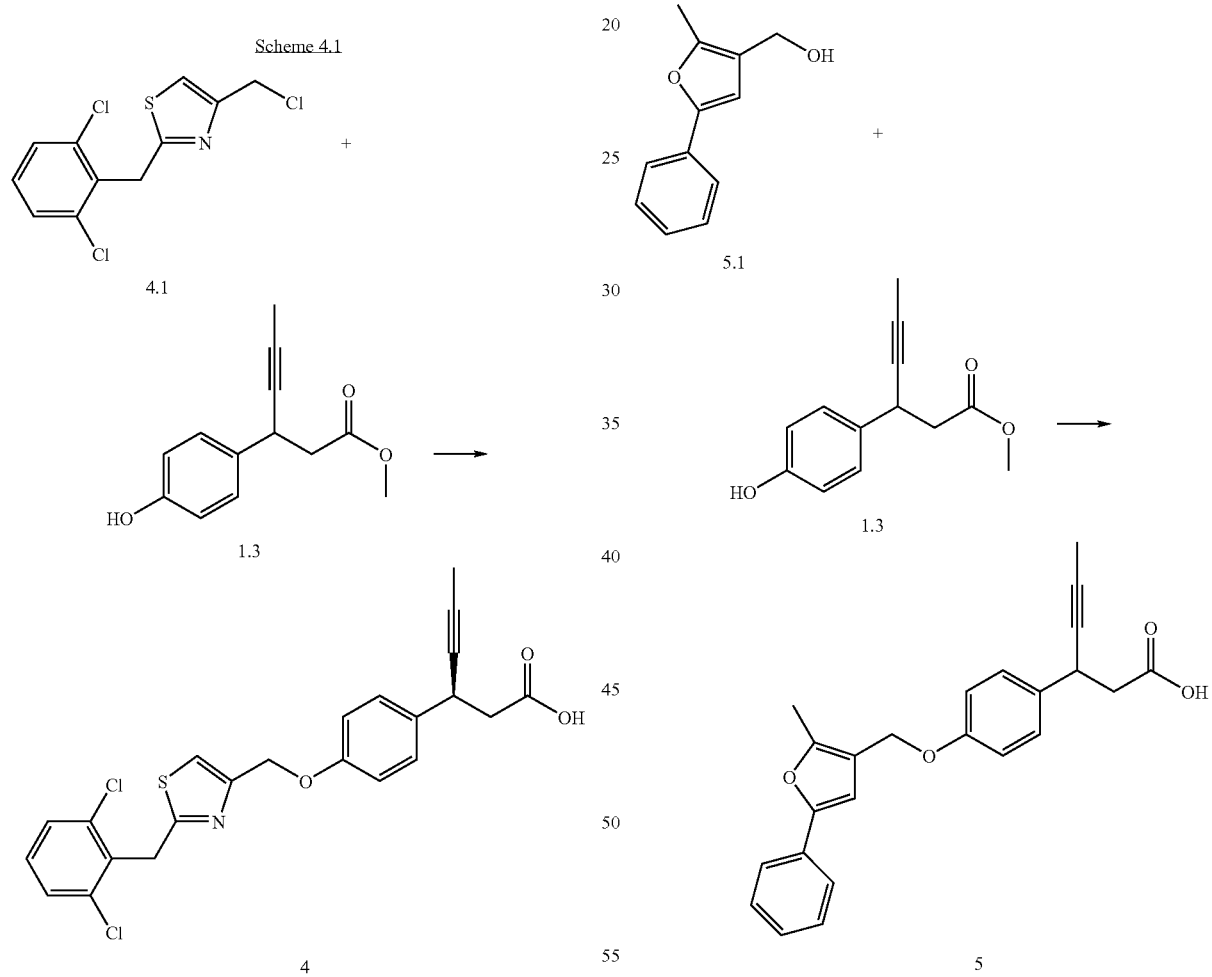

3-{4-[2-(2,6-Dichloro-benzyl)-thiazol-4-ylmethoxy]-phenyl}-hex-4-ynoic acid (4). Preparation of thiazole 4.1 was carried out according to the method of Bordwell et al. (1990) J. Amer. Chem. Soc. 112: 792-797. Compound 4.1 (58 mg, 0.2 mmol) and phenol 1 (43.6 mg, 0.2 mmol) were dissolved in anhydrous DMF (2 mL) and treated with finely powdered Cs$_2$CO$_3$ (65 mg, 0.22 mmol). The reaction mixture was stirred at room temperature for 14 hours. The reaction was poured into water and extracted with ethyl acetate (10 mL×3). The combined organic phases were dried over Na$_2$SO$_4$, con- 3-[4-(2-Methyl-5-phenyl-furan-3-ylmethoxy)-phenyl]-hex-4-ynoic acid (5). The Mitsunobu reaction was carried out according to the method of Mikó et al. (2003) J. Med. Chem. 46: 1523-1530. Commercially available 5.1 (37.6 mg, 0.2 mmol), PPh$_3$ (52 mg, 0.2 mmol) and phenol 1.3 (43.6 mg, 0.2 mmol) were added to anhydrous THF (3 mL). DEAD (45 µL, 0.22 mmol) was then added dropwise. The reaction mixture was stirred at room temperature over 14 hours. The reaction was then extracted with ethyl acetate (10 mL×3). The organic phases were combined, dried over Na$_2$SO$_4$, and concentrated in vacuo. The resulting residue was dissolved in THF/MeOH/ 10% NaOH$_{(aq)}$ (1:1:1) solution (6 mL). The resulting mixture was stirred at room temperature over 30 minutes. The resulting mixture was stirred at room temperature for 30 minutes. The mixture was acidified with 1N HCl$_{(aq.)}$ until pH=4. The aqueous phase was extracted with ethyl acetate. The organic phases were combined, dried over Na$_2$SO$_4$, and concentrated in vacuo. The crude product was triturated in 20% ethyl acetate in hexanes (10 mL). The precipitate was filtered and compound 5 was obtained as a white powder (35 mg, 0.9 mmol). MS ESI m/e: 375 (M−H). $^1$H NMR (500 MHz) (CDCl$_3$) δ 7.65 (2H, d, J=8 Hz); 7.40-7.24 (5H, m); 6.96 (2H, d, J=8.5 Hz); 6.68 (1H, s); 4.88 (2H, s); 4.1 (1H, s); 2.77 (2H, m); 2.4 (3H, s); 1.86 (3H, s).

6.6 Example 6

The following compounds were prepared by methods similar to those described in Example 2.

TABLE 1

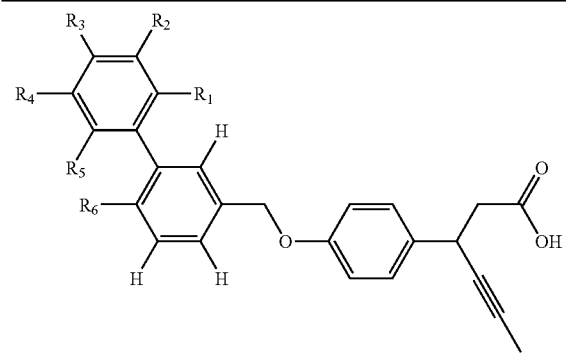

| Compound | R$_1$ | R$_2$ | R$_3$ | R$_4$ | R$_5$ | R$_6$ |
|---|---|---|---|---|---|---|
| 6.1 | H | H | H | H | H | H |
| 6.2 | OC$_2$H$_5$ | H | H | H | H | H |
| 6.3 | H | H | OC$_2$H$_5$ | H | H | H |
| 6.4 | H | —OCH$_2$O— | | H | H | H |
| 6.5 | H | H | CF$_3$ | H | H | H |
| 6.6 | H | CN | H | H | H | H |
| 6.7 | H | H | CN | H | H | H |
| 6.8 | CF$_3$ | H | H | H | H | H |
| 6.9 | H | CF$_3$ | H | H | H | H |
| 6.10 | H | H | OCF$_3$ | H | H | H |
| 6.11 | H | H | CF$_3$ | H | H | OC$_2$H$_5$ |
| 6.12 | OCH$_3$ | H | CF$_3$ | H | H | H |

NMR and MS data for compounds 6.13 and 6.14 are as follows:

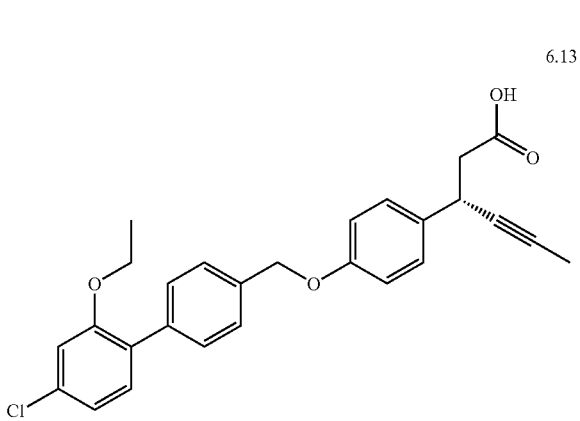

6.13

$^1$H NMR (400 MHz) ((CD$_3$)$_2$SO) δ 12.4 (s, 1H), 7.52 (d, 2H, J=8.1 Hz), 7.48 (d, 2H, J=8.1 Hz), 7.28-7.34 (m, 3H), 7.17 (s, 1H), 7.08 (d, 1H, J=8.1 Hz), 6.98 (d, 2H, J=8.2 Hz), 5.12 (s, 2H), 4.08 (q, 2H, J=7.0 Hz), 3.95 (m, 1H), 2.50-2.60 (m, 2H), 1.78 (s, 3H), 1.27 (t, 3H, J=7.0 Hz). [M+H]$^+$ Calculated for C$_{27}$H$_{25}$ClO$_4$: 449.1. Found 449.1.

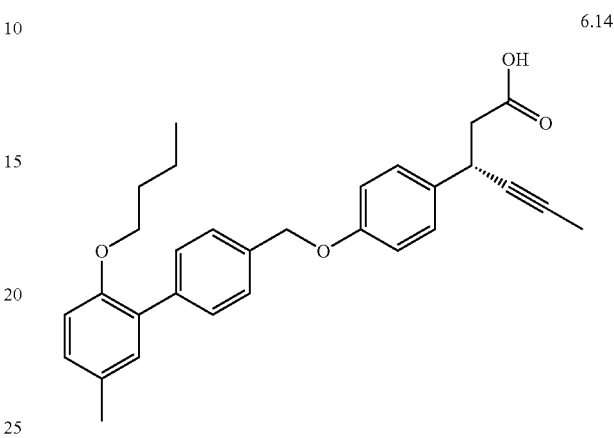

6.14

$^1$H NMR (400 MHz) ((CD$_3$)$_2$SO) δ 12.4 (s, 1H), 7.52 (d, 2H, J=8.0 Hz), 7.46 (d, 2H, J=8.6 Hz), 7.30 (d, 2H, J=8.8 Hz), 7.46 (d, 2H, J=6.0 Hz), 6.98-7.01 (m, 3H), 6.91-6.98 (m, 3H), 5.13 (s, 2H), 3.92-4.04 (m, 3H), 2.61 (d, 2H, J=7.6 Hz), 2.29 (s, 3H), 1.79 (d, 2H, J=2.0 Hz), 1.59-1.66 (m, 2H), 1.34-1.40 (m, 2H), 0.88 (t, 3H, J=7.6 Hz). [M+Na]$^+$ Calculated for C$_{30}$H$_{32}$O$_4$: 471.1. Found 471.1.

6.7 Example 7

The following compounds were prepared by methods similar to those described in Example 2.

TABLE 2

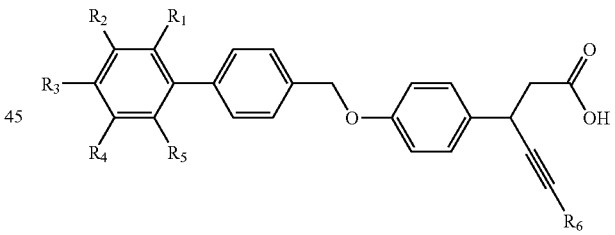

| Compound | R$_1$ | R$_2$ | R$_3$ | R$_4$ | R$_5$ | R$_6$ |
|---|---|---|---|---|---|---|
| 7.1 | H | H | H | H | H | H |
| 7.2 | CN | H | H | H | H | H |
| 7.3 | H | H | H | H | H | CH$_3$ |
| 7.4 | CN | H | H | H | H | CH$_3$ |
| 7.5 | OC$_2$H$_5$ | H | H | H | H | CH$_3$ |
| 7.6 | Cl | H | H | H | H | CH$_3$ |
| 7.7 | F | H | H | H | H | CH$_3$ |
| 7.8 | H | OC$_2$H$_5$ | H | H | H | CH$_3$ |
| 7.9 | H | H | OC$_2$H$_5$ | H | H | CH$_3$ |
| 7.10 | H | H | CF$_3$ | H | H | CH$_3$ |
| 7.11 | H | —OCH$_2$O— | | H | H | CH$_3$ |
| 7.12 | OCH$_3$ | OCH$_3$ | H | H | H | CH$_3$ |
| 7.13 | H | OCH$_3$ | H | H | H | CH$_3$ |
| 7.14 | H | CN | H | H | H | CH$_3$ |
| 7.15 | H | H | CN | H | H | CH$_3$ |

6.8 Example 8

The following compounds were prepared by methods similar to those described in Example 3.

TABLE 3

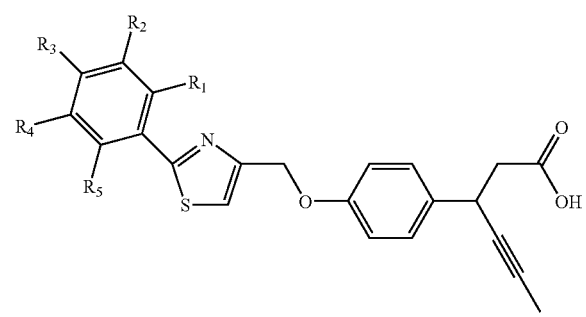

| Compound | R₁ | R₂ | R₃ | R₄ | R₅ |
|---|---|---|---|---|---|
| 8.1 | H | H | CF₃ | H | H |
| 8.2 | H | H | H | H | H |
| 8.3 | H | H | Cl | H | H |
| 8.4 | H | H | OCH₃ | H | H |
| 8.5 | H | H | CH₃ | H | H |
| 8.6 | H | OCH₃ | OCH₃ | H | H |
| 8.7 | Cl | Cl | H | H | H |

6.9 Example 9

The following compounds were prepared by methods similar to those described in Example 3.

TABLE 4

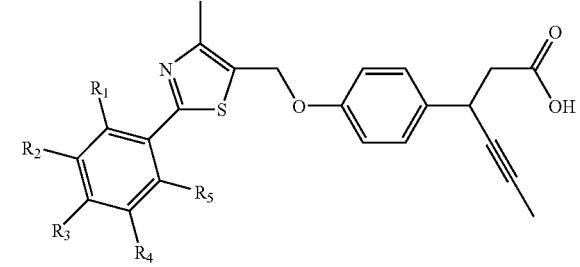

| Compound | R₁ | R₂ | R₃ | R₄ | R₅ |
|---|---|---|---|---|---|
| 9.1 | H | H | CF₃ | H | H |
| 9.2 | H | H | CH₃ | H | H |
| 9.3 | H | H | H | H | H |
| 9.4 | H | OCH₃ | OCH₃ | H | H |
| 9.5 | H | H | Cl | H | H |
| 9.6 | Cl | H | H | H | H |

6.10 Example 10

The following compounds were prepared by methods similar to those described in Examples 3-5. The carboxylic acids corresponding to 10.2 and 10.5 were prepared according to the method of Huang et al. (2003) *J. Amer. Chem. Soc.* 22: 6653-6655, and Admas et al. (1973) *Org. Synth. Coll.* Vol. V: 107, 109, respectively.

TABLE 5

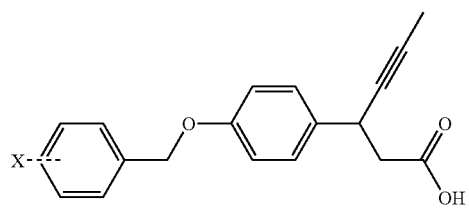

| Compound | X |
|---|---|
| 10.1 | 3-C(O)Ph |
| 10.2 | 3-N(C₂H₅)Ph |
| 10.3 | 3-Phenoxy |
| 10.4 | 4-C(O)Ph |
| 10.5 | 4-SO₂Ph |
| 10.6 | 4-CH₂Ph |
| 10.7 | 4-C₂H₄PH |
| 10.8 | 3-(2)-pyridyl |
| 10.9 | 3-(3)-pyridyl |
| 10.10 | 3-(4)-pyridyl |
| 10.11 | 4-(2)-pyridyl |
| 10.12 | 4-(3)-pyridyl |
| 10.13 | 4-(4)-pyridyl |
| 10.14 | 4-Pyrrol-1-yl |

6.11 Example 11

The following compounds were prepared by methods similar to those described in Examples 3-5.

TABLE 6

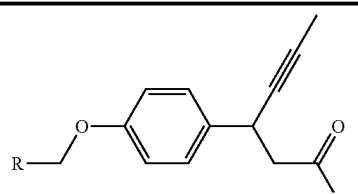

| Compound | R |
|---|---|
| 11.1 | 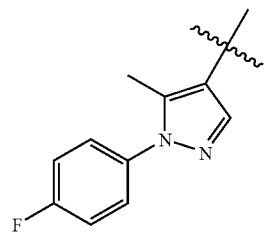 |
| 11.2 | 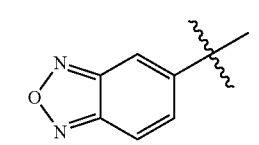 |
| 11.3 | 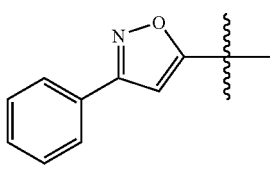 |

TABLE 6-continued

[Structure with R-O-CH2- group attached to phenyl ring with propargyl side chain and carboxylic acid]

| Compound | R |
|---|---|
| 11.4 | [2-phenyl-benzimidazole] |
| 11.5 | [benzothiazole-phenyl] |
| 11.6 | [trifluoromethylphenyl-thiazole] |
| 11.7 | [tert-butyl-thiazole-phenyl] |
| 11.8 | [dibenzofuran] |

6.12 Example 12

This example illustrates the preparation of (+/−)-3-(4-[(4-methoxyphenyl)methoxy]-phenyl)-hex-4-ynoic acid.

Scheme 12.1

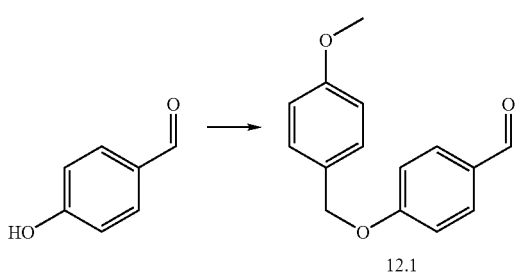

4-[(4-methoxyphenyl)methoxy]benzaldehyde (12.1). A 500 mL round bottom flask was charged with 4-hydroxyben- zaldehyde (40 g, 328 mmol) and DMF (250 mL). 4-methoxy- benzyl chloride (57.8 mL, 426 mmol) was added, followed by potassium carbonate (90 g, 656 mmol). The reaction mixture was stirred at room temperature for 5 h then poured into ice water (2.5 L). The product was collected by filtration and rinsed with water. After drying thoroughly, 78 g (98%) of aldehyde 12.1 was obtained as a light yellow powder. $^1$H NMR(400 MHz)(DMSO-d$_6$) δ 9.88 (s, 1H); 7.88 (d, 2H, J=8.7 Hz); 7.42 (d, 2H, J=8.8 Hz); 7.21 (d, 2H, J=8.8 Hz); 6.97 (d, 2H, J=8.6 Hz); 5.16 (s, 2H); 3.77 (s, 3H). MS ESI (pos.) m/e: 243.1 (M+H).

Scheme 12.2

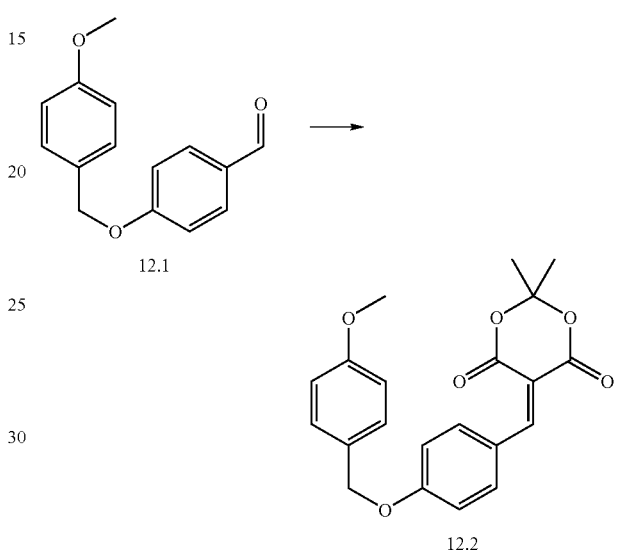

5-[[4-[(4-methoxyphenyl)methoxy]phenyl]methylene]-2,2-dimethyl-[1,3]dioxane-4,6-dione (12.2). Condensation with Meldrum's acid is carried out according to the procedure of DeWolf et al. (1989) *Biochemistry* 28: 3833-3842. A solution of Meldrum's acid (18 g, 124 mmol) compound 12.1 (30 g, 124 mmol) in toluene (100 mL) was treated with glacial acetic acid (4 mL) and piperidine (2 mL). The reaction mixture was stirred and heated at reflux until the removal of water with a Dean-Stark trap was complete. The reaction mixture was cooled to room temperature and the resulting solid was filtered and washed with cold toluene to yield 28 g (62%) of 12.2 as a bright yellow powder. $^1$H NMR(400 MHz)(DMSO-d$_6$) δ8.32 (s, 1H); 8.24 (d, 2H, J=8.9 Hz); 7.42 (d, 2H, J=8.6 Hz); 7.17 (d, 2H, J=9.0 Hz); 6.97 (d, 2H, J=8.7 Hz); 5.18 (s, 2H) 3.75 (s, 6H) 1.75 (s, 6H).

Scheme 12.3

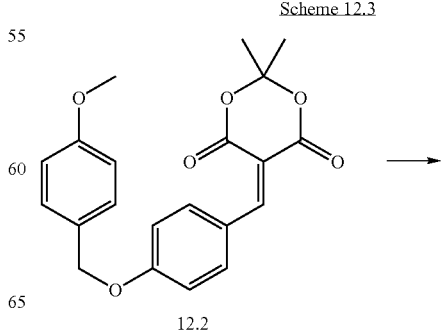

-continued

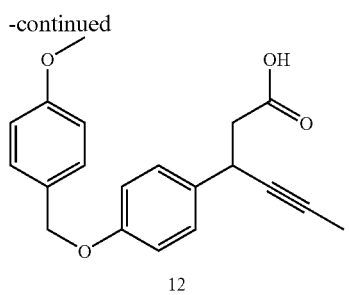

12

(+/−)-3-(4-[(4-methoxyphenyl)methoxy]phenyl)-hex-4-ynoic acid (12). To a stirring THF (120 mL) solution of compound 12.2 (13.8 g, 37.5 mmol) under nitrogen was added 1-propynylmagnesium bromide in THF (0.5 N, 97.5 mL) over a period of 20 minutes. After the addition was complete, the reaction mixture was stirred for 20 minutes, quenched with saturated aqueous NH₄Cl (50 mL) and extracted with ethyl acetate (3×50 mL). The combined extracts were washed with water, dried over MgSO₄, filtered, and concentrated to a brown oil. A solution of this brown oil in 5:1 pyridine-water (360 mL) was heated at 100° C. for 36 h. The reaction mixture was cooled to room temperature and put in an ice-water bath. Concentrated HCl was carefully added to pH ~2. The resulting suspension was extracted with ethyl acetate (200 mL×3), dried over MgSO₄, filtered, and concentrated to an off-white solid. Recrystalization from ethanol gave 9.5 g (78%) of compound 12 as a white powder. ¹H NMR(500 MHz)DMSO-d₆) δ 12.2 (s, 1H); 7.37 (d, 2H, J=8.5 Hz); 7.27 (d, 2H, J=8.5 Hz); 6.95 (d, 2H, J=8.0 Hz); 6.94 (d, 2H, J=8.5 Hz); 4.99 (s, 2H); 3.95 (m, 1H); 3.76 (s, 3H); 2.60 (m, 2H); 1.78 (d, 3H, J=1.5 Hz). MS ESI (neg.) m/e: 323.0 (M−1).

6.13 Example 13

This example illustrates the preparation of (3S)-3-[4-(2-Methyl-benzyloxy)-phenyl]-hex-4-ynoic acid sodium salt.

Scheme 13.1

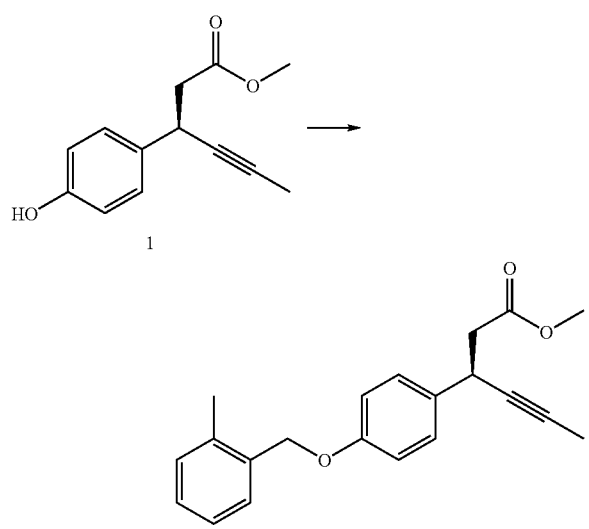

(3S)-3-[4-(2-Methyl-benzyloxy)-phenyl]-hex-4-ynoic acid methyl ester (13.1). 2-Methylbenzyl bromide (0.98 g, 5.3 mmol) and phenol 1 (0.97 g, 4.4 mmol) were dissolved in acetone (9 mL) and treated with Cs₂CO₃ (1.45 g, 4.4 mmol). The reaction was stirred at room temperature for 16 h then filtered and concentrated to an oil which was purified by radial chromatography (2 mm silica gel plate, 10% ethyl acetate in hexanes). Eluant containing compound 13.1 was concentrated to a colorless oil (1.37 g, 96%). This material was analyzed by chiral HPLC (Daicel ChiralPAK AD-H column, eluant: 0.1% TFA in 95:5 hexanes:2-propanol) and was found to have 94% ee. ¹H NMR(500 MHz)(MeOH-d₄) δ 7.39 (d, 1H, J=7 Hz); 7.28 (d, 2H, J=8.5 Hz); 7.25-7.15 (m, 3H); 5.05 (s, 2H); 4.02 (m, 1H); 3.64 (s, 3H); 2.68 (m, 2H); 2.36 (s, 3H); 1.80 (d, 3H, J=2.5 Hz). MS ESI (pos.) m/e: 323.0 (M+H); 245.1 (M+Na).

Scheme 13.2

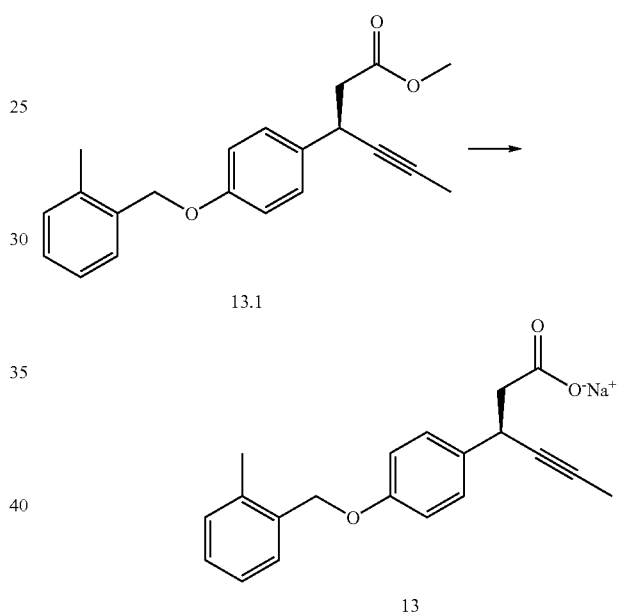

(3S)-3-[4-(2-Methyl-benzyloxy)-phenyl]-hex-4-ynoic acid sodium salt (13). 2N KOH$_{(aq)}$ (3.2 mL) was added to a solution of 13.1 (1.37 g, 4.25 mmol) in methanol (30 mL). The reaction was stirred at room temperature overnight and then taken up in copious water. The aqueous solution was adjusted to pH=2.0 with 1N HCl$_{(aq)}$ and extracted with ethyl acetate. The combined organic layers were washed with water, followed by brine. The solvent was removed under reduced pressure and the resulting residue dissolved in ethanol (4 mL) and treated with 1 equiv. of aqueous sodium bicarbonate. The solvents were removed under reduced pressure and the residue triturated with diethyl ether. After collecting by filtration and drying, sodium salt 13 (1.1 g) was obtained as a fine white powder. ¹H NMR(500 MHz)(D₂O) δ 7.34-7.18 (m, 6H); 6.95 (d, 2H, J=6.5 Hz); 5.05 (s, 2H); 3.88 (m, 1H); 2.47 (d, 2H, J=8.5 Hz); 2.28 (s, 3H); 1.72 (d, 3H, J=2.5 Hz). MS ESI (pos.) m/e: 309.1 (M+H); 331.0 (M+Na). [α]$_D$=+20.6°.

6.14 Example 14

The following compounds were prepared using similar methods to those described in Example 12.

TABLE 7

| Compounds | R |
|---|---|
| 14.1 | Me₃Si—≡—⁀ |
| 14.2 | F—(C₆H₄)—⁀ |
| 14.3 | Et |
| 14.4 | Me |
| 14.5 | —O—CH₂—≡—⁀ |
| 14.6 | Ph—≡—⁀ |

6.15 Example 15

This example illustrates the preparation of (3S)-3-[4-(2-Methyl-benzyloxy)-phenyl]-hex-4-ynoic acid.

Scheme 15.1

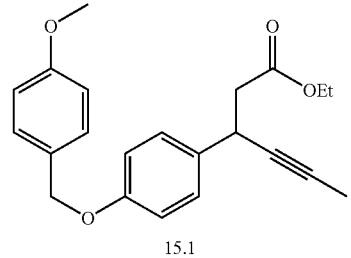

(+/−)-[4-(4-Methoxy-benzyloxy)-phenyl]-hex-4-ynoic acid ethyl ester (15.1). A 100 mL RB flask was charged with compound 12 (3.00 g, 9.25 mmol), 1-(3-dimethylaminopropyl)-3-ethylcarbodiimide hydrochloride (2.67 g, 13.9 mmol), 4-dimethylaminopyridine (1.13 g, 9.25 mmol) and dichloromethane (30 mL), the mixture was stirred into a solution. After 15 min, ethyl alcohol (absolute, 1.00 mL) was added. After 2 h, the reaction was quenched with aqueous NaHCO₃ (sat., 100 mL). The layers was separated, and the organic layer was washed with aqueous NaHCO₃ (2×100 mL), dried over MgSO₄ and concentrated to a white powder (3.19 g, 98%) which was used without further purification.

Scheme 15.2

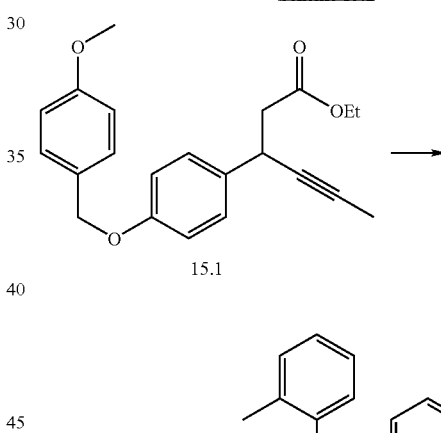

(+/−)-[4-(2-Methyl-benzyloxy)-phenyl]-hex-4-ynoic acid ethyl ester (15.2). Ester 15.1 (3.19 g, 9 mmol) was taken up in glacial acetic acid (100 mL) in a 250 mL RB Flask, and the suspension was heated to reflux for 16 h. The solvent was removed under reduced pressure, and the residue was re-dissolved in ethyl acetate (200 mL). The solution was washed with 1 N HCl$_{(aq)}$ (200 mL) and saturated brine (200 mL), dried over MgSO₄ and concentrated to a thick yellow oil, to which was added 2-methylbenyl bromide (2.57 g, 13.9 mmol), cesium carbonate (6.03 g, 18.5 mmol) and DMF (20 mL). The suspension was heated to 80° C. for overnight. After cooling, the reaction was quenched with water (200 mL) and extracted with ethyl acetate (2×100 mL). The combined organic layers were washed with NaHCO3 (sat. 2×100 mL), and NaCl (sat. 3×100 mL), dried over MgSO4, and concentrated to a white powder (2.41 g, 79%).

6.16 Example 16

This example illustrates the preparation of 3-(4-Hydroxy-phenyl)-hex-4-ynoic acid ethyl ester.

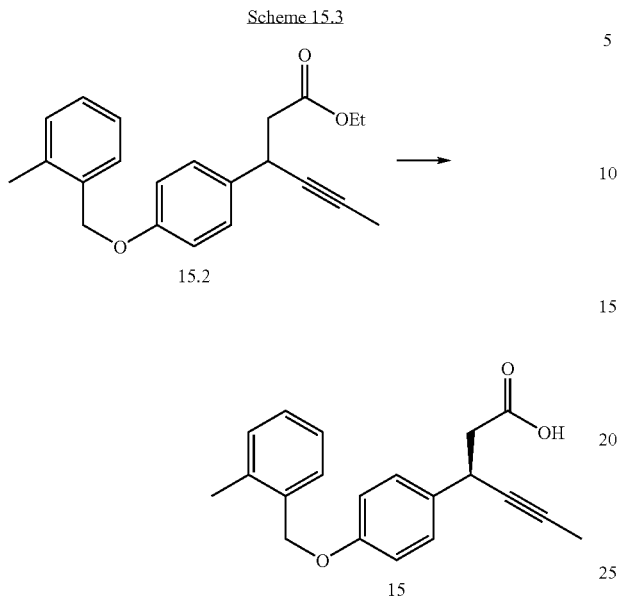

15.2

15

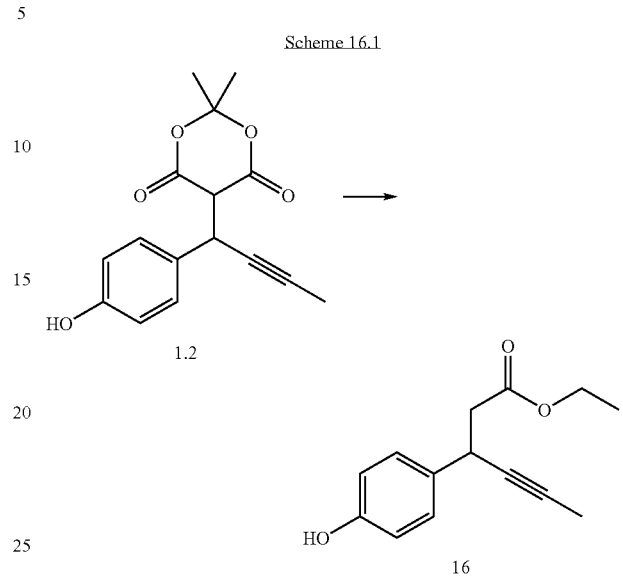

1.2

16

(3S)-3-[4-(2-Methyl-benzyloxy)-phenyl]-hex-4-ynoic acid (15). Compound 15.2 was dissolved in a mixture of 24 mL methanol and 24 mL isopropanol with the aid of sonication. The solution was filtered into a 50 mL glass vial. The racemic 15.2 was resolved with chiral normal phase HPLC using a ChiralTech AD semi-preparative column (2.0 cm×25.0 cm), eluting isocratically with hexane/isopropanol (92:8) at a flow rate 20 mL/min. Each injection contained 50 mg of ester 15 (1 mL). The absorbance at 220 nm was used for detection. Both enantiomers were collected. After 36 injections, the separated enantiomers were dried to give white solids. Analytical chiral HPLC (Chiraltech AD-H column, 0.4 cm×25.0 cm, 8% isopropanol/hexane, 1 mL/min) indicated both compounds were optically pure. The enantiomers were referred to as A (retention time=11.5 min) and B (retention time=15.6 min).

A RB flask was charged with enantiomer A (0.65 g), ethanol (10 mL) and 2N KOH (10 mL). and was stirred for 2 h at room temperature. After acidification to pH~2 with citric acid, the product was extracted into ethyl acetate (100 mL). The organic layers were washed with saturated brine (2×50 mL), dried over MgSO$_4$ and concentrated to a yellow oil (0.59 g, 42% overall). An aliquot (12.0 mg) was made into a 1 mL DMF solution, and optical rotation was measured. This enantiomer was assigned to (S) according to DeWolf Jr. et al. (1989) *Biochemistry* 28: 3833-3842.

$^1$HNMR (400 MHz, acetone-d$_6$) δ 7.45 (d, 1H, J=7.15 Hz); 7.37 (d, 2H, J=8.66 Hz); 7.25 (d, 1H, J=1.42 Hz); 7.24 (m, 2H); 7.00 (d, 2H, J=8.74 Hz); 5.11 (s, 2H); 4.05 (m, 1H); 2.70 (m, 2H); 2.39 (s, 3H); 2.10 (s, 1H); 1.80 (d, 3H, J=2.41). MS-ESI (neg.) m/e: 307.1 (M–H); 637.2 (2M–H). [α]$_D$20: +16.32 (c1.2, DMF).

3-(4-Hydroxy-phenyl)-hex-4-ynoic acid ethyl ester (16). Phenol 1.2 (1.2 g, 4 mmol) was dissolved in pyridine (3 mL) and ethanol (1 mL). The mixture was heated to 90° C. for 16 h and then concentrated to an oil which was purified by column chromatography (elution with 1-3% MeOH in dichloromethane). Phenol 16 (0.88 g, 91%) was obtained as an oil. $^1$H NMR(500 MHz)(acetone-d$_6$) δ 8.24 (s, 1H); 7.21 (d, 2H, J=9.5 Hz); 6.78 (d, 2H, J=9.0 Hz); 4.06 (m, 2H); 3.98 (m, 1H); 2.68-2.59 (m, 2H); 1.78 (d, 3H, J=2.5 Hz); 1.75 (t, 3H, J=7.0 Hz). MS ESI (pos.) m/e: 233.1 (M+H); 255.1 (M+Na).

6.17 Example 17

The following compounds were prepared by methods similar to those of Examples 12 and 15.

TABLE 8

| Compound | R |
|---|---|
| 17.1 | CF$_3$-phenyl- |
| 17.2 | 2-chlorophenyl- |

TABLE 8-continued
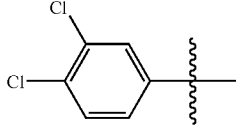
| Compound | R |
|---|---|
| 17.3 | 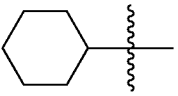 |
| 17.4 | 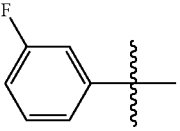 |
| 17.5 | 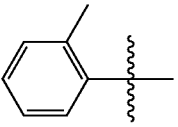 |
| 17.6 | 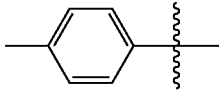 |
| 17.7 | 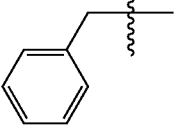 |
| 17.8 | 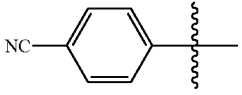 |
| 17.9 | 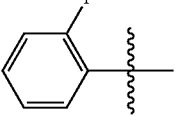 |
| 17.10 | 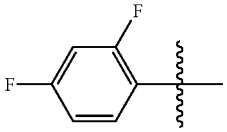 |
| 17.11 |  |
TABLE 8-continued
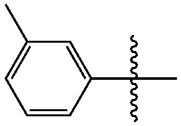
| Compound | R |
|---|---|
| 17.12 | 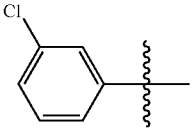 |
| 17.13 | 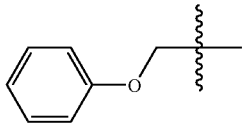 |
| 17.14 |  |
| 17.15 | 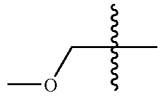 |
| 17.16 | 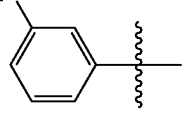 |
| 17.17 | 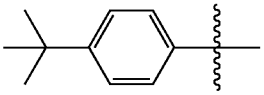 |
| 17.18 | 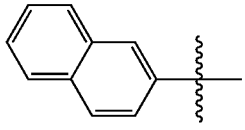 |
| 17.19 | 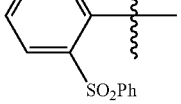 |
| 17.20 | |
| 17.21 | |

TABLE 8-continued

| Compound | R |
|---|---|
| 17.22 | 2-methoxy-5-nitrophenyl |
| 17.23 | 2,4-bis(trifluoromethyl)phenyl |
| 17.24 | 4-(trifluoromethoxy)phenyl |
| 17.25 | 3,5-dimethoxyphenyl |
| 17.26 | 3-cyanophenyl |
| 17.27 | phenyl |
| 17.28 | 4-bromophenyl |
| 17.29 | 3-(4-fluorophenoxy)phenyl |
| 17.30 | 4-phenylphenyl |
| 17.32 | 3-bromophenyl |
| 17.33 | 3,5-bis(benzyloxy)phenyl |
| 17.34 | 2-phenylphenyl |
| 17.35 | 3-(trifluoromethoxy)phenyl |
| 17.36 | 4,7-dichloro-3-methylbenzo[d]isoxazol-3-yl |
| 17.37 | 5-chlorobenzo[b]thiophen-3-yl |
| 17.38 | ethynyl |
| 17.39 | 3-(trifluoromethyl)phenyl |

TABLE 8-continued

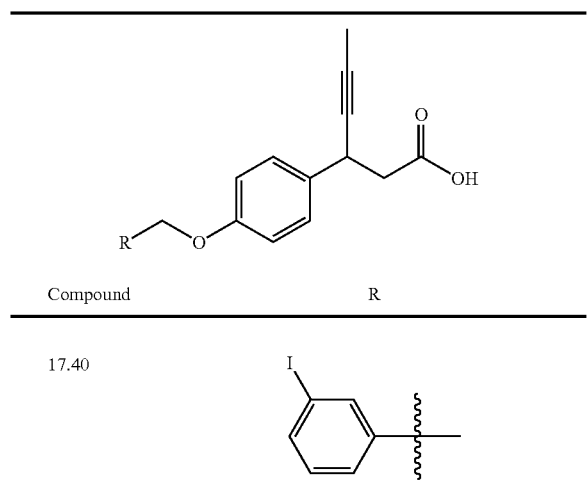

| Compound | R |
|---|---|
| 17.40 | (3-iodophenyl) |

6.18 Example 18

This example illustrates the preparation of 3-{4-[5-Methyl-2-(4-trifluoromethyl-phenyl)-oxazol-4-ylmethoxy]-phenyl}-hex-4-ynoic acid.

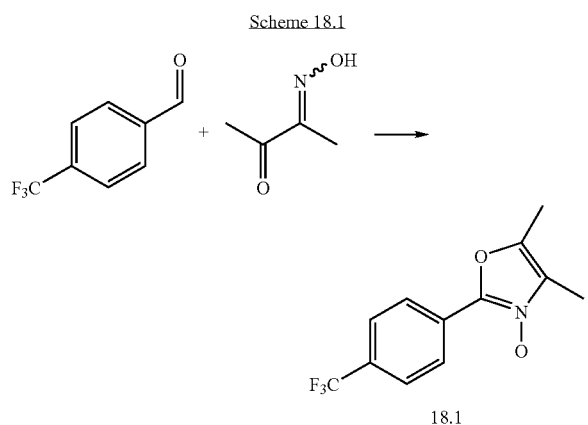

4,5-dimethyl-2-(4-trifluoromethyl-phenyl)-oxazole-3-oxide (18.1). A 100 mL pear-shaped flask was charged with butane-2,3-dione monooxime (2.1 g, 20.4 mmol), 4-(trifluoromethyl)benzaldehyde (3.0 mL, 22.4 mmol), and acetic acid (20 mL). The mixture was cooled to 0° C. A solution of 4N HCl in dioxane (7.0 mL, 28.0 mmol) was added dropwise to the reaction and the resultant mixture was stirred at 0° C. for 20 minutes. Diethyl ether (30 mL) was added to the reaction and the mixture was allowed to warm to room temperature overnight. The solvent was removed under reduced pressure and the resulting residue was taken up in water (300 mL). Conc. NH$_4$OH$_{(aq)}$ was added to adjust the pH to 9.0. The mixture was extracted with ethyl acetate (2×75 mL), and the combined organic layers were washed with water (100 mL), followed by saturated brine (100 mL). The organic layer was dried (Na$_2$SO$_4$) and the solvent removed under reduced pressure. The resulting residue was purified via radial chromatography (3% MeOH in DCM) to yield 1.8 g (35%) of 4,5-dimethyl-2-(4-trifluoromethyl-phenyl)-oxazole-3-oxide as a white solid. LC/MSD m/e: 258.1 (M+H); $^1$H NMR (400 MHz) (Acetone-d$_6$) δ 8.68 (d, 2H, J=8.0 Hz), 7.89 (d, 2H, J=8.0 Hz), 2.45 (s, 3H), 2.16 (s, 3H).

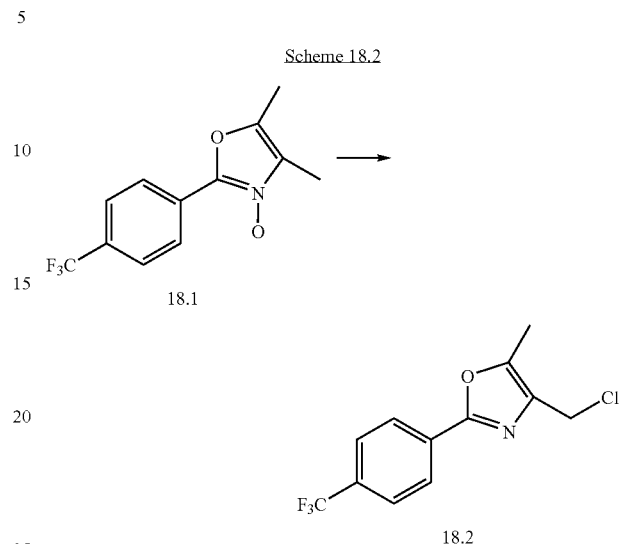

4-chloromethyl-5-methyl-2-(4-trifluoromethyl-phenyl)-oxazole (18.2). Phosphorous oxychloride (0.72 mL, 7.8 mmol) was added dropwise to an oven-dried 100 mL pear-shaped flask charged with 18.1 (1.8 g, 7.00 mmol) and dichloromethane (20 mL). The reaction was refluxed under nitrogen atmosphere for 30 minutes and then cooled to room temperature. The reaction was washed with water (2×250 mL) and the combined aqueous layers were back extracted with DCM (2×25 mL). The combined organic layers were washed with brine and dried (Na$_2$SO$_4$). The solvent was removed under reduced pressure and the resulting residue was purified via radial chromatography (15% diethyl ether in hexanes) to yield 216 mg (15%) of 4-chloromethyl-5-methyl-2-(4-trifluoromethyl-phenyl)-oxazole as a white solid. LC/MSD m/e: 276.0 (M+H); $^1$H NMR (400 MHz) (CDCl$_3$) δ 8.15 (2H, d, J=8.0 Hz), 7.73 (2H, d, J=8.0 Hz), 4.59 (2H, s), 2.48 (2H, s).

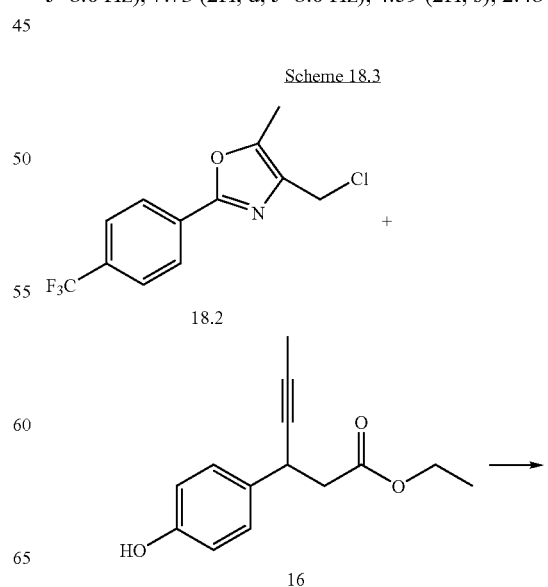

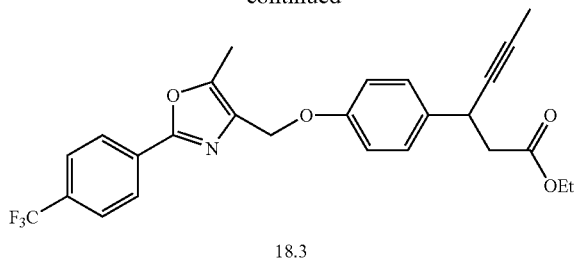

18.3

3-{4-[5-Methyl-2-(4-trifluoromethyl-phenyl)-oxazol-4-ylmethoxy]-phenyl}-hex-4-ynoic acid ethyl ester (18.3). Cesium carbonate (0.51 g, 1.57 mmol) was added to a solution of 18.2 (216 mg, 0.79 mmol) and phenol 16 (220 mg, 0.79 mmol) in DMF (8 mL). The reaction was stirred at room temperature overnight and then taken up in water (500 mL). The solution was adjusted to pH=4.0 with 1N HCl(aq) and extracted with ethyl acetate (2×25 mL). The combined organics were washed with water, followed by brine. The solvent was removed under reduced pressure and the resulting residue was purified via radial chromatography (20% diethyl ether in hexanes) to yield 304 mg (82%) of 3-{4-[5-Methyl-2-(4-trifluoromethyl-phenyl)-oxazol-4-ylmethoxy]-phenyl}-hex-4-ynoic acid ethyl ester. LC/MSD m/e: 472.0 (M+H); $^1$H NMR (400 MHz) (CDCl$_3$) δ 8.16 (2H, d, J=8.0 Hz), 7.73 (2H, d, J=8.0 Hz), 7.33 (2H, m), 6.99 (2H, m), 5.01 (2H, s), 4.14 (3H, m), 2.72 (2H, m), 2.48 (3H, s), 1.85 (3H, s), 1.26 (3H, t, J=8.0 Hz).

Scheme 18.4

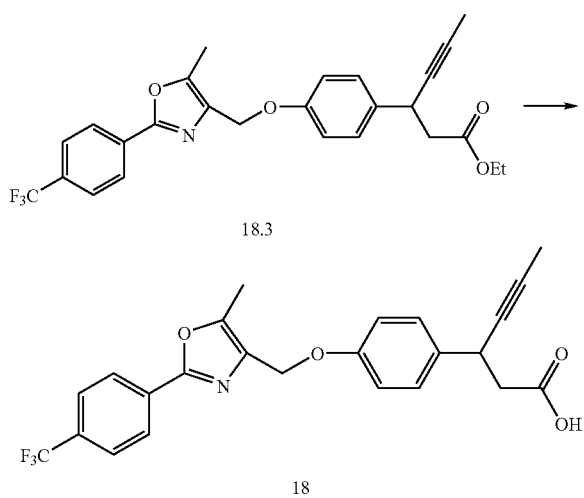

3-{4-[5-Methyl-2-(4-trifluoromethyl-phenyl)-oxazol-4-ylmethoxy]-phenyl}-hex-4-ynoic acid (18). 2N KOH$_{(aq)}$ was added to a solution of 18.3 (304 mg, 0.65 mmol) in ethanol (5 mL). The reaction was stirred at room temperature overnight and then taken up in copious water. The aqueous solution was adjusted to pH=2.0 with 1N HCl$_{(aq)}$ and extracted with ethyl acetate (2×25 mL). The combined organic layers were washed with water, followed by brine. The solvent was removed under reduced pressure and the resulting residue was purified via radial chromatography (40% ethyl acetate in Hexanes+0.1% AcOH) to yield 150 mg (52%) of compound 18 as a glass. LC/MSD m/e: 444.0 (M+H); $^1$H NMR (400 MHz) (acetone) δ 8.21 (2H, m), 7.89 (2H, d, J=8.0 Hz), 7.38 (2H, m), 7.03 (2H, m), 5.06 (2H, s), 4.06 (1H, m), 2.70 (2H, m), 2.52 (3H, s), 1.81 (3H, s).

6.19 Example 19

Examples 19-22 were prepared using methods similar to those described in Example 18.

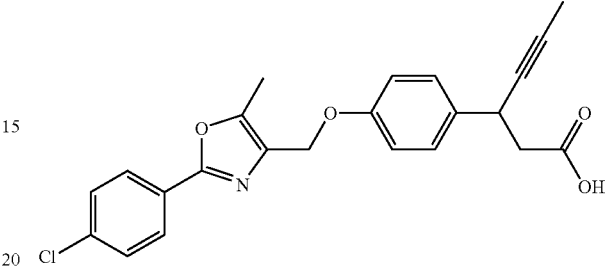

3-{4-[5-Methyl-2-(4-chloro-phenyl)-oxazol-4-ylmethoxy]-phenyl}-hex-4-ynoic acid (19). LC/MSD m/e: 410.0 (M+H). $^1$H-NMR (400 MHz) (acetone-d$_6$) δ 8.02 (2H, m), 7.49 (2H, m), 7.35 (2H, m), 7.01 (2H, m), 5.04 (2H, s), 4.09 (1H, m), 2.77 (2H, m), 2.48 (3H, s), 1.86 (3H, s).

6.20 Example 20

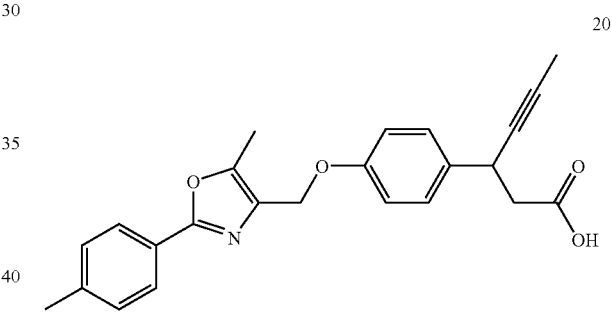

3-{4-[5-Methyl-2-(4-methyl-phenyl)-oxazol-4-ylmethoxy]-phenyl}-hex-4-ynoic acid (16). LC/MSD m/e: 390.2 (M+H). $^1$H NMR (400 MHz) (CDCl$_3$) δ 7.96 (2H, m), 7.34 (2H, m), 6.70 (2H, m), 5.02 (2H, s), 4.09 (1H, m), 2.80 (2H, m), 2.47 (3H, s), 1.85 (3H, s).

6.21 Example 21

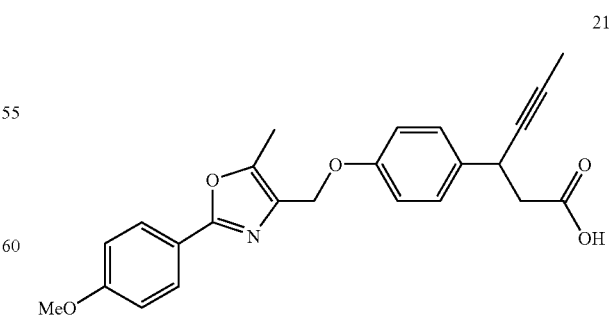

3-{4-[5-Methyl-2-(4-methoxy-phenyl)-oxazol-4-ylmethoxy]-phenyl}-hex-4-ynoic acid (21). LC/MSD m/e: 406.1 (M+H). $^1$H NMR (400 MHz) (acetone-d$_6$) δ 7.89 (2H, d, J=9.0 Hz) 7.30 (2H, m), 7.09 (2H, d, J=9.0 Hz), 7.00 (2H, m), 4.97 (3H, s), 3.90 (1H, m), 3.84 (3H, s), 2.44 (3H, s), 1.79 (3H, s).

6.22 Example 22

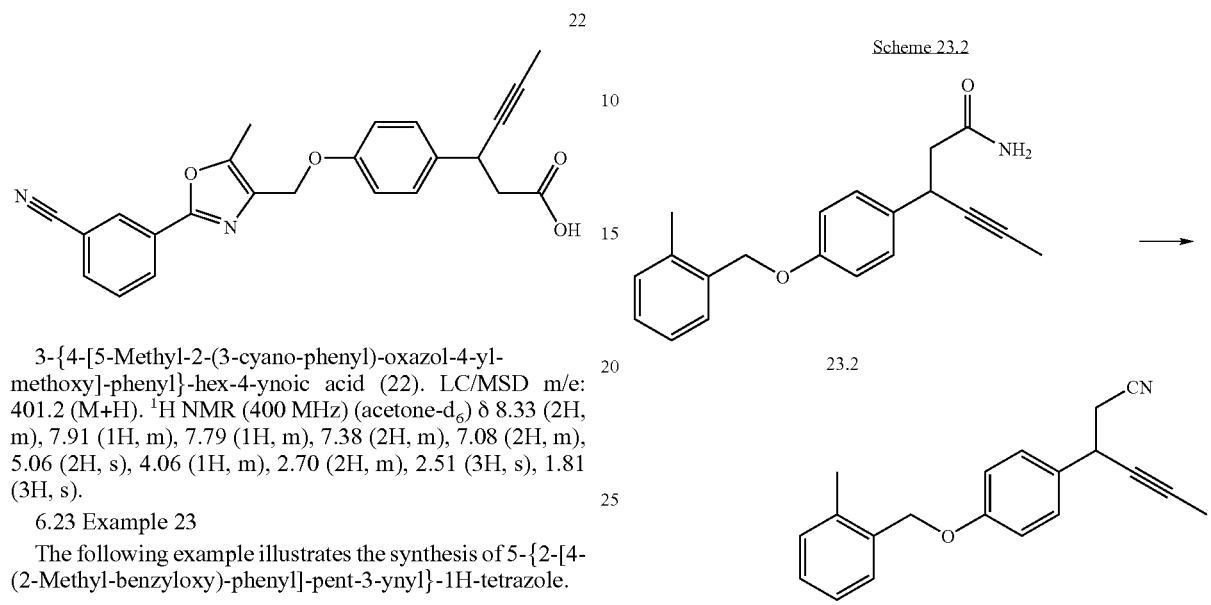

3-{4-[5-Methyl-2-(3-cyano-phenyl)-oxazol-4-yl-methoxy]-phenyl}-hex-4-ynoic acid (22). LC/MSD m/e: 401.2 (M+H). $^1$H NMR (400 MHz) (acetone-$d_6$) δ 8.33 (2H, m), 7.91 (1H, m), 7.79 (1H, m), 7.38 (2H, m), 7.08 (2H, m), 5.06 (2H, s), 4.06 (1H, m), 2.70 (2H, m), 2.51 (3H, s), 1.81 (3H, s).

6.23 Example 23

The following example illustrates the synthesis of 5-{2-[4-(2-Methyl-benzyloxy)-phenyl]-pent-3-ynyl}-1H-tetrazole.

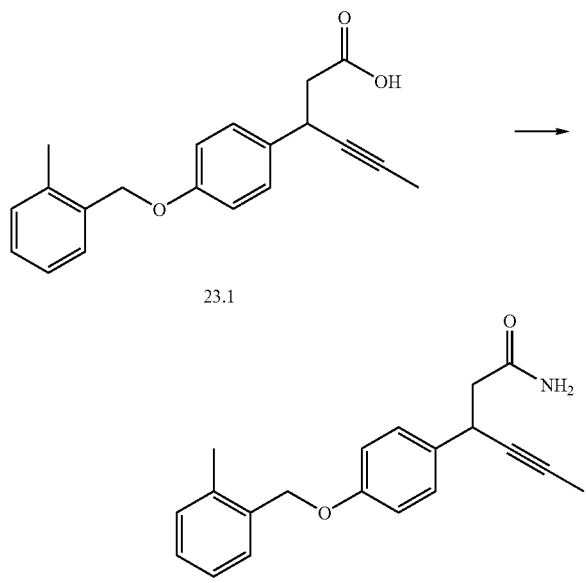

3-[4-(2-Methyl-benzyloxy)-phenyl]-hex-4-ynoic acid amide (23.2). Carbonyl diimidazole (0.46 g, 2.84 mmol) was added to a solution of 3-[4-(2-Methyl-benzyloxy)-phenyl]-hex-4-ynoic acid (See Example 13) (0.73 g, 2.37 mmol) in anhydrous THF (10 mL). The mixture was stirred at room temperature for 2 hours. Concentrated NH$_4$OH (10 mL) was then added to the mixture, and the reaction was stirred at room temperature overnight. The reaction mixture was poured into water (300 mL) and the solution was adjusted to pH=7 with conc. HCl. The aqueous layer was then extracted with 3×25 mL ethyl acetate. The combined organic layers were washed with water, followed by brine. The organic layer was then dried (Na$_2$SO$_4$) and concentrated under reduced pressure to yield 0.48 g (70%) of 3-[4-(2-Methyl-benzyloxy)-phenyl]-hex-4-ynoic acid amide (23.2) as a light yellow solid. LC/MSD m/e: 308.4 (M+H)

3-[4-(2-Methyl-benzyloxy)-phenyl]-hex-4-ynenitrile (23.3). An oven-dried 50 mL round-bottomed flask was charged with DMF (8 mL) and a stir bar. The solution was cooled to 0° C. in an ice bath. Thionyl chloride (160 μL, 1.0 mmol) was added slowly via syringe. The mixture was stirred at 0° C. for an additional 45 minutes. Nitrile 23.2 (300 mg, 0.98 mmol) was then added to the mixture as solution in DMF (2 mL). The reaction was stirred at 0° C. for an hour, and was then allowed to gradually warm to room temperature overnight. The reaction mixture was partitioned between ice water and ethyl acetate. The aqueous layer was extracted 2 additional times with 25 mL ethyl acetate. Saturated NaHCO$_3$ was then added to the aqueous layer and the aqueous layer was extracted a third time with ethyl acetate. The combined organic layers were washed with saturated NaHCO$_3$ and concentrated under reduced pressure. The resulting residue was purified via radial chromatography (15% ethyl acetate in hexanes) to yield 203 mg (72%) of 3-[4-(2-Methyl-benzyloxy)-phenyl]-hex-4-ynenitrile (23.3). $^1$H NMR (400 MHz) (acetone-$d_6$) δ 7.44 (3H, m), 7.24 (3H, m), 7.05 (2H, m), 5.13 (2H, s), 4.09 (1H, m), 2.89 (2H, m), 2.39 (3H, s), 1.88 (3H, s).

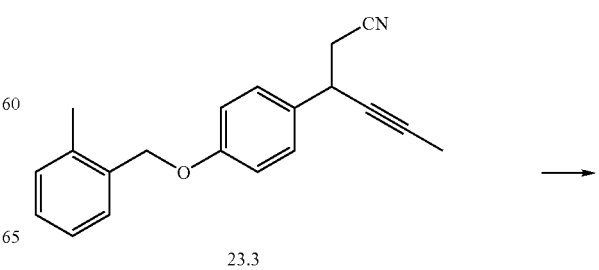

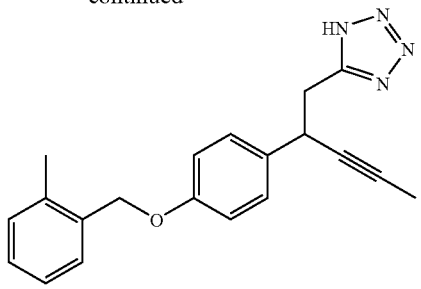

23

5-{2-[4-(2-Methyl-benzyloxy)-phenyl]-pent-3-ynyl}-1H-tetrazole (23). To a solution of 23.3 (200 mg, 0.51 mmol) in DMF (5 mL) was added sodium azide (35 mg, 0.54 mmol) and ammonium chloride (29 mg, 0.54 mmol). The solution was stirred at 110° C. for 48 hours. The reaction mixture was poured into 50 mL of water and extracted with ethyl acetate (2×25 mL). The combined organic layers were concentrated under reduce pressure, and the resulting residue was purified via HPLC to yield 5 mg (3%) of 5-{2-[4-(2-Methyl-benzyloxy)-phenyl]-pent-3-ynyl}-1H-tetrazole (23) as a film. LC/MSD m/e: 333.1 (M+H). $^1$H NMR (400 MHz) (acetone-$d_6$) δ 7.45 (1H, m), 7.34 (2H, m), 7.25 (3H, m), 7.00 (2H, m), 5.11 (2H, s), 4.17 (1H, m), 3.37 (2H, d, J=7 Hz), 2.39 (3H, s), 1.79 (3H, s).

6.24 Example 24

The following example illustrates the synthesis of 3-[4-(4-Methoxy-benzyloxy)-phenyl]-hex-4-ynoic acid thiazol-2-ylamide.

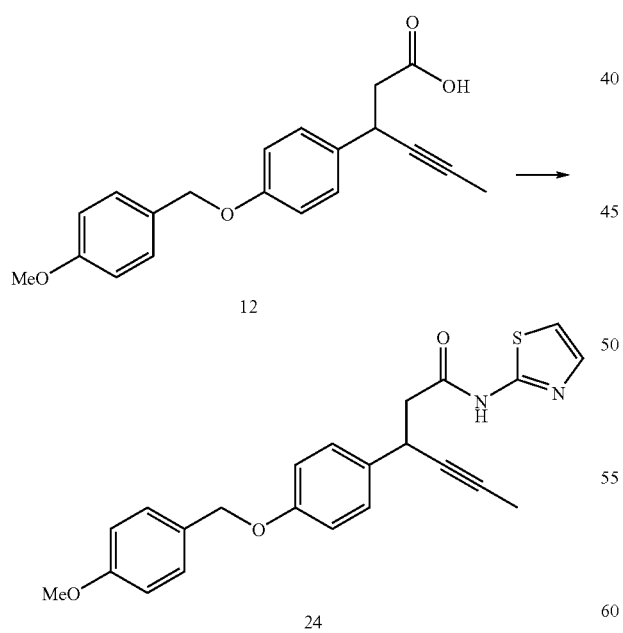

Scheme 24.1

3-[4-(4-Methoxy-benzyloxy)-phenyl]-hex-4-ynoic acid thiazol-2-ylamide (24). A pear-shaped flask was charged with a stir bar, compound 12 (50 mg, 0.154 mmol), carbonyl diimidazole (25 mg, 0.154 mmol) and THF (4 mL). The mixture was refluxed for 1 hour, and 2-amino thiazole (16 mg, 0.154 mmol) was then added. The reaction was refluxed for 48 hours, poured into water and extracted with ethyl acetate. The organic layer was concentrated and the resulting residue was purified via HPLC to yield 1.0 mg (2%) of 3-[4-(4-Methoxy-benzyloxy)-phenyl]-hex-4-ynoic acid thiazol-2-ylamide (24) as a film. $^1$H NMR (400 MHz) (acetone-$d_6$) δ 7.39 (4H, m), 7.11 (1H, s), 6.95 (3H, m), 5.03 (2H, s), 3.82 (3H, s), 2.95 (2H, m), 1.79 (3H, s).

6.25 Example 25

The compounds in the following table were prepared using the method described in Example 24.

TABLE 9

| Compound | HAR |
|---|---|
| 25.1 | Tetrazole-5-yl |
| 25.2 | pyrimidin-2-yl |
| 25.3 | Pyridin-2-yl |

6.26 Example 26

The following example illustrates the preparation of 3-[4-(5-Methyl-2-phenyl-2H-[1,2,3]triazol-4-ylmethoxy)-phenyl]-hex-4-ynoic acid (26).

Scheme 26.1

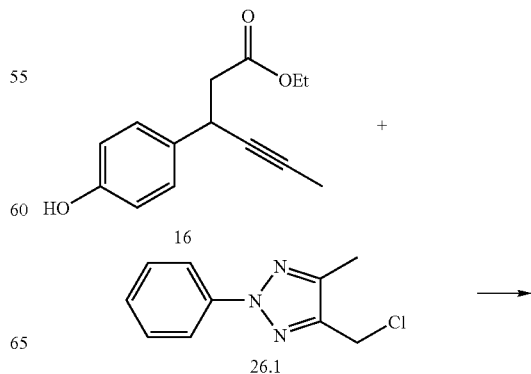

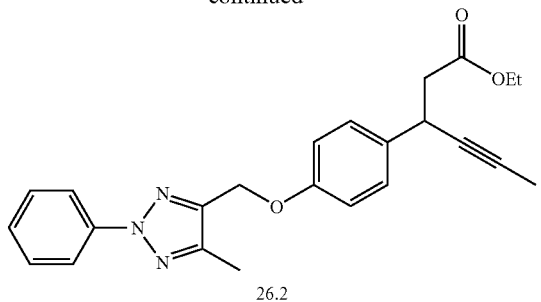

26.2

3-[4-(5-Methyl-2-phenyl-2H-[1,2,3]triazol-4-yl-methoxy)-phenyl]-hex-4-ynoic acid ethyl ester (26.2). Cesium carbonate (107 mg, 0.33 mmol) was added to a solution of 16 (60 mg, 0.22 mmol) in DMF (5 mL). The mixture was stirred at room temperature for 5 minutes, and 4-Chloromethyl-5-methyl-2-phenyl-2H-[1,2,3]triazole (55 mg, 0.22 mmol) was added. The reaction was heated to 60° C. and stirred overnight. The reaction mixture was then poured into copious water. 1N HCl$_{(aq)}$ was added to adjust the pH to 4.0. The aqueous layer was extracted with ethyl acetate. The organic layer was then washed with water, followed with brine. The organic layer was dried (Na$_2$SO$_4$) and concentrated. The resulting residue was purified via radial chromatography (20% ethyl acetate in hexanes) to yield 60 mg (66%) of 3-[4-(5-Methyl-2-phenyl-2H-[1,2,3]triazol-4-yl-methoxy)-phenyl]-hex-4-ynoic acid ethyl ester (26.2). LC/MSD m/e: 404.2 (M+H).

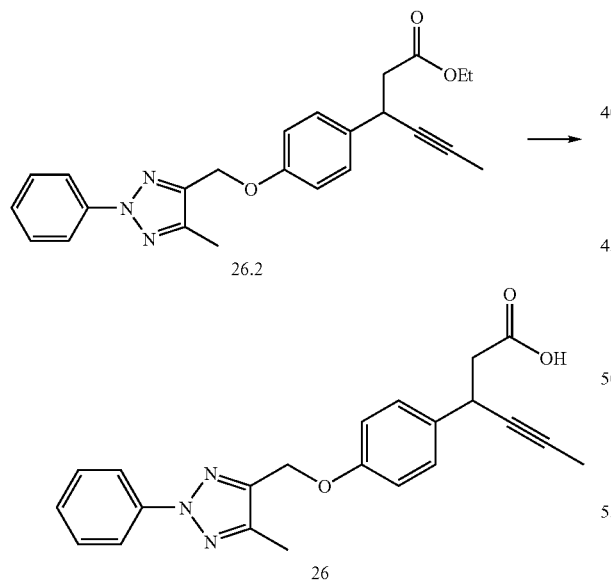

3-[4-(5-Methyl-2-phenyl-2H-[1,2,3]triazol-4-yl-methoxy)-phenyl]-hex-4-ynoic acid (26). 2N KOH(aq) (1 mL) was added to a solution of 26.2 (68 mg, 0.17 mmol) in EtOH (2 mL). The reaction was stirred at room temperature overnight and then poured into water. The aqueous mixture was acidified to pH=2 with 1N HCl(aq), and then extracted with ethyl acetate. The organic layer was washed with water, followed by brine. The organic layer was then concentrated under reduced pressure and the resulting residue was purified via radial chromatography (20% ethyl acetate in hexanes) to yield 60.3 mg (95%) of compound 26 as a colorless oil. LC/MSD m/e: 374.0 (M−H); $^1$H NMR (400 MHz) (acetone-d$_6$) δ 8.05 (2H, d, J=8.0 Hz), 7.56 (2H, t, J=8.0 Hz), 7.40 (3H, t, J=8.0 Hz), 7.06 (2H, d, J=8.0 Hz), 5.28 (2H, s), 4.05 (1H, m), 2.70 (2H, m), 2.44 (3H, s), 1.80 (3H, s).

6.27 Example 27

The compounds in the following table were prepared using methods similar to those described in Example 26.

TABLE 10

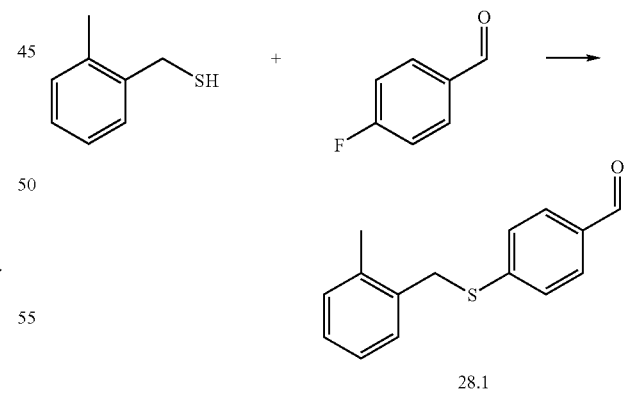

| Compound | HAR |
|---|---|
| 27.1 | F$_3$C-[4-phenyl-1,2,4-oxadiazol-3-yl with methyl] |
| 27.2 | [pyrazol-1-yl-phenyl] |
| 27.3 | [1,2,3-thiadiazol-4-yl-phenyl] |

6.28 Example 28

The following example illustrates the preparation of 3-[4-(2-Methyl-benzylsulfanyl)-phenyl]-hex-4-ynoic acid (28).

Scheme 28.1

4-(2-Methyl-benzylsulfanyl)-benzaldehyde (28.1). 4-fluoro-benzaldehyde (1.16 g, 9.32 mmol) was added dropwise over 2 minutes to a solution of o-tolyl-methanethiol (1.35 g, 9.79 mmol) and Cesium carbonate (3.19 g, 9.79 mmol) in DMF (20 mL). The solution was stirred at 40° C. overnight and then poured into copious water. The pH of the solution was adjusted to 4 with 1N HCl$_{(aq)}$, and the aqueous solution was extracted with ethyl acetate (2×35 mL). The combined organic layers were washed with water, followed by brine. The combined organic layers were then dried (Na₂SO₄) and the solvent removed under reduced pressure. The resulting residue was purified via radial chromatography (15% ethyl acetate in hexanes) to yield 1.29 g (54%) of 4-(2-Methyl-benzylsulfanyl)-benzaldehyde (28.1). LC/MSD m/e: 243.0 (M+H).

Scheme 28.2

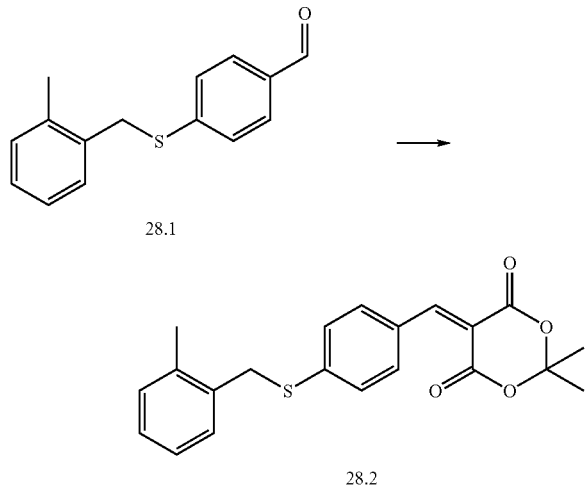

2,2-Dimethyl-5-[4-(2-methyl-benzylsulfanyl)-benzylidene]-[1,3]dioxane-4,6-dione (28.2). Pyrrolidine (0.45 mL, 5.27 mmol) was added to a solution of aldehyde 28.1 in diethyl ether (20 mL) and the mixture was sonicated for 5 minutes. The mixture was then added to a solution of Meldrum's acid (0.73 g, 5.08 mmol) in diethyl ether (20 mL) and the resultant mixture was sonicated for 5 minutes, forming a solid. The solid was filtered, rinsed with diethyl ether, and then suspended in DCM (10 mL). p-Toluenesulfonic acid (0.97 g, 5.10 mmol) was then added to the suspension and the suspension was sonicated until clear. The solvent was removed under reduced pressure, and the resulting residue was taken up in diethyl ether and partitioned between water and ethyl acetate. The aqueous layer was extracted 2 additional times with ethyl acetate. The combined organic layers were washed with water, dried (Na₂SO₄), and concentrated in vacuo to yield 1.05 g (54%) of 2,2-Dimethyl-5-[4-(2-methyl-benzylsulfanyl)-benzylidene]-[1,3]dioxane-4,6-dione (28.2) as a yellow oil The resulting yellow oil was used without further purification. LC/MSD m/e: 391.1 (M+Na).

Scheme 28.3

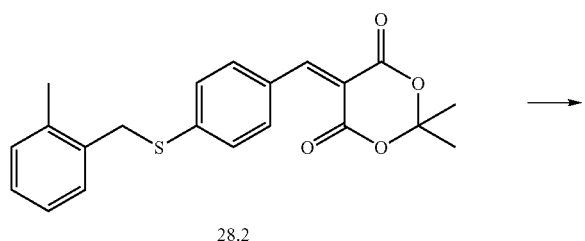

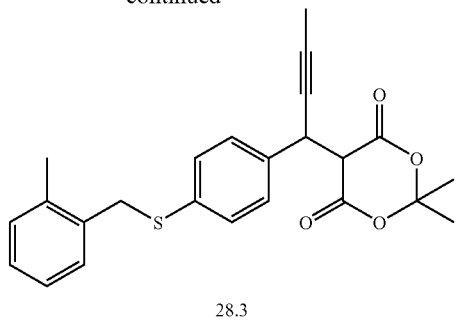

2,2-Dimethyl-5-{1-[4-(2-methyl-benzylsulfanyl)-phenyl]-but-2-ynyl}-[1,3]dioxane-4,6-dione (28.3). An oven-dried 100 mL pear-shaped flask, fitted with an oven-dried stir bar, was charged with a 0.5 M solution of 1-propynyl magnesium bromide in THF (12.5 mL, 6.27 mmol) via cannula. The solution was cooled to 0° C., and then a solution of 28.2 (1.05 g, 2.85 mmol) in anhydrous THF (6 mL) was added over 3 minutes via cannula. The reaction was stirred at 0° C. for 5 minutes and then stirred at room temperature for 1.5 hours. The reaction mixture was poured into saturated NH₄Cl$_{(aq)}$ and extracted with ethyl acetate. The combined organic layers were washed with water, followed by brine. The combined organic layers were dried (Na₂SO₄) and concentrated in vacuo. The resulting residue was purified via radial chromatography (20% ethyl acetate in hexanes) followed by recrystallization from hot ethyl acetate and hexanes to yield 162 mg (15%) of 2,2-Dimethyl-5-{1-[4-(2-methyl-benzylsulfanyl)-phenyl]-but-2-ynyl}-[1,3]dioxane-4,6-dione (28.3). LC/MSD m/e: 409.1 (M+H).

Scheme 28.4

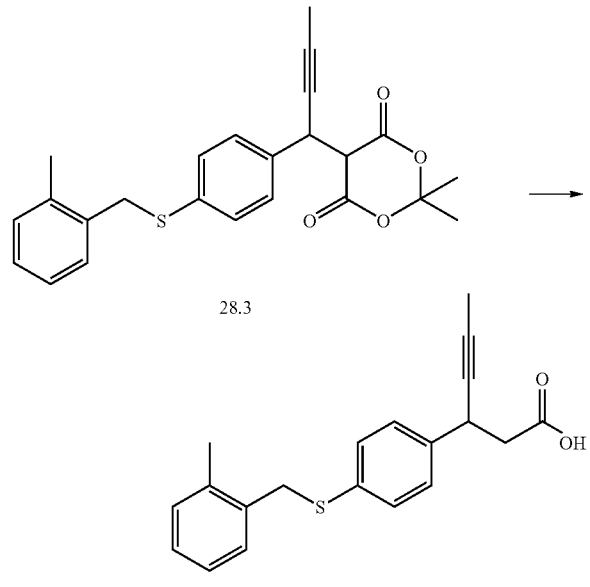

3-[4-(2-Methyl-benzylsulfanyl)-phenyl]-hex-4-ynoic acid (28). A solution of 28.3 (20 mg, 0.05 mmol) in 5:1 pyridine: water (6 mL) was heated to 80° C. for 72 hours. The reaction was poured into 500 mL of water and the solution was acidified with 1N HCl$_{(aq)}$ (65 mL). The aqueous solution was extracted with ethyl acetate and the combined organic layers were washed with water, followed by brine. The combined organic layers were then dried (Na₂SO₄) and concentrated in vacuo. The resultant residue was then purified via radial chromatography (30% ethyl acetate in hexanes) to yield 18 mg (quantitative) 3-[4-(2-Methyl-benzylsulfanyl)-phenyl]-hex-4-ynoic acid (28). LC/MSD m/e: 323.1 (M−H).

6.29 Example 29

The following example illustrates the preparation of 3-(4-O—Tolylmethanesulfinyl-phenyl)-hex-4-ynoic acid.

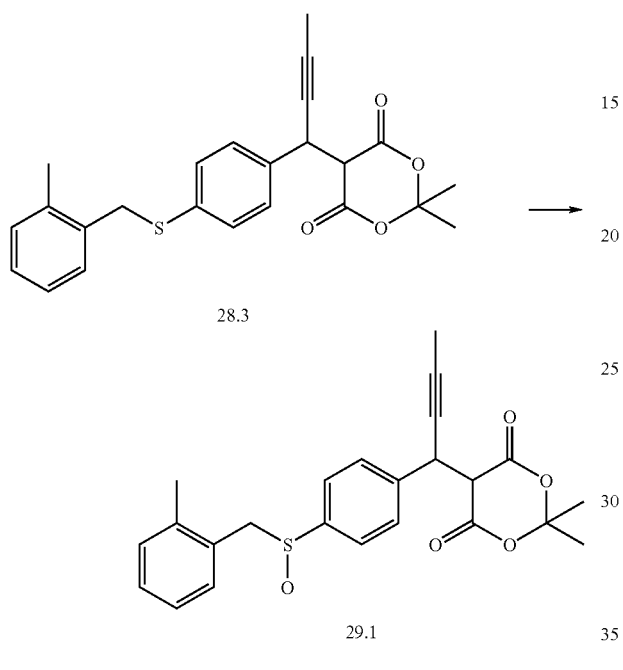

2,2-Dimethyl-5-[1-(4-o-tolylmethanesulfinyl-phenyl)-but-2-ynyl]-[1,3]dioxane-4,6-dione (29.1). Hydrogen peroxide (20 μL, 0.05 mmol) was added to a 0° C. solution of 28.3 (20 mg, 0.05 mmol) in AcOH (2 mL). The reaction was stirred at 80° C. for 1.5 hours, then cooled to room temperature and stirred for 16 hours. The reaction mixture was poured into cold water and the resulting solution was acidified to pH=2 with 6N HCl(aq). The aqueous layer was extracted with ethyl acetate and sec-butanol. The combined organic layers were concentrated to yield 10 mg (50%) of 2,2-Dimethyl-5-[1-(4-o-tolylmethanesulfinyl-phenyl)-but-2-ynyl]-[1,3]dioxane-4,6-dione (29.1). LC/MSD m/e: 383.0 (consistent with di-acid —H).

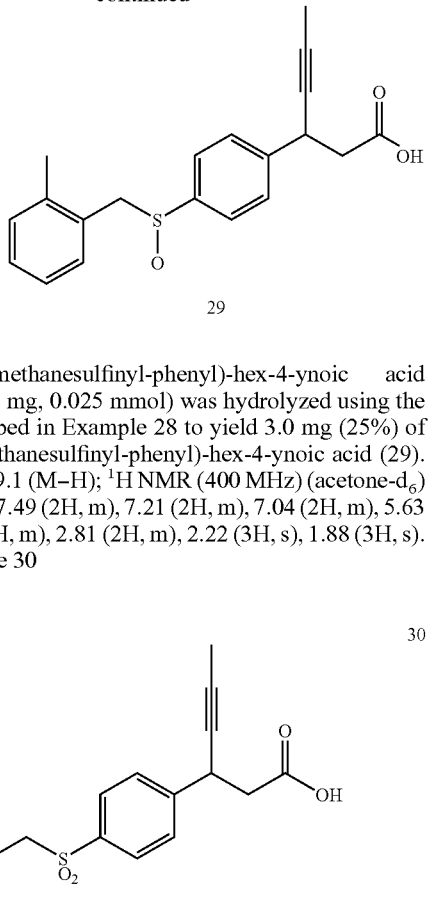

3-(4-o-Tolylmethanesulfinyl-phenyl)-hex-4-ynoic acid (29). 29.1 (10.0 mg, 0.025 mmol) was hydrolyzed using the methods described in Example 28 to yield 3.0 mg (25%) of 3-(4-o-Tolylmethanesulfinyl-phenyl)-hex-4-ynoic acid (29). LC/SD m/e: 339.1 (M−H); $^1$H NMR (400 MHz) (acetone-d$_6$) δ 7.60 (2H, m), 7.49 (2H, m), 7.21 (2H, m), 7.04 (2H, m), 5.63 (2H, s), 4.17 (1H, m), 2.81 (2H, m), 2.22 (3H, s), 1.88 (3H, s).

6.30 Example 30

3-(4-o-Tolylmethanesulfonyl-phenyl)-hex-4-ynoic acid (30) was prepared using methods similar to those described in Example 29. LC/MSD m/e: 357.2 (M+H); $^1$H NMR (400 MHz) (acetone-d$_6$) δ 7.69 (3H, m), 7.50 (1H, m), 7.17 (4H, m), 4.53 (2H, s), 4.22 (1H, m), 2.79 (2H, m), 2.27 (3H, s), 1.82 (3H, s).

6.31 Example 31

The following example illustrates the preparation of 3-[2-Methyl-4-(2-methyl-benzyloxy)-phenyl]-hex-4-enoic acid (31).

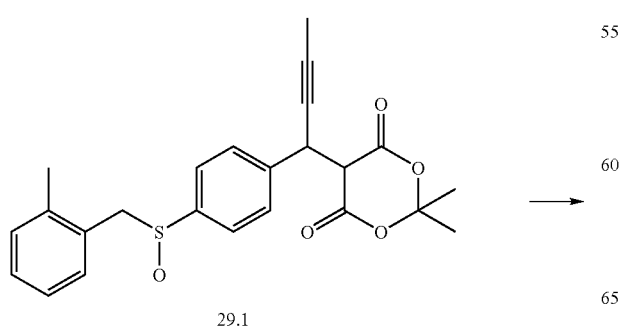

2-(2-methyl-benzyloxy)toluene (31.1). α-bromo-o-xylene (2.0 g, 10.81 mmol) was added to a solution of 2-methyl-phenol (1.06 g, 9.82 mmol) and cesium carbonate (7.99 g, 24.55 mmol) in DMF (20 mL). The reaction was stirred at 80° C. overnight. The reaction mixture was acidified with 25 mL 1N HCl(aq) and poured into copious water. The aqueous layer was extracted with ethyl acetate and the organic layer was dried (Na$_2$SO$_4$) and concentrated in vacuo. The resulting residue was purified via radial chromatography (20% ethyl acetate in hexanes) to yield 1.82 g (88%) of 2-(2-methyl-benzyloxy)toluene (31.1). LC/MSD m/e: 213.2 (M+H).

for 15 minutes and then DMF (3.3 mL) was added. Cooling was removed after 5 minutes and the reaction was allowed to warm to room temperature. The reaction was partitioned between ethyl acetate and water and the aqueous layer was extracted 1 additional time with ethyl acetate. The combined organic layers were dried (Na$_2$SO$_4$) and concentrated. The resulting residue was purified via radial chromatography (50% ethyl acetate in hexanes0 to yield 269 mg (22%) of 2-Methyl-4-(2-methyl-benzyloxy)-benzaldehyde (31.3). LC/MSD m/e: 241.2 (M+H).

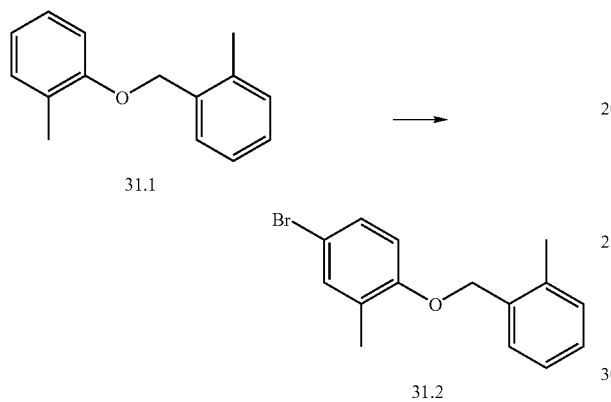

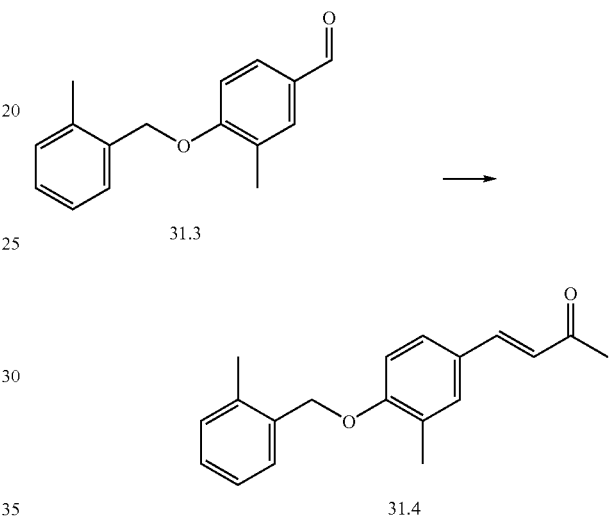

2-(2-methyl-benzyloxy)-5-bromotoluene (31.2). NBS (1.46 g, 8.23 mmol) was added to a solution of 31.1 (1.59 g, 7.48 mmol) in carbon tetrachloride (8 mL). The reaction was stirred at 60° C. overnight and filtered to remove succinimide. The filtrate was concentrated in vacuo and purified via radial chromatography (15% diethyl ether in hexanes) to yield 0.65 g (25%) of 2-(2-methyl-benzyloxy)-5-bromotoluene (31.2). LC/MSD m/e: 314.2 (M+Na).

4-[2-Methyl-4-(2-methyl-benzyloxy)-phenyl]-but-3-en-2-one (31.4). 2N NaOH$_{(aq)}$ (0.6 mL) was added to a solution of 31.3 (100 mg, 0.42 mmol) in acetone (1 mL). The reaction was stirred at room temperature overnight and then taken up in water. The aqueous solution was acidified with 1N HCl$_{(aq)}$ (1.5 mL) and extracted with ethyl acetate. The organic extracts were washed with brine, dried (Na$_2$SO$_4$), and concentrated in vacuo. The resultant residue was purified via radial chromatography (20% ethyl acetate in hexanes) to yield 74 mg (63%) of 4-[2-Methyl-4-(2-methyl-benzyloxy)-phenyl]-but-3-en-2-one (31.4). LC/MSD m/e: 281.4 (M+H); $^1$H NMR (400 MHz) (acetone-d$_6$) δ 7.83 (1H, d, J=16), 7.70 (1H, m), 7.46 (1H, m), 7.25 (3H, m), 6.96 (2H, m), 6.63 (1H, d, J=16 Hz).

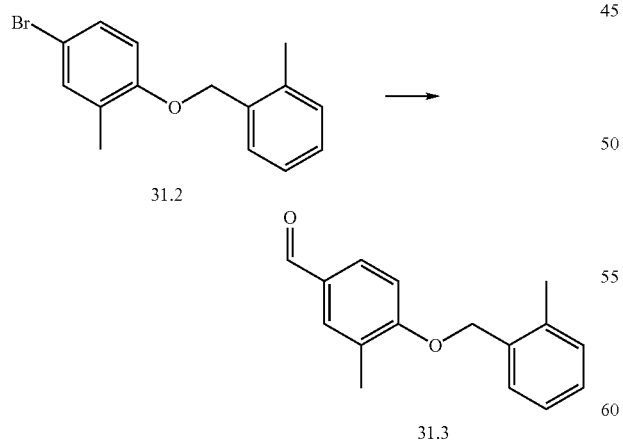

2-Methyl-4-(2-methyl-benzyloxy)-benzaldehyde (31.3). A 2.5M solution of n-BuLi (2.1 mL, 5.26 mmol) in THF was added dropwise to a −78° C. solution of 31.2 (1.46 g, 5.01 mmol) in THF (25 mL). The reaction was stirred at −78° C.

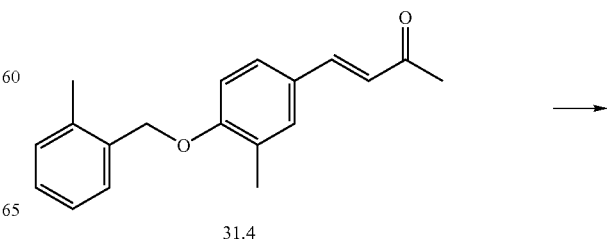

-continued

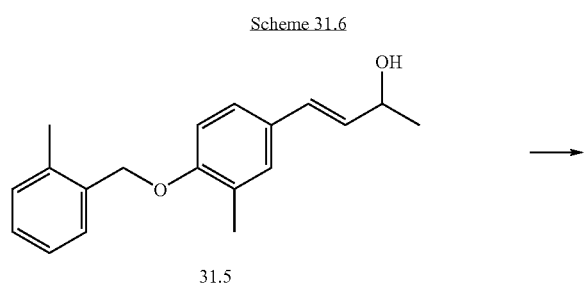

31.5

4-[2-Methyl-4-(2-methyl-benzyloxy)-phenyl]-but-3-en-2-ol (31.5). NaBH$_4$ (20 mg, 0.51 mmol) was added to a 0.4 M solution of CeCl$_3$ in MeOH (0.65 mL, 0.26 mmol), 31.4 (74 mg, 0.26 mmol), and THF (1 mL). The reaction was stirred, uncapped, until gas evolution ceased. The reaction was quenched with water (1.5 mL) and partitioned between water and diethyl ether. The aqueous layer was extracted 2 times with diethyl ether and the combined organic layers were washed with brine and concentrated in vacuo to yield 69 mg (93%) of 4-[2-Methyl-4-(2-methyl-benzyloxy)-phenyl]-but-3-en-2-ol (31.5). LC/MSD m/e: 266.3 (M−OH); $^1$H NMR (400 MHz) (DMSO-d$_6$) δ 7.44 (2H, m), 7.25 (3H, m0, 6.86 (2H, m), 6.75 (1H, m), 6.08 (1H, m), 5.11 (2H, s), 4.40, (1H, m), 2.38 (3H, s), 2.32 (3H, s), 1.29 (3H, m).

Scheme 31.6

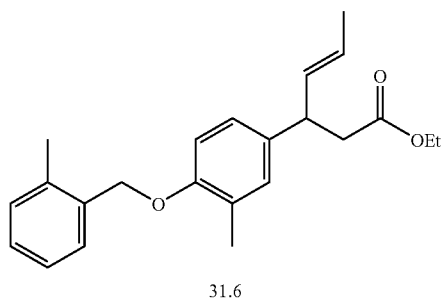

31.5

→

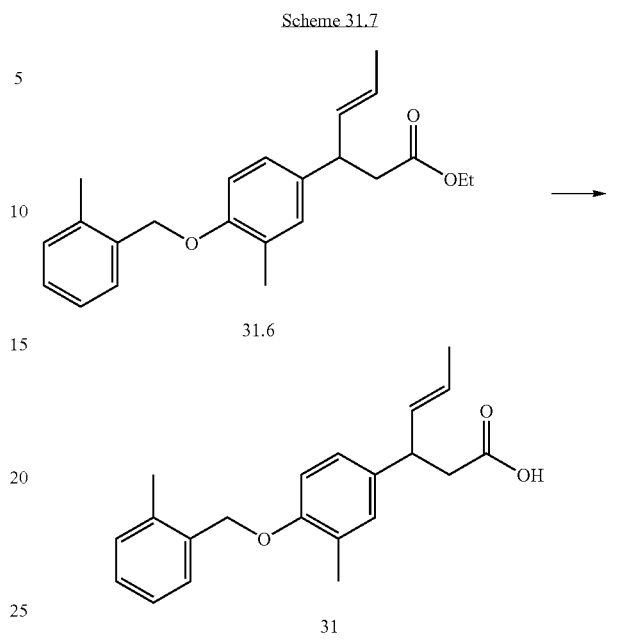

31.6

3-[2-Methyl-4-(2-methyl-benzyloxy)-phenyl]-hex-4-enoic acid ethyl ester (31.6). Propionic acid (cat.) was added to a solution of 31.5 (69 mg, 0.24 mmol) in 1,1,1-triethoxyethane (440 μL, 2.4 mmol). The reaction was stirred at 105° C. overnight. The solvent was removed under reduced pressure and the resulting residue was purified via radial chromatography (5% ethyl acetate in hexanes) to yield 33 mg (39%) of 3-[2-Methyl-4-(2-methyl-benzyloxy)-phenyl]-hex-4-enoic acid ethyl ester (31.6). LC/MSD m/e: 375.0 (M+Na).

Scheme 31.7

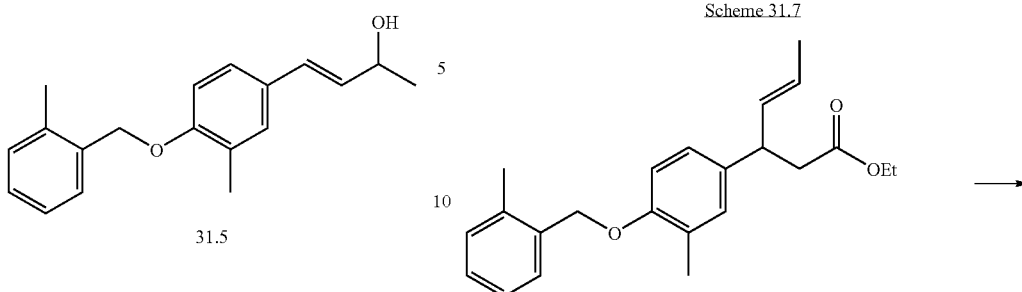

31.6

31

3-[2-Methyl-4-(2-methyl-benzyloxy)-phenyl]-hex-4-enoic acid (31). The hydrolysis of 31.6 (33 mg, 0.094 mmol) was carried out using methods similar to those described in Example 26 to yield 5.7 mg (19%) of 3-[2-Methyl-4-(2-methyl-benzyloxy)-phenyl]-hex-4-enoic acid (31). $^1$H NMR (400 MHz) (acetone) a 7.44 (2H, m), 7.25 (3H, m), 6.86 (2H, m), 6.73 (1H, m), 6.10 (1H, m), 5.64 (2H, s), 4.42 (1H, m), 2.38 (3H, s), 2.32 (3H, s), 1.29 (3H, d, J=7.0 Hz).

6.32 Example 32

The following compounds were made using methods similar to those described in Examples 28 and 31.

TABLE 11

32

| Compound | R1 | R2 | R3 | R4 | R5 |
|---|---|---|---|---|---|
| 32.1 | Me | H | Me | H | —C≡CH (propynyl) |
| 32.2 | H | Ph | H | H | —CH=CH-CH$_3$ |
| 32.3 | Me | Me | H | H | —CH=CH-CH$_3$ |

TABLE 11-continued

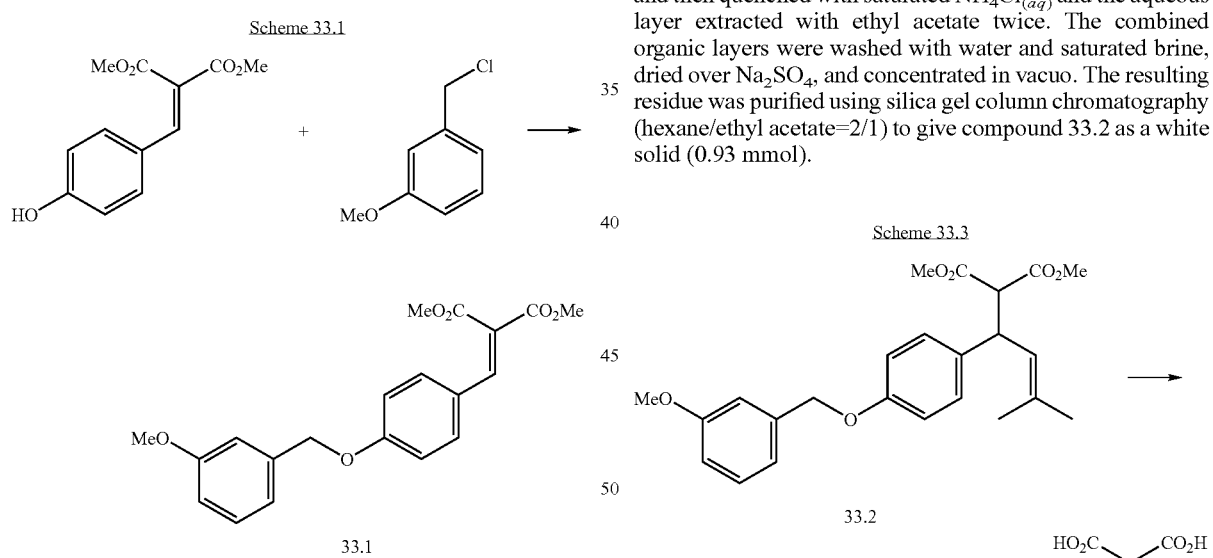

| Compound | R1 | R2 | R3 | R4 | R5 |
|---|---|---|---|---|---|
| 32.4 | Ph | H | H | H | (but-2-enyl) |

6.33 Example 33

The following example illustrates the preparation 3-[4-(3-Methoxy-benzyloxy)-phenyl]-5-methyl-hex-4-enoic acid (33).

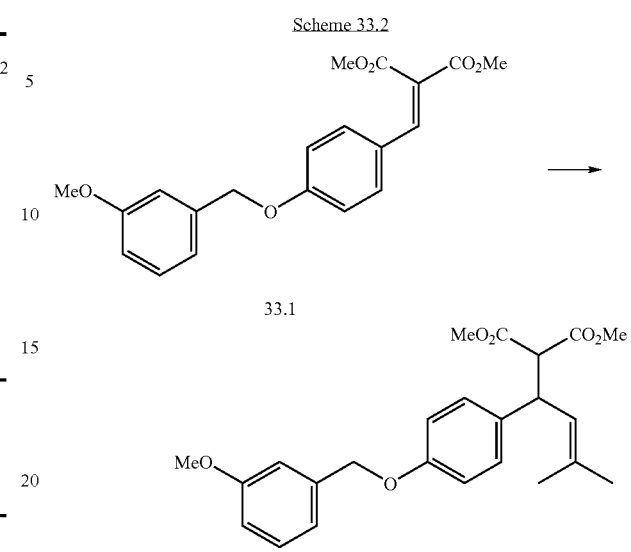

2-[4-(3-Methoxy-benzyloxy)-benzylidene]-malonic acid dimethyl ester (33.1). $K_2CO_3$ was added to a solution of 4-hydroxybenzylidene-malonic acid dimethyl ester (6.95 mmol) and 4-methyoxybenzyl chloride (7.64 mmol) in DMF (15 ml). It was stirred at room temperature overnight. The reaction was poured into water, and the product was extracted with ethyl acetate twice. The organic layer was washed with water and saturated brine, dried over $Na_2SO_4$, and concentrated in vacuo. The resulting residue was purified using silica gel column chromatography (hexane/ethyl acetate=2/1) to give compound 33.1 as a white solid (3.2 mmol).

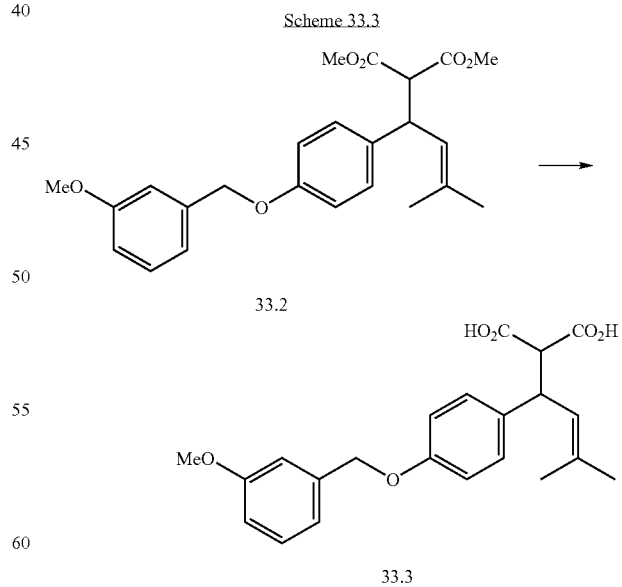

2-{1-[4-(3-Methoxy-benzyloxy)-phenyl]-3-methyl-but-2-enyl}-malonic acid dimethyl ester (33.2). 2-methyl-1-propenylmagnesium bromide (3 mL, 0.5 M in THF) was added dropwise to a solution of compound 33.1 (1.0 mmol) in THF. The reaction mixture was stirred at room temperature for 1 hr and then quenched with saturated $NH_4Cl_{(aq)}$ and the aqueous layer extracted with ethyl acetate twice. The combined organic layers were washed with water and saturated brine, dried over $Na_2SO_4$, and concentrated in vacuo. The resulting residue was purified using silica gel column chromatography (hexane/ethyl acetate=2/1) to give compound 33.2 as a white solid (0.93 mmol).

2-{1-[4-(3-Methoxy-benzyloxy)-phenyl]-3-methyl-but-2-enyl}-malonic acid (33.3). To a solution of compound 33.2 (0.50 g, 1.21 mmol) in THF (5 ml), methanol (5 ml) and water (2.5 ml) was added lithium hydroxide monohydrate (1.17 g, 28 mmol). The reaction mixture was stirred at room temperature overnight. The reaction mixture was acidified with 1N HCl to pH 2-3, and then extracted with ethyl acetate twice. The organic layer was washed with water and brine, dried over Na₂SO₄, and concentrated in vacuo. The resulting residue was used for the next reaction without purification.

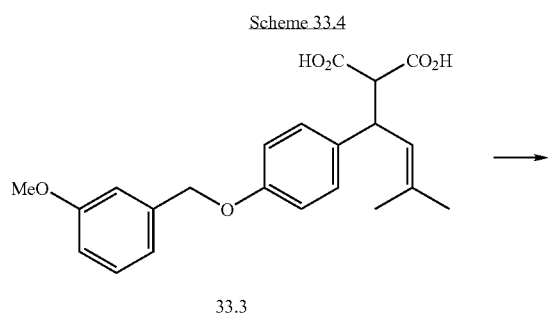

3-[4-(3-Methoxy-benzyloxy)-phenyl]-5-methyl-hex-4-enoic acid (33). A suspension of compound 33.3 (0.136 mmol) in toluene was refluxed for 16 h. After removing the solvent, the residue was purified using silica gel column chromatography (TFA/Dichloromethane/ethyl acetate=Jan. 5, 1940) to give compound 33 as a white solid (0.088 mmol). MS ESI m/e: 339 (M–H) $^1$H NMR (500 MHz) (DMSO-d₆) δ 11.97 (1H, s); 7.31 (1H, t, J=10 Hz); 7.14 (2H, d, J=11 Hz); 6.99 (2H, m); 6.87 (3H, m); 5.22 (1H, m); 5.03 (2H, s); 3.75 (1H, m); 3.75 (3H, s); 2.44-2.53 (2H, m); 1.63 (3H, s); 1.62 (3H, s).

6.34 Example 34

The following compounds were made using the method described in Example 33.

TABLE 12

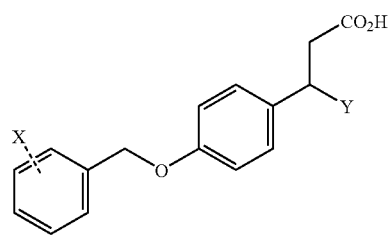

| Compound | X | Y |
|---|---|---|
| 34.1 | 4-Methoxy | 1-Propenyl |
| 34.2 | 4-Methoxy | 3-Propenyl |
| 34.3 | 4-Methoxy | Vinyl |
| 34.4 | 4-Methoxy | 2-Propenyl |
| 34.5 | 4-Methoxy | 2-Methyl-1-propenyl |
| 34.6 | 4-Methoxy | 1-Methyl-1-propenyl |
| 34.7 | 4-Methoxy | Thiophen-2-yl |
| 34.9 | 2-Methoxy | 2-Methyl-1-propenyl |

TABLE 12-continued

| Compound | X | Y |
|---|---|---|
| 34.10 | 3-Methoxy | 1-Propynyl |
| 34.11 | 3-Ethoxy | 2-Methyl-1-propenyl |

Compound 34.1. MS ESI m/e: 325 (M–H). $^1$H NMR (500 MHz) (DMSO-d₆) δ 12.05 (1H, s); 7.36 (2H, d, J=10 Hz); 7.16 (2H, d, J=10 Hz); 6.94 (2H, d, J=10 HZ); 6.90 (2H, d, J=5 Hz); 5.48-5.58 (1H, m); 5.39-5.43 (1H, m); 4.98 (2H, s); 3.99-4.03 (1H, m); 3.76 (3H, s); 2.46-2.60 (2H, m); 1.64 (3H, d, J=5 HZ).

Compound 34.2. MS ESI m/e: 325 (M–H). $^1$H NMR (500 MHz) (DMSO-d₆) δ 11.98 (1H, s); 7.38 (2H, d, J=10 Hz); 7.13 (2H, m); 6.95 (2H, m); 6.09 (2H, m); 5.63 (1H, m); 4.97 (2H, s); 4.92 (2H, d, J=10 Hz); 3.76 (3H, s); 3.03 (1H, m); 2.28-2.56 (4H, m).

Compound 34.3. MS ESI m/e: 311 (M–H). $^1$H NMR (500 MHz) (DMSO-d₆) δ 12.06 (1H, s); 7.37 (2H, d, J=10 Hz); 7.14 (2H, d, J=10 Hz); 6.92-6.95 (4H, m); 5.92 (1H, m); 5.00 (2H, m); 4.98 (2H, s); 3.76 (3H, s); 3.35 (1H, m); 2.54-2.64 (2H, m).

Compound 34.4. MS ESI m/e: 325 (M–H). $^1$H NMR (500 MHz) (DMSO-d₆) δ 12.03 (1H, s); 7.37 (2H, d, J=10 Hz); 7.09-7.19 (4H, m); 6.91-6.99 (4H, m); 4.97 (2H, s); 3.76 (3H, s); 3.63 (1H, m); 2.57-2.71 (2H, m); 2.09 (3H, s).

Compound 34.5. MS ESI m/e: 339 (M–H). $^1$H NMR (500 MHz) (DMSO-d₆) δ 11.97 (1H, s); 7.36 (2H, d, J=10 Hz); 7.14 (2H, d, J=10 Hz); 6.94 (2H, d, J=10 Hz); 6.89 (2H, d, J=5 Hz); 5.24 (2H, d, J=10 Hz); 3.85-3.90 (1H, m); 3.76 (3H, s); 2.44-2.57 (2H, m); 1.68 (3H, s); 1.63 (3H, d, J=10 Hz).

Compound 34.6. MS ESI m/e: 339 (M–H). $^1$H NMR (500 MHz) (DMSO-d₆) δ 11.97 (1H, s); 7.37 (2H, d, J=8.5 Hz); 7.10 (2H, d, m); 6.90-6.95 (4H, m); 5.23 (1H, d, J=6.5 Hz); 4.97 (2H, s); 4.29 (1H, m); 3.76 (3H, s); 2.47-2.75 (2H, m); 1.71 (3H, d, J=6 Hz); 1.56 (3H, s).

Compound 34.7. MS ESI m/e: 367 (M–H). $^1$H NMR (500 MHz) (DMSO-d₆) δ 12.18 (1H, s); 7.37 (2H, d, J=5 Hz); 7.32 (1H, m); 7.21 (2H, d, J=10 Hz); 6.92-6.95 (6H, m); 4.98 (2H, s); 4.58 (1H, m); 3.76 (3H, s); 3.01 (1H, m); 2.94 (1H, m).

Compound 34.9. MS ESI m/e: 339 (M–H). $^1$H NMR (500 MHz) (DMSO-d₆) δ 11.99 (1H, s); 7.37 (2H, m); 7.14 (2H, d, J=10 Hz); 7.04 (2H, d, J=10 Hz); 6.96 (1H, t, J=10 Hz); 6.88 (2H, d, J=10 Hz); 5.24 (2H, d, J=10 Hz); 5.00 (2H, s); 3.87 (1H, m); 3.87(3H, s); 2.45-2.55 (2H, m); 1.63 (3H, s).

Compound 34.10. MS ESI m/e: 323 (M–H). $^1$H NMR (500 MHz) (DMSO-d₆) δ 12.10 (1H, s); 7.25-7.32 (3H, m); 7.01

(2H, d, J=9 Hz); 6.94 (2H, d, J=10 Hz); 6.88 (1H, m); 5.05 (2H, s); 3.92-3.95 (1H, m); 3.75 (3H, s); 2.58 (2H, d, J=10 Hz); 1.77 (3H, s).

Compound 34.11. MS ESI m/e: 353.0 (M−H).

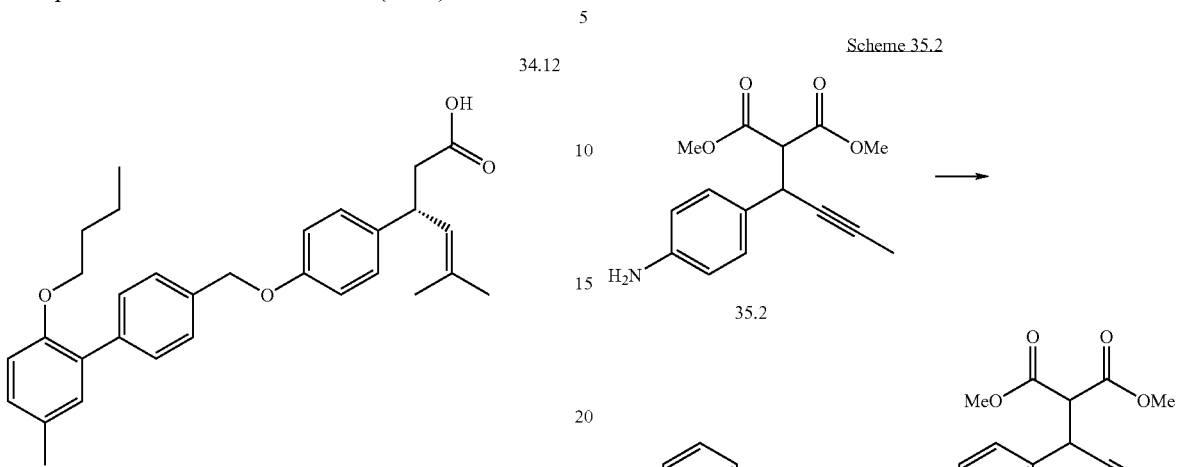

34.12

¹H NMR (400 MHz) ((CD₃)₂SO) δ 11.95 (s, 1H), 7.49 (d, 2H, J=8.2 Hz), 7.15 (d, 2H, J=8.6 Hz), 7.08-7.10 (m, 2H), 6.91-6.98 (m, 3H), 5.25 (d, 1H, 9.0 Hz), 5.07 (s, 2H), 3.78-3.94 (m, 3H), 2.44-2.59 (m, 2H), 2.26 (s, 3H), 1.55-1.63 (m, 8H), 1.30-1.38 (m, 2H), 0.85 (t, 3H, J=7.3 Hz). [M+1]⁺ Calculated for C₃₁H₃₆O₄: 473.3. Found 473.5.

6.35 Example 35

The following example illustrates the preparation 3-[4-(3-Methoxy-benzyloxy)-phenyl]-5-methyl-hex-4-enoic acid.

Scheme 35.1

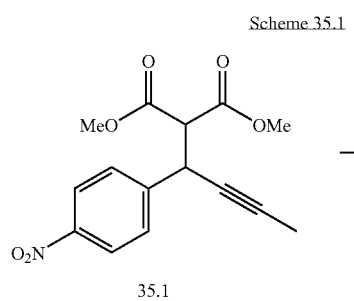

35.1

2-[1-(4-Amino-phenyl)-but-2-ynyl]-malonic acid dimethyl ester (35.2). Tin chloride dihydrate (46 mmol) was added to solution of compound 35.1 (15.3 mmol, prepared from commercially available dimethyl-4-nitrobenzylidine-malonate and 1-propynylmagnesium bromide according to the method in Example 33) in ethanol (200 ml). The mixture was stirred at 70° C. for 17 h. After removing solvent under reduced pressure, aqueous sodium carbonate solution was added and the aqueous layer was extracted with ethyl acetate twice. The combined organic layers were washed with water and brine, dried over Na₂SO₄, concentrated in vacuo. The resulting residue was filtered through short plug of silica gel, eluting with ethyl acetate. The eluant was concentrated to obtain compound 35.2 (12.8 mmol).

Scheme 35.2

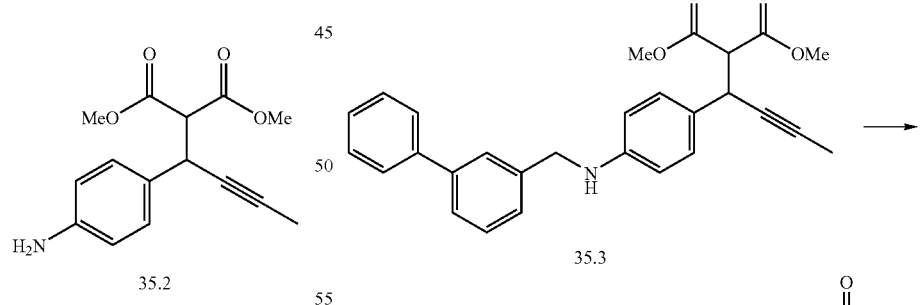

35.3

2-(1-{4-[(Biphenyl-3-ylmethyl)-amino]-phenyl}-but-2-ynyl)-malonic acid dimethyl ester (35.3). A mixture of compound 35.2 (1.0 mmol), 3-(bromomethyl)biphenyl (1.3 mmol) and K₂CO₃ (2.0 mmol) in DMF (10 ml) was stirred at 90° C. for 19 h. After diluting with ethyl acetate, the mixture was washed with aqueous Na₂CO₃ and then with brine, dried over Na₂SO₄, and concentrated in vacuo. The resulting residue was purified using silica gel column chromatography (hexane/ethyl acetate=2/1) to give compound 35.3.

Scheme 35.3

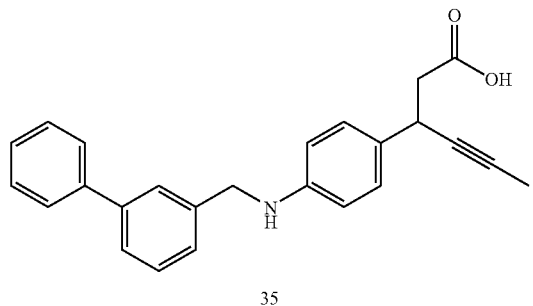

35

3-{4-[(Biphenyl-3-ylmethyl)-amino]-phenyl-hex-4-ynoic acid (35). Compound 35 was prepared from compound 35.3 by hydrolysis with base and decarboxylation as described in Example 33. MS ESI m/e: 368 (M−H). $^1$H NMR (500 MHz) (DMSO-$d_6$) δ 7.63-7.66 (2H, m); 7.51(1H, m); 7.34-7.44 (6H, m); 7.05 (2H, d, J=10 Hz); 6.60 (2H, d, J=10 Hz); 4.33 (2H, s); 3.79-3.83 (1H, m); 2.44-2.53 (2H, m); 2.09 (1H, s); 1.74 (3H, s).

6.36 Example 36

The following compounds were prepared according to the methods described in Example 35.

TABLE 13

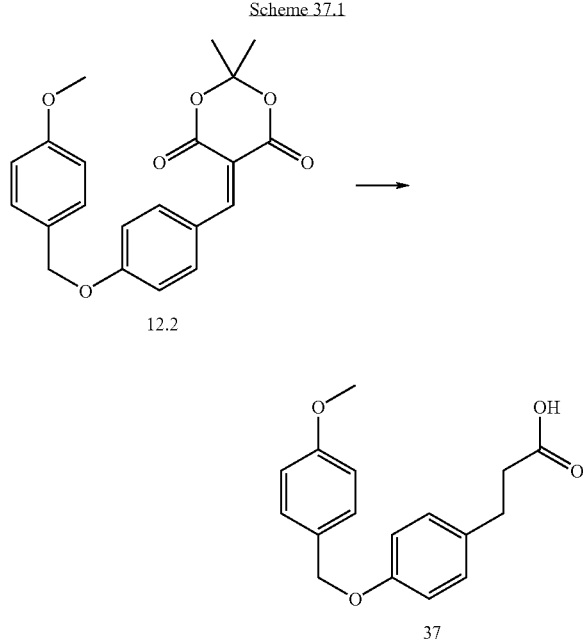

| Compound | X | Y | Z |
| --- | --- | --- | --- |
| 36.1 | 3-Methoxy | H | 1-Propynyl |
| 36.2 | 3-Methoxy | 3-Methoxy-benzyl | 1-Propynyl |
| 36.3 | 4-Phenyl | H | 1-Propynyl |
| 36.4 | 4-(2-cyanophenyl) | H | 1-Propynyl |

6.37 Example 37

This example illustrates the preparation of (+/−)-3-(4-[(4-methoxyphenyl)methoxy]-phenyl)-propanoic acid.

Scheme 37.1

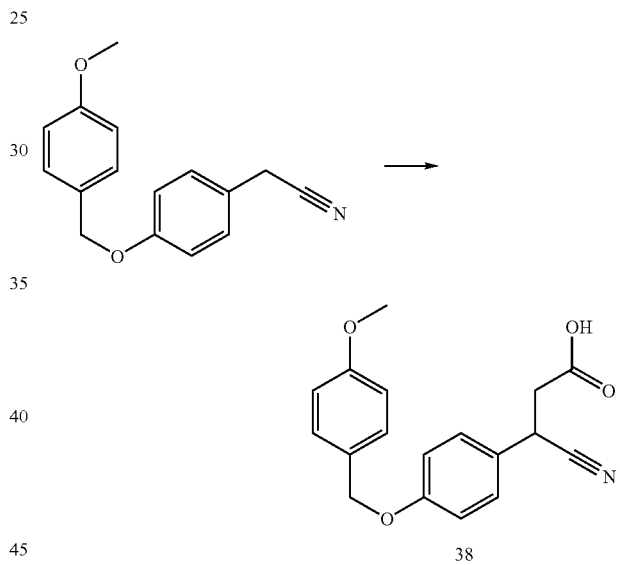

(+/−)-3-(4-[(4-methoxyphenyl)methoxy]phenyl)-propanoic acid (37). To a stirring ethyl acetate (100 mL) solution of 5-[[4-[(4-methoxyphenyl)methoxy]phenyl]-methylene]-2,2-dimethyl-[1,3]dioxane-4,6-dione (200 mg, 0.543 mmol) was added EtOH (4 mL), followed by NaBH$_4$ (62 mg, 1.63 mmol). The reaction mixture was stirred at room temperature for 15 minutes, quenched with water (5 mL), extracted with EtOAc (10 mL). The extract was washed with brine, dried over MgSO$_4$, filtered, and concentrated to a white solid. A solution of this white solid in 3:1 pyridine-water (5 mL) was heated at 100° C. for 24 h. The reaction mixture was cooled to room temperature and put in an ice-water bath. Concentrated HCl was carefully added to pH ~2. The resulting suspension was extracted with ethyl acetate (10 mL×3), dried over MgSO$_4$, filtered, and concentrated to an off-white solid. Preparative HPLC gave compound 37 as a white solid. MS ESI (neg.) m/e: 285.0 (M−1).

6.38 Example 38

This example illustrates the preparation of (+/−)-3-(4-[(4-methoxyphenyl)methoxy]-phenyl)-3-cyano-propanoic acid.

(+/−)-3-(4-[(4-methoxyphenyl)methoxy]phenyl)-3-cyano-propanoic acid (38). To a stirred DMF (10 mL) solution of 2-[4-[(4-Methoxyphenyl)methoxy]phenyl]-acetonitrile (500 mg, 1.97 mmol) was added ethyl bromoacetate (330 μL, 2.96 mmol), followed by K$_2$CO$_3$ (820 mg, 5.9 mmol). The reaction mixture was stirred at room temperature for 2 h, poured into ice water (100 mL), filtered, and dried to a white solid. 20 mg of this white solid in 1:1 THF/1N NaOH in MeOH (4 mL) was stirred for 5 h. The reaction mixture was concentrated, diluted with water (10 mL), washed with EtOAc (5 mL×2). The aqueous layer was acidified with 3N HCl to pH ~2, extracted with EtOAc (10 mL×2), dried over MgSO$_4$, filtered, and concentrated to a white solid. MS ESI (neg.) m/e: 310.0 (M−1).

6.39 Example 39

The following compounds were prepared by the methods described in Example 15 using the enantiomer with the shorter retention time from the chiral HPLC resolution.

TABLE 14

| Compounds | R |
|---|---|
| 15 | 2-CH₃ |
| 39.1 | 3-CH₃ |
| 39.2 | 3-CF₃O |
| 39.3 | 3-Cl |
| 39.4 | 4-(2-CN)Ph |
| 39.5 | 3-CF₃ |
| 39.6 | 4-Br |
| 39.7 | 4-CH₃O |

(3S)-3-[4-(3-Methyl-benzyloxy)-phenyl]-hex-4-ynoic acid (39.1). MS-ESI (neg.) m/e: 307.1 (M–H). [α]20: +21.26 (c0.188, DMF).

(3S)-3-[4-(3-Trifluoromethoxy-benzyloxy)-phenyl]-hex-4-ynoic acid (39.2). MS-ESI (neg.) m/e: 377.0 (M–H). [α]$^{20}$: +18.30 (c0.259, DMF).

(3S)-3-[4-(3-chlorobenzyloxy)-phenyl]-hex-4-ynoic acid (39.3). MS-ESI (neg.) m/e: 327.1 (M–H). [α]$^{20}$: +14.36 (c0.440, DMF).

(3S)-3-[4-(2'-Cyano-biphenyl-4-ylmethoxy)-phenyl]-hex-4-ynoic acid (39.4). MS-ESI (neg.) m/e: 394.1 (M–H). [α]$^{20}$: +16.07 (c0.331, DMF).

(3S)-3-[4-(2-Trifluoromethyl-benzyloxy)-phenyl]-hex-4-ynoic acid (39.5). MS-ESI (neg.) m/e: 361.1 (M–H). [α]$^{20}$: +12.80 (c0.285, DMF).

(3S)-3-[4-(4-Bromobenzyloxy)-phenyl]-hex-4-ynoic acid (39.6). MS-ESI (neg.) m/e: 371.0, 373.0 (M–H). [α]$^{20}$: +19.19 (c0.238, DMF).

(3S)-3-[4-(4-Methoxy-benzyloxy)-phenyl]-hex-4-ynoic acid (39.7). MS-ESI (neg.) m/e: 323.0 (M–H). [α]$^{20}$: +23.30 (c0.329, DMF).

6.40 Example 40

The following compounds were prepared by the methods described in Example 15 using the enantiomer with longer retention time from the chiral HPLC resolution.

TABLE 15

| Compounds | R |
|---|---|
| 40.1 | 2-CH₃ |
| 40.2 | 3-Cl |
| 40.3 | 4-(2-CN)Ph |
| 40.4 | 3-CF₃ |
| 40.5 | 4-CH₃O |

(3R)-3-[4-(2-Methyl-benzyloxy)-phenyl]-hex-4-ynoic acid (40.1). $^1$H NMR (400 MHz, acetone-d₆) δ 7.45 (d, 1H, J=7.11 Hz); 7.37 (d, 2H, J=8.58 Hz); 7.26 (d, 1H, J=1.62 Hz); 7.22-7.27 (m, 2H); 7.00 (d, 2H, J=8.76 Hz); 5.11 (s, 2H); 4.05 (m, 1H); 3.33 (s, 1H); 2.69 (m, 2H); 2.38 (s, 3H); 1.80 (d, 3H, J=2.44). MS-ESI (neg.) m/e: 307.1 (M–H). [α]$^{20}$: -19.78 (c0.286, DMF).

(3R)-3-[4-(3-chlorobenzyloxy)-phenyl]-hex-4-ynoic acid (40.2). MS-ESI (neg.) m/e: 327.0 (M–H). [α]$^{20}$: -20.50 (c0.158, DMF).

(3R)-3-[4-(2'-Cyano-biphenyl-4-ylmethoxy)-phenyl]-hex-4-ynoic acid (40.3). MS-ESI (neg.) m/e: 394.1 (M–H). [α]$^{20}$: -25.04 (c0.143, DMF).

(3R)-3-[4-(2-Trifluoromethyl-benzyloxy)-phenyl]-hex-4-ynoic acid (40.4). MS-ESI (neg.) m/e: 361.0 (M–H). [α]$^{20}$: -14.69 (c0.286, DMF).

(3R)-3-[4-(4-Methoxy-benzyloxy)-phenyl]-hex-4-ynoic acid (40.5). MS-ESI (neg.) m/e: 323.0 (M–H). [α]$^{20}$: -27.20 (c0.324, DMF).

6.41 Example 41

The following compounds were prepared by the methods similar to those of Example 15.

(3S)-3-[4-(4-Methoxy-benzyloxy)-phenyl]-pent-4-ynoic acid (41.1). MS-ESI (pos.) m/e: 333.1 (M+H). [α]$^{20}$: +11.80 (c0.166, DMF).

(3R)-3-[4-(4-Methoxy-benzyloxy)-phenyl]-pent-4-ynoic acid (41.2). MS-ESI (pos.) m/e: 333.1 (M+H). [α]$^{20}$: −10.20 (c0.206, DMF).

6.42 Example 42

Scheme 42.1 presents a general procedure for preparation of diaryl ether compounds.

Scheme 42.1

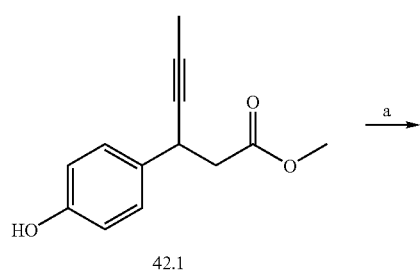

42.1

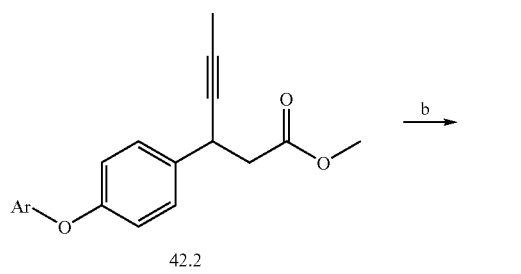

42.2

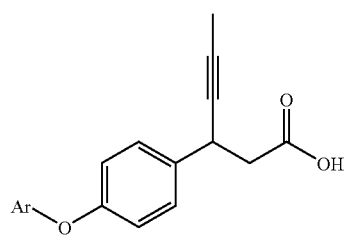

42.3

Scheme 42.1. a. ArB(OH)$_2$, CuO(Ac)$_2$, Et$_3$N, DCM, 4A MS, r.t., 16 h; b. LiOH/THF, MeOH, and water, r.t., 2 h.

General procedure for preparation of diaryl ether compounds: A flask is charged with phenol (1.0 equiv.), Cu(OAc)$_2$ (1.0 equiv.), arylboronic acid (1.0-3.0 equiv.), powdered 4 Å molecular sieves. The reaction mixture was diluted with CH$_2$Cl$_2$ to yield a solution approximately 0.1 M in phenol, and Et$_3$N (5.0 equiv.) is added. After stirring the heterogeneous reaction mixture for 16 h at 25° C. under ambient atmosphere, the resulting slurry is filtered and the diaryl ether is isolated from the organic filtrate by flash chromatography. The resulted ester was then hydrolyzed with LiOH (2.0 equiv.) in a 1:1:1 mixture of MeOH, THF, and water for 2 h at 25° C. The reaction mixture was acidified with 1N HCl, extracted with CH$_2$Cl$_2$ and concentrated to give the pure acid.

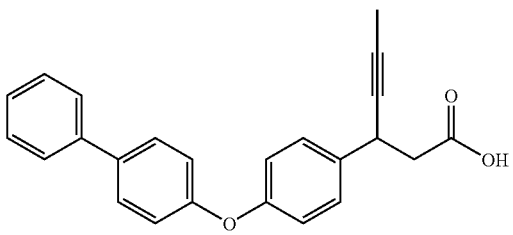

42.4

3-[4-(Biphenyl-4-yloxy)-phenyl]-hex-4-ynoic acid (42.4). MS ESI m/e: 357.0 (+H). $^1$H NMR (500 MHz) (CDCl$_3$) δ 7.60-7.57 (4H, m); 7.46 (2H, dd, J=8.0, 8.0 Hz); 7.39 (2H, d, J=8.5 Hz); 7.36 (1H, d, J=7.3 Hz); 7.09 (2H, d, J=8.6 Hz); 7.04 (2H, d, J=8.6 Hz); 4.2-4.1 (1H, m); 2.87 (1H, dd, J=15.8, 8.6 Hz); 2.77 (1H, dd, J=15.8, 6.7 Hz); 1.88 (3H, d, J=2.3 Hz).

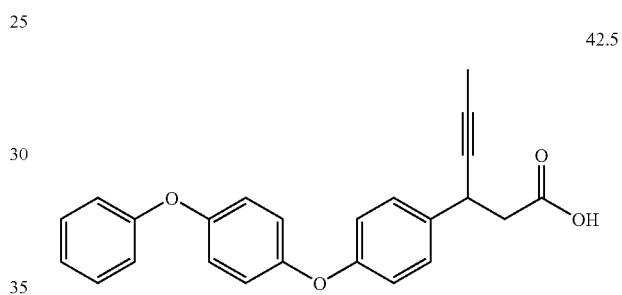

42.5

3-[4-(4-Phenoxy-phenoxy)-phenyl]-hex-4-ynoic acid (42.5). MS ESI m/e: 373.0 (M+H). $^1$H NMR (500 MHz) (CDCl$_3$) δ 7.37-7.32 (5H, m); 7.12 (2H, dd, J=8.0, 8.0 Hz); 7.03 (2H, d, J=7.5 Hz); 7.02 (2H, s); 6.97 (2H, d, J=8.6 Hz); 4.1 (1H, m); 2.85 (1H, dd, J=15.8, 8.6 Hz); 2.75 (1H, dd, J=15.8, 6.7 Hz); 1.87 (3H, d, J=2.3 Hz).

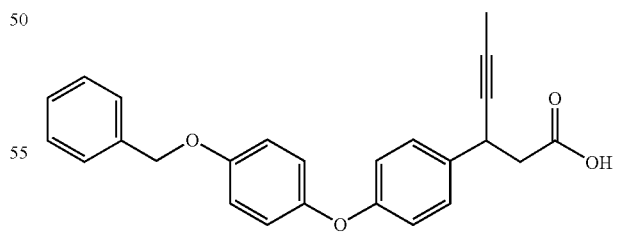

42.6

3-[4-(4-Benzyloxy-phenoxy)-phenyl]-hex-4-ynoic acid (42.6). MS ESI m/e: 387.0 (M+H). $^1$H NMR (500 MHz) (CDCl$_3$) δ 7.47 (2H, d, J=7.2 Hz); 7.42 (2H, dd, J=7.5, 7.5 Hz); 7.37 (1H, d, J=7.3 Hz); 7.33 (2H, d, J=8.7 Hz); 6.98 (4H, br. s); 6.93 (2H, d, J=9.7 Hz); 5.07 (2H, s); 4.10 (1H, m); 2.84 (1H, dd, J=15.7, 8.5 Hz); 2.75 (1H, dd, J=15.7, 6.7 Hz); 1.86 (3H, d, J=2.3 Hz).

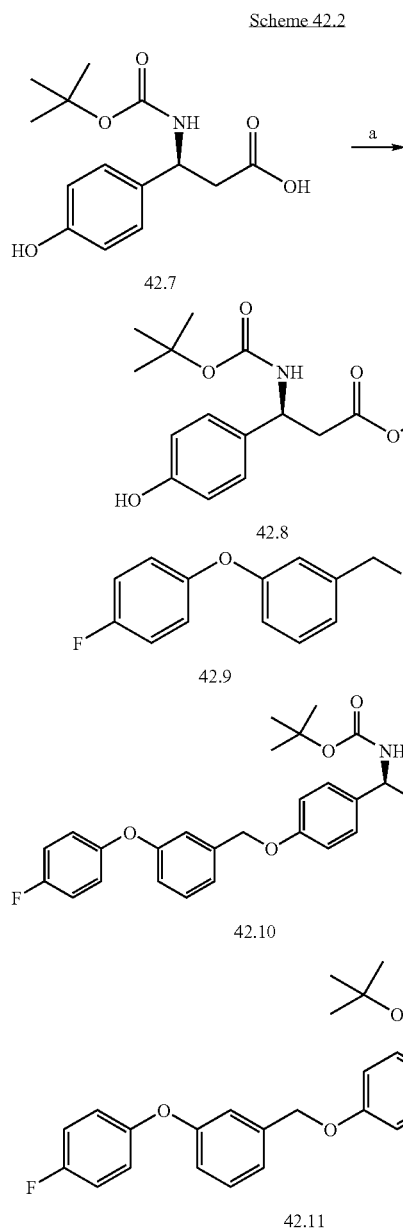

Scheme 42.2. a. TMSCHN₂, MeOH, benzene, r.t., 1 h; b. K₂CO₃, DMF, r.t., overnight; c. LiOH/THF, MeOH, and water, r.t., 2 h.

(S)-3-tert-Butoxycarbonylamino-3-{4-[3-(4-fluoro-phenoxy)-benzyloxy]-phenyl}-propionic acid (42.11). 3-Boc-amino-3(4-hydroxyphenyl)-propanoic acid (42.7) (703 mg, 2.5 mmol) in 25 mL of MeOH/Benzene (4:1) was slowly added 2.5 mL of 2M solution of trimethylsilyldiazomethane in hexane at 25° C. The reaction mixture was stirred for 1 h and concentrated in vacuo to give the methyl ester. MS ESI m/e: 296.0 (M+H). To a solution of the methyl ester 42.8 (2.5 mmol) and 4-fluorophenoxybenzyl bromide 42.9 (700 mg, 2.5 mmol) in DMF (10 mL), was added K₂CO₃ (414 mg, 3 mmol) and the resulting mixture was stirred overnight (14~16 h) at 25° C. The solution was diluted with water (20 mL0 and extracted with EtOAc twice (20 mL). The organic extraction was concentrated and the product was purified by flash chromatography. MS ESI m/e: 518.0 (M+Na). The methyl ester 42.10 (39 mg, 0.08 mmol) was hydrolyzed with LiOH (10 mg, 0.25 mmol) in a 1.5 mL of 1:1:1 mixture of MeOH, THF, and water for 2 h at 25° C. The reaction mixture was acidified with 1N HCl, extracted with CH₂Cl₂ and concentrated to give the pure acid (42.11). MS ESI m/e: 504.0 (M+Na). ¹H NMR (400 MHz) (CDCl₃) δ 8.5 (1H, br. s); 7.34 (1H, dd, J=8.0, 8.0 Hz); 7.24 (2H, d, J=8.8 Hz); 7.16 (1H, d, J=7.7 Hz); 7.07-6.98 (5H, m); 6.93 (2H, d, J=1.7 Hz); 6.92 (1H, d); 5.3 (1H, br. s); 5.03 (2H, s); 3.0-2.8 (2H, m); 2.1-1.9 (1H, m); 1.44 (9H, s).

Scheme 42.3. a. TFA, DCM, r.t., 1 h; b. formaldehyde, NaBH(OAc)₃, AcOH, DMF, r.t., overnight; c. LiOH/THF, MeOH, and water, r.t., 2 h.

3-Dimethylamino-3-{4-[3-(4-fluoro-phenoxy)-benzyloxy]-phenyl}-propionic acid (42.14). (S)-3-tert-Butoxycarbonylamino-3-{4-[3-(4-fluoro-phenoxy)-benzyloxy]-phenyl}-propionic acid methyl ester (42.10) (1.0 g, 2 mmol) was treated with 10 mL of 10% TFA solution in CH₂Cl₂ at 25° C. for 1 h. The solvent was concentrated in vacuo to give the free amine (42.12). MS ESI m/e: 418.0 (M+Na). The amine (60 mg, 0.15 mmol) was treated with excess formaldehyde (2 equiv.), NaBH(OAc)₃ (85 mg, 0.4 mmol) and catalytic amount of AcOH in DMF overnight (14-16 h) at 25° C. The product was purified by reverse phase HPLC. MS ESI m/e: 424.1 (M+H). The methyl ester was hydrolyzed with LiOH (19 mg, 0.45 mmol) in a 3 mL of 1:1:1 mixture of MeOH, THF, and water for 2 h at 25° C. The reaction mixture was acidified with 1N HCl, extracted with CH₂Cl₂ and concentrated to give the pure acid (42.14) (23 mg). MS ESI m/e:

410.2 (M+H). ¹H NMR (500 MHz) (CDCl₃) δ 9.46 (1H, br. s); 7.72 (1H, d, J=16.0 Hz); 7.51 (2H, d, J=8.7 Hz); 7.36 (1H, dd, J=8.0, 8.0 Hz); 7.17 (2H, d, J=7.0 Hz); 7.08-6.98 (5H, m); 6.94 (1H, d, J=8.2 Hz); 6.34 (1H, d, J=16.0 Hz); 5.10 (2H, s); 3.4-2.9 (2H, m); 2.73 (6H, s); 2.1-1.9 (1H, m).

6.43 Example 43

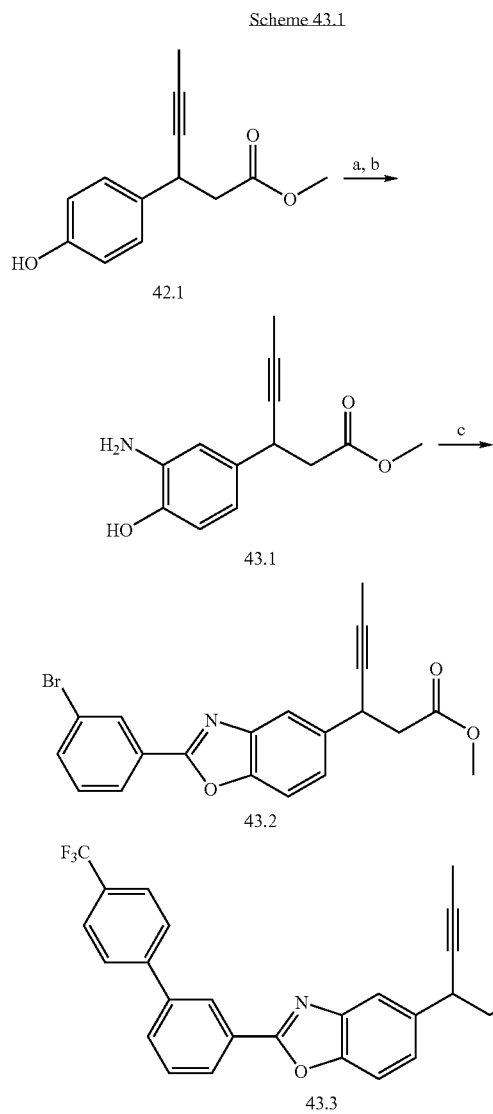

Scheme 43.1. a. HNO₃, HOAc, 80° C., 3 h; b. SnCl₂ ETOAc/EtOH, 70° C., 3 h; c. 3-bromobenzaldehyde, DDQ, DMF, r.t. 2 h; d. 4-trifluoromethylbezeneboronic acid, Pd(PPh₃)₄, DME, Na₂CO₃, 80° C., 14 h; e. LiOH/THF, MeOH, and water, r.t., 2 h.

3-[2-(4'-Trifluoromethyl-biphenyl-3-yl)-benzooxazol-5-yl]-hex-4-ynoic acid (43.3). 3-(4-Hydroxy-phenyl)-hex-4-ynoic acid methyl ester (1.32 g, 6 mmol) was treated with HNO₃ (0.30 mL, 7.2 mmol) in AcOH (10 mL) at 80° C. for 3 h. The solvent was concentrated in vacuo and 3-(3-nitro-4-hydroxy-phenyl)-hex-4-ynoic acid methyl ester (613 mg, 2.3 mmol) was isolated from flash chromatography. MS ESI m/e: 264.0 (M+H). The nitro group was then reduced with SnCl₂ (2.62 g, 11.6 mmol) in EtOH (10 mL0 and EtOAc (10 mL) at 70° C. for 3 h. The reaction mixture was cooled to 25° C., washed with saturated aqueous Na₂CO₃, water, brine, dried over MgSO₄, filtered and concentrated in vacuo. The crude product was then purified by reverse phase HPLC to give 3-(3-amino-4-hydroxy-phenyl)-hex-4-ynoic acid methyl ester (174 mg, 0.74 mmol). MS ESI m/e: 234.0 (M+H). 3-(3-amino-4-hydroxy-phenyl)-hex-4-ynoic acid methyl ester (174 mg, 0.74 mmol) and 3-bromobenzaldehyde (278 mg, 1.5 mmol) in DMF (3 mL) was treated with DDQ (204 mg, 0.9 mmol) for 2 h at 25° C. The producted was purified by reverse phase HPLC. MS ESI m/e: 398.0 (M+H). 3-[2-(3-Bromo-phenyl)-benzooxazol-5-yl]-hex-4-ynoic acid methyl ester (19.6 mg, 0.05 mmol) and trifluorophenylboronic acid (38 mg, 0.2 mmol) in DME (1 mL) and 0.2 mL of 2M solution of aqueous Na₂CO₃ was treated with Pd(PPh₃)₄ at 80° C. for 14 h. The product was isolated from flash chromatography. MS ESI m/e: 464.0 (M+H). The methyl ester (7.8 mg, 0.017 mmol) was hydrolyzed with LiOH (4 mg, 0.1 mmol) in a 1 mL of 1:1:1 mixture of MeOH, THF, and water for 2 h at 25° C. The reaction mixture was acidified with 1N HCl, extracted with CH₂Cl₂ and concentrated to give the pure acid (7.6 mg). MS ESI m/e: 450.1 (M+H). ¹H NMR (500 MHz) (CDCl₃) δ 8.52 (1H, s); 8.30 (1H, d, J=7.8 Hz); 7.91 (1H, s); 7.83 (2H, d, J=8.2 Hz); 7.82 (1H, s); 7.78 (2H, dd, J=8.0, 8.0 Hz); 7.67 (1H, dd, J=7.8, 7.8 Hz); 7.58 (2H, d, J=8.4 Hz); 7.46 (1H, dd, J=8.4, 1.5 Hz); 4.29 (1H, m); 2.94 (1H, dd, J=15.8, 8.1 Hz); 2.84 (1H, dd, J=15.8, 6.9 Hz); 1.89 (3H, d, J=2.3 Hz).

6.44 Example 44

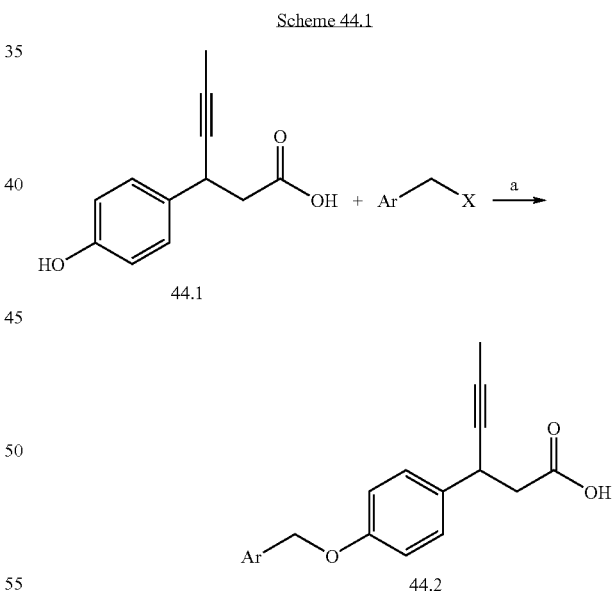

Scheme 44.1. a. NaOH, EtOH, water, r.t., 3 h (X = Br, Cl).

General procedure for the preparation of aryl benzyl ethers: 3-(4-Hydroxy-phenyl)-hex-4-ynoic acid in EtOH (0.4M) was added 1N NaOH solution (3 equiv.) in water at 25° C. and stirred for 5 minutes at 70° C. ArCH₂X (X=Br, Cl, 1 equiv.) in EtOH (0.2M) was slowly added, stirred for 3 h at 70° C. The reaction mixture was acidified with 1N HCl and purified from reverse phase HPLC.

44.3

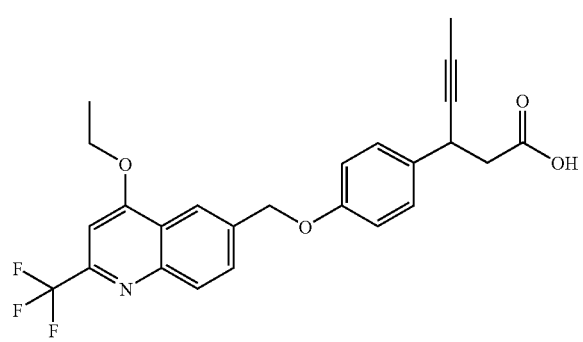

3-[4-(4-Ethoxy-2-trifluoromethyl-quinolin-6-yl-methoxy)-phenyl]-hex-4-ynoic acid (44.3). MS ESI m/e: 458.0 (M+H). ¹H NMR (400 MHz) (DMSO-d₆) δ 12.6 (1H, br. s); 8.31 (1H, s); 8.12 (1H, d, J=8.7 Hz); 7.95 (1H, dd, J=8.7, 1.3 Hz); 7.41 (1H, s); 7.31 (2H, d, J=8.5 Hz); 7.03 (2H, d, J=8.5 Hz); 5.36 (2H, s); 4.47 (2H, q, J=8.0 Hz); 3.96 (1H, m); 2.62 (2H, d, J=7.6 Hz); 1.79 (3H, d, J=1.9 Hz); 1.21 (3H, t, J=8.0 Hz).

44.4

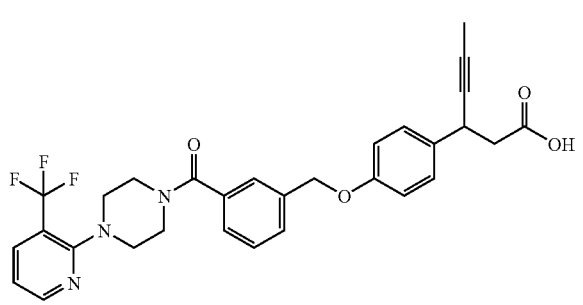

3-(4-{3-[4-(3-Trifluoromethyl-pyridin-2-yl)-piperazine-1-carbonyl]-benzyloxy}-phenyl)-hex-4-ynoic acid. MS ESI m/e: 552.0 (M+H). ¹H NMR (400 MHz) (DMSO-d₆) δ 12.5 (1H, br. s); 8.57 (1H, d, J=3.5 Hz); 8.12 (1H, dd, J=7.9, 1.6 Hz); 7.56-7.48 (3H, m); 7.41 (1H, d, J=7.5 Hz); 7.30-7.25 (3H, m); 6.98 (2H, d, J=8.7 Hz); 5.16 (2H, s); 3.95 (1H, m); 3.2 (4H, m); 2.60 (2H, d, J=7.6 Hz); 2.52 (4H, m); 1.77 (3H, d, J=2.4 Hz).

44.5

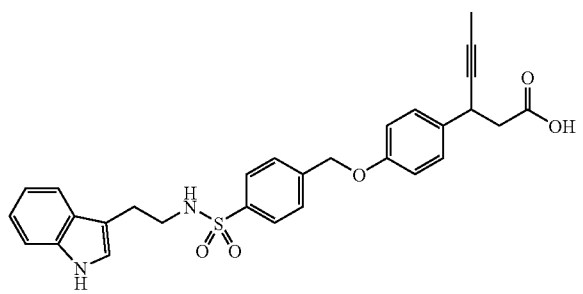

3-(4-{4-[2-(1H-Indol-3-yl)-ethylsulfamoyl]-benzyloxy}-phenyl)-hex-4-ynoic acid. MS ESI m/e: 517.2 (M+H). ¹H NMR (400 MHz) (DMSO-d₆) δ 12.5 (1H, br. s); 10.82 (1H, s); 7.83 (2H, d, J=8.3 Hz); 7.77 (1H, dd, J=7.8, 7.8 Hz); 7.39 (1H, d, J=8.0 Hz); 7.32 (1H, d, J=8.0 Hz); 7.29 (2H, d, J=8.7 Hz); 7.13 (1H, d, J=2.2 Hz); 7.06 (1H, dd, J=7.0, 8.0 Hz); 6.97 (2H, d, J=8.7 Hz); 5.19 (2H, s); 3.95 (1H, m); 3.02 (2H, t, J=7.6 Hz); 2.81 (2H, t, J=7.6 Hz); 2.61 (2H, d, J=8.0 Hz); 1.78 (3H, d, J=2.4 Hz).

6.45 Example 45

This example illustrates the preparation of (+/−)-3-[4-(2'-butoxy-5'-methyl-biphenyl-4-ylmethoxy)-phenyl]-3-(4-fluorophenyl)-propionic acid (45).

Scheme 45.1

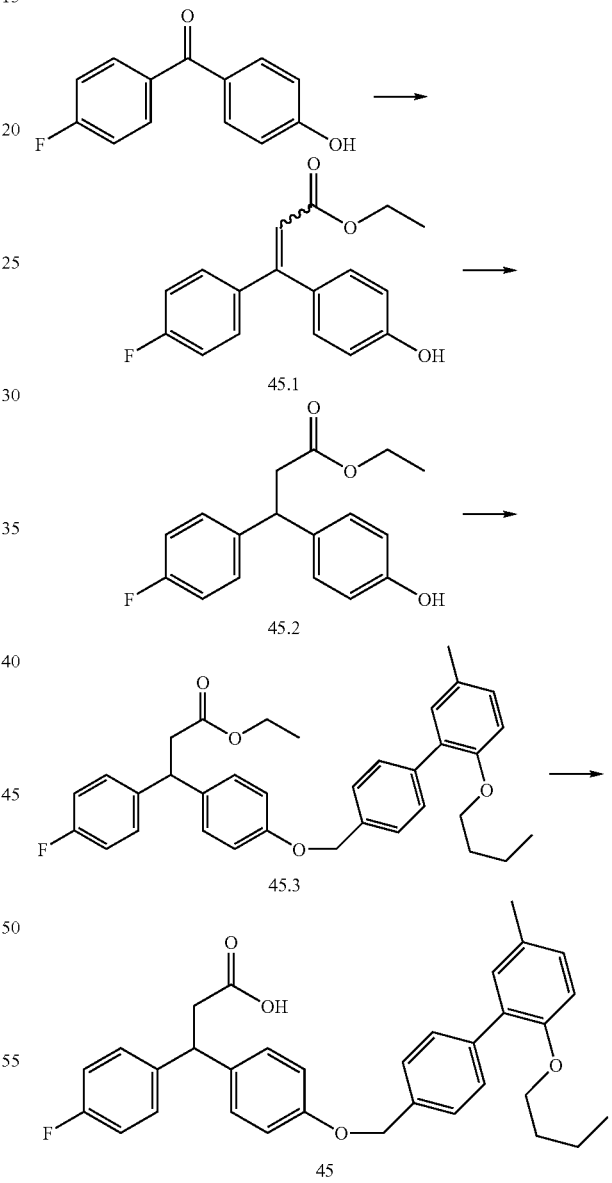

Ethyl 3-(4-fluorophenyl)-3-(4-hydroxyphenyl)-acrylate (45.1). A solution of lithium hexamethyldisilazide (23.1 mL, 1 M in THF) was added to a stirred solution of ethyl (trimethylsilyl)acetate (2.53 mL, 13.9 mmol) in THF (15 mL) in 10 min. at −78° C. The reaction mixture was further stirred at this temperature for 20 min. A solution of (4-fluorophenyl)-(4- hydroxyphenyl)-methanone (2 g, 9.2 mmol) in THF (30 mL) was slowly added to the reaction mixture. The reaction mixture was brought to 0° C. in 5 h. The reaction mixture was quenched with saturated ammonium chloride solution, extracted into ethyl acetate and washed with dilute ammonium chloride solution. The organic layer was dried over magnesium sulfate. The solvent was removed under vacuum and product was purified flash chromatography on silica gel, giving 45.1 as an oil (1.405 g).

3-(4-Fluorophenyl)-3-(4-hydroxyphenyl)-propionic acid ethyl ester (45.2). A solution of 45.1 (385 mg) in ethanol (12 mL) and ethyl acetate (10 mL) was stirred with 10% Pd—C (50 mg) under a hydrogen atmosphere at room temperature for 3 h. The reaction mixture was filtered and concentrated to provide 45.2 (350 mg).

3-[4-(2'-Butoxy-5'-methyl-biphenyl-4-ylmethoxy)-phenyl]-3-(4-fluorophenyl)-propionic acid ethyl ester (45.3). A mixture of 45.2 (48 mg, 0.166 mmol), 4'-Bromomethyl-2-butoxy-5-methyl-biphenyl (67 mg, 0.2 mmol) and cesium carbonate (81 mg, 0.25 mmol) in DMF (2 mL) was stirred at room temperature overnight. The reaction mixture was diluted with water, acidified with dilute HCl, extracted into ethyl acetate, washed with water and dried over magnesium sulfate. The residue obtained after concentration was flash chromatographed on silica gel to obtain 45.3 (71 mg).

(+/−)-3-[4-(2'-Butoxy-5'-methyl-biphenyl-4-ylmethoxy)-phenyl]-3-(4-fluorophenyl)-propionic acid (45). A mixture of 45.3 (56 mg, 0.1 mmol) and 2N NaOH$_{(aq)}$ solution (0.31 mL, 0.62 mmol) in THF (3 mL) was stirred at room temperature overnight. The reactor mixture was concentrated, treated with dilute HCl, and extracted into ethyl acetate. The organic layer washed with water and concentrated to yield product which was purified by flash chromatography to give compound 45 (40 mg). $^1$H NMR (500 MHz, CDCl$_3$, ppm), δ 0.9 (t, 3H), 1.4 (m, 2H), 1.65 (m, 2H), 2.35 (s, 3H), 3.05 (m, 2H), 3.9 (t, 2H), 4.5 (t, 1H), 5.05 (s, 2H), 6.8-7.5 (m, 15H). MS ESI (neg.) m/e: 511.0 (M−H).

6.46 Example 46

The following compounds were prepared according to methods analogous to those described in Example 45: 3-(4-fluorophenyl)-3-[4-(4'-trifluoromethyl-biphenyl-3-ylmethoxy)-phenyl]-propionic acid (46.1), 3-(4-fluorophenyl)-3-[4-(4-methyl-2-p-tolyl-thiazol-5-ylmethoxy)-phenyl]-propionic acid (46.2) and 3-(4-fluorophenyl)-3-{4-[2-(3-trifluoromethyl-phenoxy)-ethoxy]-phenyl}-propionic acid (46.3).

Starting from (4-hydroxyphenyl)-phenyl-methanone, the following compounds were prepared according to methods analogous to those described in Example 45: 3-[4-(2-methyl-benzyloxy)-phenyl]-3-phenyl-propionic acid (46.4), 3-[4-(2'-butoxy-5'-methyl-biphenyl-4-ylmethoxy)-phenyl]-3-phenyl-propionic acid (46.5), 3-[4-(4-methyl-2-p-tolyl-thiazol-5-ylmethoxy)-phenyl]-3-phenyl-propionic acid (46.6), 3-phenyl-3-{4-[2-(3-trifluoromethyl-phenoxy)-ethoxy]-phenyl}-propionic acid (46.7), 3-[4-(2'-cyano-biphenyl-4-ylmethoxy)-phenyl]-3-phenyl-propionic acid (46.8) and 3-phenyl-3-[4-(4'-trifluoromethyl-biphenyl-3-ylmethoxy)-phenyl]-propionic acid (46.9).

Starting from (4-hydroxyphenyl)-pyridin-4-yl-methanone, the following compounds were prepared according to methods analogous to those described in Example 45: 3-[4-(2'-butoxy-5'-methyl-biphenyl-4-ylmethoxy)-phenyl]-3-pyridin-4-yl-propionic acid (46.10) and 3-pyridin-4-yl-3-[4-(4'-trifluoromethyl-biphenyl-3-ylmethoxy)-phenyl]-propionic acid (46.11).

6.47 Example 47

This example illustrates the preparation of (+/−)-3-(4-[3-(4-chloro-2-methylphenyl) benzyloxy]phenyl)-3-(4-fluorophenyl)-propanoic acid (47).

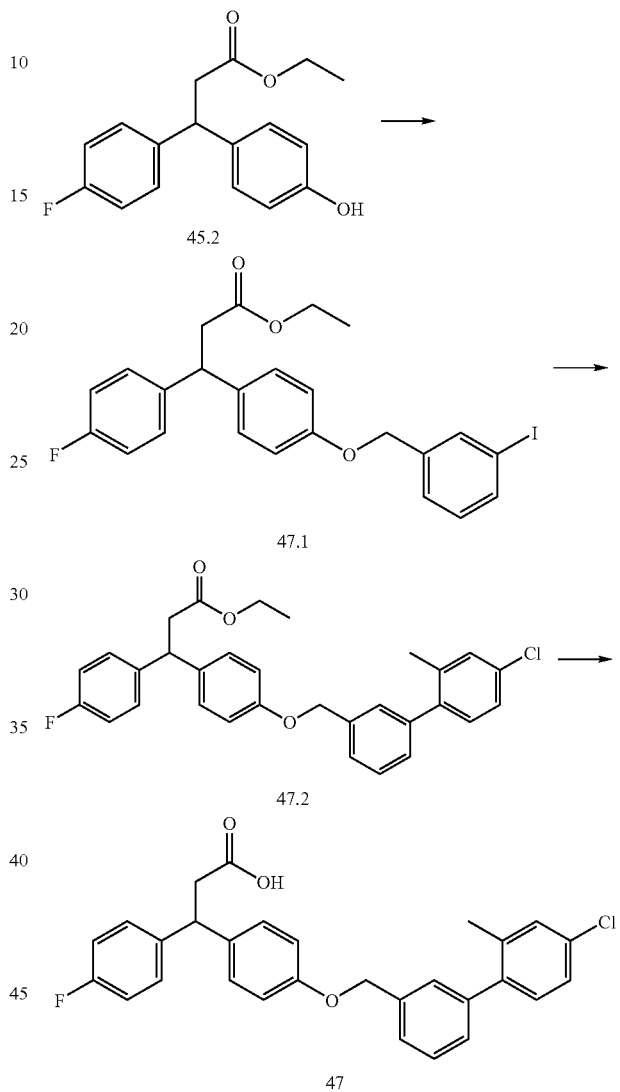

Scheme 47.1

Ethyl 3-(4-(3-iodobenzyloxy)phenyl)-3-(4-fluorophenyl) propanoate (47.1). Cs$_2$CO$_3$ (4.89 g 15 mmol) and 1-(bromomethyl)-3-iodobenzene (4.45 g, 15 mmol) were added successively to a dry DMF (20 mL) solution of 45.2 (2.88 g, 10 mmol). The reaction mixture was stirred at room temperature overnight, diluted with ethyl acetate (200 mL), washed with water (100 mL×2) and brine (100 mL), and dried over Na$_2$SO$_4$. The solvent was removed under vacuum and the residue was purified by flash chromatography to give compound 47.1 as a colorless oil. MS ESI (pos.) m/e: 505.0 (1+H).

3-(4-[3-(4-Chloro-2-methylphenyl)benzyloxy]phenyl)-3-(4-fluorophenyl)-propanoate (47.2). CsF (96 mg, 0.6 mmol), 4-chloro-2-methylphenylboronic acid (102 mg, 0.6 mmol) and Pd(PPh$_3$)$_4$ (70 mg, 0.06 mmol) were added successively to a dry 1,2-dimethoxyethane (DME, 2 mL) solution of 47.1 (108 mg, 0.2 mmol) with stirring under a nitrogen atmosphere. The reaction mixture was stirred at 80° C. overnight.

The solvent was removed under nitrogen flow and the residue was dissolved in $CH_2Cl_2$ (2 mL) and purified by flash chromatography. Compound 47.2 was obtained as a colorless oil. MS ESI (pos.) m/e 503.0 (M+1).

(+/−)-3-{4-[3-(4-Chloro-2-methylphenyl)phenyl]-methoxy]phenyl}-3-(4-fluorophenyl)-propanoic acid (47). LiOH (48 mg, 2 mmol) was added to the THF—$H_2O$ (1/1, 4 mL) solution of compound 47.2 (104 mg, 0.2 mmol). The reaction mixture was stirred at room temperature overnight. 1N $HCl_{(aq)}$ was added to acidify the mixture to pH 3 at 0° C. The mixture was extracted with ethyl acetate (20 mL×2), washed with water and brine, dried over $Na_2SO_4$, and purified by flash chromatography to obtain compound 47 (82 mg) as colorless oil. $^1H$ NMR (400 MHz)($CDCl_3$) δ 2.22 (s, 3H), 3.05 (dd, J=7.8, 1.1 Hz, 2H), 4.49 (t, J=8.0 Hz, 1H), 5.09 (s, 2H), 6.92-7.43 (m, 12H). MS ESI (neg.) m/e 473.0 (M−H).

6.48 Example 48

The following compounds were prepared according to the methods described in Example 47.

TABLE 16

| Compound | X |
| --- | --- |
| 48.1 | 4-iodo |
| 48.2 | 3-iodo |
| 48.3 | 4-(3-benzyloxyphenyl) |
| 48.4 | 4-(3-butoxyphenyl) |
| 48.5 | 4-(5-ethoxy-2-fluorophenyl) |
| 48.6 | 4-(2-ethoxy-6-fluorophenyl) |
| 48.7 | 4-(2-butoxy-5-fluorophenyl) |
| 48.8 | 4-(3-isopropoxyphenyl) |
| 48.9 | 4-(2-fluoro-5-propoxyphenyl) |
| 48.10 | 4-(4-chloro-2-methylphenyl) |
| 48.11 | 4-(4-methoxy-2-methylphenyl) |
| 48.12 | 4-(4-methoxy-2,6-dimethylphenyl) |
| 48.13 | 4-(2,4,6-trimethylphenyl) |
| 48.14 | 4-(4-chloro-2-ethoxyphenyl) |
| 48.15 | 4-(4-fluoro-2-ethoxyphenyl) |
| 48.16 | 4-(2-isopropoxyphenyl) |
| 48.17 | 3-(2,5-dimethylphenyl) |
| 48.18 | 3-(3-benzyloxyphenyl) |
| 48.19 | 3-(5-ethoxy-2-fluorophenyl) |
| 48.20 | 3-(4-chloro-2-methylphenyl) |
| 48.21 | 3-(2-ethoxy-5-methylphenyl) |
| 48.22 | 3-(4-chloro-2-ethoxyphenyl) |
| 48.23 | 3-(2-butoxy-5-methylphenyl) |
| 48.24 | 3-(2-butoxy-5-fluorophenyl) |
| 48.25 | 3-(4-ethoxyphenyl) |
| 48.26 | 3-(5-fluoro-2-methoxyphenyl) |
| 48.27 | 3-(3-isopropoxyphenyl) |

6.49 Example 49

This example illustrates the preparation of (+/−)-3-(4-(3-(4-(trifluoromethyl)phenyl) benzyloxy)phenyl)-4-(diethylamino)-3-methyl-4-oxobutanoic acid.

Scheme 49.1

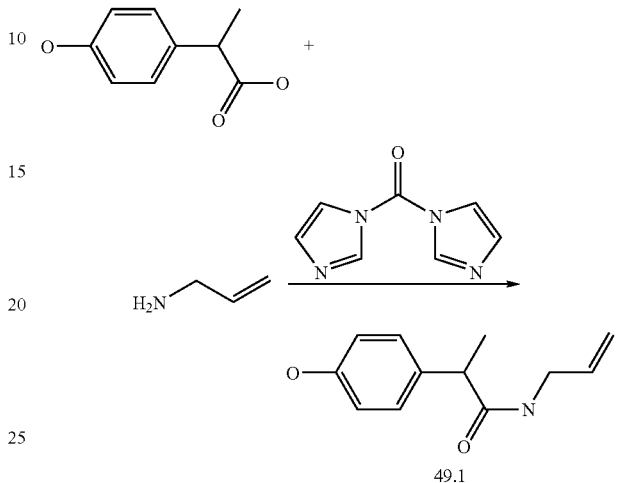

N-Allyl-2-(4-hydroxyphenyl)propanamide (49.1). N,N'-Carbonyldiimidazole (22.65 g, 140 mmol) was added to commercially available 2-(4-hydroxyphenyl)propionic acid (21 g, 127 mmol) in THF (100 mL). Gentle warming and gas evolution was observed. The resulting mixture was stirred for 3 h. Allylamine (10.9 g, 190.5 mmol) and $Et_3N$ (19.2 mL, 190.5 mmol) were added dropwise, and the mixture was stirred overnight. The reaction was quenched with water (200 mL) and the organic phase was extracted with ethyl acetate (50 mL×3). The combined organic extracts were dried over $MgSO_4$ and concentrated in vacuo. The product was purified by flash chromatography (elution with ethyl acetate). Phenol 49.1 was obtained as a white solid. MS ESI m/e: 206 (M−H).

Scheme 49.2

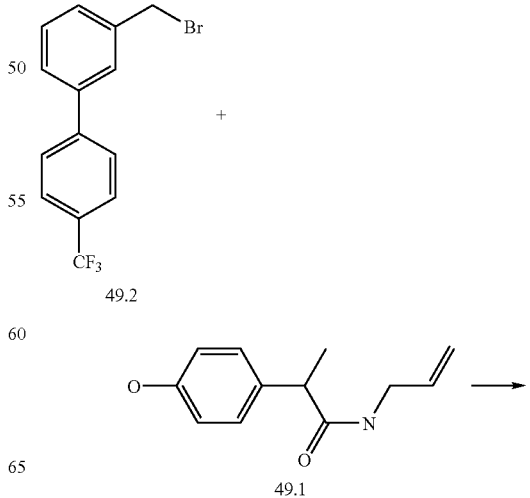

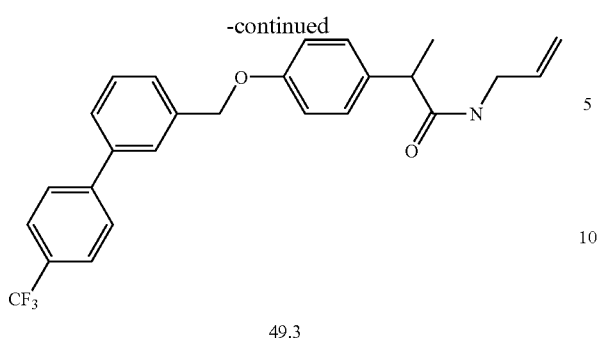

49.3

2-(4-(3-(4-(Trifluoromethyl)phenyl)benzyloxy)phenyl)-N-allylpropanamide (49.3). Cs₂CO₃ (23.1 g, 71 mmol) was added to a mixture of compound 49.2 (20.33 g, 64.5 mmol) and phenol 49.1 (13.23 g 64.5 mmol) in DMF (50 mL). The resulting mixture was stirred overnight. The reaction was quenched with water (500 mL). The organic phase was extracted with ethyl acetate (75 mL×3). The combined organic phases were dried over MgSO₄ and the solvent was removed under reduced pressure. The resulting residue was purified via flash chromatography (10% Acetone in dichloromethane) to yield 15.9 g of 49.3. MS ESI m/e: 440 (M–H).

Scheme 49.3

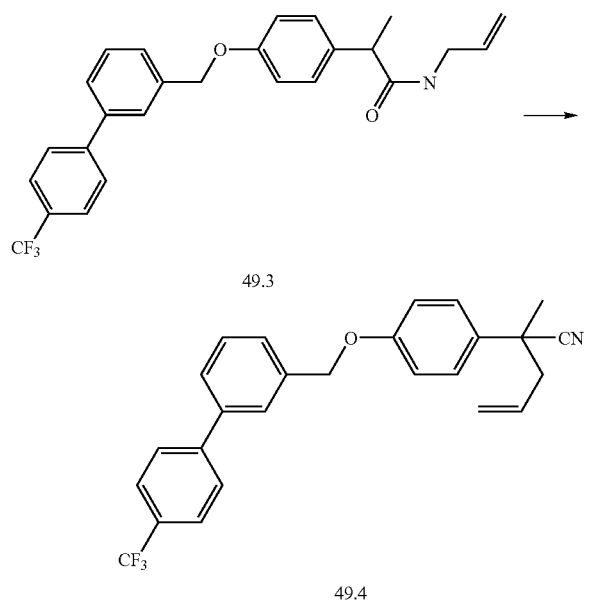

2-(4-(3-(4-(Trifluoromethyl)phenyl)benzyloxy)phenyl)-2-methylpent-4-enenitrile (49.4). The 3-aza-claisen reaction was carried out according to the method of Walters et al. (1991) *Tetrahedron Lett.* 2: 179-182. Amide 49.3 (15.9 g, 36.2 mmol) and PPh₃ (21 g, 80 mmol) were dissolved in anhydrous dichloromethane (160 mL). Et₃N (12 g, 119.5 mmol) and CCl₄ (18.4 g, 119.5 mmol) were added dropwise. The resulting mixture was stirred at room temperature overnight. The reaction was quenched with saturated brine (250 mL). The organic phase was extracted with ethyl acetate (50 mL×3). The combined organic phases were dried over MgSO₄ and concentrated under reduced pressure. The resulting residue was purified via flash chromatography (25% ethyl acetate in hexanes) to yield 12.3 g of 49.4. ¹H NMR (400 MHz) (CDCl₃) δ 7.73 (4H, s); 7.70 (1H, s); 7.61-7.51 (3H, m); 7.41 (2H, d, J=8.9 Hz); 7.05 (2H, d, J=8.9 Hz); 5.76-5.72 (1H, m); 5.21-5.17 (4H, m); 2.71-2.59 (2H, m); 1.72 (3H, s).

Scheme 49.4

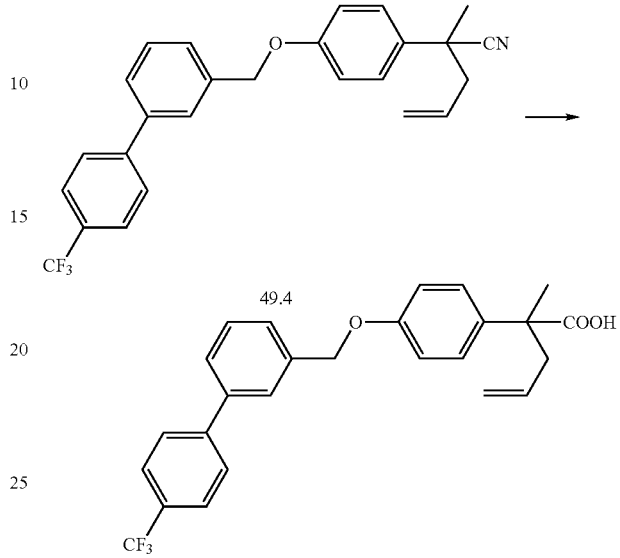

2-(4-(3-(4-(Trifluoromethyl)phenyl)benzyloxy)phenyl)-2-methylpent-4-enoic acid (49.5). 49.4 was added to a mixture of ethylene glycol (8 mL), H₂O (0.25 mL) and KOH (750 mg). The resulting mixture was heated to 190° C. for 6 h. The reaction mixture was cooled to room temperature. The aqueous phase was extracted with ethyl acetate (10 mL×3). The extracts were combined, dried over MgSO₄ and concentrated under reduced pressure. The resulting residue was purified via flash chromatography (10% acetone in dichloromethane) to yield 632 mg of 49.5. MS ESI m/e: 441 (M–H).

Scheme 49.5

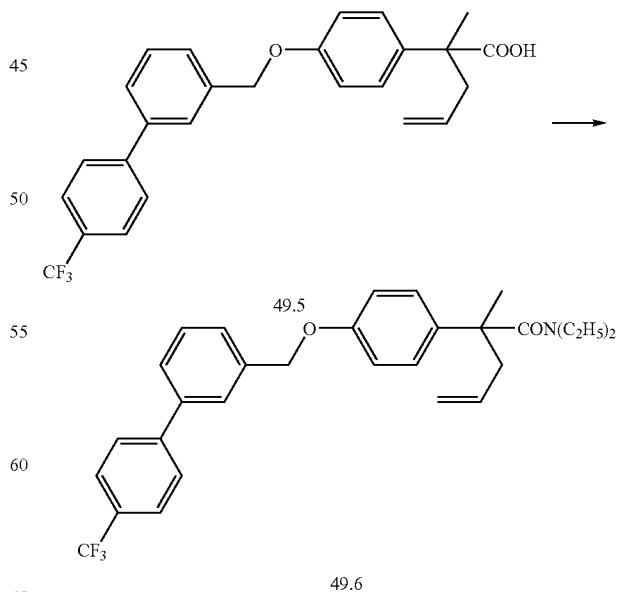

2-(4-(3-(4-(Trifluoromethyl)phenyl)benzyloxy)phenyl)-N,N-diethyl-2-methylpent-4-enamide (49.6). Oxalyl chloride (57.7 mg, 0.45 mmol) was added dropwise to 49.5 (100 mg, 0.23 mmol) in anhydrous dichloromethane (4 mL). The resulting mixture was refluxed in a sealed tube at 50° C. overnight. The dichloromethane was removed under a stream of $N_2$. Anhydrous ether (2 mL) was added dropwise, followed by diethyl amine (50 mg, 0.69 mmol) and $Et_3N$ (70 mg, 0.69 mmol). The mixture was refluxed overnight. The reaction mixture was concentrated under reduced pressure, and the resulting residue was purified via flash chromatography (25% ethyl acetate in hexanes). 82 mg of 49.6 was obtained. MS ESI m/e: 496 (M−H). $^1$H NMR (500 MHz) (CDCl$_3$) δ 7.72 (4H, s); 7.69 (1H, s); 7.6-7.5 (3H, m); 7.14 (2H, d, J=8.5 Hz); 7.05 (2H, d, J=8.5 Hz); 5.7-5.6 (1H, m); 5.15 (2H, s); 5.03-5 (2H, m); 3.5-3.2 (2H, m); 3.0-2.9 (2H, m); 2.74-2.64 (2H, m); 1.62 (3H, s); 1.13 (3H, s); 0.72 (3H, s).

Scheme 49.6

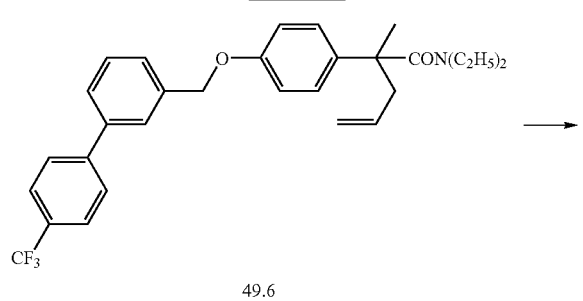

49.6

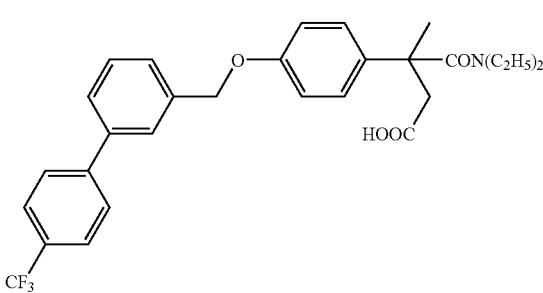

49

(+/−)-3-(4-(3-(4-(Trifluoromethyl)phenyl)benzyloxy)phenyl)-4-(diethylamino)-3-methyl-4-oxobutanoic acid (49). The oxidation reaction was carried out according to the method of Henry et al. (1993) *J. Org. Chem.* 58: 4745. A catalytic amount of OsO$_4$ was added to a solution of 49.6 (50 mg, 0.1 mmol) in acetone (4 mL), followed by an excess of Jones reagent (0.25 mL). The reaction mixture was stirred at room temperature overnight. The reaction was quenched with water (2 mL), and the aqueous phase was extracted with dichloromethane (2 mL×3). The combined organic extracts were dried over MgSO$_4$ and removed under reduced pressure. The resulting residue was purified on reversed phase HPLC. MS ESI m/e: 514 (M−H).

6.50 Example 50

This example illustrates the preparation of 3-{4-[4'-(1,1-difluoro-ethyl)-biphenyl-3-ylmethoxy]-phenyl}-N,N-dimethyl-succinamic acid.

Scheme 50.1

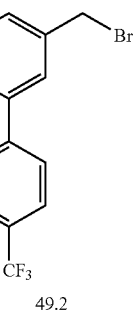 + 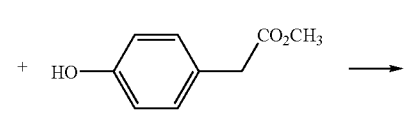

49.2

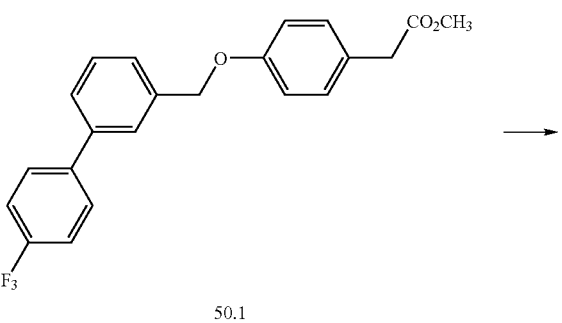

50.1

[4-(4'-Trifluoromethyl-biphenyl-3-ylmethoxy)-phenyl]-acetic acid methyl ester (50.1). Compound 49.2 (15.8 g, 50.1 mmol) was added to methyl 4-hydroxyphenylacetate (8.3 g 50 mmol) in DMF (30 mL), followed by Cs$_2$CO$_3$ (17.9 g, 55 mmol). The resulting mixture was stirred overnight. The reaction was quenched with water (300 mL). The organic phase was extracted with ethyl acetate (50 mL×3). The combined organic phase was rinsed with saturated brine, dried over MgSO$_4$, and concentrated under reduced pressure. The product (16.3 g) was used in the next step without further purification. MS ESI (pos.) m/e: 423 (M+Na).

Scheme 50.2

50.1

-continued

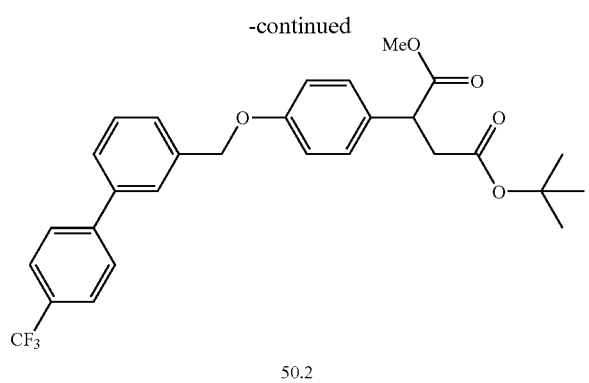

50.2

2-{4-[4'-Trifluoromethyl-biphenyl-3-ylmethoxy]-phenyl}-succinic acid 4-tert-butyl ester 1-methyl ester (50.2). Compound 50.1 (4 g, 10 mmol) in THF (12 mL) was added dropwise to LDA in THF (1M, 12 mL) at −78° C. The resulting mixture was stirred for 30 min. before tert-butyl bromoacetate (2.15 g, 11 mmol) in THF (2 mL) was added over 10 min. The reaction mixture was stirred for 2 h at −78° C. and allowed to warm slowly to 0° C. The reaction was quenched with saturated aqueous NH$_4$Cl (20 mL). The organic phase was extracted with ethyl acetate (25 mL×3). The organic extracts were combined, dried over MgSO$_4$ and concentrated under reduced pressure. The resulting residue was purified via flash chromatography (50% ethyl acetate in hexanes) to yield 3.3 g of 50.2. MS ESI (pos.) m/e: 537 (M+Na). $^1$H NMR (400 MHz) (CDCl$_3$) δ 7.72 (4H, s); 7.68 (1H, s); 7.58-7.49 (3H, m); 7.25-7.24 (2H, m); 6.98-6.97 (2H, m); 5.14 (2H, s); 4.04-4.0 (1H, m); 3.7 (3H, s); 3.1 (1H, m); 2.63 (1H, m); 1.42 (9H, s).

2-{4-[4'-Trifluoromethyl-biphenyl-3-ylmethoxy]-phenyl}-succinic acid 4-tert-butyl ester (50.3). Lithium hydroxide (121 mg, 5 mmol) was added to a solution of 50.2 in MeOH/THF/H$_2$O (1:1:1, 90 mL). The resulting mixture was stirred at room temperature overnight. The organic solvent was removed under reduced pressure. The reaction mixture was extracted with dichloromethane (10 mL><3). The organic extracts were combined, dried over MgSO$_4$ and concentrated under reduced pressure. The resulting residue was purified via flash chromatography (50% ethyl acetate in hexanes) to yield acid 50.3 (860 mg) MS ESI (pos.) m/e: 523 (M+Na). $^1$H NMR (400 MHz) (CDCl$_3$) δ 7.72 (4H, s); 7.67 (1H, s); 7.59-7.47 (3H, m); 7.29-7.25 (2H, m); 6.98-6.97 (2H, m); 5.14 (2H, s); 4.04-4.0 (1H, m); 3.1-3.053 (1H, m); 2.64-2.60 (1H, m); 1.4 (9H, s).

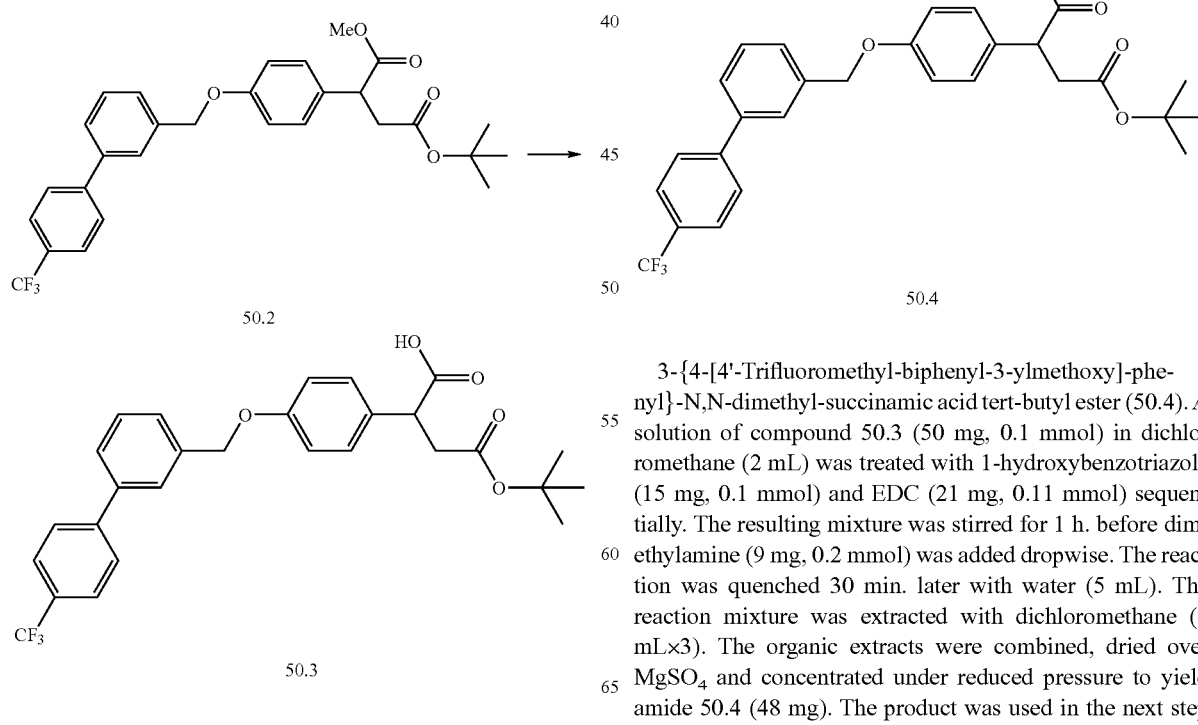

3-{4-[4'-Trifluoromethyl-biphenyl-3-ylmethoxy]-phenyl}-N,N-dimethyl-succinamic acid tert-butyl ester (50.4). A solution of compound 50.3 (50 mg, 0.1 mmol) in dichloromethane (2 mL) was treated with 1-hydroxybenzotriazole (15 mg, 0.1 mmol) and EDC (21 mg, 0.11 mmol) sequentially. The resulting mixture was stirred for 1 h. before dimethylamine (9 mg, 0.2 mmol) was added dropwise. The reaction was quenched 30 min. later with water (5 mL). The reaction mixture was extracted with dichloromethane (2 mL×3). The organic extracts were combined, dried over MgSO$_4$ and concentrated under reduced pressure to yield amide 50.4 (48 mg). The product was used in the next step without further purification. MS ESI (pos.) m/e: 527 (M+).

Scheme 50.5

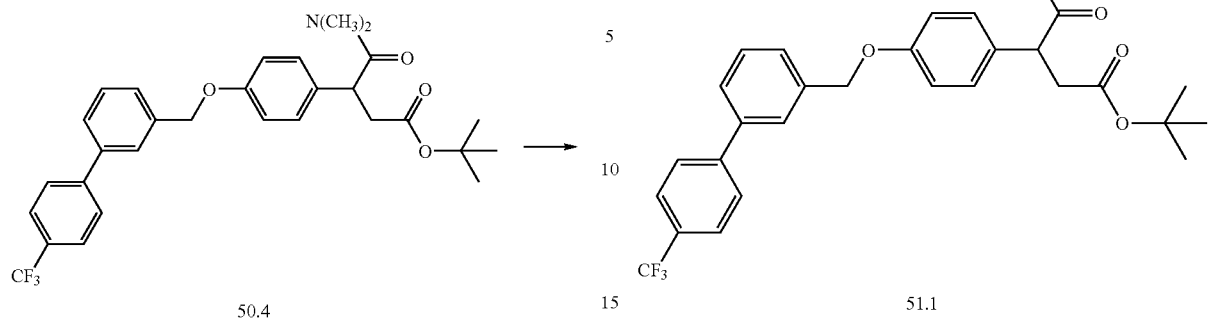

50.4

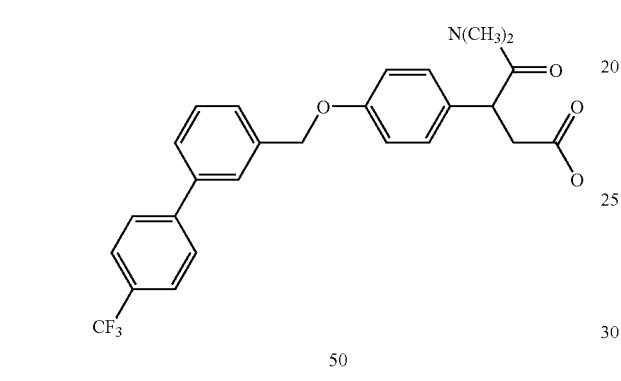

50

(+/−)-3-{4-[4'-Trifluoromethyl-biphenyl-3-ylmethoxy]-phenyl}-N,N-dimethyl-succinamic acid (50). Ester 50.4 (48 mg, 0.09 mmol) was dissolved in dichloromethane/TFA solution (3:1, 2 mL). The resulting mixture was stirred at room temperature for 2 h. The solvent removed under reduced pressure, and the product was purified on reserve phase HPLC to yield acid 50 (30 mg). MS ESI (pos.) m/e: 472 (M+H).

$^1$H NMR (400 MHz) (CDCl$_3$) δ 7.72 (4H, s); 7.67 (1H, s); 7.59-7.28 (3H, m); 7.2 (2H, d, J=8.6 Hz); 7.0 (2H, d, J=8.6 Hz); 5.13 (2H, s); 4.24-4.21 (1H, m); 3.20-3.13 (1H, m); 3.0 (3H, s); 2.95 (3H, s); 2.76-2.71 (1H, m).

6.51 Example 51

This example illustrates the preparation of 3-(4-methyl-thiazol-2-yl)-3-[4-(4'-trifluoromethyl-biphenyl-3-yl-methoxy)-phenyl]-propionic acid.

Scheme 51.1

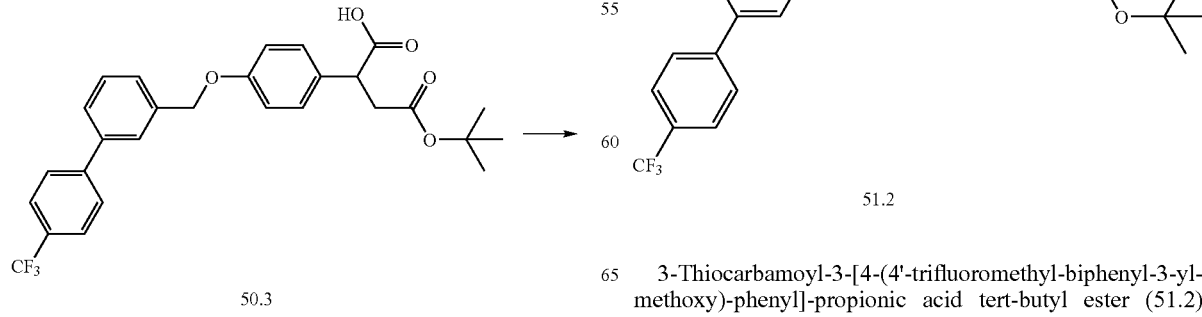

50.3

-continued

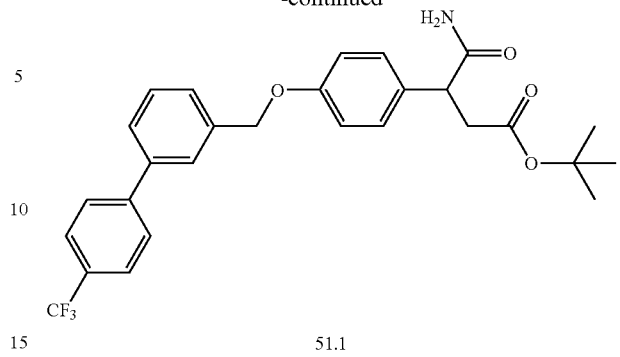

51.1

3-[4-(4'-Trifluoromethyl-biphenyl-3-ylmethoxy)-phenyl]-succinamic acid tert-butyl ester (51.1). 1-hydroxybenzotriazole (225 mg, 1.65 mmol) and EDC (315 mg, 1.65 mmol) were added sequentially to compound 50.3 (750 mg, 1.5 mmol) in dichloromethane (25 mL). The resulting mixture was stirred for 1 h before ammonium hydroxide (25% in water, 630 mg, 4.5 mmol) was added dropwise. The reaction was quenched after 30 min. with water (10 mL). The reaction mixture was extracted with dichloromethane (10 mL×3). The organic extracts were combined, dried over MgSO$_4$ and concentrated under reduced pleasure. The product was purified via flash chromatography (50% ethyl acetate in hexanes) to yield 51.1 (720 mg) as a white solid. MS ESI (pos.) m/e: 500 (M+H). $^1$H NMR (400 MHz) (CDCl$_3$) δ 7.72 (4H, s); 7.68 (1H, s); 7.57-7.48 (3H, m); 7.29-7.25 (2H, m); 7.0-6.97 (2H, d, J=6,8 Hz); 5.14 (2H, s); 3.91-3.88 (1H, m); 3.19-3.13 (1H, m); 2.60-2.55 (1H, m); 1.4 (9H, s).

Scheme 51.2

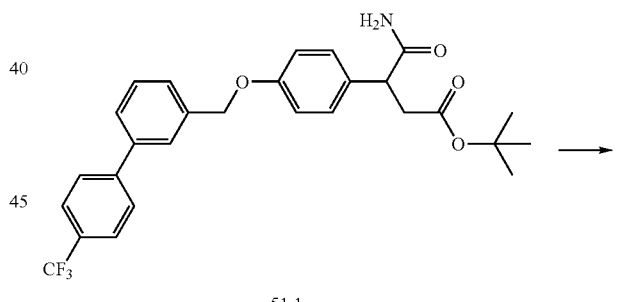

51.1

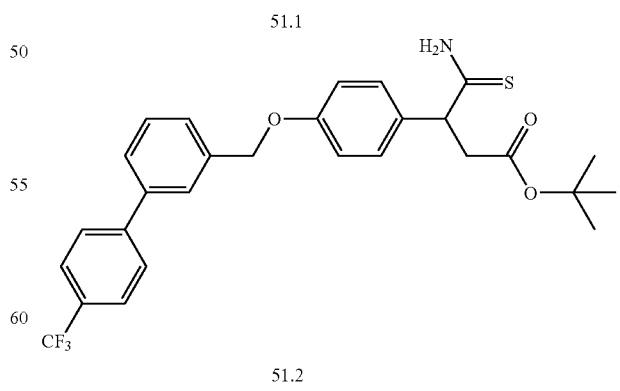

51.2

3-Thiocarbamoyl-3-[4-(4'-trifluoromethyl-biphenyl-3-yl-methoxy)-phenyl]-propionic acid tert-butyl ester (51.2). Lawesson's reagent (81 mg, 0.2 mmol) was added to a solution of compound 51.1 (50 mg, 0.1 mmol) in THF (2 mL). The resulting mixture was stirred at room temperature for 6 h. The reaction was quenched with water (5 mL). The reaction mixture was extracted with dichloromethane (3 mL×3). The organic extracts were combined, dried over MgSO$_4$ and concentrated under reduced pressure. The product was purified via flash chromatography (50% ethyl acetate in hexanes) to yield compound 51.2 (40 mg) as a clear film. MS ESI (pos.) m/e: 516 (M+H). $^1$H NMR (400 MHz) (CDCl$_3$) δ 7.72 (4H, s); 7.67 (1H, s); 7.51-7.48 (3H, m); 7.31-7.28 (2H, m); 7.0-6.97 (2H, m); 5.14 (2H, s); 4.25-4.22 (1H, m); 3.51-3.46 (1H, m); 2.78-2.72 (1H, m); 1.38 (9H, s).

Scheme 51.3

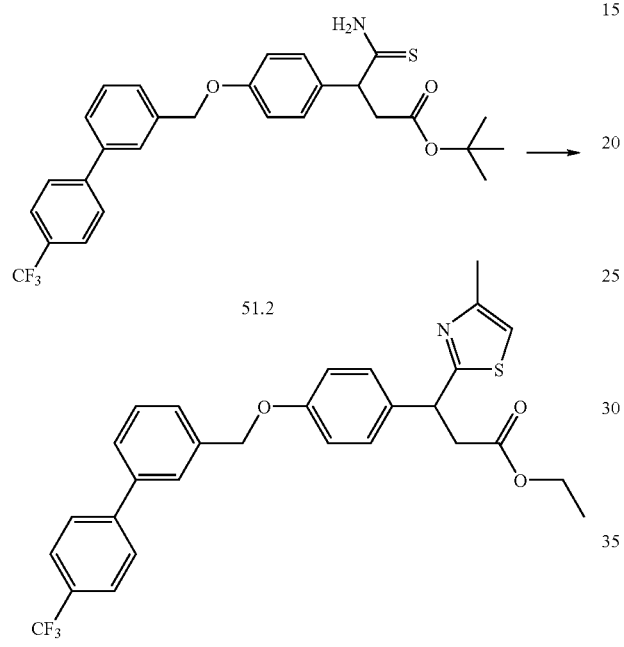

Ethyl 3-(4-Methyl-thiazol-2-yl)-3-[4-(4'-trifluoromethyl-biphenyl-3-ylmethoxy)-phenyl]-propanoate (51.3). A solution of 51.2 (100 mg, 0.19 mmol) in EtOH (3 mL) was treated with chloroacetone (88 mg, 0.95 mmol). The resulting mixture was refluxed for 5 h. Aqueous HCl (6N, 25 µL) was added into above reaction mixture and the reaction was heated at 50° C. overnight. The solvent was removed under reduced pressure. The product was purified via flash chromatography (50% ethyl acetate in hexanes) to yield 51.3 (50 mg). MS ESI (pos.) m/e: 526 (M+H).

Scheme 51.4

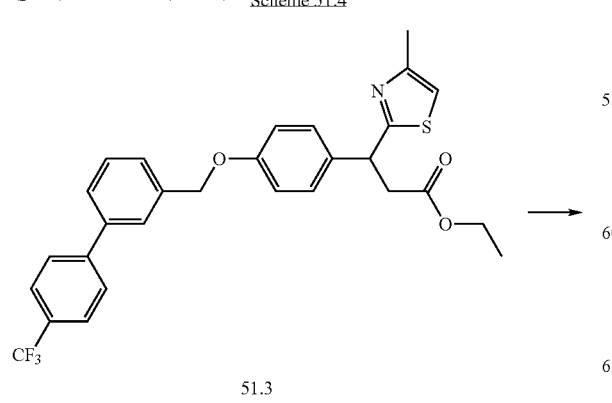

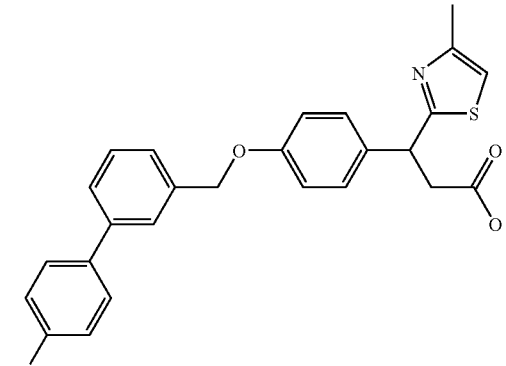

(+/−)-3-(4-Methyl-thiazol-2-yl)-3-[4-(4'-trifluoromethyl-biphenyl-3-ylmethoxy)-phenyl]-propionic acid (51). Compound 51.3 (50 mg, 0.1 mmol) was dissolved in MeOH/THF/H$_2$O (1:1:1, 3 mL). The resulting mixture was stirred at room temperature for 2 h. The reaction mixture was acidified to PH=4 and extracted with dichloromethane (3 mL×3). The product was purified on reverse phase HPLC to yield compound 51 (40 mg). MS ESI (pos.) m/e: 498 (M+H). $^1$H NMR (400 MHz) (DMSO) δ 7.92 (2H, d, J=8.1 Hz); 7.84 (3H, d, J=8.8 Hz); 7.71 (1H, t, J=5.1 Hz); 7.54 (2H, d, J=7 Hz); 7.29 (2H, d, J=8.7 Hz); 7.09 (1H, s); 7.01 (2H, d, J=8.7 Hz); 5.18 (2H, s); 4.66 (1H, m); 3.2 (1H, m); 2.93 (1H, m); 2.33 (3H, s).

6.52 Example 52

This example illustrates the preparation of (+/−)-3-(4-((4-methyl-2-p-tolylthiazol-5-yl)methoxy)phenyl)-3-(thiophen-2-yl)propanoic acid.

Scheme 52.1

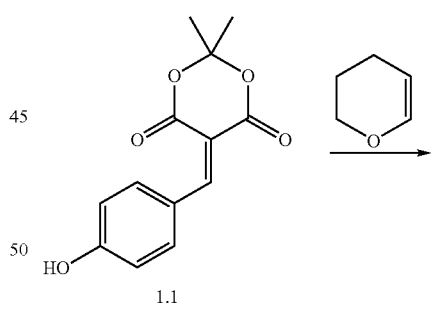

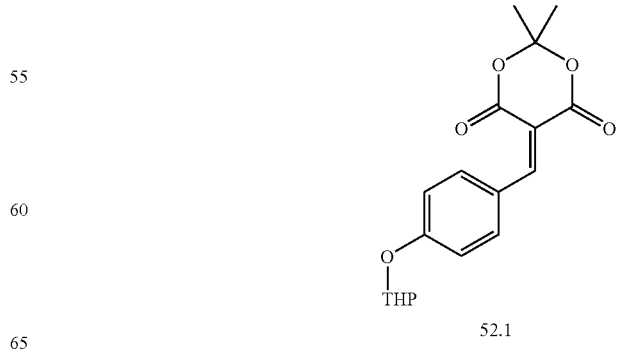

2,2-Dimethyl-5-[4-(tetrahydro-pyran-2-yloxy)-benzylidene]-[1,3]dioxane-4,6-dione (52.1). Protection of the phenol with dihydropyran was carried out based on the method given in Miyashita et al. (1977) *J. Org. Coed.* 42: 3772. Compound 1.1 (500 g, 2 mol) was dissolved in dichloromethane (4 L). 3,4-Dihydro-2H-pyran (250 g, 3 mol) was added to the suspension followed by PPTS (5 g, 20 mmol). The reaction mixture heated to a gentle reflux (3.5 h). HPLC showed ~90% completion of the reaction. The reaction was concentrated under reduced pressure to ~2 L of volume. 1 L of acetone was added, and 2 L of solvent was removed under reduced pressure. 1 L of acetone was added, and 1 L of solvent was removed under reduced pressure. 0.5 L of acetone was added, and 0.5 L of solvent was removed under reduced pressure. The resulting slurry of very fine, light yellow crystals was filtered and rinsed sequentially with two 500 mL portions of acetone. The product was dried in a vacuum oven at 50° C. until no further solvent collected in the traps. Compound 52.1 (528 g) was obtained as fine, light yellow crystals. $^1$H NMR(400 MHz)(DMSO-$d_6$) δ 8.29 (s, 1H); 8.18 (d, 2H, J=8.9 Hz); 7.13 (d, 2H, J=8.9 Hz); 5.67 (m, 1H); 3.70 (m, 1H); 3.60 (m, 1H). 1.9-1.5 (m, 12H). MS ESI (pos.) m/e: 355.1 (M+Na).

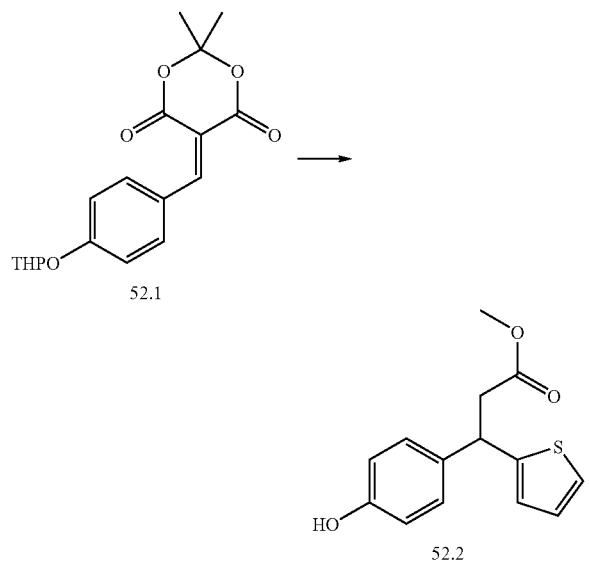

Scheme 52.2

(+/−)-Methyl 3-(4-hydroxyphenyl)-3-(thiophen-2-yl)propanoate (52.2). A 500 mL flask was equipped with a magnetic stir bar, nitrogen inlet, nitrogen outlet and placed in a room temperature water bath. Compound 52.1 (5.00 g, 15.1 mmol) was added to the flask along with anhydrous THF (150 mL). After purging with nitrogen for 30 min, a solution of thiophene-2-yl-magnesium bromide in THF (1 M, 18.1 mL) was added by cannula. After the addition was complete, the reaction mixture was stirred for 1.5 h and quenched with aqueous NH$_4$Cl (1 M, 100 mL) diluted with ethyl acetate (100 mL). The aqueous layer was acidified to pH ~2 with Conc. HCl and extracted with ethyl acetate (150 mL×2). The extract was washed with brine and concentrated. The residue was dissolved in 100 mL of 10:1 DMF-water heated to 100° C. for 8 h. The reaction was cooled and the diluted with 500 mL water and extracted with ethyl acetate (150 mL×3). The organic was dried with MgSO$_4$, filtered, and concentrated on a rotary evaporator. The residue was dissolved in MeOH (200 mL) and 5 drops of conc. H$_2$SO$_4$ were added and the solution was refluxed for 24 h. The solution was concentrated to a residue on a rotary evaporator and purified using flash column chromatography with 30% ethyl acetate/hexanes as the eluant. The fractions were combined and concentrated to afford 2.69 g (10.3 mmol) of 5 2.2 as a viscous oil.

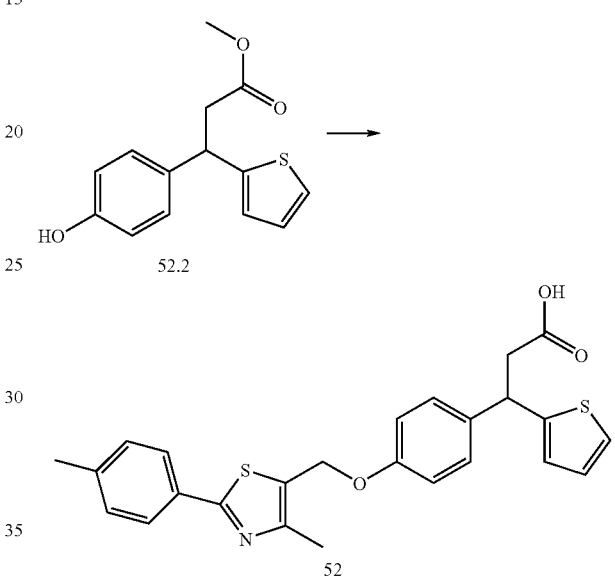

Scheme 52.3

(+/−)-3-(4-((4-Methyl-2-p-tolylthiazol-5-yl)methoxy)phenyl)-3-thiophen-2-yl)propanoic acid (52). Thiazole chloride 3.1 (108 mg, 0.457 mmol) and phenol 52.2 (100 mg, 0.381 mmol) were dissolved in DMF (1 mL) and treated with Cs$_2$CO$_3$ (371 mg, 1.14 mmol). The reaction was stirred at 50° C. for 16 h diluted with water (15 mL) and methylene chloride (15 mL). The organic layer was washed with water, dried with MgSO$_4$, filtered, and concentrated. The residue was purified by column chromatography (silica gel, 33% to 66% ethyl acetate in hexanes). Eluant containing desired compound was concentrated dissolved in a THF/MeOH/2N LiOH(aq) (1:1:1) solution (2 mL). The mixture was stirred at room temperature for 90 min., and the solution was poured into 0.65 N HCl (aq.) (2 mL). The aqueous phase was extracted with dichloromethane (3×10 mL) and the combined organic phases were dried over Na$_2$SO$_4$. After filtration and drying, 156 mg (0.323 mmol) of carboxylic acid 52 was obtained. $^1$H NMR (400 MHz) (CDCl$_3$) δ 7.77 (d, 2H, J=8.1 Hz), 7.23-7.30 (m, 5H), 6.89-6.97 (m, 4H), 5.24 (s, 2H), 4.58 (t, 1H, J=7.8 Hz), 3.02 (m, 1H), 2.92 (m, 1H), 2.40 (s, 3H), 2.33 (s, 3H).

6.53 Example 53

This example illustrates the preparation of (+/−)-3-[4-(4'-trifluoromethyl-biphenyl-3-ylmethoxy)-phenyl]-3-(thiazol-2-yl)-propionic acid.

Scheme 53.1

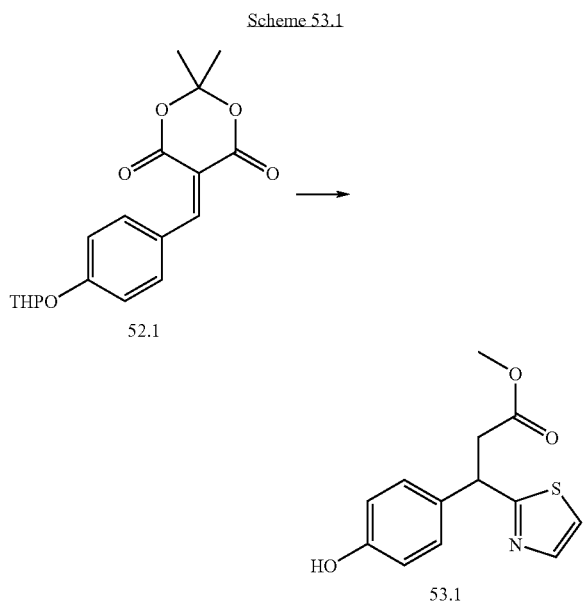

52.1

(+/−)-Methyl 3-(4-hydroxyphenyl)-3-(thiazol-2-yl)propanoate (53.1). A 500 mL flask was equipped with a magnetic stir bar, nitrogen inlet, nitrogen outlet and placed in a room temperature water bath. Compound 52.1 (5.00 g, 15.1 mmol) was added to the flask along with anhydrous THF (150 mL). After purging with nitrogen for 30 min, a solution of thiozole-2-yl-magnesium bromide in THF (1 M, 18.1 mL) was added by cannula. After the addition was complete, the reaction mixture was stirred for 1.5 h, quenched with aqueous $NH_4Cl$ (1 M, 100 mL) diluted with ethyl acetate (100 mL). The aqueous layer was acidified to pH ~2 with conc. HCl and extracted with ethyl acetate (150 mL×2). The extract was washed with brine and concentrated. The residue was dissolved in 100 mL of 10:1 DMF-water and heated to 100° C. for 8 h. The reaction was cooled and the diluted with 500 mL water and extracted with ethyl acetate (150 mL×3). The organic was dried with $MgSO_4$, filtered, and concentrated on a rotary evaporator. The residue was dissolved in MeOH (200 mL) and 5 drops of Conc. $H_2SO_4$ were added and the solution was refluxed for 24 h. The solution was concentrated to a residue on a rotary evaporator and purified using flash column chromatography with 50% ethyl acetate/hexanes as the eluant. The fractions were combined and concentrated to afford 1.90 g (7.25 mmol) of 53.1 as a viscous oil.

Scheme 53.2

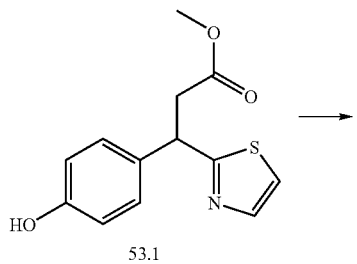

53.1

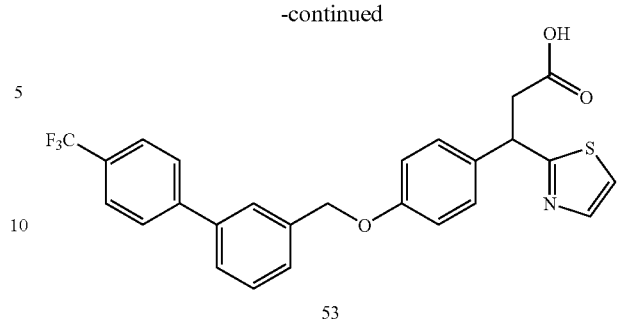

53

(+/−)-3-[4-(4'-Trifluoromethyl-biphenyl-3-ylmethoxy)-phenyl]-3-(thiazol-2-yl)-propionic acid (53). Benzyl chloride 2.3 (123 mg, 0.456 mmol) and phenol 53.1 (100 mg, 0.380 mmol) were dissolved in acetone (1 mL) and treated with $Cs_2CO_3$ (371 mg, 1.14 mmol). The reaction was stirred at 50° C. for 16 h, filtered and concentrated. The residue was purified by column chromatography (silica gel, 30% to 70% ethyl acetate in hexanes). Eluant containing desired compound was concentrated and dissolved in a THF/MeOH/2N $LiOH_{(aq)}$ (1:1:1) solution (2 mL). The mixture was stirred at room temperature for 90 min., and the solution was poured into 0.65 N $HCl_{(aq.)}$ (2 mL). The aqueous phase was extracted with dichloromethane (3×10 mL) and the combined organic phases were dried over $Na_2SO_4$. After filtration and drying, 150 mg (0.311 mmol) of carboxylic acid 53 was obtained. $^1H$ NMR (400 MHz) ($CDCl_3$) δ 7.47-7.77 (m, 9H), 7.24-7.27 (m, 3H), 6.99-7.00 (m, 2H), 5.14 (s, 2H), 4.78 (dd, 1H, J=6.8, 4.4 Hz), 3.47 (dd, 1H, J=12.8, 6.8 Hz), 3.09 (dd, 1H, J=12.8, 4.4 Hz).

6.54 Example 54

This example illustrates the preparation of (+/−)-3-[4-(4'-Trifluoromethyl-biphenyl-3-ylmethoxy)-phenyl]-3-(3-methylthiophen-2-yl)-propionic acid.

Scheme 54.1

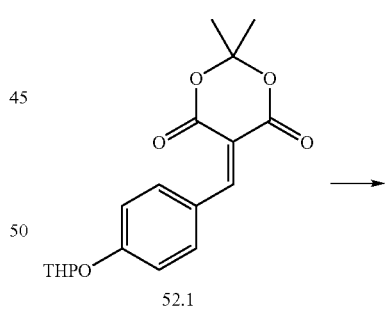

52.1

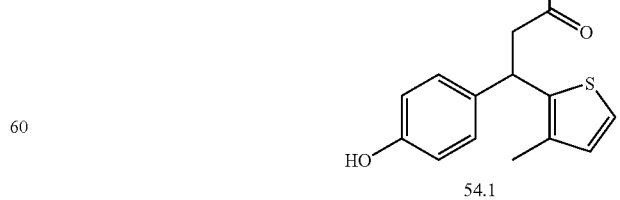

54.1

(+/−)-Methyl 3-(4-hydroxyphenyl)-3-(3-methylthiophen-2-yl)propanoate (54.1). A 500 mL flask was equipped with a magnetic stir bar, nitrogen inlet, nitrogen outlet and placed in a room temperature water bath. Compound 52.1 (5.00 g, 15.1 mmol) was added to the flask along with anhydrous THF (150 mL). After purging with nitrogen for 30 min, a solution of 3-methylthiophen-2-yl-magnesium bromide in THF (1 M, 18.1 mL) was added by cannula. After the addition was complete, the reaction mixture was stirred for 1.5 h, quenched with aqueous NH₄Cl (1 M, 100 mL) and diluted with ethyl acetate (100 mL). The aqueous layer was acidified to pH ~2 with Conc. HCl and extracted with ethyl acetate (150 mL×2). The extract was washed with brine and concentrated. The residue was dissolved in 100 mL of 10:1 DMF-water and heated to 100° C. for 8 h. The reaction mixture was cooled, diluted with 500 mL water, and extracted with ethyl acetate (150 mL×3). The combined organic layers were dried with MgSO₄, filtered, and concentrated on a rotary evaporator. The residue was dissolved in MeOH (200 mL) and 5 drops of Conc. H₂SO₄ were added and the solution was refluxed for 24 h. The solution was concentrated to a residue on a rotary evaporator and purified using flash column chromatography with 30% ethyl acetate/hexanes as the eluant. The fractions were combined and concentrated to afford 2.33 g (7.25 mmol) of 54.1 as a viscous oil.

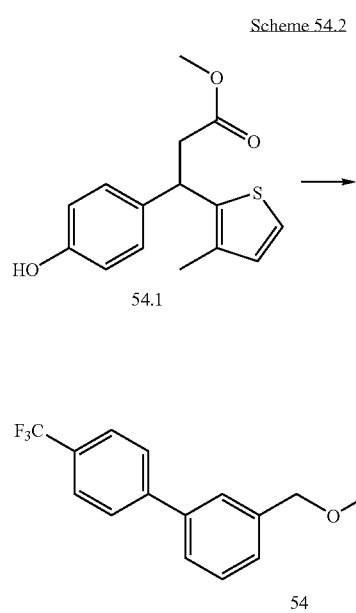

(+/−)-3-[4-(4-Trifluoromethyl-biphenyl-3-ylmethoxy)-phenyl]-3-(3-methylthiophen-2-yl)-propionic acid (54). Benzyl chloride 2.3 (113 mg, 0.434 mmol) and phenol 54.1 (100 mg, 0.362 mmol) were dissolved in acetone (1 mL) and treated with Cs₂CO₃ (371 mg, 1.14 mmol). The reaction was stirred at 50° C. for 16 h, filtered and concentrated. The residue was purified by column chromatography (silica gel, 30% to 60% ethyl acetate in hexanes). Eluant containing desired compound was concentrated and dissolved in a THF/MeOH/2N LiOH$_{(aq)}$ (1:1:1) solution (2 mL). The mixture was stirred at room temperature for 90 min., the solution was poured into 0.65 N HCl (aq.) (2 mL). The aqueous phase was extracted with dichloromethane (3×10 mL) and the combined organic phases were dried over Na₂SO₄. After filtration and drying, 154 mg (0.311 mmol) of carboxylic acid 54 was obtained. ¹H NMR (400 MHz) (CDCl₃) δ 7.43-7.70 (m, 8H), 7.21 (d, 2H, J=8.6 Hz), 7.05 (d, 1H, J=5.0 Hz), 6.92 (d, 2H, J=8.6 Hz), 6.76 (d, 1H, 5.0 Hz), 5.09 (s, 2H), 4.74 (t, 1H, J=7.8 Hz), 3.05 (d, 2H, J=7.8 Hz), 2.15 (s, 3H).

6.55 Example 55

This example illustrates the preparation of methyl 3-(4-hydroxyphenyl)-3-(1H-pyrrol-1-yl)propanoate.

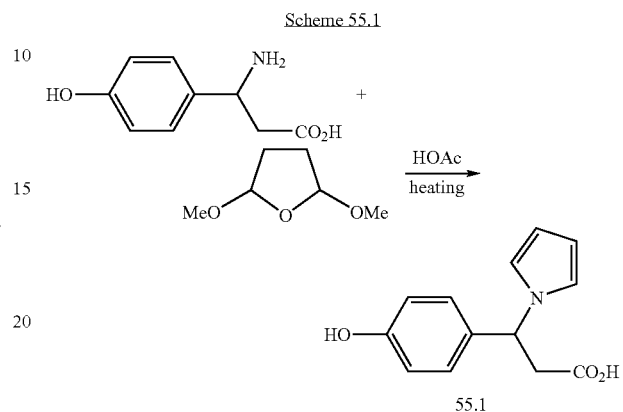

3-(4-Hydroxyphenyl)-3-(1H-pyrrol-1-yl)propanoic acid (55.1). At 100° C., 2,5-dimethoxytetrahydrofuran (8.5 mmol) was added to a mixture of 3-amino-3-(4-hydroxyphenyl) propanoic acid (7.7 mmol) and sodium acetate (46 mmol) in acetic acid (34 mL). After stirring for 1 h, acetic acid was removed under reduced pressure. The residue was extracted with ethyl acetate (300 mL). The organic layer was washed with brine and dried over anhydrous Na₂SO₄ and concentrated. The residue was purified via column chromatography (10% methanol in dichloromethane) to compound 55.1. LC-MS (neg.) m/e: 230.2 (M−H).

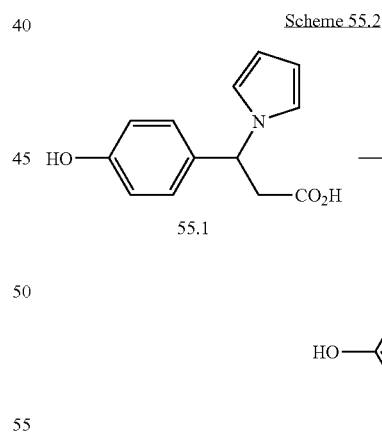

(+/−)-Methyl 3-(4-hydroxyphenyl)-3-(1H-pyrrol-1-yl) propanoate (55). Trimethysilyldiazomethane (8 mL, 2M in diethyl ether, 16 mmol) was added to a solution of compound 55.1 (7 mmol) in methanol (25 mL). After 10 min., the solvent was removed to yield methyl compound 55. MS ESI (pos.) m/e: 246.1 (M+H).

6.56 Example 56

The following compounds were prepared from compound 55 according to the methods described in Example 18.

TABLE 17

Structure: R-O-C6H4-CH(pyrrol-1-yl)-CH2-CO2H (with pyrrole N attached to the benzylic carbon and CO2H on the alpha carbon)

| Compound | R |
|---|---|
| 56.1 | 4-methyl-phenyl-(4-methylthiazol-5-yl-methyl)— (2-(p-tolyl)-4-methylthiazol-5-ylmethyl) |
| 56.2 | 4'-(trifluoromethyl)biphenyl-3-ylmethyl |
| 56.3 | biphenyl-3-ylmethyl |
| 56.4 | 3-methoxybenzyl |
| 56.5 | 3-ethoxybenzyl |
| 56.6 | 3-phenoxybenzyl |
| 56.7 | 4-phenyl-phenyl-methyl (biphenyl-4-ylmethyl, meta connection) |
| 56.8 | 3'-cyanobiphenyl-4-ylmethyl |

TABLE 17-continued

| Compound | R |
|---|---|
| 56.9 | 2'-cyanobiphenyl-4-ylmethyl |

Compound 56.1. MS ESI (neg.) m/e: 431 (M−H). $^1$H NMR (500 MHz) (DMSO-d$_6$) δ 12.3 (1H, s); 7.81 (2H, d, J=8 Hz); 7.30 (4H, m); 6.99 (2H, d, J=9 Hz); 6.92 (2H, m); 5.98 (2H, m); 5.56 (1H, t, J=8 Hz), 5.29 (2H, s); 3.18 (2H, m); 2.44 (3H, s); 2.38 (3H, s).

Compound 56.2. MS ESI (neg.) m/e: 464 (M−H). $^1$H NMR (500 MHz) (DMSO-d$_6$) δ 7.92 (2H, m); 7.84 (3H, m); 7.72 (1H, d, J=8 Hz); 7.53 (2H, m); 7.26 (2H, d, J=9 Hz); 7.00 (2H, d, J=9 Hz), 6.91 (2H, m); 5.55 (1H, d, J=8 Hz); 5.19 (2H, s); 3.16 (2H, m).

Compound 56.3. MS ESI (neg.) m/e: 396 (M−H). $^1$H NMR (500 MHz) (DMSO-d$_6$) δ 12.37 (1H, s); 7.65-7.77 (4H, m); 7.41-7.51 (5H, m); 67.27 (2H, m); 7.01 (2H, d, J=5 Hz)); 6.92 (2H, m); 5.99(2H, m), 5.56 (1H, m); 5.18 (2H, s), 3.21 (2H, m).

Compound 56.4. MS ESI (neg.) m/e: 350 (M−H). $^1$H NMR (500 MHz) (DMSO-d$_6$) δ 12.4 (1H, s); 7.30-7.34 (1H, t, J=8 Hz); 7.26 (2H, d, J=9 Hz); 7.01 (2H, m); 6.96 (2H, d, J=9 Hz)); 6.90-6.92 (3H, m); 5.98 (2H, m), 5.55 (1H, t, J=8 Hz); 5.07(2H, s); 3.78 (3H, s); 3.21(2H, m).

Compound 56.5. MS ESI (neg.) m/e: 364 (M−H). $^1$H NMR (500 MHz) (DMSO-d$_6$) δ 7.24-7.31 (3H, m); 6.99 (2H, m); 6.88 (3H, m); 5.97 (2H, s); 5.55 (1H, m); 5.06(2H, s), 4.04 (2H, q, J=7 Hz); 3.16 (2H, m); 1.34 (3H, t, J=7 Hz).

Compound 56.6. MS ESI (neg.) m/e: 412 (M−H). $^1$H NMR (500 MHz) (DMSO-d$_6$) δ 7.40-7.43 (3H, m); 7.16-7.26 (4H, m); 7.08 (1H, s); 7.03 (2H, d, J=8 Hz)); 6.90-6.97 (5H, m); 5.98(2H, s), 5.54 (1H, t, J=8 Hz); 5.09 (2H, s); 3.17 (2H, m)

Compound 56.7. MS ESI (neg.) m/e: 396 (M−H). $^1$H NMR (500 MHz) (DMSO-d$_6$) δ 7.70-7.71 (4H, m); 7.41-7.55 (4H, m); 7.39 (1H, m); 7.25 (2H, d, J=8 Hz)); 6.98 (2H, d, J=9 Hz); 6.89 (2H, s), 5.97 (2H, s); 5.55 (1H, t, J=8 Hz); 5.12 (2H, s); 3.10 (2H, m).

Compound 56.8. MS ESI (neg.) m/e: 421 (M−H). $^1$H NMR (500 MHz) (DMSO-d$_6$) δ 8.19 (1H, s); 8.05 (1H, d, J=8 Hz); 7.87 (1H, d, J=8 Hz); 7.80 (2H, d, J=8 Hz); 7.71 (1H, t, J=8 Hz); 7.56 (2H, d, J=8 Hz); 7.26 (2H, d, J=8 Hz); 6.98 (2H, d, J=8 Hz); 6.90 (2H, d, J=8 Hz); 5.98 (2H, m); 5.55 (2H, t, J=8 Hz)); 5.17 (2H, s); 3.13 (2H, m).

Compound 56.9. MS ESI (neg.) m/e: 421 (M−H). $^1$H NMR (500 MHz) (DMSO-d$_6$) δ 7.99 (1H, d, J=8 Hz); 7.84 (1H, t, J=8 Hz); 7.68 (1H, d, J=8 Hz); 7.58-7.64 (5H, m); 7.17 (2H, d, J=8 Hz); 6.96 (2H, d, J=8 Hz); 6.81 (2H, m); 5.95 (2H, m); 5.55 (1H, t, J=7 Hz); 5.18 (2H, s); 2.73 (2H, d, J=7 Hz).

6.57 Example 57

The following compounds were prepared according to the methods described in Examples 55 and 56.

TABLE 18

[Structure: R—O—(phenyl)—CH(pyrrol-1-yl)—CO₂H]

| Compound | R |
|---|---|
| 57.1 | 2-(p-tolyl)-4-methylthiazol-5-ylmethyl |
| 57.2 | 4'-(trifluoromethyl)biphenyl-3-ylmethyl |
| 57.3 | biphenyl-3-ylmethyl |
| 57.4 | 3-methoxybenzyl |
| 57.5 | 3-phenoxybenzyl |
| 57.6 | 4-(2-cyanophenyl)benzyl |

Compound 57.1. MS ESI (neg.) m/e: 431 (M−H). $^1$H NMR (500 MHz) (DMSO-$d_6$) δ 7.81 (2H, m); 7.28-7.32 (4H, m); 7.00 (2H, d, J=8 Hz); 6.92 (2H, s); 5.99 (2H, s); 5.57 (1H, m); 5.30 (2H, s); 3.23 (2H, m); 2.44(3H, s); 2.38 (3H, s).

Compound 57.2. MS ESI (neg.) m/e: 464 (M−H). $^1$H NMR (500 MHz) (DMSO-$d_6$) δ 7.93 (2H, d, J=8 Hz); 7.83-7.86 (3H, m); 7.72 (1H, d, J=8 Hz); 7.56 (2H, m); 7.27 (2H, d, J=9 Hz); 7.01 (2H, d, J=9 Hz); 6.91 (2H, m); 5.98 (2H, s); 5.55 (1H, d, J=8 Hz); 3.14 (2H, m).

Compound 57.3. MS ESI (neg.) m/e: 396 (M−H). $^1$H NMR (500 MHz) (CDCl$_3$) δ 7.63-7.76 (4H, m); 7.39-7.59 (5H, m); 7.15 (2H, d, J=8 Hz); 6.77 (2H, s); 6.19 (2H, s); 5.64 (1H, s); 5.13 (2H, s); 3.22-3.26 (2H, m).

Compound 57.4. MS ESI (neg.) m/e: 350 (M−H). $^1$H NMR (500 MHz) (DMSO-$d_6$) δ 7.33 (1H, t, J=8 Hz); 7.25 (2H, d, J=8 Hz); 7.01 (2H, m); 6.95 (2H, d, J=9 Hz); 6.90 (3H, m); 5.98 (2H, s); 5.55 (1H, t, J=8 Hz); 5.07 (2H, s); 3.78 (3H, s); 3.16 (2H, m).

Compound 57.5. MS ESI (neg.) m/e: 412 (M−H). $^1$H NMR (500 MHz) (DMSO-$d_6$) δ 7.40-7.43 (3H, m); 7.24-7.26 (3H, m); 7.20 (1H, m); 7.10 (1H, s); 7.03 (2H, d, J=9 Hz); 6.90-6.93 (5H, m); 5.98 (2H, m); 5.55 (1H, m); 5.10 (2H, s); 3.18 (2H, m).

Compound 57.6. MS ESI (neg.) m/e: 421 (M−H). $^1$H NMR (500 MHz) (DMSO-$d_6$) δ 7.99 (1H, d, J=8 Hz); 7.81(1H, m); 7.68 (1H, d, J=8 Hz); 7.61-7.65 (5H, m); 6.92 (2H, m); 5.99 (2H, s); 5.56 (1H, t, J=8 Hz); 5.20(2H, s); 3.19 (2H, m).

6.58 Example 58

This example illustrates the preparation of (+/−)-3-(−4-(Benzyloxy)phenyl)-3-(1H-pyrazol-1-yl)propanoic acid (58.3).

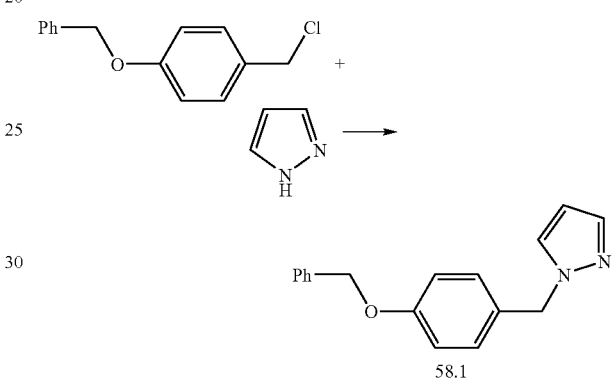

Scheme 58.1

1-(4-(Benzyloxy)benzyl)-1H-pyrazole (58.1). After a mixture of pyrazole (7.73 mmol) and potassium hydroxide (7.73 mmol) in DMF (35 mL) was stirred at room temperature for 30 min., a solution of 1-(benzyloxy)-4-(chloromethyl)benzene (6.44 mmol) in DMF (7 mL) was added dropwise. The reaction mixture was stirred at room temperature overnight and the product obtained from a standard aqueous work up. Column chromatography (1:2 ethyl acetate/hexane) of the residue yielded compound 58.1 as a white solid. LC-MS ESI (pos.) m/e: 265 (M+H); $^1$H NMR (500 MHz) (DMSO-$d_6$) δ 7.79 (1H, m); 7.46 (3H, m); 7.40 (2H, m); 7.36 (1H, m); 7.21 (2H, d, J=9 Hz)); 5.27 (2H, s); 5.11 (2H, m).

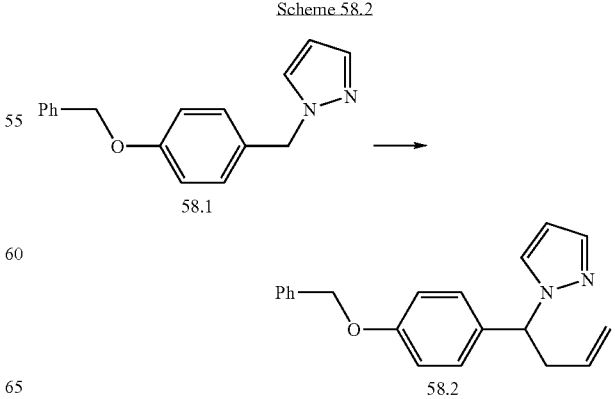

Scheme 58.2

1-(4-(Benzyloxy)phenyl)but-3-enyl)-1H-pyrazole (58.2). To a solution of compound 58.1 (3.41 mmol) in THF (30 mL) at −78° C. was added dropwise n-butyllithium in hexanes (3.75 mmol). The mixture was stirred for 10 min. followed by addition of allyl bromide (3.75 mmol). The reaction mixture was allowed to warm to room temperature overnight, quenched by addition of water. After extraction with ethyl acetate, the organic layer was washed with brine, dried over Na$_2$SO$_4$, and concentrated under reduced pressure. Column chromatography (1:3 ethyl acetate/hexane) of the residue yielded compound 58.2 as a white solid. LC-MS ESI (pos.) m/e: 305 (M+H).

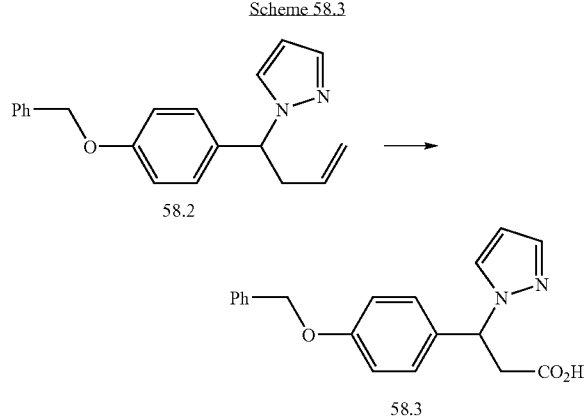

3-(-4-(Benzyloxy)phenyl)-3-(1H-pyrazol-1-yl)propanoic acid (58.3). A solution of KMnO$_4$ (1.68 mmol) in water (19 mL) was added dropwise to a mixture of compound 58.2 (1.08 mmol), NaIO$_4$ (2.2 mmol), acetone (6 mL), and acetic acid (6 mL). After stirring at room temperature for 1 h, ethylene glycol (2 mL) was added and stirred for additional 1 h. MnO$_2$ was removed by filtration through silica gel (eluting with 1:9 methanol:dichloromethane). After concentration under reduced pressure, the residue was purified by column chromatography (1:9 methanol:dichloromethane), yielding compound 58.3 (243 mg, 0.75 mmol). LC-MS ESI (pos.) m/e: 323 (+H).

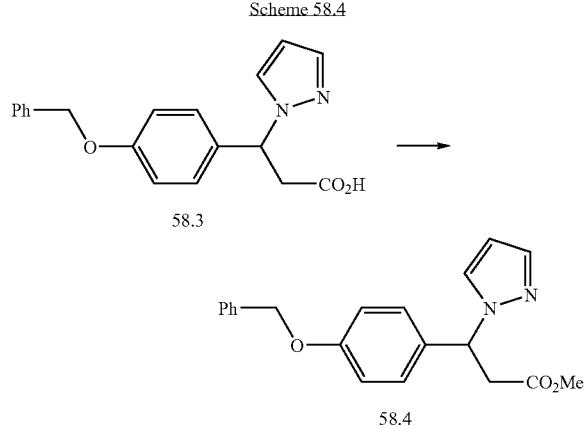

Methyl 3-(4-(benzyloxy)phenyl)-3-(1H-pyrazol-1-yl)propanoate (58.4). Compound 58.3 was esterified similarly to the method discussed in connection with Scheme 55.2.

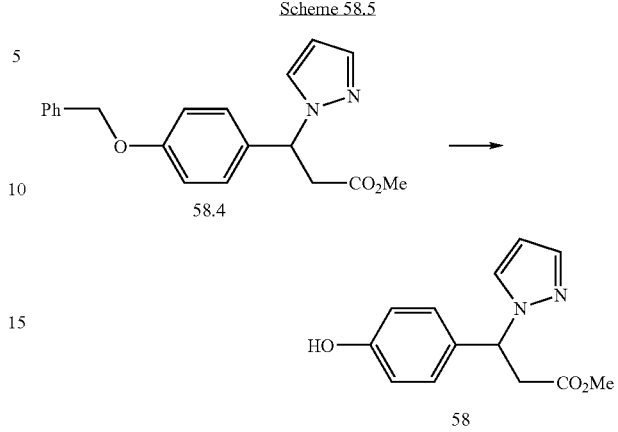

(+/−)-Methyl 3-(4-hydroxyphenyl)-3-(1H-pyrazo-1-l)propanoate (58). A mixture of compound 58.4 (0.37 mmol) and a small amount of Pd—C in methanol (8 mL) was stirred at room temperature under hydrogen atmosphere for 20 min. After filtration and concentration, the residue was purified by column chromatography. Compound 58 was obtained (81 mg, 0.33 mmol). LC-MS ESI (pos.) m/e: 247 (M+H).

6.59 Example 59

The following compounds were prepared from compound 58 according to the methods described in Example 18.

TABLE 19

| Compound | R | R' |
|---|---|---|
| 59.1 | benzyl | H |
| 59.2 | biphenyl-3-ylmethyl | H |
| 59.3 | 4'-(trifluoromethyl)biphenyl-3-ylmethyl | H |

TABLE 19-continued

[Structure: R-O-C6H4-CH(pyrazole-R')-CH2-CO2H]

| Compound | R | R' |
|---|---|---|
| 59.4 | 4-(trifluoromethyl)biphenyl-3-ylmethyl | 3-Methyl |
| 59.5 | biphenyl-3-ylmethyl | 3-Methyl |
| 59.6 | 4-(trifluoromethyl)biphenyl-3-ylmethyl | 5-Methyl |
| 59.7 | biphenyl-3-ylmethyl | 5-Methyl |

Compound 59.1. MS ESI (neg.) m/e: 321 (M−H). $^1$H NMR (500 MHz) (DMSO-$d_6$) δ 7.84 (1H, d, J=2 Hz); 7.40-7.50 (5H, m); 7.35 (1H, m); 7.27(2H, d, J=9 Hz); 6.97 (2H, d, J=9 Hz); 6.24 (1H, s); 5.79 (1H, m); 5.06 (2H, s); 3.3(1H, m); 3.12 (1H, m).

Compound 59.2. MS ESI (neg.) m/e: 397 (M−H). $^1$H NMR (500 MHz) (DMSO-$d_6$) δ 7.85 (1H, s); 7.64-7.77 (4H, m); 7.41-7.50 (6H, m); 7.29(2H, d, J=8 Hz); 7.01 (2H, d, J=9 Hz); 6.24 (1H, s); 5.80 (1H, m); 5.18 (2H, s); 3.3(1H, m); 3.12 (1H, m).

Compound 59.3. MS ESI (neg.) m/e: 465 (M−H). $^1$H NMR (500 MHz) (DMSO-$d_6$) δ 7.93 (2H, d, J=8 Hz); 7.85 (4H, m); 7.73 (1H, d, J=7 Hz); 7.54(2H, m); 7.29 (1H, s); 7.28 (2H, m); 7.00 (2H, m); 6.23(1H, s); 5.80 (1H, m); 5.20 (2H, s); 3.3(1H, m); 3.14 (1H, m).

Compound 59.4. MS ESI (neg.) m/e: 479 (M−H). $^1$H NMR (500 MHz) (DMSO-$d_6$) δ 7.92 (2H, m); 7.82-7.86 (3H, m); 7.72 (1H, m); 7.52-7.56 (2H, m); 7.36 (1H, s); 7.20 (2H, d, J=9 Hz); 6.99 (2H, d, J=9 Hz); 6.02 (1H, m); 5.69 (1H, m); 5.14 (2H, s); 3.3 (1H, m); 2.98 (1H, m); 2.24 (3H, s).

Compound 59.5. MS ESI (neg.) m/e: 411 (M−H). $^1$H NMR (500 MHz) (DMSO-$d_6$) δ 7.63-7.73 (4H, m); 7.36-7.52 (6H, m); 7.20 (2H, d, J=8 Hz); 6.99 (2H, d, J=8 Hz); 6.01 (1H, s); 5.70 (1H, m); 5.17 (2H, s); 3.3 (1H, m); 2.99 (1H, m); 2.24 (3H, s).

Compound 59.6. MS ESI (neg.) m/e: 479 (M−H). $^1$H NMR (500 MHz) (DMSO-$d_6$) δ 7.93 (2H, d); 7.84 (3H, m); 7.71 (2H, m); 7.55 (2H, m); 7.26(2H, d, J=9 Hz); 7.00 (2H, d, J=9 Hz); 6.00 (1H, s); 5.69 (1H, m); 5.19 (2H, s); 3.3 (1H, m); 3.05 (1H, m); 2.15 (3H, s).

Compound 59.7. MS ESI (neg.) m/e: 411 (M−H). $^1$H NMR (500 MHz) (DMSO-$d_6$) δ 7.64-7.74 (5H, m); 7.39-7.52 (5H, m); 7.26 (2H, d, J=9 Hz); 6.99 (2H, d, J=9 Hz); 5.99 (1H, s); 5.68 (1H, m); 5.17 (2H, s); 3.3 (1H, m); 3.06 (1H, m); 2.15 (3H, s).

6.60 Example 60

This example illustrates the preparation of ethyl 3-(4-hydroxyphenyl)-3-(5-methyloxazol-2-yl)propanoate.

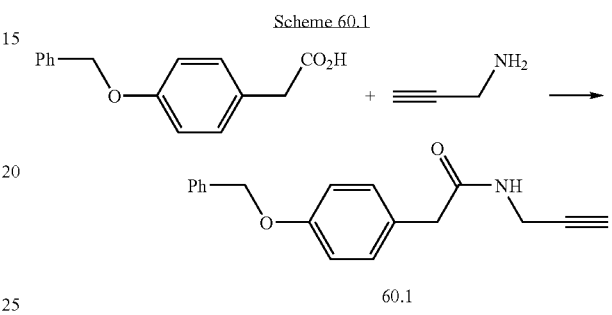

Scheme 60.1

2-(4-(Benzyloxy)phenyl)-N-(prop-2-ynyl)acetamide (60.1). A mixture of 4-(benzyloxy)phenylacetic acid (20.7 mmol), 1-hydroxybenzotrizole hydrate (37 mmol), 1-(3-dimethylaminopropyl)-3-ethylcarbodiimide (37 mmol), propargylamine (20.7 mmol) and N-methylmorpholine (62 mmol) in DMF (60 mL) were stirred at room temperature overnight. The reaction mixture was diluted with ethyl acetate (400 mL), washed with 1N HCl, water, saturated $Na_2CO_3$ solution, brine and dried over $Na_2SO_4$. After removing solvent under reduced pressure, the residue was triturated with dichloromethane. Compound 60.1 was obtained as a white solid after filtration and drying. LC-MS ESI (pos.) m/e: 280 (M+H).

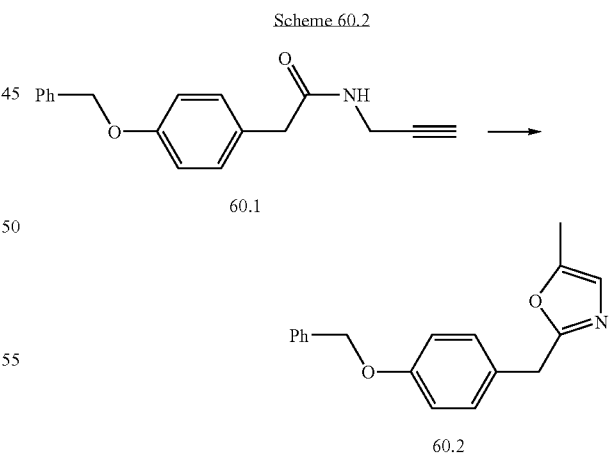

Scheme 60.2

2-(4-Benzyloxy)benzyl)-5-methyl oxazole (60.2). A mixture of compound 60.1 (10.1 mmol), $AuCl_3$ (1 mmol) in dichloromethane (100 mL) was stirred at room temperature overnight. Additional dichloromethane (100 L) was added and the reaction mixture was washed with $NaHCO_3$ solution and saturated brine. After drying over $Na_2SO_4$ and concentration under reduced pressure, the residue was purified by column chromatography (1:2 ethyl acetate-hexanes) to obtain compound 60.2. LC-MS ESI (pos.) m/e: 280 (M+H).

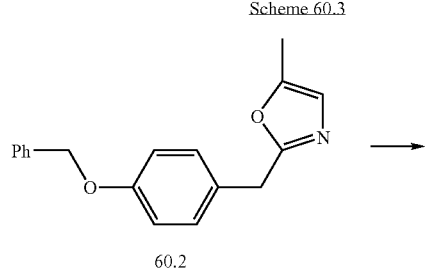

Ethyl 3-(4-(benzyloxy)phenyl)-3-(5-methyloxazol-2-yl)propanoate (60.3). Compound 60.3 was obtained from compound 60.2 according to the method of Example 58.

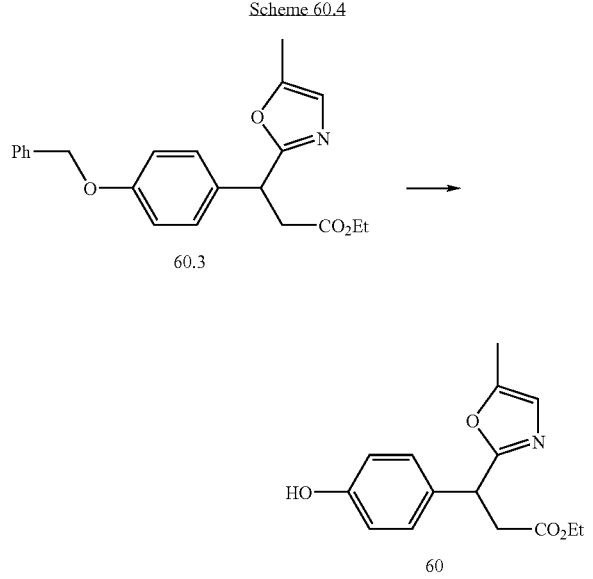

(+/−)-Ethyl 3-(4-hydroxyphenyl)-3-(5-methyloxazol-2-yl)propanoate (60). Compound 60 was obtained from compound 60.3 according to the method of Example 58.

6.61 Example 61

The following compounds were prepared from compound 60 according to the methods described in Example 18.

TABLE 20

| Compound | R |
|---|---|
| 61.1 | benzyl |
| 61.2 | 4'-(trifluoromethyl)biphenyl-3-ylmethyl |
| 61.3 | (4-methyl-2-p-tolylthiazol-5-yl)methyl |
| 61.4 | 3-methoxybenzyl |
| 61.5 | 2-butoxy-5'-methylbiphenyl-4-ylmethyl |

Compound 61.1. MS ESI (neg.) m/e: 336 (M−H). $^1$H NMR (500 MHz) (DMSO-$d_6$) δ 7.41-7.46 (4H, m); 7.36 (1H, m); 7.17 (2H, d, J=9 Hz); 6.97 (2H, d, J=9 Hz); 6.73 (1H, s); 5.09 (2H, s); 4.44 (1H, m); 3.08 (1H, m); 2.71 (1H, m); 2.22 (3H, s).

Compound 61.2. MS ESI (neg.) m/e: 480 (M−H). $^1$H NMR (500 MHz) (DMSO-$d_6$) δ 7.91-7.93 (2H, m); 7.82-7.85 (3H, m); 7.72 (2H, d, J=7 Hz); 7.54 (2H, m); 7.18 (2H, d, J=8 Hz); 6.99 (2H, d, J=8 Hz); 6.72 (1H, s); 5.17 (2H, s); 4.44 (1H, m); 3.08 (1H, m); 2.74 (1H, m); 2.21 (3H, s).

Compound 61.3. MS ESI (neg.) m/e: 447 (M−H). $^1$H NMR (500 MHz) (DMSO-$d_6$) δ 7.80 (2H, d, J=8 Hz); 7.30 (2H, d, J=8 Hz); 7.19 (2H, d, J=8 Hz); 7.00 (2H, d, J=8 Hz); 6.73 (1H, s); 5.27 (2H, s); 4.44 (1H, m); 3.10 (1H, m); 2.73 (1H, m); 2.43 (3H, s); 2.34 (3H, s); 2.21 (3H, s).

Compound 61.4. MS ESI (neg.) m/e: 366 (M−H). $^1$H NMR (500 MHz) (DMSO-$d_6$) δ 7.32 (1H, t, J=8 Hz); 7.16 (2H, d, J=8 Hz); 7.00 (2H, m); 6.96 (2H, m); 6.89 (1H, m); 6.72 (1H, s); 5.05 (2H, s); 4.42 (1H, m); 3.76 (3H, s); 3.06 (1H, m); 2.76 (1H, m); 2.21 (3H, s).

Compound 61.5. MS ESI (pos.) m/e: 500 (M+H). $^1$H NMR (500 MHz) (DMSO-$d_6$) δ 7.50 (2H, d, J=8 Hz); 7.44 (2H, d, J=8 Hz); 7.11-7.18 (4H, m); 6.97 (3H, m); 6.71 (1H, s); 5.10

(2H, s); 4.43 (1H, m); 3.93 (2H, t, J=7 Hz); 3.06 (1H, m); 2.70 (1H, m); 2.20 (3H, s); 1.61 (2H, m); 1.36 (2H, m); 0.86 (3H, t, J=7 Hz).

6.62 Example 62

This example illustrates the preparation 3-(4-(3-(4-(trifluoromethyl)phenyl) benzyloxy)phenyl)-3-(isoxazol-5-yl)propanoic acid (62).

Scheme 62.1

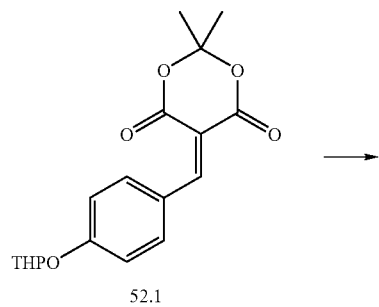

52.1

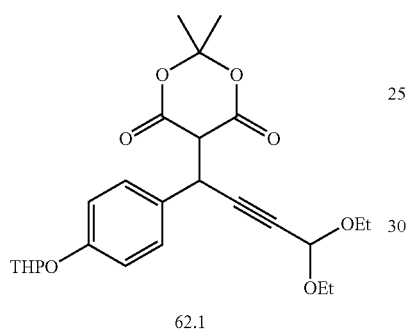

62.1

5-(4,4-Diethoxy-1-(4-(tetrahydro-2H-pyran-2-yloxy)phenyl)but-2-ynyl)-2,2-dimethyl-1,3-dioxane-4,6-dione (62.1). Propiolaldehyde diethyl acetal (5 g, 39 mmol) in anhydrous THF (65 mL) was cooled to −5° C. and treated with ethylmagnesium bromide (39 mmol in 14 mL of anhydrous THF) dropwise over 10 min. After 45 min., the solution of Grignard reagent was added to compound 52.1 in anhydrous THF (50 mL). After stirring 1 h, the reaction was quenched with saturated NH$_4$Cl$_{(aq)}$ (20 mL) and diluted with hexanes (100 mL). After mixing vigorously, the layers were separated and the organic layer discarded. The aqueous layer was acidified and extracted twice with diethyl ether. The combined organic layers were washed with saturated brine, dried over Na$_2$SO$_4$, filtered, and concentrated under reduced pressure. The residue was used immediately without further purification. MS ESI (pos.) m/e: 478.3 (M+NH$_4$)$^+$.

Scheme 62.2

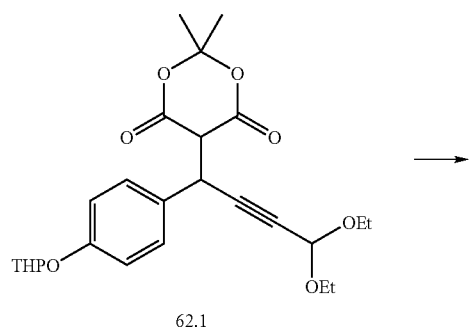

62.1

-continued

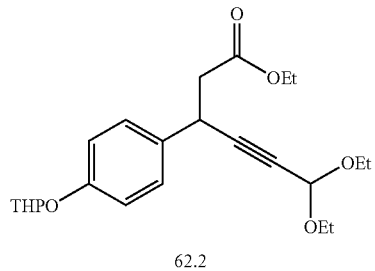

62.2

Ethyl 6,6-diethoxy-3-(4-(tetrahydro-2H-pyran-2-yloxy)phenyl)hex-4-ynoate (62.1). Ethanolysis and decarboxylation was carried out according to the method of Example 16. Ester 62.2 was obtained as a light yellow oil (8 g).

Scheme 62.3

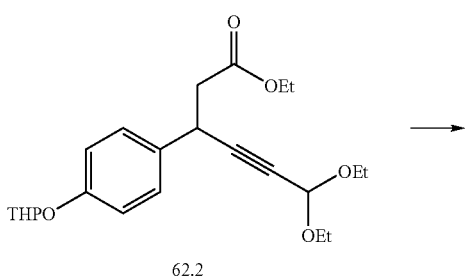

62.2

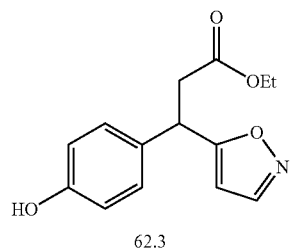

62.3

Ethyl 3-(4-hydroxyphenyl)-3-(isoxazol-5-yl)propanoate (62.3). Compound 62.2 (1 g, 2.5 mmol) and hydroxylamine hydrochloride (0.43 g, 6.2 mmol) were dissolved in a mixture of ethanol (10 mL) and water (1 mL). After refluxing 2 h, the reaction mixture was diluted with 200 mL of water and extracted with diethyl ether (2×100 mL). The combined organic layers were washed with saturated brine, dried over MgSO$_4$, filtered, and concentrated under reduced pressure. The residue was purified by flash chromatography (silica gel, 5% methanol in dichloromethane eluant). Compound 62.3 was obtained as a thick oil (0.38 g). $^1$H NMR (500 MHz) (CDCl$_3$) δ 8.14 (d, J=1.5 Hz, 1H); 7.12 (d, J=8.5 Hz, 2H); 6.77 (d, J=8.5, 2H); 5.98 (d, J=1.0 Hz, 1H); 5.30 (s, 1H); 4.64 (t, J=8.0 Hz, 1H); 4.06 (m, 2H); 3.15 (dd, J=16, 7.5 Hz, 1H); 2.95 (dd, J=16, 8.0 Hz, 1H); 1.17 (t, J=7.2 Hz, 3H).

Scheme 62.4

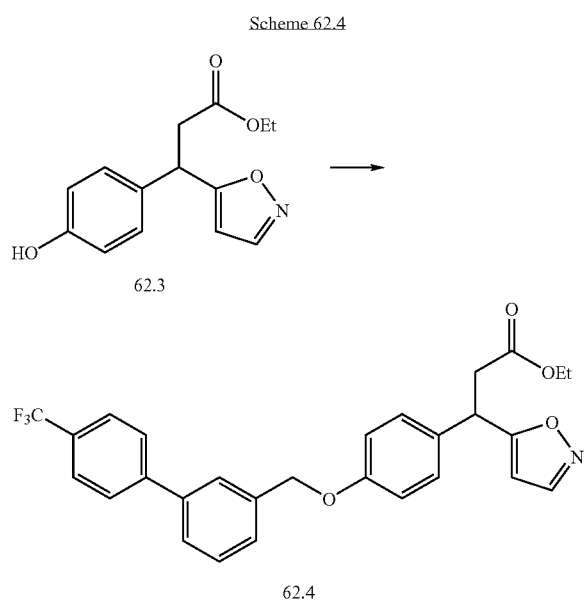

Ethyl 3-(4-(3-(4-(trifluoromethyl)phenyl)benzyloxy)phenyl)-3-(isoxazol-5-yl)propanoate (62.4). Compound 62.3 was alkylated according to the procedure of Example 2. LC-MS ESI (pos.) m/e: 496.1 (M+H). ¹H NMR (500 MHz) (CDCl₃) δ 8.14 (s, 1H); 7.70 (s, 4H); 7.66 (s, 1H); 7.56 (d, J=7.5 Hz, 1H); 7.50-7.45 (m, 2H); 7.22 (d, J=8.5 Hz, 2H); 6.96 (d, J=8.5, 2H); 5.99 (s, 1H); 5.12 (s, 2H); 4.67 (t, J=7.7 Hz, 1H); 4.08 (m, 2H); 3.16 (dd, J=16, 7.5 Hz, 1H); 2.95 (dd, J=16, 8.0 Hz, 1H); 1.17 (t, J=7.2 Hz, 3H).

Scheme 62.5

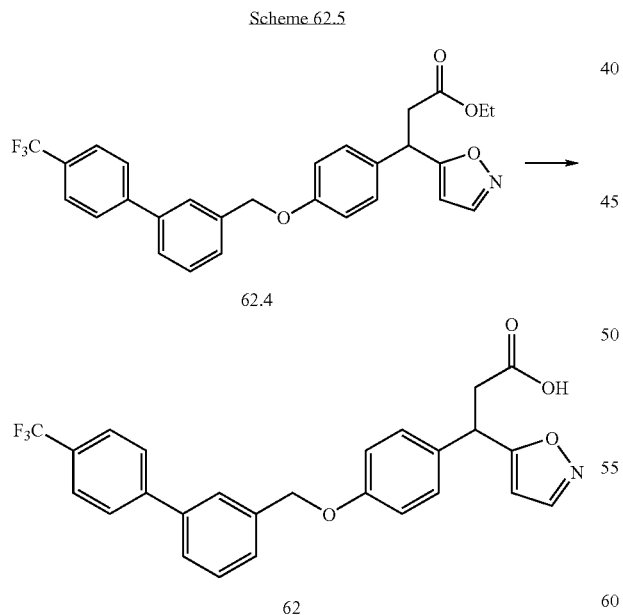

(+/−)-3-(4-(3-(4-(Trifluoromethyl)phenyl)benzyloxy)phenyl)-3-(isoxazol-5-yl)propanoic acid (62). Compound 62.4 was dissolved in glacial acetic acid (1 mL) and water (0.3 mL) and heated to 95° C. for 16 h. 1N HCl (0.1 mL) was added and the reaction mixture was heated for another 16 h. The reaction mixture was poured into deionized water (50 mL) and extracted twice with diethyl ether. The combined organic layers were washed with saturated brine, dried over Na₂SO₄, filtered, and concentrated under reduced pressure. The residue was purified by flash chromatography (silica gel, 5% methanol in dichloromethane eluant). Compound 62 was obtained as a thick oil (26 mg). LC-MS ESI (pos.) m/e: 468.1 (M+H). ¹H NMR (500 MHz) (CDCl₃) δ 8.14 (s, 1H); 7.70 (s, 4H); 7.66 (s, 1H); 7.56 (d, J=7.5 Hz, 1H); 7.50-7.45 (m, 2H); 7.22 (d, J=8.5 Hz, 2H); 6.96 (d, J=8.5, 2H); 5.99 (s, 1H); 5.12 (s, 2H); 4.67 (t, J=7.7 Hz, 1H); 4.08 (n, 2H); 3.16 (dd, J=16, 7.5 Hz, 1H); 2.95 (dd, J=16, 8.0 Hz, 1H); 1.17 (t, J=7.2 Hz, 3H).

6.63 Example 63

This example illustrates the preparation 3-[4-(2'-butoxy-5'-methyl-biphenyl-4-ylmethoxy)-phenyl]-3-(1-methyl-1H-pyrazol-5-yl) propionic acid and 3-[4-(2'-butoxy-5'-methyl-biphenyl-4-ylmethoxy)-phenyl]-3-(1-methyl-1H-pyrazol-3-yl) propionic acid.

Scheme 63.1

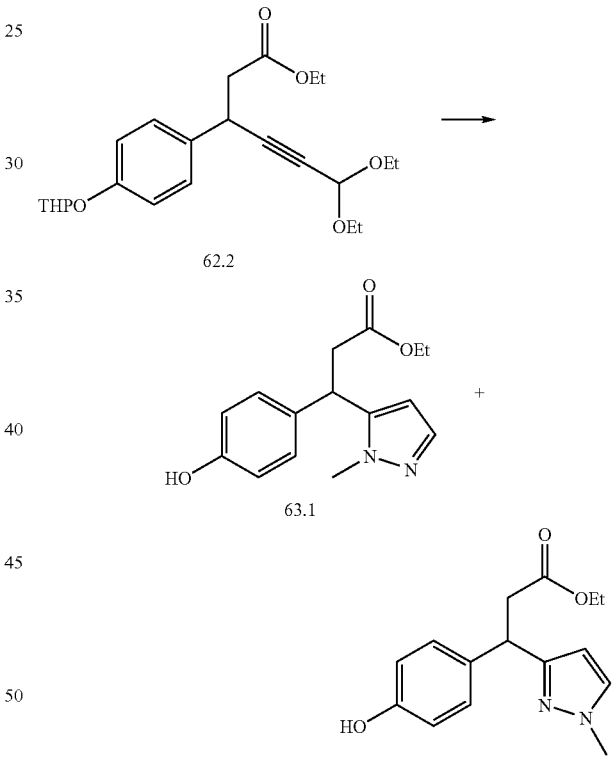

Ethyl 3-(4-hydroxyphenyl)-3-(1-methyl-1H-pyrazol-5-yl)propanoate (63.1) and ethyl 3-(4-hydroxyphenyl)-3-(1-methyl-1H-pyrazol-3-yl)propanoate (63.2). Compound 62.2 was dissolved in abs. Ethanol (6 mL). A solution of methylhydrazine (173 mg, 3.7 mmol) in 6N HCl₍aq₎ (0.6 mL) was added and the reaction mixture heated to reflux. After 2 h, the reaction mixture was diluted with 200 mL of water, neutralized with saturated aqueous NaHCO₃, and extracted with diethyl ether (2×100 mL). The combined organic layers were washed with saturated brine, dried over MgSO₄, filtered, and concentrated under reduced pressure. The residue was purified by flash chromatography (silica gel, 5% methanol in dichloromethane). Compounds 63.1 and 63.2 were obtained as an inseparable mixture in a 4:5 ratio by $^1$H-NMR. LC-MS ESI (pos.) m/e: 275.2 (M+H).

Scheme 63.2

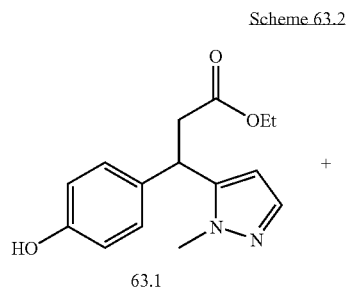

63.1

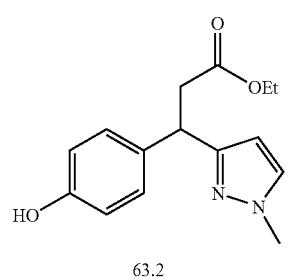

63.2

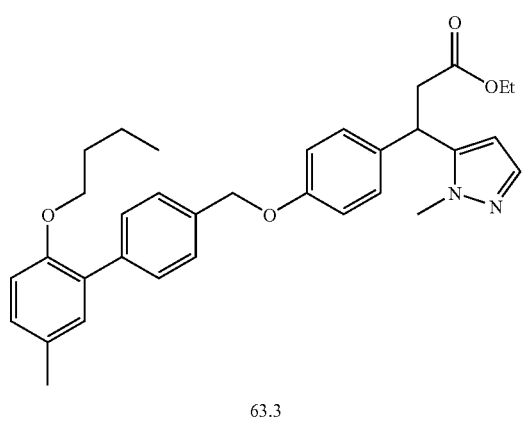

63.3

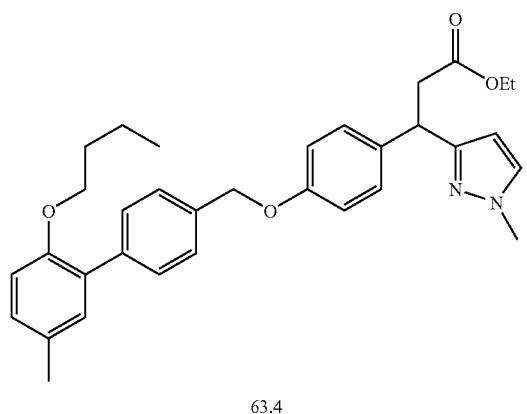

63.4

Ethyl 3-[4-(2'-Butoxy-5'-methyl-biphenyl-4-ylmethoxy)-phenyl]-3-(1-methyl-1H-pyrazol-5-yl) propionic (63.3) and Ethyl 3-[4-(2'-butoxy-5'-methyl-biphenyl-4-ylmethoxy)-phenyl]-3-(1-methyl-1H-pyrazol-3-yl) propanoate (63.4). The mixture of 63.1 and 63.2 was alkylated with 4-(2-butoxy-5-methyl)phenyl)benzyl bromide according to the method of Example 2. Separation of 63.3 and 63.4 could be accomplished by flash chromatography (silica gel, 3% acetone in dichloromethane).

Scheme 63.3

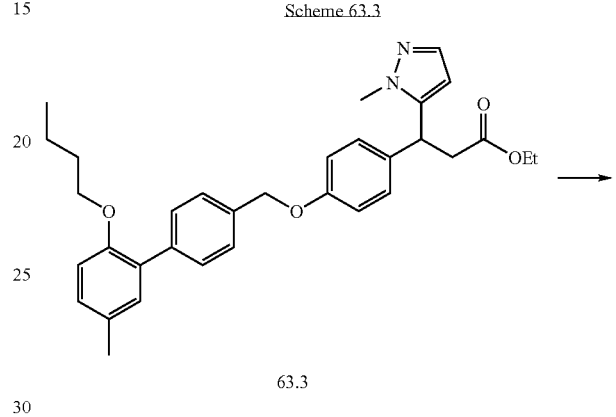

63.3

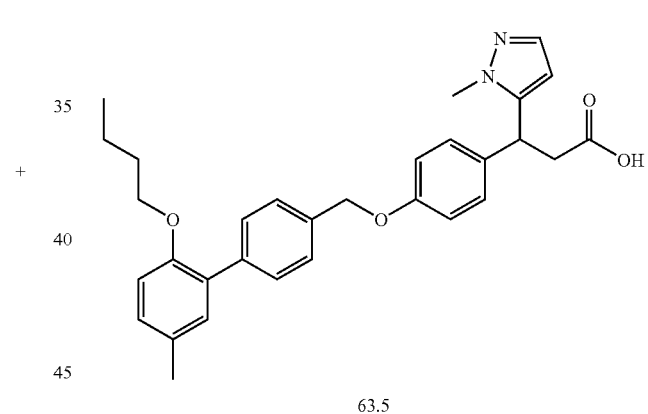

63.5

(+/−)-3-[4-(2'-Butoxy-5'-methyl-biphenyl-4-ylmethoxy)-phenyl]-3-(1-methyl-1H-pyrazol-5-yl) propionic acid (63.5). A 25 mL pear-shaped flask was charged with ethanol (1 mL), compound 63.3 (20 mg, 0.04 mmol), and 2N NaOH$_{(aq)}$ (2 mL, 4.0 mmol). The resulting mixture was stirred overnight at room temperature. The mixture was acidified to a pH of 3 with 1 N HCl and extracted with ethyl acetate (2×10 mL). The combined extracts were washed with brine and concentrated. The resulting residue was purified via preparatory TLC (30% Acetone in dichloromethane) to yield compound 63.5 (4.0 mg). $^1$H NMR(400 MHz)(CDCl$_3$) δ 7.55 (d, 2H, J=2 Hz); 7.42 (d, 2H, J=2 Hz); 7.29 (m, 1H); 7.19-7.08 (m, 4H); 6.95-6.86 (m, 3H); 5.98 (s, 1H); 5.05 (s, 2H); 4.46 (m, 1H); 3.94 (s, 3H); 3.31 (m, 1H); 3.01 (m, 1H); 2.33 (s, 3H); 1.67 (m, 3H); 1.40 (m, 3H); 0.90 (t, 3H, J=6 Hz). MS ESI (neg.) m/e: 497.2 (M−H).

Scheme 63.4

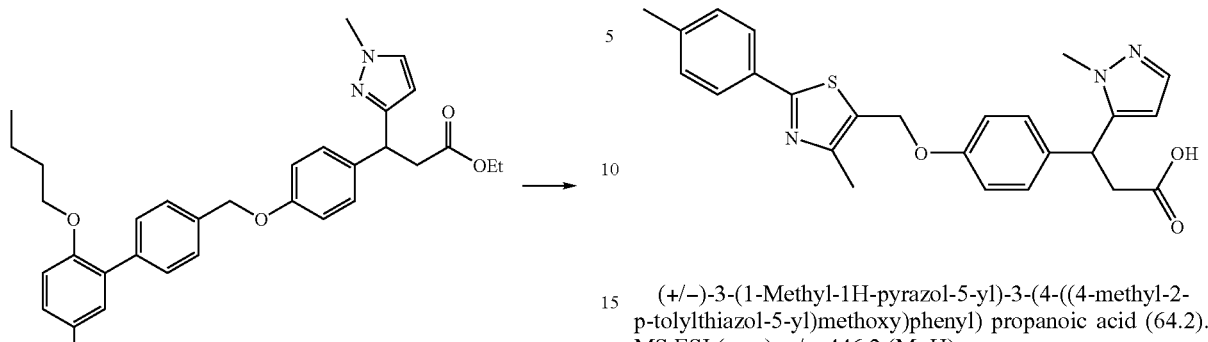

63.4

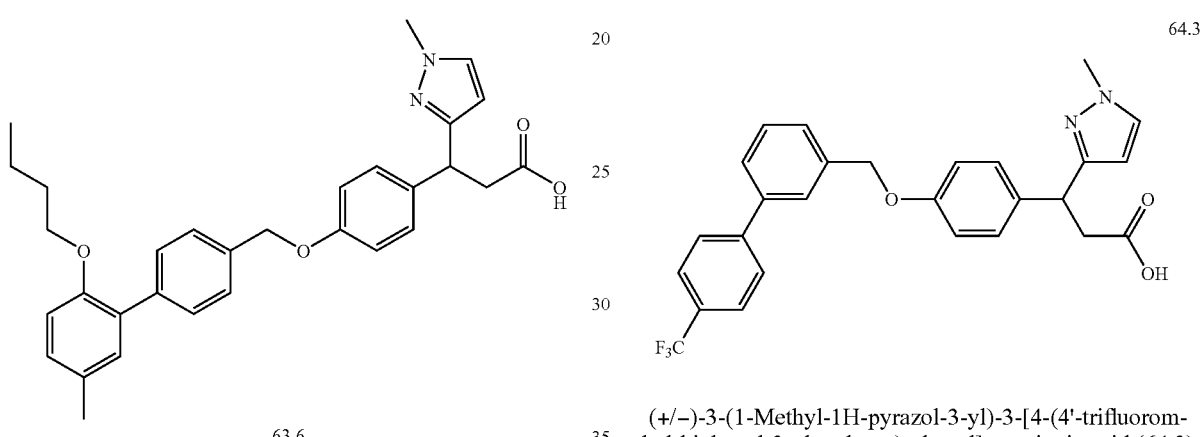

63.6

(+/−)-3-[4-(2'-Butoxy-5'-methyl-biphenyl-4-ylmethoxy)-phenyl]-3-(1-methyl-1H-pyrazol-3-yl) propionic acid (63.6). Hydrolysis of 63.4 was carried out as described above. MS ESI (neg.) m/e: 497.2 (M−H).

6.64 Example 64

The following compounds were prepared from compounds 63.1 and 63.2 according to the methods described in Example 63.

64.1

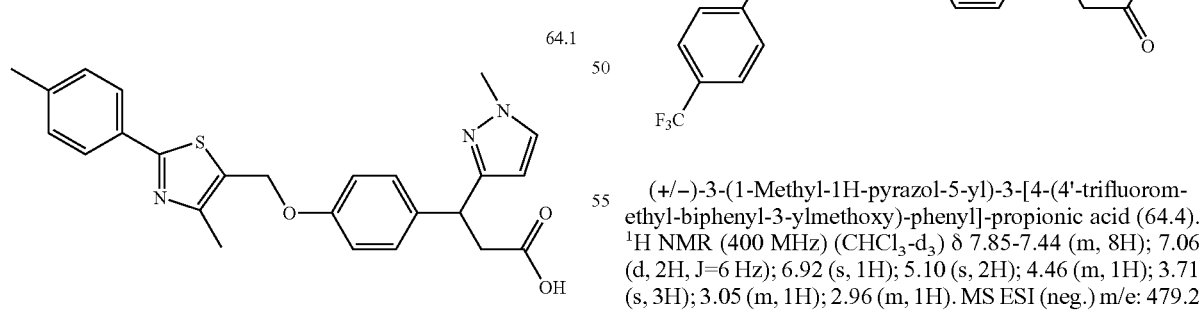

(+/−)-3-(1-Methyl-1H-pyrazol-3-yl)-3-(4-((4-methyl-2-p-tolylthiazol-5-yl)methoxy)phenyl) propanoic acid (64.1). $^1$H NMR (400 MHz) (CDCl$_3$) δ 7.84 (m, 2H); 7.12 (m, 5H); 6.89 (m, 2H); 5.92 (s, 1H); 5.13 (s, 2H); 4.46 (q, 1H, J=6 Hz); 3.88 (s, 3H); 3.23 (m, 1H); 2.98 (m, 1H); 2.50 (s, 3H); 2.39 (s, 3H). MS ESI (neg.) m/e: 446.2 (M−H).

(+/−)-3-(1-Methyl-1H-pyrazol-5-yl)-3-(4-((4-methyl-2-p-tolylthiazol-5-yl)methoxy)phenyl) propanoic acid (64.2). MS ESI (neg.) m/e: 446.2 (M−H).

(+/−)-3-(1-Methyl-1H-pyrazol-3-yl)-3-[4-(4'-trifluoromethyl-biphenyl-3-ylmethoxy)-phenyl]-propionic acid (64.3). $^1$H NMR (400 MHz) (CDCl$_3$) δ 7.69-7.46 (m, 8H); 7.26-6.92 (m, 5H); 5.96 (s, 1H); 5.01 (s, 2H); 4.47 (m, 1H); 3.91 (s, 3H); 3.25 (m, 1H); 2.99 (m, 1H). MS ESI (neg.) m/e: 479.2 (M−H).

(+/−)-3-(1-Methyl-1H-pyrazol-5-yl)-3-[4-(4'-trifluoromethyl-biphenyl-3-ylmethoxy)-phenyl]-propionic acid (64.4). $^1$H NMR (400 MHz) (CHCl$_3$-d$_3$) δ 7.85-7.44 (m, 8H); 7.06 (d, 2H, J=6 Hz); 6.92 (s, 1H); 5.10 (s, 2H); 4.46 (m, 1H); 3.71 (s, 3H); 3.05 (m, 1H); 2.96 (m, 1H). MS ESI (neg.) m/e: 479.2 (M−H).

6.65 Example 65 Cell-based Aequorin Assay

A cell-based aequorin assay may be employed to characterize the modulatory activity of compounds on the GPR40 signaling pathway. In an exemplary assay, CHO cells are transfected in a 15 cm plated containing 14 million cells with 5 μg of GPR40 expression vector and 5 μg of Aequorin expression vector (Euroscreen) using Lipofectamine 2000

(Invitrogen). After 17-24 hours post-transfection, cells are washed with phosphate buffered saline (PBS) and detached from the tissue culture dish with 2 mL of trypsin (0.25% (w/v)). Trypsinization is halted with 28 mL of Hanks Buffered Salt Solution containing 20 mM Hepes (H/HBSS) and 0.01% fatty acid-free bovine serum albumin (BSA) or 0.625% fatty acid-free human serum albumin (HSA). Coelantrazine is added to 1 μg/mL and the cells are incubated for 2 hours at room temperature. Cells are gently mixed every 15 minutes. Compounds are dissolved in dimethyl sulfoxide for preparation of 10 mM stock solutions. Compounds are diluted in H/HBSS containing either 0.01% BSA or 0.625% HSA. Serial dilutions of the test compounds are prepared to determine dose response.

Aequorin luminescence measurements are made using an EG&G Berthold 96-well luminometer and the response is measured over a 20 second interval after cells and compounds were mixed. The area-under-curve from 2-20 seconds is plotted to determine dose response. The $EC_{50}$ (effective concentration to reach 50% maximal response) is determined from the dose response plot.

Table 21 presents representative data ($EC_{50}$ values) obtained for exemplary compounds of the invention for the relative activation of human GPR40.

The stereoisomers in Table 21 are as specified, i.e., S-enantiomers or R-enantiomers, and if not specified, are mixtures of S-enantiomers and R-enantiomers. In addition, the present invention provides the S-enantiomers, the R-enantiomers, and mixtures of both S-enantiomers and R-enantiomers including racemates of each compound prepared according to the synthetic methods described herein or adapted with the necessary minor modifications from these methods.

6.66 Example 66 Insulin Secretion Assay

C57/B16 mice are euthanized with carbon dioxide gas. The pancreatic bile duct is clamped proximal to the duodenum and then cannulated. H/HBSS containing 0.75 mg/ml collagenase XI (Sigma) is then infused into the pancreas through the cannula. The pancreas is excised and then incubated at 37° C. for 13 minutes to complete enzymatic digestion. The collagenase digestion is quenched in H/HBSS containing 1% BSA and washed once in the same buffer. Islets can be purified using density gradient centrifugation using Histopaque (Sigma) and are hand-picked under a stereomicroscope.

Islets are cultured overnight in Roswell Park Memorial Institute (RMPI) media containing 10% fetal bovine serum and 50 uM beta-mercaptoethanol. Following overnight culture, islets are incubated in Dulbecco's Modification of Eagle's medium (DMEM) containing 2.8 mM glucose for one hour.

For determination of insulin secretion, islets are incubated in DMEM containing 12.5 mM glucose and test compounds for one hour. Insulin released into the culture medium from the islets is measured using an insulin ELISA.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 21

Aequorin Assay Using Human GPR40

| No. | Structure | Relative $EC_{50}{}^a$ |
|---|---|---|
| 2 | 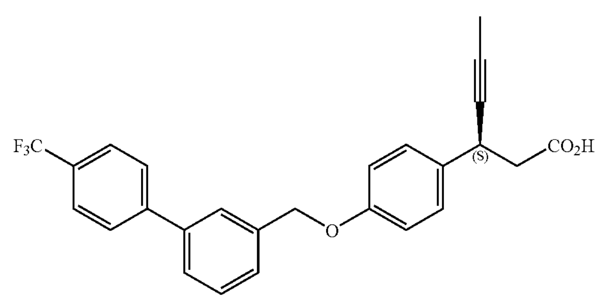 | ++++ |
| 3 | 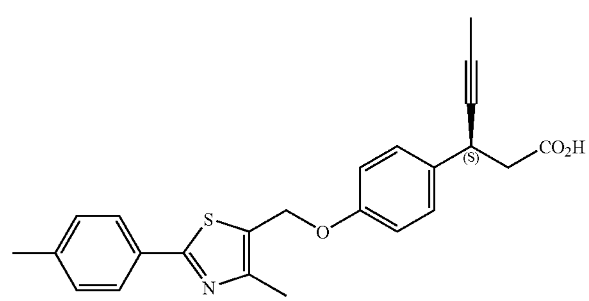 | +++++ |

TABLE 21-continued

Aequorin Assay Using Human GPR40

| No. | Structure | Relative $EC_{50}^a$ |
|---|---|---|
| 5 | 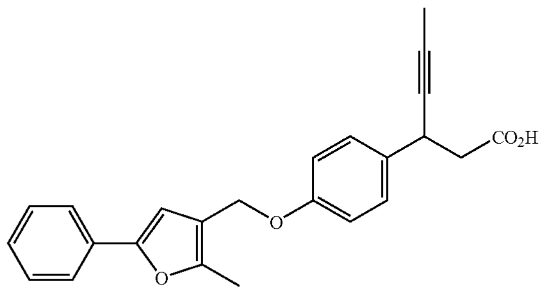 | ++++ |
| 6.1 | 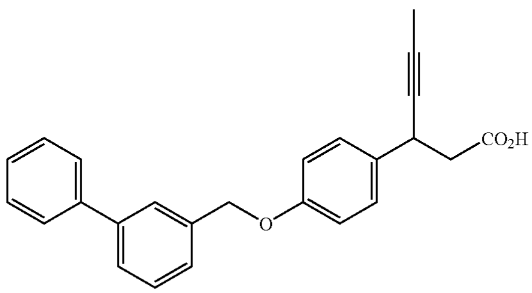 | ++++ |
| 6.2 | 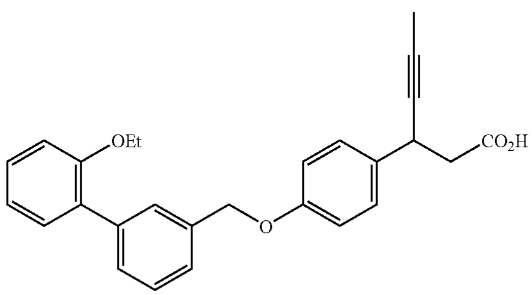 | ++++ |
| 6.3 | 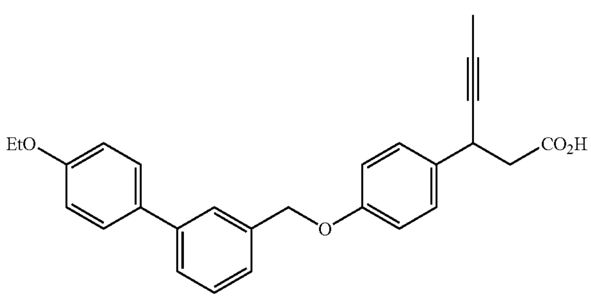 | ++++ |
| 6.5 | 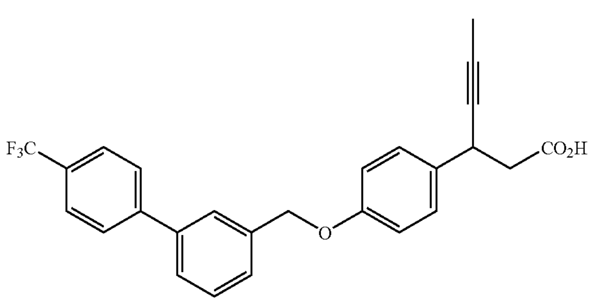 | ++++ |

TABLE 21-continued

Aequorin Assay Using Human GPR40

| No. | Structure | Relative EC$_{50}$$^a$ |
|---|---|---|
| 6.7 | NC-C6H4-C6H4-CH2-O-C6H4-CH(C≡CCH3)-CH2-CO2H | ++++ |
| 6.8 | 2-CF3-C6H4-C6H4-CH2-O-C6H4-CH(C≡CCH3)-CH2-CO2H | ++++ |
| 6.9 | 3-CF3-C6H4-C6H4-CH2-O-C6H4-CH(C≡CCH3)-CH2-CO2H | ++++ |
| 7.3 | C6H5-C6H4-CH2-O-C6H4-CH(C≡CCH3)-CH2-CO2H | ++ |

TABLE 21-continued
Aequorin Assay Using Human GPR40
| No. | Structure | Relative EC$_{50}$$^a$ |
|---|---|---|
| 7.5 | 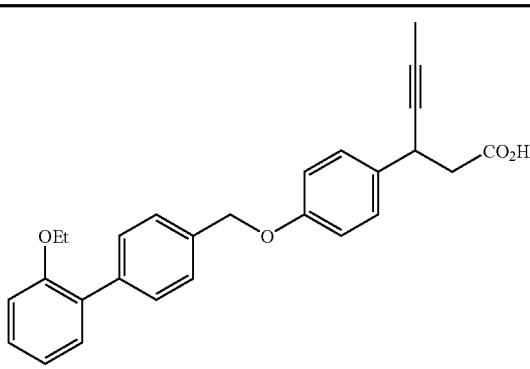 | ++++ |
| 7.8 | 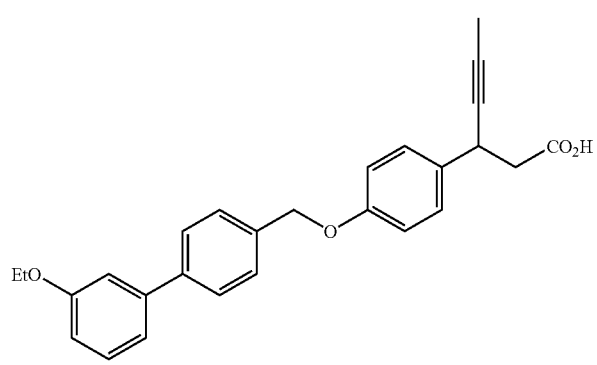 | +++ |
| 7.9 | 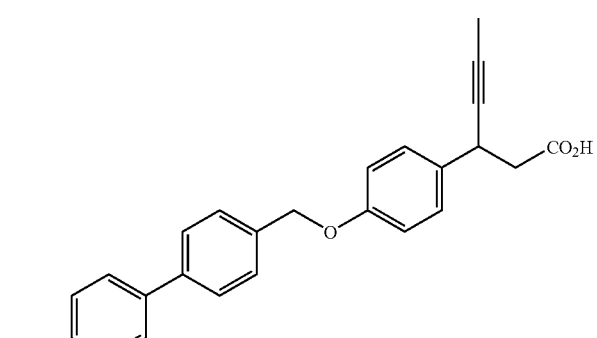 | +++ |
| 7.10 | 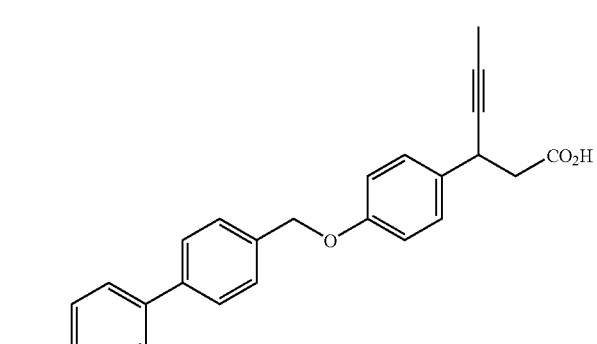 | +++ |

TABLE 21-continued
Aequorin Assay Using Human GPR40
| No. | Structure | Relative EC$_{50}$$^a$ |
|---|---|---|
| 7.15 | 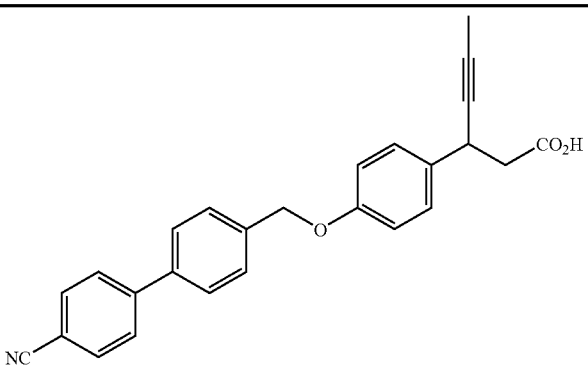 | ++++ |
| 8.1 | 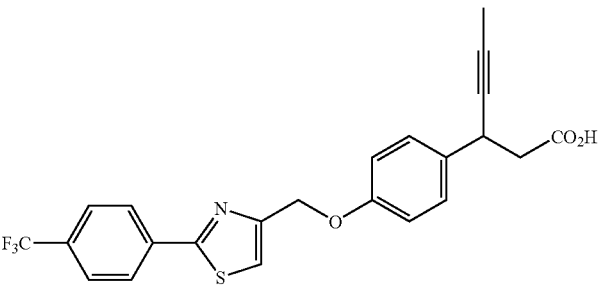 | ++++ |
| 8.2 | 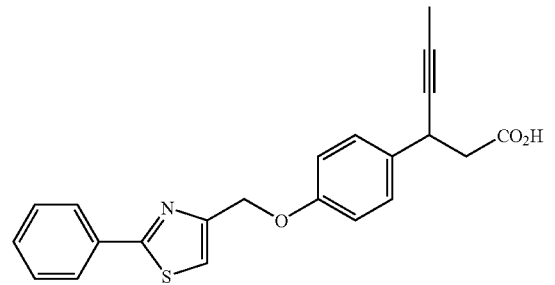 | ++++ |
| 8.3 | 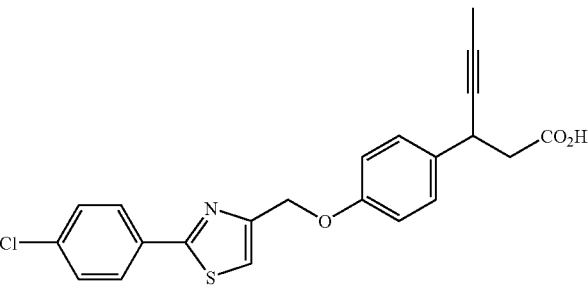 | ++++ |
| 8.4 | 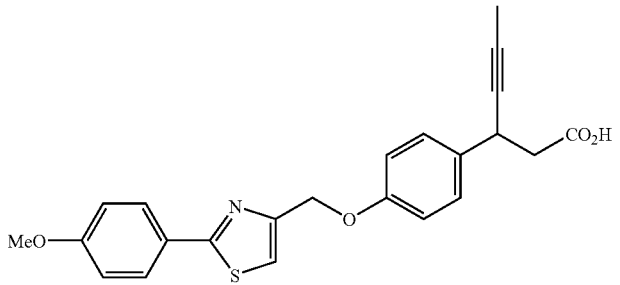 | ++++ |

TABLE 21-continued

Aequorin Assay Using Human GPR40

| No. | Structure | Relative EC$_{50}$$^a$ |
|---|---|---|
| 8.5 | 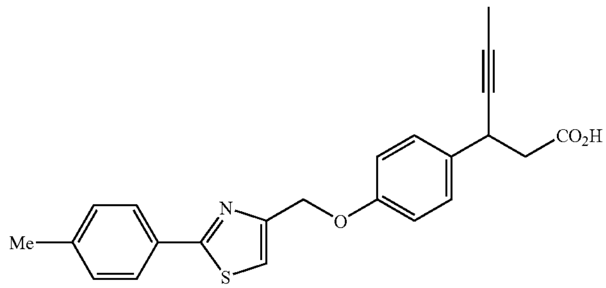 | ++++ |
| 8.6 | 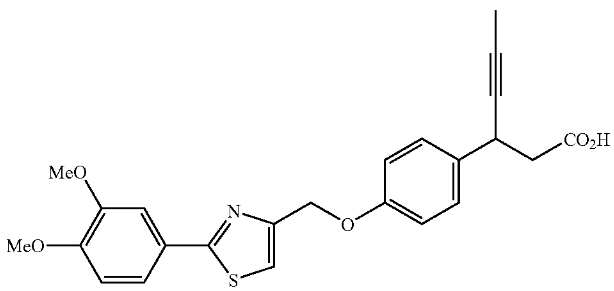 | +++ |
| 9.1 | 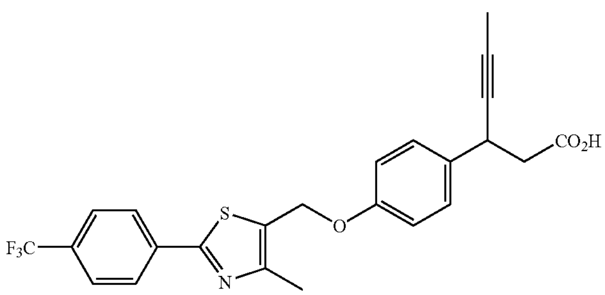 | ++++ |
| 9.2 | 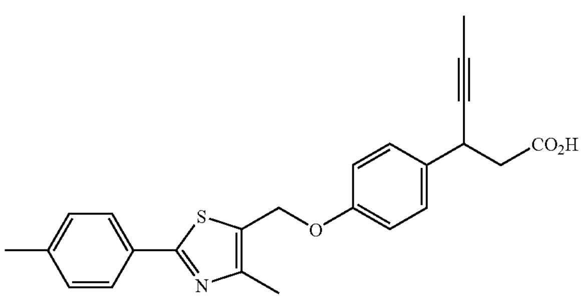 | +++++ |
| 9.3 | 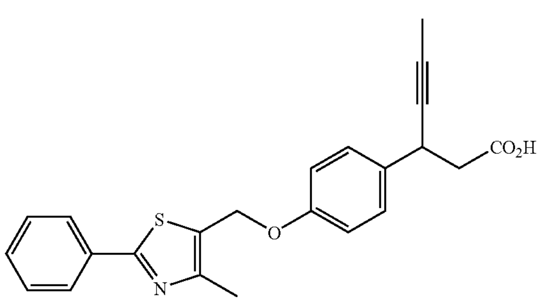 | ++++ |

TABLE 21-continued

Aequorin Assay Using Human GPR40

| No. | Structure | Relative $EC_{50}{}^a$ |
|---|---|---|
| 9.4 | 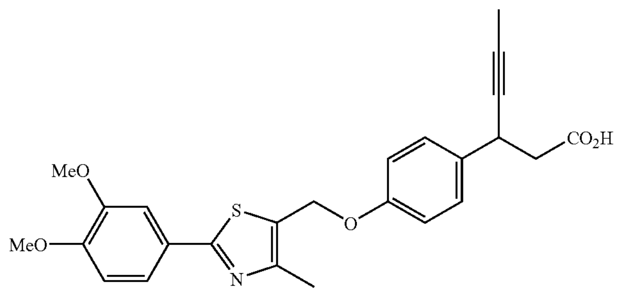 | ++++ |
| 10.2 | 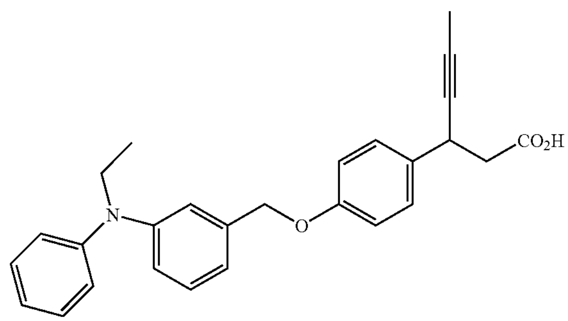 | ++++ |
| 10.3 | 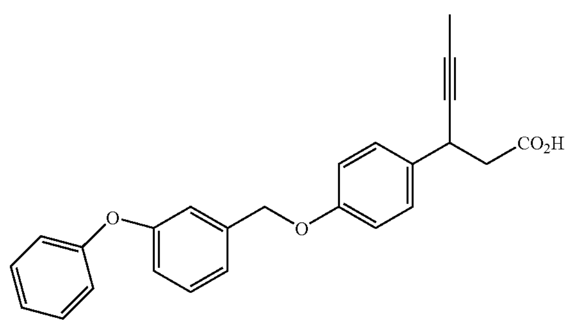 | ++++ |
| 10.4 | 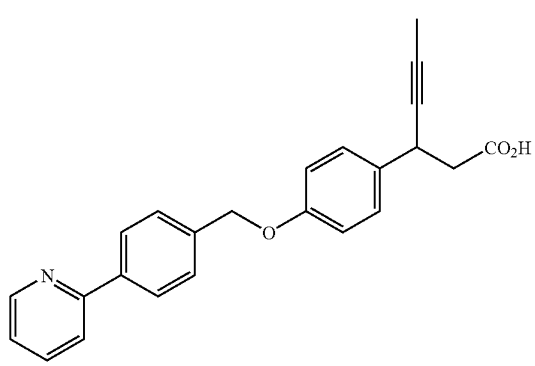 | ++++ |

TABLE 21-continued
Aequorin Assay Using Human GPR40
| No. | Structure | Relative EC$_{50}$$^a$ |
|---|---|---|
| 10.5 | 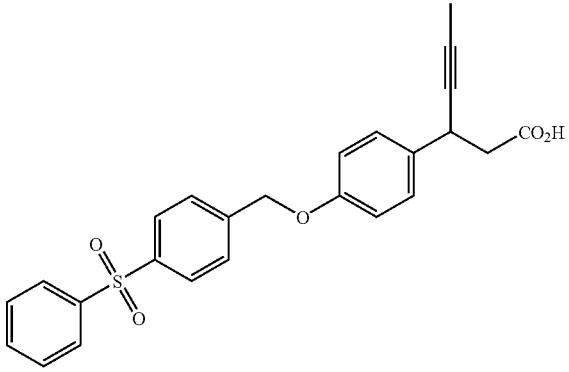 | +++ |
| 10.6 | 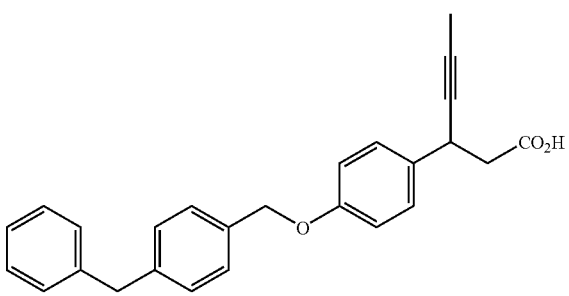 | ++++ |
| 10.7 | 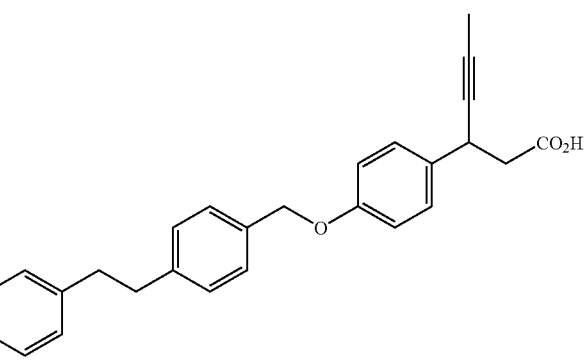 | +++ |
| 10.8 | 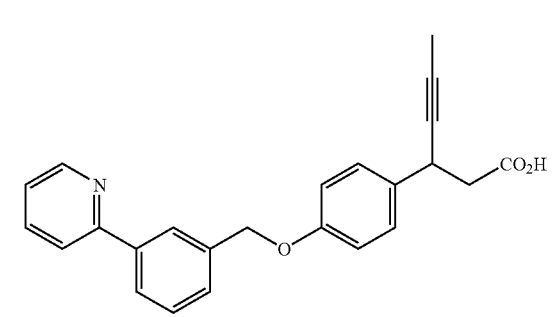 | +++ |

TABLE 21-continued

Aequorin Assay Using Human GPR40

| No. | Structure | Relative EC$_{50}$$^a$ |
|---|---|---|
| 10.9 | 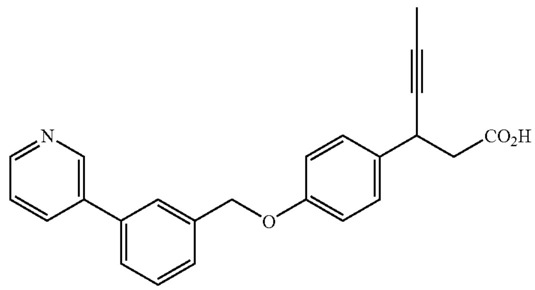 | +++ |
| 10.10 | 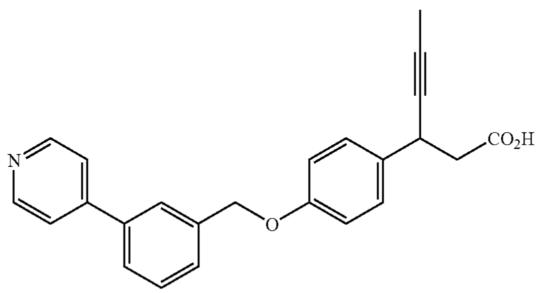 | +++ |
| 10.12 | 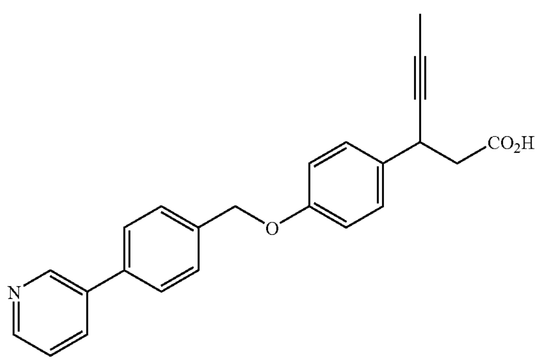 | ++ |
| 10.13 | 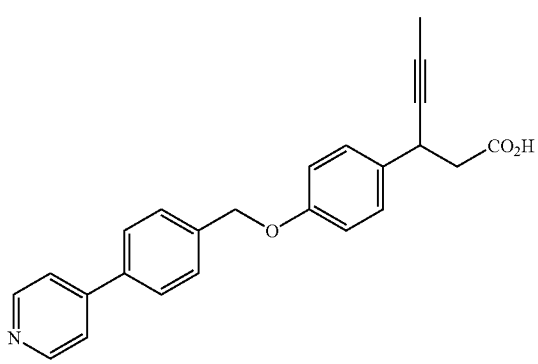 | +++ |

TABLE 21-continued

Aequorin Assay Using Human GPR40

| No. | Structure | Relative EC$_{50}$$^a$ |
|---|---|---|
| 10.14 | 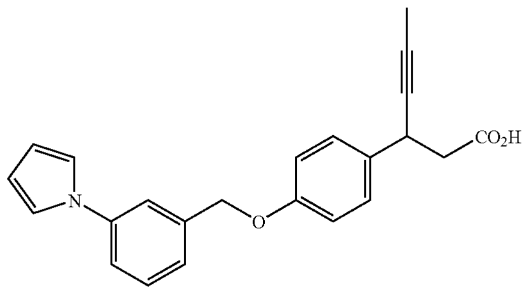 | ++++ |
| 11.1 | 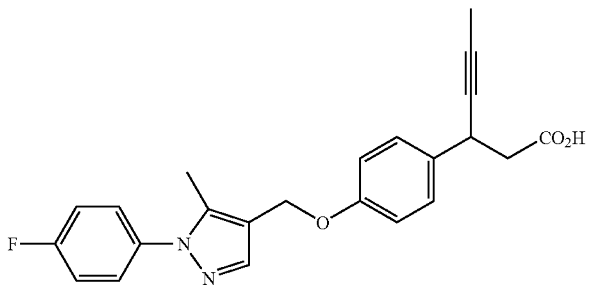 | +++ |
| 12 | 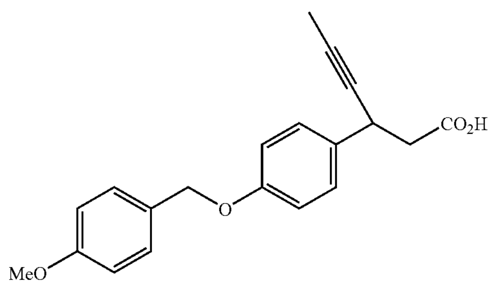 | +++ |
| 14.1 | 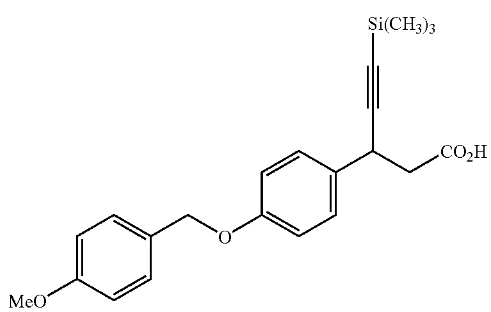 | ++ |
| 14.2 | 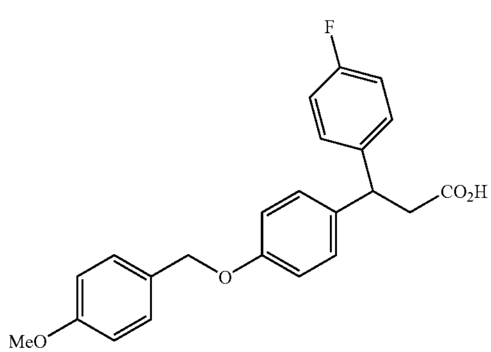 | +++ |

TABLE 21-continued
Aequorin Assay Using Human GPR40
| No. | Structure | Relative $EC_{50}{}^a$ |
|---|---|---|
| 14.3 | 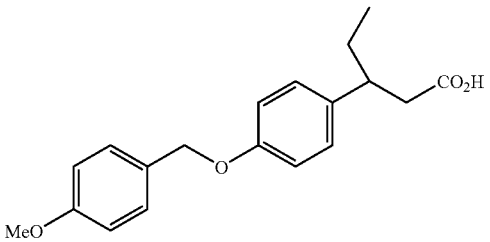 | ++ |
| 14.4 | 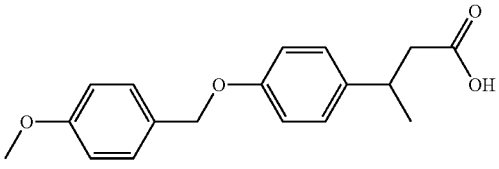 | + |
| 14.5 | 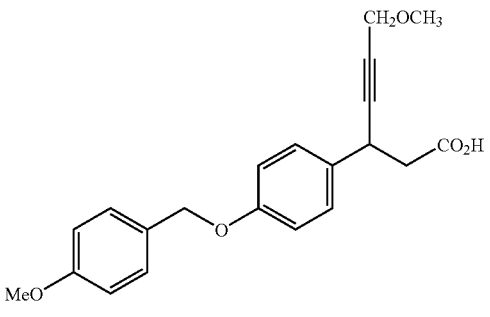 | ++ |
| 14.6 | 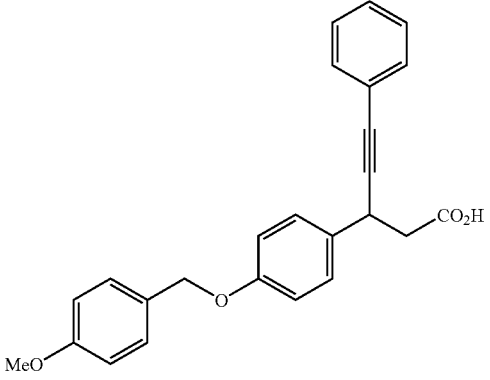 | ++ |
| 15 | 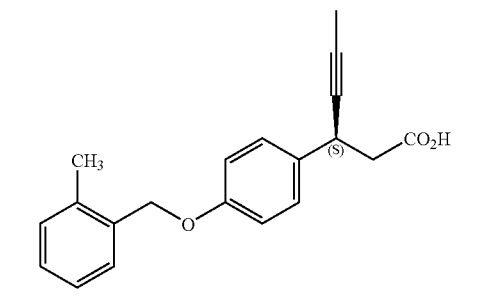 | ++++ |

TABLE 21-continued

Aequorin Assay Using Human GPR40

| No. | Structure | Relative $EC_{50}{}^a$ |
|---|---|---|
| 17.6 | 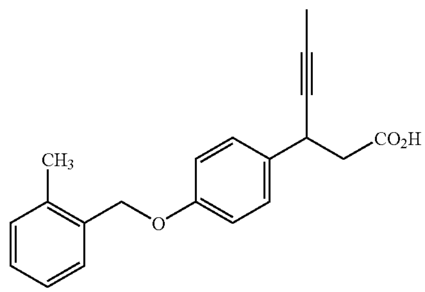 | +++ |
| 17.8 | 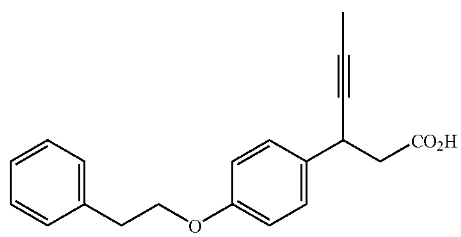 | ++ |
| 18 | 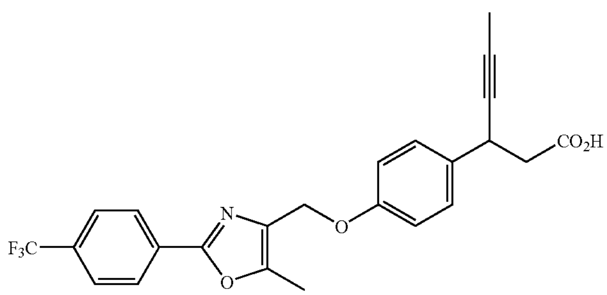 | ++++ |
| 23 | 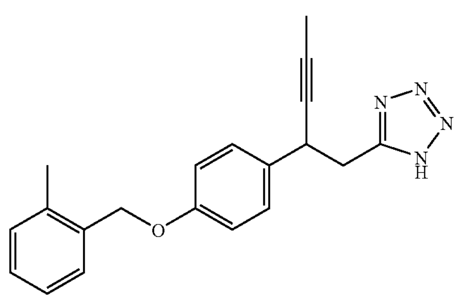 | ++ |
| 24 | 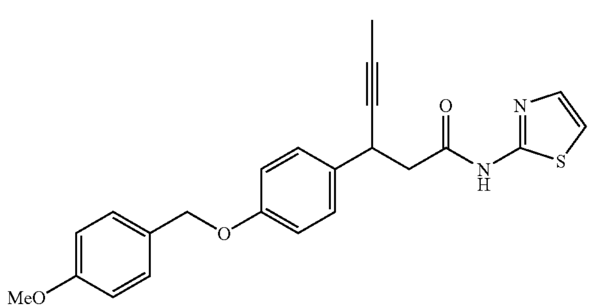 | +++ |

TABLE 21-continued

Aequorin Assay Using Human GPR40

| No. | Structure | Relative EC$_{50}$$^a$ |
|---|---|---|
| 25.1 | 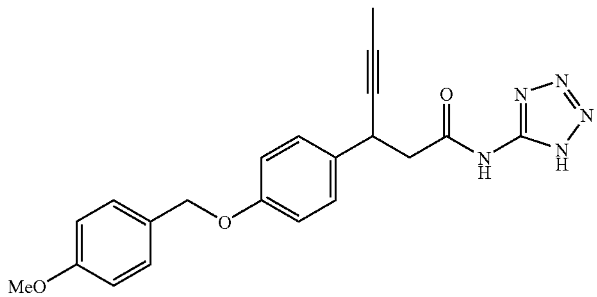 | ++ |
| 26 | 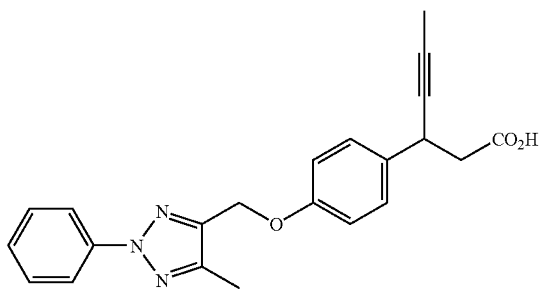 | ++++ |
| 27.1 | 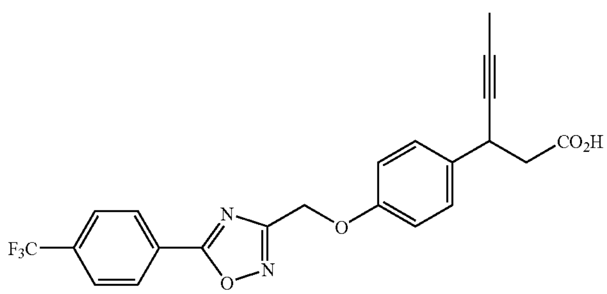 | +++ |
| 28 | 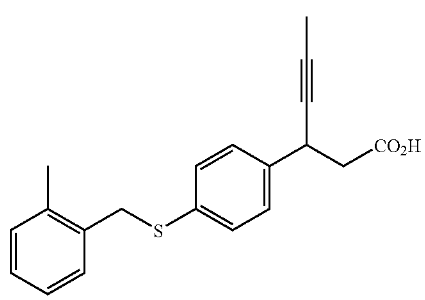 | +++ |
| 34.4 | 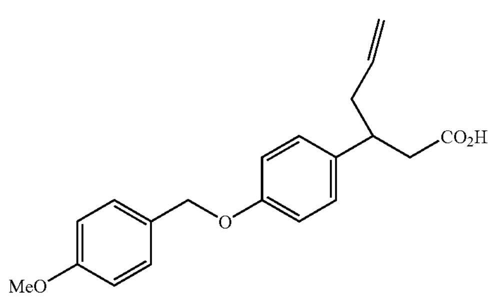 | ++ |

TABLE 21-continued
| | Aequorin Assay Using Human GPR40 | |
|---|---|---|
| No. | Structure | Relative $EC_{50}^{a}$ |
| 34.5 | 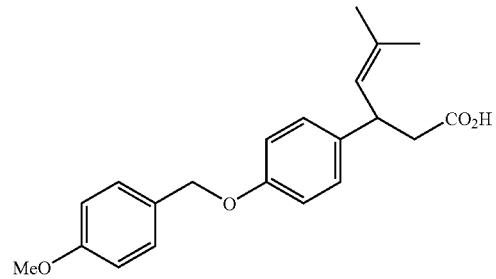 | +++ |
| 36.1 | 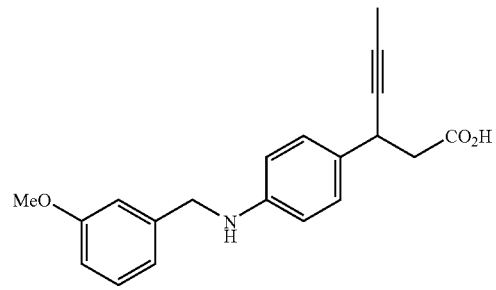 | +++ |
| 36.2 | 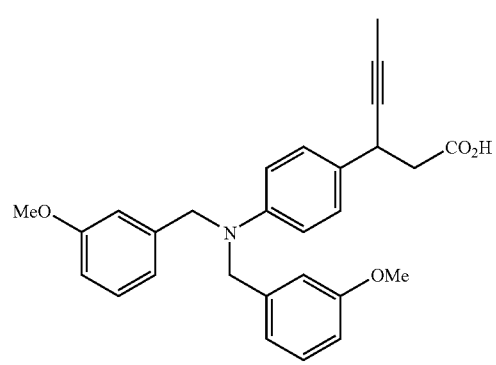 | +++ |
| 39.7 | 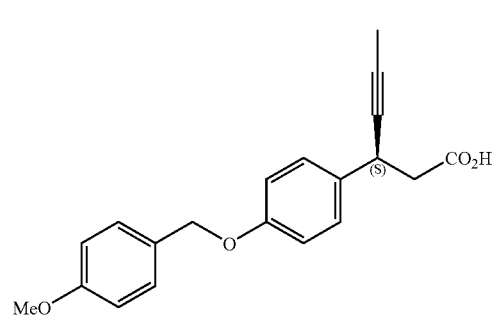 | ++++ |

TABLE 21-continued
Aequorin Assay Using Human GPR40
| No. | Structure | Relative EC$_{50}$$^a$ |
|---|---|---|
| 40.5 | 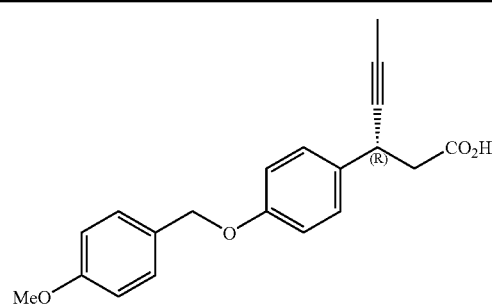 | ++ |
| 41 | 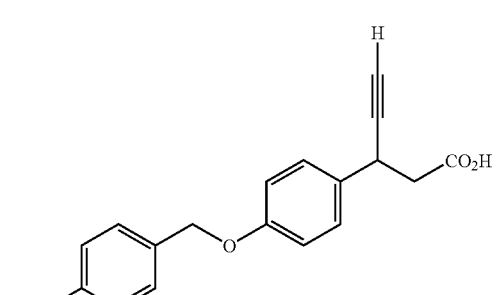 | +++ |
| 42.11 | 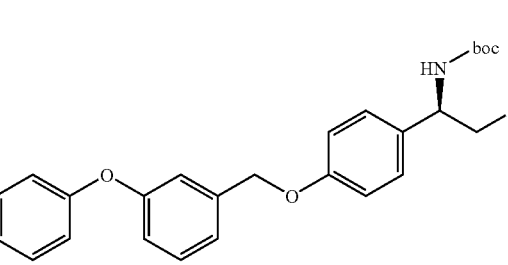 | +++ |
| 42.14 | 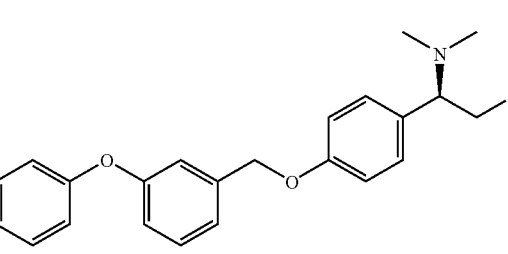 | +++ |
| 46.1 | 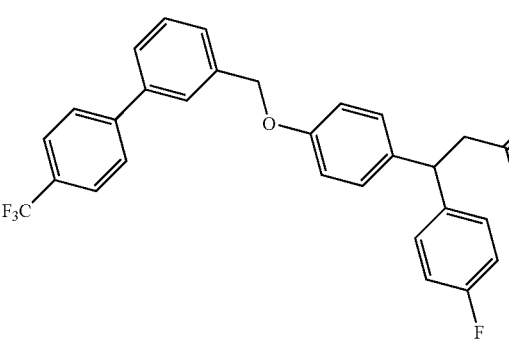 | +++ |

TABLE 21-continued

Aequorin Assay Using Human GPR40

| No. | Structure | Relative EC$_{50}$$^a$ |
|---|---|---|
| 53 | 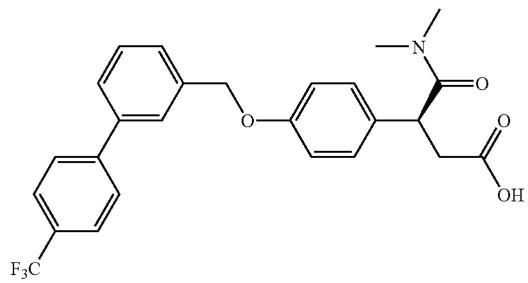 | ++++ |
| 56 | 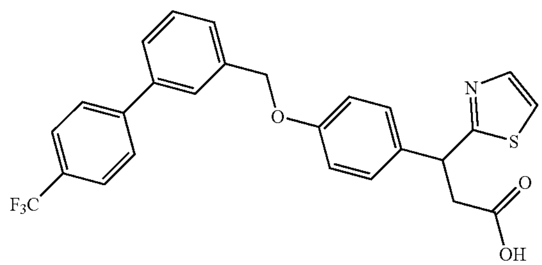 | +++ |
| 62.3 | 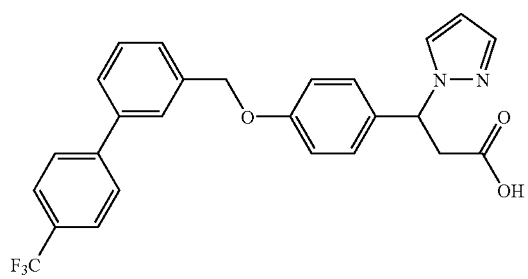 | ++++ |
| 66.5 | 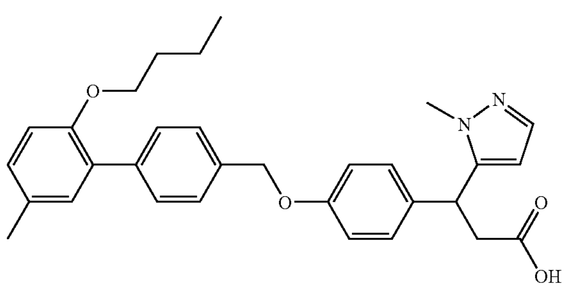 | +++ |
| 70.1 | 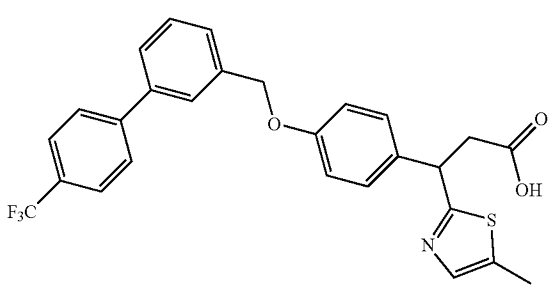 | ++ |

TABLE 21-continued

Aequorin Assay Using Human GPR40

| No. | Structure | Relative $EC_{50}{}^a$ |
|---|---|---|
| 70.2 | 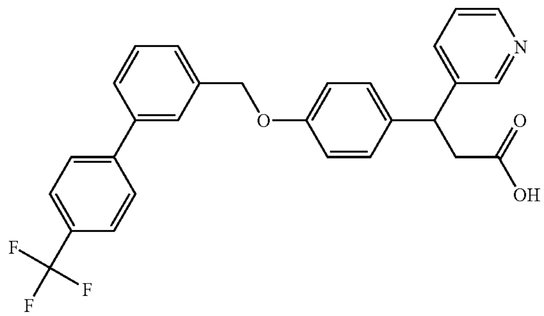 | +++ |
| 71 | 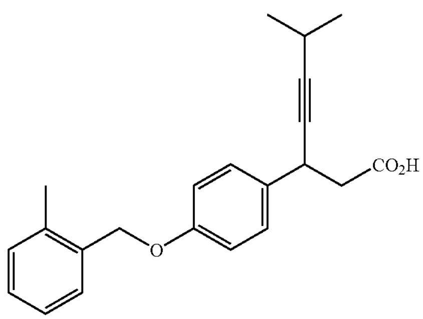 | +++ |
| 72 | 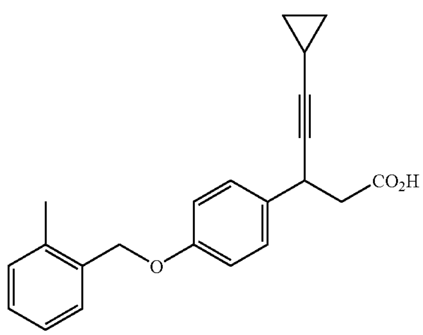 | +++ |
| 73 | 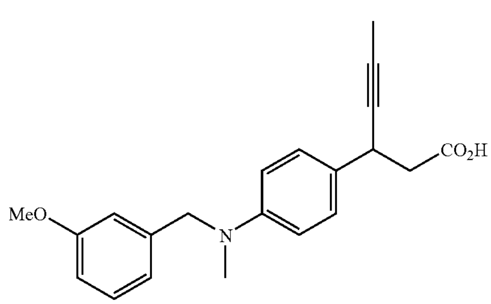 | ++ |

TABLE 21-continued

Aequorin Assay Using Human GPR40

| No. | Structure | Relative EC$_{50}$$^a$ |
|---|---|---|
| 74 | 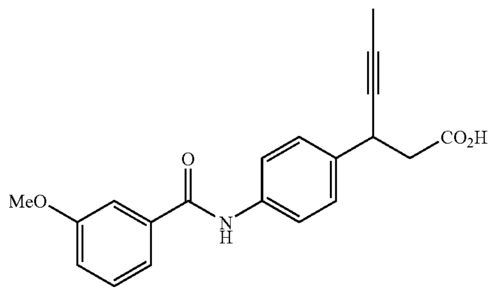 | ++ |
| 75 | 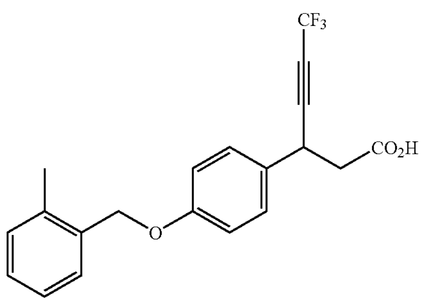 | + |
| 76 | 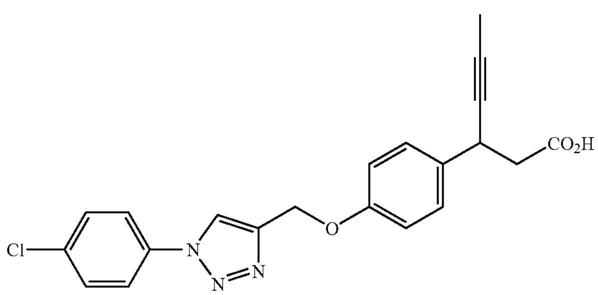 | ++ |
| 77 | 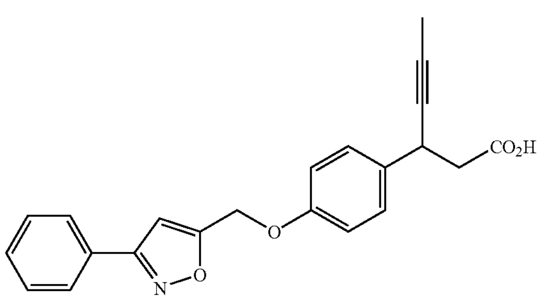 | +++ |

TABLE 21-continued

Aequorin Assay Using Human GPR40

| No. | Structure | Relative EC$_{50}$$^a$ |
|---|---|---|
| 78 | 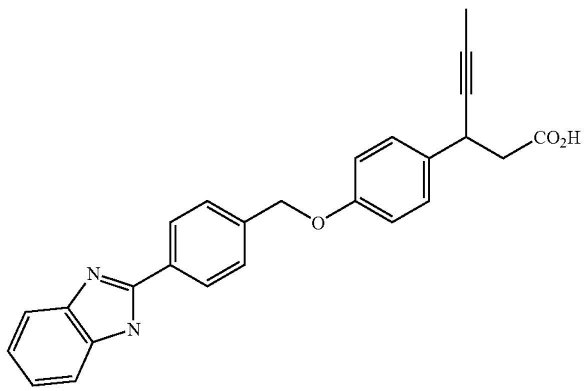 | ++ |
| 79 | 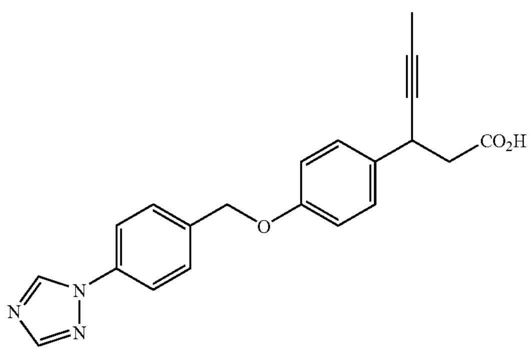 | ++ |
| 80 | 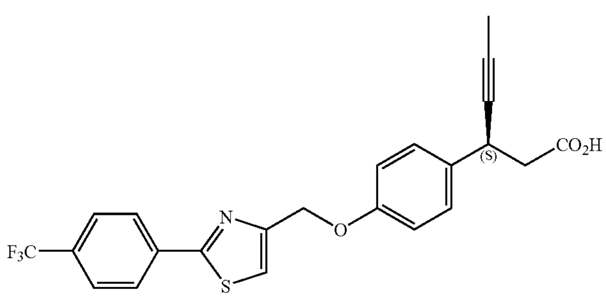 | +++++ |
| 81 | 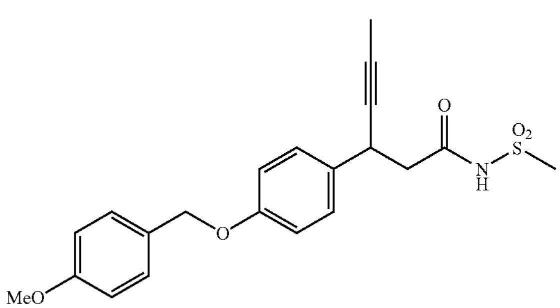 | ++ |

TABLE 21-continued

Aequorin Assay Using Human GPR40

| No. | Structure | Relative EC$_{50}$$^a$ |
|---|---|---|
| 82.1$^b$ | | ++++ + |
| 82.2$^b$ | | ++++ + |
| 82.3$^b$ | | ++++ + |
| 82.4$^b$ | | +++ + |
| 82.5$^b$ | | ++++ + |

TABLE 21-continued
Aequorin Assay Using Human GPR40
| No. | Structure | Relative EC$_{50}$$^a$ |
|---|---|---|
| 82.6$^b$ | 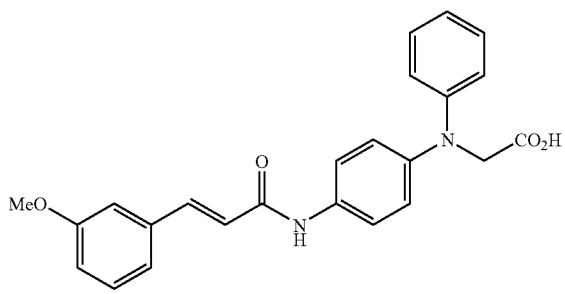 | ++++ + |
| 82.7$^b$ | 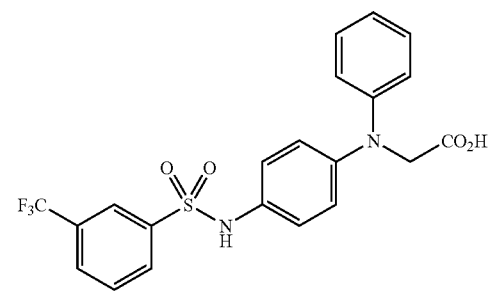 | +++++ + |
| 82.8$^b$ | 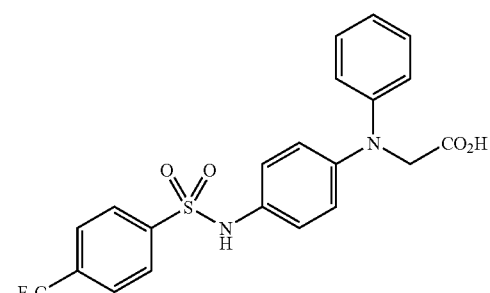 | +++++ + |
| 83 | 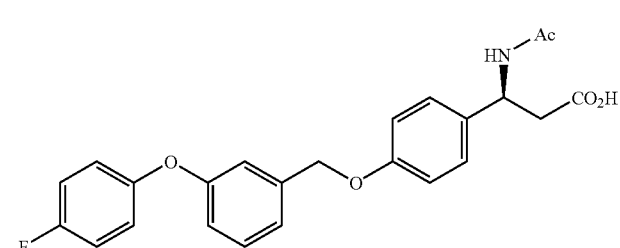 | ++ |
| 84.1 | 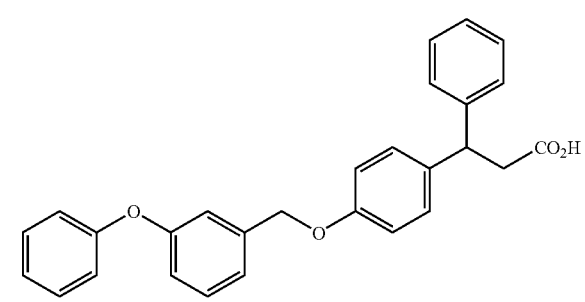 | ++++ |

TABLE 21-continued
Aequorin Assay Using Human GPR40
| No. | Structure | Relative EC$_{50}$$^a$ |
|---|---|---|
| 84.2 | 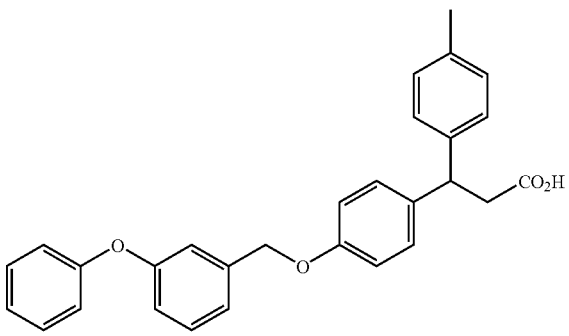 | ++ |
| 84.3 | 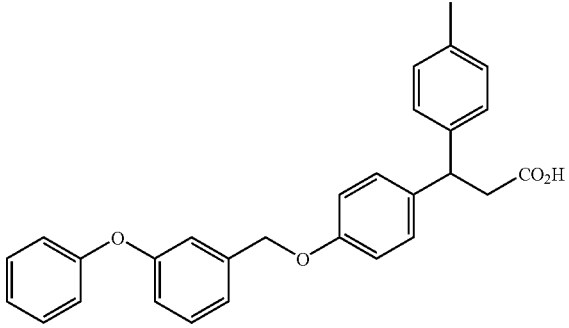 | +++ |
| 84.4 | 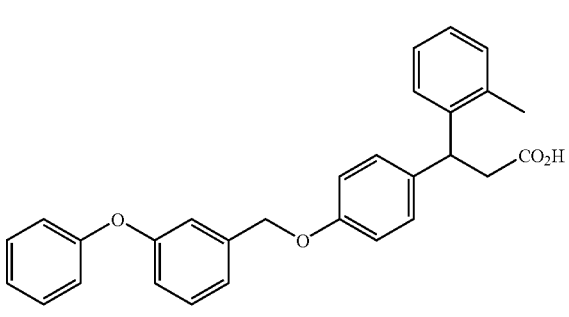 | +++ |
| 84.5 | 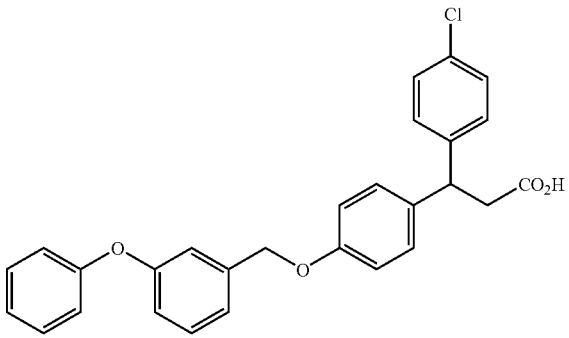 | +++ |

TABLE 21-continued

Aequorin Assay Using Human GPR40

| No. | Structure | Relative $EC_{50}{}^a$ |
|---|---|---|
| 84.6 | 3-chlorophenyl derivative | +++ |
| 84.7 | 4-methoxyphenyl derivative | +++ |
| 84.8 | 3-methoxyphenyl derivative | +++ |
| 85.1 | 4-trifluoromethylphenyl derivative | ++ |

TABLE 21-continued

Aequorin Assay Using Human GPR40

| No. | Structure | Relative $EC_{50}{}^a$ |
|---|---|---|
| 85.2 | 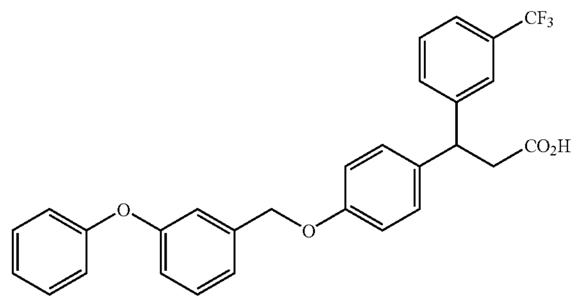 | +++ |
| 86 | 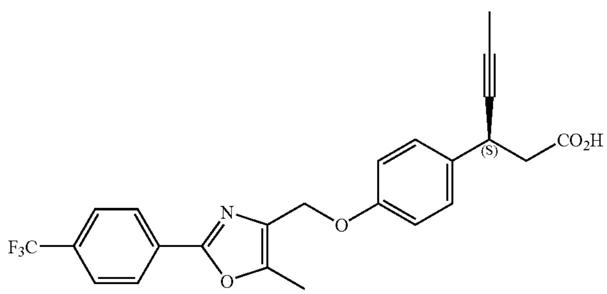 | +++++ |
| 87 | 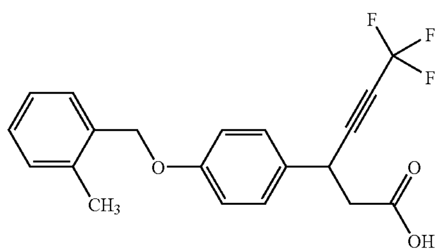 | + |
| 88.1 | 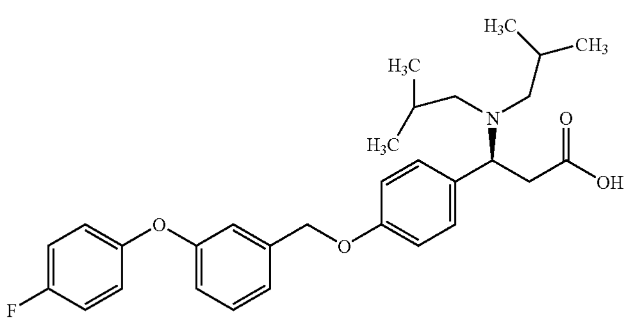 | + |
| 88.2 | 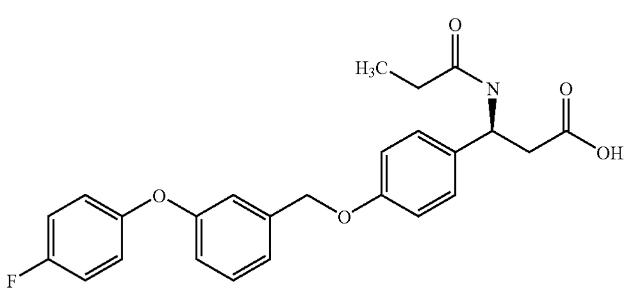 | + |

TABLE 21-continued

Aequorin Assay Using Human GPR40

| No. | Structure | Relative EC$_{50}$$^a$ |
|---|---|---|
| 88.3 | 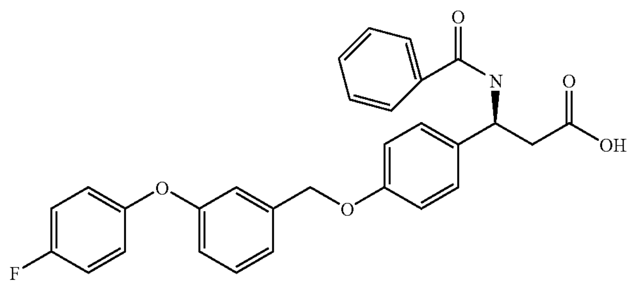 | + |
| 88.4 | 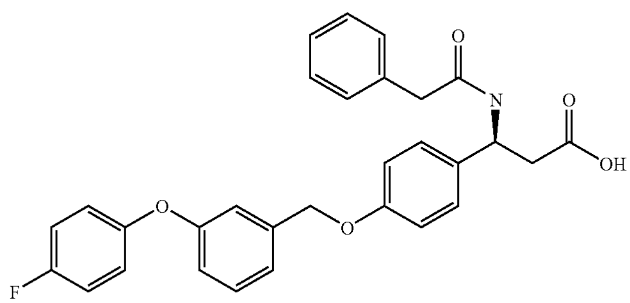 | + |
| 88.5 | 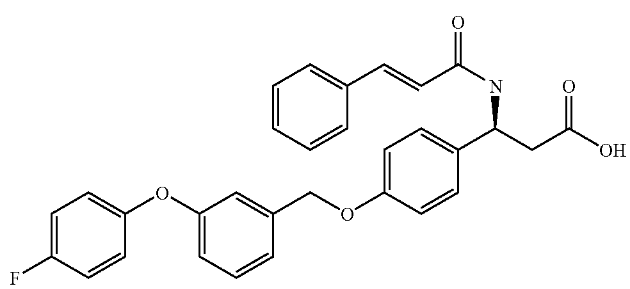 | + |
| 88.6 | | + | ns
TABLE 21-continued
Aequorin Assay Using Human GPR40
| No. | Structure | Relative EC$_{50}$$^a$ |
|---|---|---|
| 88.7 | 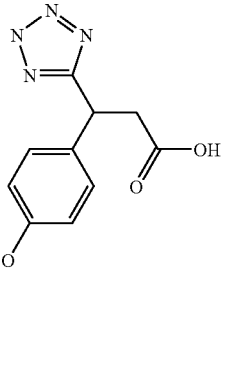 | ++ |
| 89 | 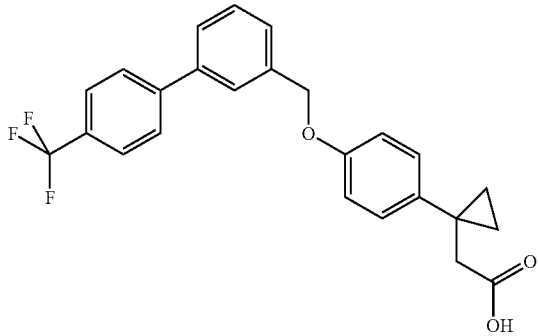 | ++ |
| 90 | 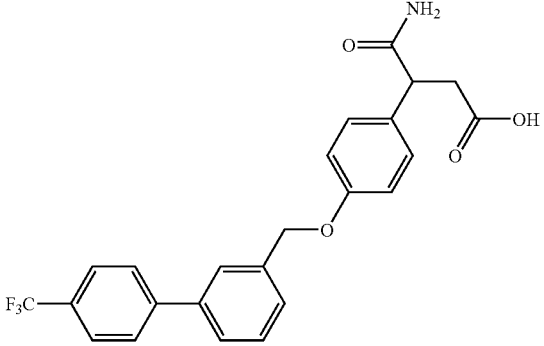 | ++ |

TABLE 21-continued

Aequorin Assay Using Human GPR40

| No. | Structure | Relative EC$_{50}$$^a$ |
|---|---|---|
| 91 | 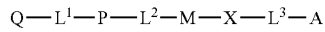 | ++ |

$^a$EC$_{50}$ Ranges:
+ EC$_{50}$ > 10 μM
++ 1 μM ≤ EC$_{50}$ ≤ 10 μM
+++ 0.1 μM ≤ EC$_{50}$ < 1 μM
++++ 0.01 μM ≤ EC$_{50}$ < 0.1 μM
+++++ EC$_{50}$ < 0.01 μM $^b$Each relative EC$_{50}$ range indicated for this compound reflects the range for an observed EC$_{50}$ for the compound when determined in seperately performed assays.

What is claimed:

1. A compound having the formula (I):

$$Q-L^1-P-L^2-M-X-L^3-A \qquad I$$

or a pharmaceutically acceptable salt, or ester thereof, wherein

Q is heteroaryl $L^1$ is a bond;

P is an aromatic ring;

$L^2$ is oxymethylene or thiomethylene;

M is an aromatic ring;

X is $CR^3R^4$;

$L^3$ is ($C_1$-$C_5$)alkylene;

A is —$CO_2H$;

$R^1$ is ($C_1$-$C_6$)alkyl, aryl($C_1$-$C_3$) alkyl or ($C_2$-$C_6$)heteroalkyl;

$R^3$ is cyano, aryl, heteroaryl, ($C_1$-$C_8$)alkyl, ($C_2$-$C_8$)alkyl, ($C_2$-$C_8$)alkenyl, ($C_3$-$C_8$)alkenyl, ($C_2$-$C_8$)alkynyl, ($C_3$-$C_8$)alkynyl, —$NR^8R^9$, —$C(O)NR^{10}R^{11}$, —$NR^{12}C(O)R^{13}$ or —$NR^{12}S(O)_pR^{13}$;

$R^4$ is hydrogen, cyano, aryl, heteroaryl, ($C_1$-$C_8$)alkyl, ($C_2$-$C_8$)alkenyl or ($C_2$-$C_8$)alkynyl;

$R^8$ and $R^9$ are independently hydrogen, ($C_1$-$C_5$)alkyl, oxy($C_1$-$C_5$)alkyl or carboxy($C_1$-$C_5$)alkyl;

optionally, $R^8$ and $R^9$ are combined to form a 4-, 5-, 6- or 7-membered ring containing the nitrogen atom to which they are attached and from 0 to 2 additional heteroatoms selected from N, O and S;

$R^{10}$, $R^{11}$ and $R^{12}$ are independently selected from hydrogen, aryl, heteroaryl, ($C_1$-$C_8$)alkyl, ($C_2$-$C_8$)heteroalkyl, ($C_3$-$C_8$)cycloalkyl and ($C_3$-$C_8$)heterocycloalkyl;

optionally, $R^{10}$ and $R^{11}$ are combined to form a 4-, 5-, 6- or 7-membered ring containing the nitrogen atom to which they are attached and from 0 to 2 additional heteroatoms selected from N, O and S;

$R^{13}$ is aryl, heteroaryl, ($C_1$-$C_8$)alkyl, ($C_2$-$C_8$)heteroalkyl, ($C_3$-$C_8$)cycloalkyl or ($C_3$-$C_8$)heterocycloalkyl;

the subscript p is 1 or 2; and wherein the aromatic rings, aryl groups, and heteroaryl groups set forth above are optionally substituted with substituents selected from -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic, aryl, or heteroaryl ring; and further wherein R', R" and R'" are independently selected from hydrogen, ($C_1$-$C_8$) alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

2. The compound of claim 1, wherein P and M are benzene.

3. The compound of claim 1, wherein the compound has the following structure:

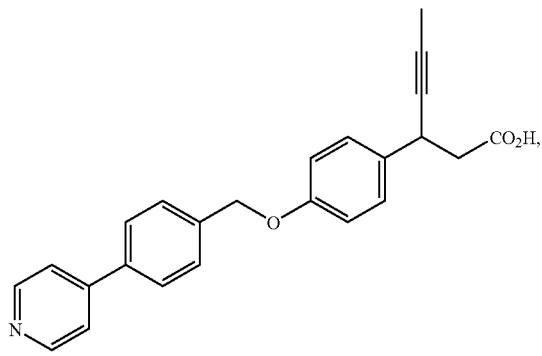

or is a salt thereof.

4. The compound of claim 1, wherein $R^3$ is cyano, aryl, heteroaryl, $(C_1-C_8)$alkyl, $(C_2-C_8)$alkenyl, $(C_2-C_8)$alkynyl or —$NR^8R^9$.

5. The compound of claim 4, wherein $R^4$ is hydrogen.

6. The compound of claim 1, wherein M is benzene.

7. The compound of claim 6, wherein $R^3$ is cyano, aryl, heteroaryl, $(C_1-C_8)$alkyl, $(C_2-C_8)$alkenyl, $(C_2-C_8)$alkynyl or —$NR^8R^9$.

8. The compound of claim 7, wherein P is benzene.

9. The compound of claim 1, wherein P is benzene.

10. The compound of claim 9, wherein $R^3$ is cyano, aryl, heteroaryl, $(C_1-C_8)$alkyl, $(C_2-C_8)$alkenyl, $(C_2-C_8)$alkynyl or —$NR^8R^9$.

11. The compound of claim 10, wherein $R^4$ is hydrogen.

12. The compound of claim 11, wherein M is benzene.

13. The compound of claim 9, wherein M is benzene and X is para to $L^2$.

14. The compound of claim 13, wherein $L^3$ is methylene.

15. The compound of claim 14, wherein $R^3$ is cyano, aryl, heteroaryl, $(C_1-C_8)$alkyl, $(C_2-C_8)$alkenyl, $(C_2-C_8)$alkynyl or —$NR^8R^9$.

16. The compound of claim 15, wherein $L^2$ is oxymethylene.

17. The compound of claim 15, wherein $R^4$ is hydrogen.

18. The compound of claim 1, wherein $L^2$ is oxymethylene.

19. The compound of claim 17, wherein $L^2$ is oxymethylene.

20. A pharmaceutical composition comprising a pharmaceutically acceptable carrier, diluent or excipient and the compound of claim 1.

21. A method for treating a disease or condition, the method comprising administering to a subject in need thereof a therapeutically effective amount of the compound of claim 1, wherein the disease or condition is type II diabetes.

22. The method of claim 21, wherein said compound is administered orally, parentally or topically.

23. The method of claim 21 wherein said compound is administered in combination with a second therapeutic agent.

24. The method of claim 23 wherein said second therapeutic agent is a metformin or a thiazolidinedione.

25. A method for increasing circulating insulin concentration in a subject, comprising administering the compound of claim 1 to the subject.

* * * * *